(12) United States Patent
Vechorkin et al.

(10) Patent No.: US 11,111,247 B2
(45) Date of Patent: Sep. 7, 2021

(54) PYRAZOLOPYRIMIDINE COMPOUNDS AND USES THEREOF

(71) Applicant: Incyte Corporation, Wilmington, DE (US)

(72) Inventors: Oleg Vechorkin, Wilmington, DE (US); Minh Nguyen, Claymont, DE (US); Chao Qi, Newark, DE (US); Anlai Wang, Wilmington, DE (US); Liangxing Wu, Wilmington, DE (US); Wenqing Yao, Chadds Ford, PA (US); Peng Zhao, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 16/580,766

(22) Filed: Sep. 24, 2019

(65) Prior Publication Data

US 2020/0095250 A1 Mar. 26, 2020

Related U.S. Application Data

(60) Provisional application No. 62/736,121, filed on Sep. 25, 2018.

(51) Int. Cl.
*C07D 487/04* (2006.01)
*C07D 487/02* (2006.01)
*A61P 35/00* (2006.01)
*C07D 519/00* (2006.01)
*A61K 45/06* (2006.01)

(52) U.S. Cl.
CPC ............ *C07D 487/02* (2013.01); *A61P 35/00* (2018.01); *C07D 487/04* (2013.01); *C07D 519/00* (2013.01); *A61K 45/06* (2013.01)

(58) Field of Classification Search
CPC .................................................. C07D 487/04
See application file for complete search history.

(56) References Cited

U.S. PATENT DOCUMENTS

| | | |
|---|---|---|
| 5,250,534 A | 10/1993 | Bell et al. |
| 6,200,980 B1 | 3/2001 | Piazza et al. |
| 6,251,904 B1 | 6/2001 | Bunnage et al. |
| 6,333,330 B1 | 12/2001 | Bunnage et al. |
| 6,458,951 B1 | 10/2002 | Bunnage et al. |
| 6,512,002 B2 | 1/2003 | Lee et al. |
| 6,670,366 B1 | 12/2003 | Bunnage et al. |
| 6,723,719 B1 | 4/2004 | Bunnage et al. |
| 6,743,799 B2 | 6/2004 | Westbrook et al. |
| 6,756,373 B1 | 6/2004 | Allerton et al. |
| 6,770,645 B2 | 8/2004 | Denton et al. |
| 6,784,185 B2 | 8/2004 | Allerton et al. |
| 6,916,927 B2 | 7/2005 | Bunnage et al. |
| 7,105,532 B2 | 9/2006 | Rawlings |
| 7,166,293 B2 | 1/2007 | Teng et al. |
| 7,259,165 B2 | 8/2007 | Bernotas et al. |
| 7,345,178 B2 | 3/2008 | Nunes et al. |
| 7,576,087 B2 | 8/2009 | Bernotas et al. |
| 7,919,487 B2 | 4/2011 | Sun et al. |
| 7,968,719 B2 | 6/2011 | Zoller et al. |
| 8,106,190 B2 | 1/2012 | Kuramochi et al. |
| 8,450,335 B2 | 5/2013 | Singh et al. |
| 8,546,403 B2 | 10/2013 | Whitten et al. |
| 8,637,507 B2 | 1/2014 | Zhou et al. |
| 8,722,691 B2 | 3/2014 | He et al. |
| 8,987,273 B2 | 3/2015 | Rehwinkel et al. |
| 9,090,593 B2 | 7/2015 | Wang et al. |
| 9,260,425 B2 | 2/2016 | Do et al. |
| 9,284,319 B2 | 3/2016 | Eis et al. |
| 9,320,737 B2 | 4/2016 | Eis et al. |
| 9,718,818 B2 | 8/2017 | DeMong et al. |
| 9,730,929 B2 | 8/2017 | Eis et al. |
| 10,266,530 B2 | 4/2019 | Vechorkin et al. |
| 10,280,164 B2 | 5/2019 | Ye et al. |
| 10,435,405 B2 | 10/2019 | Vechorkin et al. |
| 2002/0013327 A1 | 1/2002 | Lee et al. |
| 2002/0198223 A1 | 12/2002 | Allerton et al. |
| 2003/0018036 A1 | 1/2003 | Westbrook et al. |
| 2003/0064990 A1 | 4/2003 | Denton et al. |
| 2003/0114440 A1 | 6/2003 | Lee et al. |
| 2003/0162782 A1 | 8/2003 | Grossman et al. |
| 2003/0186996 A1 | 10/2003 | Teng et al. |
| 2004/0063730 A1 | 4/2004 | Eggenweiler et al. |
| 2004/0077681 A1 | 4/2004 | Rawlings et al. |
| 2004/0147546 A1 | 7/2004 | Tanaka et al. |
| 2004/0157866 A1 | 8/2004 | Takasugi et al. |
| 2004/0167030 A1 | 8/2004 | Bernotas et al. |
| 2004/0204417 A1 | 10/2004 | Perez et al. |
| 2005/0043325 A1 | 2/2005 | Bell et al. |
| 2005/0070557 A1 | 3/2005 | Fryburg et al. |

(Continued)

FOREIGN PATENT DOCUMENTS

| | | |
|---|---|---|
| CN | 102206172 | 10/2011 |
| CN | 102503959 | 6/2012 |

(Continued)

OTHER PUBLICATIONS

RN 2104991-77-5 Registry, 2017.*

(Continued)

*Primary Examiner* — Brian E McDowell
(74) *Attorney, Agent, or Firm* — Fish & Richardson P.C.

(57) ABSTRACT

Disclosed are compounds of Formula (I), methods of using the compounds for inhibiting ALK2 activity and/or FGFR activity, and pharmaceutical compositions comprising such compounds. The compounds are useful in treating, preventing or ameliorating diseases or disorders associated with ALK2 activity and/or FGFR activity, such as cancer.

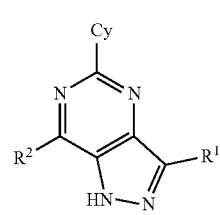

48 Claims, No Drawings
Specification includes a Sequence Listing.

(56) References Cited

U.S. PATENT DOCUMENTS

| | | |
|---|---|---|
| 2005/0075795 A1 | 4/2005 | Pandit |
| 2005/0119278 A1 | 6/2005 | Teng et al. |
| 2005/0137226 A1 | 6/2005 | Ji et al. |
| 2005/0208582 A1 | 9/2005 | Ohi et al. |
| 2005/0261339 A1 | 11/2005 | Ohi et al. |
| 2006/0106032 A1 | 5/2006 | Kuo et al. |
| 2007/0087988 A1 | 4/2007 | Sawasdikosol et al. |
| 2007/0161673 A1 | 7/2007 | Barker et al. |
| 2007/0185152 A1 | 8/2007 | Yamashita et al. |
| 2007/0270412 A1 | 11/2007 | Bell et al. |
| 2008/0280891 A1 | 11/2008 | Kelly et al. |
| 2009/0247559 A1 | 10/2009 | Brown et al. |
| 2010/0035891 A1 | 2/2010 | Bunnage et al. |
| 2010/0087464 A1 | 4/2010 | Mi et al. |
| 2010/0216798 A1 | 8/2010 | Nakai et al. |
| 2012/0129852 A1 | 5/2012 | Duan et al. |
| 2012/0225869 A1 | 9/2012 | Liu et al. |
| 2012/0295884 A1 | 11/2012 | Altmann et al. |
| 2013/0039906 A1 | 2/2013 | Do et al. |
| 2013/0040949 A1 | 2/2013 | Gray et al. |
| 2013/0281433 A1 | 10/2013 | Babaoglu et al. |
| 2014/0171405 A1 | 6/2014 | Zhuo et al. |
| 2014/0225073 A1 | 8/2014 | Lee et al. |
| 2014/0288045 A1 | 9/2014 | Ren et al. |
| 2014/0288069 A1 | 9/2014 | Eis et al. |
| 2014/0350017 A1 | 11/2014 | Williams et al. |
| 2014/0364605 A1 | 12/2014 | Li et al. |
| 2015/0038485 A1 | 2/2015 | Eis et al. |
| 2015/0191462 A1 | 7/2015 | Hommel et al. |
| 2015/0239868 A1 | 8/2015 | Pais et al. |
| 2015/0239889 A1 | 8/2015 | Nakajima et al. |
| 2015/0243908 A1 | 8/2015 | Lee et al. |
| 2015/0274639 A1 | 10/2015 | Williams et al. |
| 2015/0328188 A1 | 11/2015 | Orlemans et al. |
| 2016/0013427 A1 | 1/2016 | Kim et al. |
| 2016/0046648 A1 | 2/2016 | Petrukhin et al. |
| 2016/0068529 A1 | 3/2016 | KC et al. |
| 2016/0068547 A1 | 3/2016 | KC et al. |
| 2016/0068548 A1 | 3/2016 | KC et al. |
| 2016/0068551 A1 | 3/2016 | KC et al. |
| 2016/0200722 A1 | 7/2016 | DeMong et al. |
| 2017/0107216 A1 | 4/2017 | Wu et al. |
| 2017/0145025 A1 | 5/2017 | Li et al. |
| 2017/0174671 A1 | 6/2017 | Wu et al. |
| 2017/0174679 A1 | 6/2017 | Lajkiewicz et al. |
| 2017/0320875 A1 | 11/2017 | Li et al. |
| 2017/0342060 A1 | 11/2017 | Lu et al. |
| 2017/0362253 A1 | 12/2017 | Xiao et al. |
| 2018/0016260 A1 | 1/2018 | Yu et al. |
| 2018/0057486 A1 | 3/2018 | Wu et al. |
| 2018/0072718 A1 | 3/2018 | Liu et al. |
| 2018/0072719 A1 | 3/2018 | Ye et al. |
| 2018/0072720 A1 | 3/2018 | Vechorkin et al. |
| 2018/0072741 A1 | 3/2018 | Vechorkin et al. |
| 2018/0177784 A1 | 6/2018 | Wu et al. |
| 2018/0177870 A1 | 6/2018 | Liu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0228786 A1 | 8/2018 | Sokolsky |
| 2019/0076401 A1 | 3/2019 | Vechorkin et al. |
| 2019/0106419 A1 | 4/2019 | Vechorkin et al. |
| 2019/0256500 A1 | 8/2019 | Vechorkin et al. |
| 2019/0256520 A1 | 8/2019 | Sokolsky |
| 2019/0315717 A1 | 10/2019 | Hummel et al. |
| 2019/0315743 A1 | 10/2019 | Liu et al. |
| 2019/0343814 A1 | 11/2019 | Sokolsky |
| 2019/0382380 A1 | 12/2019 | Vechorkin et al. |
| 2020/0048241 A1 | 2/2020 | Hummel et al. |

FOREIGN PATENT DOCUMENTS

| | | |
|---|---|---|
| CN | 102516263 | 6/2012 |
| CN | 103570709 | 2/2014 |
| DE | 10 2004 054 666 | 5/2006 |
| EP | 2543372 | 1/2013 |
| EP | 2824099 | 1/2015 |
| IN | 187433 | 8/2002 |
| JP | H03287584 | 12/1991 |
| JP | 2000-038350 | 2/2000 |
| JP | 2007/055940 | 3/2007 |
| JP | 2010-111624 | 5/2010 |
| JP | 2011-246389 | 12/2011 |
| KR | 963644 | 2/1996 |
| KR | 2009053594 | 5/2009 |
| KR | 10 2014 0019055 | 2/2014 |
| MX | 9910322 | 7/2003 |
| MY | 146643 | 9/2012 |
| RU | 2239637 | 11/2004 |
| WO | WO 1989/008263 | 9/1989 |
| WO | WO 2000/043394 | 7/2000 |
| WO | WO 2001/019827 | 3/2001 |
| WO | WO 2001/019828 | 3/2001 |
| WO | WO 2001/021576 | 3/2001 |
| WO | WO 2001/046124 | 6/2001 |
| WO | WO 2002/000196 | 1/2002 |
| WO | WO 2002/016348 | 2/2002 |
| WO | WO 2002/019975 | 3/2002 |
| WO | WO 2002/050073 | 6/2002 |
| WO | WO 2002/090347 | 11/2002 |
| WO | WO 2003/037432 | 5/2003 |
| WO | WO 2003/049681 | 6/2003 |
| WO | WO 2004/072069 | 8/2004 |
| WO | WO 2004/096810 | 11/2004 |
| WO | WO 2004/108133 | 12/2004 |
| WO | WO 2005/004799 | 1/2005 |
| WO | WO 2005/011681 | 2/2005 |
| WO | WO 2005/028475 | 3/2005 |
| WO | WO 2005/051906 | 6/2005 |
| WO | WO 2005/066167 | 7/2005 |
| WO | WO 2005/073199 | 8/2005 |
| WO | WO 2005/073232 | 8/2005 |
| WO | WO 2003/101968 | 9/2005 |
| WO | WO 2005/085227 | 9/2005 |
| WO | WO 2005/085248 | 9/2005 |
| WO | WO 2005/085249 | 9/2005 |
| WO | WO 2006/013095 | 2/2006 |
| WO | WO 2006/028958 | 3/2006 |
| WO | WO 2006/038001 | 4/2006 |
| WO | WO 2006/045010 | 4/2006 |
| WO | WO 2006/047415 | 5/2006 |
| WO | WO 2006/050097 | 5/2006 |
| WO | WO 2006/053109 | 5/2006 |
| WO | WO 2006/053121 | 5/2006 |
| WO | WO 2006/053227 | 5/2006 |
| WO | WO 2006/074428 | 7/2006 |
| WO | WO 2006/105289 | 10/2006 |
| WO | WO 2006/128172 | 11/2006 |
| WO | WO 2007/019344 | 2/2007 |
| WO | WO 2007/019345 | 2/2007 |
| WO | WO 2007/019346 | 2/2007 |
| WO | WO 2007/019417 | 2/2007 |
| WO | WO 2007/020050 | 2/2007 |
| WO | WO 2007/023110 | 3/2007 |
| WO | WO 2007/023111 | 3/2007 |
| WO | WO 2007/023114 | 3/2007 |
| WO | WO 2007/030582 | 3/2007 |
| WO | WO 2007/056280 | 5/2007 |
| WO | WO 2007/063925 | 6/2007 |
| WO | WO 2007/065924 | 6/2007 |
| WO | WO 2007/080382 | 7/2007 |
| WO | WO 2007/093402 | 8/2007 |
| WO | WO 2007/112093 | 10/2007 |
| WO | WO 2007/114848 | 10/2007 |
| WO | WO 2007/137030 | 11/2007 |
| WO | WO 2008/008059 | 1/2008 |
| WO | WO 2008/008539 | 1/2008 |
| WO | WO 2008/012027 | 1/2008 |
| WO | WO 2008/045627 | 4/2008 |
| WO | WO 2008/070313 | 6/2008 |
| WO | WO 2008/089307 | 7/2008 |
| WO | WO 2008/089310 | 7/2008 |
| WO | WO 2008/113856 | 9/2008 |

(56) References Cited

FOREIGN PATENT DOCUMENTS

| | | |
|---|---|---|
| WO | WO 2009/019167 | 2/2009 |
| WO | WO 2009/024341 | 2/2009 |
| WO | WO 2009/032651 | 3/2009 |
| WO | WO 2009/038784 | 3/2009 |
| WO | WO 2009/100130 | 8/2009 |
| WO | WO 2009/139834 | 11/2009 |
| WO | WO 2009/152356 | 12/2009 |
| WO | WO 2010/036380 | 1/2010 |
| WO | WO 2010/029300 | 3/2010 |
| WO | WO 2010/035217 | 4/2010 |
| WO | WO 2010/035219 | 4/2010 |
| WO | WO 2010/035221 | 4/2010 |
| WO | WO 2010/046780 | 4/2010 |
| WO | WO 2010/080503 | 7/2010 |
| WO | WO 2010/104306 | 9/2010 |
| WO | WO 2010/107765 | 9/2010 |
| WO | WO 2010/107768 | 9/2010 |
| WO | WO 2010/111624 | 9/2010 |
| WO | WO 2010/118367 | 10/2010 |
| WO | WO 2011/019780 | 2/2011 |
| WO | WO 2011/031628 | 3/2011 |
| WO | WO 2011/050245 | 4/2011 |
| WO | WO 2011/051535 | 5/2011 |
| WO | WO 2011/062253 | 5/2011 |
| WO | WO 2011/078143 | 6/2011 |
| WO | WO 2011/082400 | 7/2011 |
| WO | WO 2011/082488 | 7/2011 |
| WO | WO 2011/107186 | 9/2011 |
| WO | WO 2011/112766 | 9/2011 |
| WO | WO 2011/133920 | 10/2011 |
| WO | WO 2011/139489 | 11/2011 |
| WO | WO 2011/141756 | 11/2011 |
| WO | WO 2011/147765 | 12/2011 |
| WO | WO 2011/153553 | 12/2011 |
| WO | WO 2011/157653 | 12/2011 |
| WO | WO 2011/158108 | 12/2011 |
| WO | WO 2012/048058 | 4/2012 |
| WO | WO 2012/049277 | 4/2012 |
| WO | WO 2012/078777 | 6/2012 |
| WO | WO 2012/080376 | 6/2012 |
| WO | WO 2012/109263 | 8/2012 |
| WO | WO 2012/130780 | 10/2012 |
| WO | WO 2012/141487 | 10/2012 |
| WO | WO 2012/143144 | 10/2012 |
| WO | WO 2012/158810 | 11/2012 |
| WO | WO 2012/163959 | 12/2012 |
| WO | WO 2013/007708 | 1/2013 |
| WO | WO 2013/021276 | 2/2013 |
| WO | WO 2013/024002 | 2/2013 |
| WO | WO 2013/024011 | 2/2013 |
| WO | WO 2013/042137 | 3/2013 |
| WO | WO 2013/064445 | 5/2013 |
| WO | WO 2013/123215 | 8/2013 |
| WO | WO 2013/130660 | 9/2013 |
| WO | WO 2013/130890 | 9/2013 |
| WO | WO 2013/146942 | 10/2013 |
| WO | WO 2014/003405 | 1/2014 |
| WO | WO 2014/024125 | 2/2014 |
| WO | WO 2014/047616 | 3/2014 |
| WO | WO 2014/055955 | 4/2014 |
| WO | WO 2014/151616 | 9/2014 |
| WO | WO 2015/026683 | 2/2015 |
| WO | WO 2015/037965 | 3/2015 |
| WO | WO 2015/038503 | 3/2015 |
| WO | WO 2015/058163 | 4/2015 |
| WO | WO 2015/061247 | 4/2015 |
| WO | WO 2015/089327 | 6/2015 |
| WO | WO 2015/089479 | 6/2015 |
| WO | WO 2015/090235 | 6/2015 |
| WO | WO 2015/091426 | 6/2015 |
| WO | WO 2015/104662 | 7/2015 |
| WO | WO 2015/117718 | 8/2015 |
| WO | WO 2015/164956 | 11/2015 |
| WO | WO 2015/192939 | 12/2015 |
| WO | WO 2015/193506 | 12/2015 |
| WO | WO 2015/193846 | 12/2015 |
| WO | WO 2015/200682 | 12/2015 |
| WO | WO 2016/040180 | 3/2016 |
| WO | WO 2016/040181 | 3/2016 |
| WO | WO 2016/041618 | 3/2016 |
| WO | WO 2016/057500 | 4/2016 |
| WO | WO 2016/071293 | 5/2016 |
| WO | WO 2016/083433 | 6/2016 |
| WO | WO 2016/090300 | 6/2016 |
| WO | WO 2016/124304 | 8/2016 |
| WO | WO 2016/144351 | 9/2016 |
| WO | WO 2016/144702 | 9/2016 |
| WO | WO 2016/164285 | 10/2016 |
| WO | WO 2016/174183 | 11/2016 |
| WO | WO 2016/205942 | 12/2016 |
| WO | WO 2017/009798 | 1/2017 |
| WO | WO 2017/009806 | 1/2017 |
| WO | WO 2017/023972 | 2/2017 |
| WO | WO 2017/027400 | 2/2017 |
| WO | WO 2017/045955 | 3/2017 |
| WO | WO 2017/058915 | 4/2017 |
| WO | WO 2017/108744 | 6/2017 |
| WO | WO 2017/023894 | 9/2017 |
| WO | WO 2018/049152 | 3/2018 |
| WO | WO 2018/049214 | 3/2018 |
| WO | WO 2018/068017 | 4/2018 |
| ZA | 2003005330 | 7/2003 |

OTHER PUBLICATIONS

RN 1897639-01-8 Registry, 2016.*
RN 1893801-43-8 Registry, 2016.*
RN 1889812-00-3 Registry, 2016, RN 1494809-54-9 Registry, 2013,RN 1369234-83-2 Registry, Apr. 2012 , RN 1368329-77-4 Registry, 2012, RN 1367941-73-8 Registry, 2012.*
Alzabin et al., "Hematopoietic progenitor kinase 1 is a critical component of prostaglandin E2-mediated suppression of the antitumor immune response," Cancer Immunol Immunother, 2010, 59(3):419-429.
Alzabin et al., "Hematopoietic progenitor kinase 1 is a negative regulator of dendritic cell activation," J Immunol, 2009, 182(10):6187-6194.
Andriopoulos et al., "BMP6 is a key endogenous regulator of hepcidin expression and iron metabolism," Nature Genetics Mar. 1, 2009, 41:482-487.
Anonymous, "Crystalline APX," IP.com #IPCOM000233879, Dec. 25, 2013, 3 pages.
Anonymous, "Crystalline ethyl 1-(4-methoxyphenyl)-6-(4-nitrophenyl)-7-oxo-,5,6,7-tetrahydro-1H-pyrazolo[3,4-c]pyridine-3-carboxylate," IP.com #IPCOM000233229D, Dec. 3, 2019, 4 pages.
Antoine et al., "Efficient synthesis of novel disubstituted pyrido[3,4-b]pyrazines for the design of protein kinase inhibitors," Med Chem Common., 2016, 6:224-229.
Antunes et al., "In silico prediction of novel phosphodiesterase type-5 inhibitors derived from Sildenafil, Vardenafil and Tadalafil," Bioorg Med Chem., Aug. 15, 2008, 16(16):7599-7606.
Asshoff et al., "Momelotinib inhibits ACVR1/ALK2, decreases hepcidin production, and ameliorates anemia of chronic disease in rodents," Blood, Mar. 30, 2017, 129:1823-1830.
Atzrodt et al., "The Renaissance of H/D Exchange," Angew. Chem. Int. Ed., Oct. 4, 2007, 46(41):7744-7765.
Ballell et al., "Fueling Open-Source Drug Discovery: 177 Small-Molecule Leads against Tuberculosis," ChemMedChem., 2013, 8(2):313-321.
Balog et al., "The synthesis and evaluation of [2.2.1]-bicycloazahydantoins as androgen receptor antagonists," Bioorg. Med. Chem. Lett., Dec. 20, 2004, 14(24):6107-6111.
Batliwalla et al., "Microarray analyses of peripheral blood cells identifies unique gene expression signature in psoriatic arthritis," Mol Med, 2005, 11(1-12):21-29.
Berge et al., "Pharmaceutical Salts," J. Pharm. Sci., Jan. 1977, 66:1-19.
Blobe et al., "Role of Transforming Growth Factor β in Human Disease," New England Journal of Medicine, May 4, 2000, 342:1350-1358.

(56) References Cited

OTHER PUBLICATIONS

Blom et al., "Optimizing Preparative LC-MS Configurations and Methods for Parallel Synthesis Purification," J. Combi. Chem., Jul. 29, 2003, 5:670-683.

Blom et al., "Preparative LCMS Purification: Improved Compound Specific Method Optimization," J. Comb. Chem., Sep. 24, 2004, 6:874-883.

Blom et al., "Two-Pump at Column Dilution Configuration for Preparative LC-MS," J. Combi. Chem., Apr. 12, 2002, 4:295-301.

Brioche et al., "Chiral Phosphoric Acid-Catalyzed Enantioselective Three-Component Aza-Diels-Alder Reactions of Aminopyrroles and Aminopyrazoles," Advanced Synthesis & Catalysis, 2014, 356(8):1719-1724.

Buczkowicz et al., "Genomic analysis of diffuse intrinsic pontine gliomas identifies three molecular subgroups and recurrent activating ACVR1 mutations," Nature Genetics, Apr. 6, 2014, 46, 451-456.

Chessari et al., "Fragment-Based Drug Discovery Targeting Inhibitor of Apoptosis Proteins: Discovery of a Non-Alanine Lead Series with Dual Activity Against cIAP1 and XIAP," J. Med. Chem., Jul. 18, 2015, 58(16):6574-6588.

Cheung et al., "A Parallel Synthesis Approach to the Identification of Novel Diheteroalylamide-Based Compounds Blocking HIV Replication: Potential Inhibitors of HIV-1 Pre-mRNA Alternative Splicing," J Med Chem., Mar. 10, 2016, 59(5):1869-1879.

Chinchilla and Najera, "Recent advances in Sonogashira reactions," Chem. Soc. Rev., 2011, 40: 5084-5121.

Choi et al., "In vitro metabolism of a novel phosphodiesterase-5 inhibitor DA-8159 in rat liver preparations using liquid chromatography/electrospray mass spectrometry," Biomed Chromatogr., Sep. 2002, 16(6):395-399

Cordovilla et al., "The Stille Reaction, 38 Years Later," ACS Catalysis, 2015, 5: 3040-3053.

Devegowda et al., "Novel 6-N-arylcarboxamidopyrazolo[4,3-d]pyrimidin-7-one derivatives as potential anti-cancer agents," Bioorg Med Chem Lett., Mar. 1, 2010, 20(5):1630-1633.

Di Bartolo et al., "A novel pathway down-modulating T cell activation involves HPK-1-dependent recruitment of 14-3-3 proteins on SLP-76," J. Exp. Med., Mar. 2007, 204(3): 681-691.

Dinther et al., "ALK2 R206H mutation linked to fibrodysplasia ossificans progressiva confers constitutive activity to the BMP type I receptor and sensitizes mesenchymal cells to BMP-induced osteoblast differentiation and bone formation," Journal of Bone and Mineral Research, Jun. 2010, 25:1208-1215.

Dong et al., "Pharmacophore identification, virtual screening and biological evaluation of prenylated flavonoids derivatives as PKB/Akt1 inhibitors," Eur J Med Chem., Dec. 2011, 46(12):5949-5958.

Dong et al., "QSAR study of Akt/protein kinase B (PKB) inhibitors using support vector machine," Eur J Med Chem., Oct. 2009, 44(10):4090-4097.

Dornow et al., "Syntheses of nitrogen-containing heterocycles. XXXVIII. Preparation and reaction of several substituted 3-nitropyridines," Chemische Berichte, 1966, 99(1):244-253 (Machine Translation).

Dumestre-Toulet et al., "Last performance with VIAGRA: postmortem identification of sildenafil and its metabolites in biological specimens including hair sample," Forensic Sci Int., Mar. 28, 2002, 126(1):71-76.

Edmondson et al., "Aminopiperidine-fused imidazoles as dipeptidyl peptidase-IV inhibitors," Bioorg Med Chem Lett., Aug. 2009, 19(15):4097-4101.

El Sayed et al., "New route for the preparation of pyrazolo[4,3-c]pyridines," Bulletin of the Chemical Society of Japan (1973), 46(6), 1801-1803.

El-Aziz et al., "Synthesis and in vitro anti-breast cancer activity of some novel 1,4-dihydropyridine derivatives," Int J of Pharm Pharma Sci., 2013, 5(Suppl. 3):183-189.

Elgemeie et al., "A new general method for substituted 4-alkylthio-N-arylsulfonylamino-2-pyridones: Reaction of ketene-S,S-acetals with arylsulfonylhydrazides," Phosphorus, Sulfur and Silicon and the Related Elements, 2001, 170:171-179.

Elgemeie et al., "Novel N-Substituted Amino-4-methylsulfanyl-2-pyridones and Deazapurine Analogues from Ketene Dithioacetals," J Chem Res., 1998, 3:164-165.

Elgemeie et al., "Novel Nucleoside Analogues: First Synthesis of Pyridine-4-Thioglycosides and Their Cytotoxic Evaluation," Nucleosides, Nucleotides and Nucleic Acids, Jun. 27, 2015, 34:659-673.

Elgemeie et al., "Novel synthesis of N-aroylaminated pyridones via reaction of ketene dithioacetals with cyanoaceto-N-aroylhydrazides," Synth Comm., 2003, 33(2):253-258.

Elgemeie et al., "Synthesis of Novel Derivatives of 4-Methylthio-N-Aryl-2-Pyridone and Deazapurine Analogues: The Reaction of Ketene Dithioacetals with Substituted Acetanilides," Phosphorus, Sulfur and Silicon, 2000, 164:189-197.

Erian, "2-Aryl-1,1-dicyano-3-phenylsulfonylpropenes in heterocyclic synthesis. A synthetic strategy towards heterocyclic sulfone," Monatshefte fuer Chemie, Oct. 1998, 129(10):1049-1056.

Eswarakumar et al., "Cellular signaling by fibroblast growth factor receptors.," Cytokine & Growth Factor Reviews, Apr. 2005, 16:139-149.

Figueiredo et al., "A chemometric study of phosphodiesterase 5 inhibitors," J Mol Graph Model., Jan. 2006, 24(4):227-232.

Fukuda et al., "A unique mutation of ALK2, G356D, found in a patient with fibrodysplasia ossificans progressiva is a moderately activated BMP type I receptor," Biochemical and Biophysical Research Communications, Dec. 18, 2008, 377:905-909.

Fukuda et al., "Constitutively Activated ALK2 and Increased SMAD1/5 Cooperatively Induce Bone Morphogenetic Protein Signaling in Fibrodysplasia Ossificans Progressiva,*" Journal of Biological Chemistry Mar. 13, 2009, 284:7149-7156.

Gao, "Slidenafil" Handbook of Metabolic Pathways of Xenobiotics, 2014, 5:2151-2154.

Goodarzi et al., "Feature Selection and Linear/Nonlinear Regression Methods for the Accurate Prediction of Glycogen Synthase Kinase-3β Inhibitory Activities," J. Chem. Inf. Model, 2009, 49(4):824-832.

Haas et al., "Recent Developments in Negishi Cross-Coupling Reactions," ACS Catalysis, 2016, 6: 1540-1552.

Haning et al., "Comparison of different heterocyclic scaffolds as substrate analog PDE5 inhibitors," Sep. 1, 2005, 15(17):3900-3907.

Hanson, "Diterpenoids of Terrestrial Origin", National Product Reports, 2016, 33:1227-1238.

He et al., "Predicting the Genotoxicity of Polycyclic Aromatic Compounds from Molecular Structure with Different Classifiers," Chemical Research in Toxicology (2003), 16(12):1567-1580.

Ho et al., "Discovery of 4-phenyl-2-phenylaminopyridine based TNIK inhibitors," Boorg Med Chem Lett, 2013, 23(2):569-573.

Hopkins, "Inhibitors of the bone morphogenetic protein (BMP) signaling pathway: a patent review (2008-2015)," Expert Opinion on Therapeutic Patents, Aug. 4, 2016, 26(10):1115-1128.

Howard et al., "Identification of potent phosphodiesterase inhibitors that demonstrate cyclic nucleotide-dependent functions in apicomplexan parasites," ACS Chem Biol., Apr. 17, 2015, 10(4):1145-1154.

Hu et al., "Discovery of 3,5-substituted 6-azaindazoles as potent pan-Pim inhibitors," Bioorg Med Chem Lett., 2015, 25(22):5258-5264.

Hu et al., "Human HPK1, a novel human hematopoietic progenitor kinase that activates the JNK/SAPK kinase cascade," Genes Dev, 1996, 10(18): p. 2251-2264.

Ikegami et al., "The expression of prostaglandin E receptors EP2 and EP4 and their different regulation by lipopolysaccharide in C3H/HeN peritoneal macrophages," J. Immunol., Apr. 2001, 166(7): 4689-4696.

International Preliminary Report on Patentability in International Application No. PCT/US2017/050669, dated Mar. 12, 2019, 8 pages.

International Preliminary Report on Patentability in International Application No. PCT/US2017/050727, dated Mar. 12, 2019, 8 pages.

International Preliminary Report on Patentability in International Application No. PCT/US2017/050737, dated Mar. 12, 2019, 8 pages.

(56) References Cited

OTHER PUBLICATIONS

International Preliminary Report on Patentability in International Application No. PCT/US2017/050757, dated Mar. 12, 2019, 10 pages.
International Preliminary Report on Patentability in International Application No. PCT/US2018/018205, dated Aug. 20, 2019, 10 pages.
International Search Report and Written Opinion in International Application No. PCT/US2017/048880, dated Nov. 2, 2017, 15 pages.
International Search Report and Written Opinion in International Application No. PCT/US2017/050669, dated Nov. 6, 2017, 16 pages.
International Search Report and Written Opinion in International Application No. PCT/US2017/050727, dated Nov. 2, 2017, 16 pages.
International Search Report and Written Opinion in International Application No. PCT/US2017/050737, dated Nov. 2, 2017, 16 pages.
International Search Report and Written Opinion in International Application No. PCT/US2017/050757, dated Nov. 10, 2017, 20 pages.
International Search Report and Written Opinion in International Application No. PCT/US2018/018205, dated Apr. 30, 2018, 16 pages.
International Search Report and Written Opinion in International Application No. PCT/US2018/049908, dated Nov. 7, 2018, 15 pages.
International Search Report and Written Opinion in International Application No. PCT/US2019/018608, dated Apr. 16, 2019, 14 pages.
International Search Report and Written Opinion in International Application No. PCT/US2019/018609, dated May 13, 2019, 12 pages.
International Search Report and Written Opinion in International Application No. PCT/US2019/052567, dated Nov. 14, 2019, 15 pages.
Ivon et al., "Synthesis of a 2,5-Diazabicyclo[2.2.1]heptane-Derived α,β-Diamino Acid," Synthesis, 2015, 47(8):1123-1130.
Karaman "Analyzing the efficiency in intramolecular amide hydrolysis of Kirby's N-alkylmaleamic acids—A computational approach," Computational and Theoretical Chemistry, 2011, 974(1-3):133-142.
Katritzky et al., "QSAR modeling of the inhibition of Glycogen Synthase Kinase-3," Bioorganic & Medicinal Chemistry, 2006, 14(14):4987-5002.
Kerekes et al., "Aurora kinase inhibitors based on the imidazo[1,2-a]pyrazine core: fluorine and deuterium incorporation improve oral absorption and exposure," J. Med. Chem., 2011, 54(1): 201-210.
Kiefer et al., "HPK1, a hematopoietic protein kinase activating the SAPK/JNK pathway," EMBO. J., Dec. 1996, 15(24): 7013-7025.
Kim et al., "Reliable screening and confirmation of 156 multi-class illegal adulterants in dietary supplements based on extracted common ion chromatograms by ultra-high-performance liquid chromatography-quadrupole/time of flight-mass spectrometry," J Chromatogr A., Mar. 31, 2017, 1491:43-56.
Knights et al., "De-regulated FGF receptors as therapeutic targets in cancer," Pharmacology & Therapeutics, Jan. 2010, 125:105-117.
Kotha et al., "Recent applications of the Suzuki—Miyaura cross-coupling reaction in organic synthesis," Tetrahedron, 2002, 58:9633-9695.
Kumar et al., "3-(1H-Indol-2-yl)-1H-pyrazolo[4,3-b]pyridines as Wnt pathway modulators and their preparation," retrieved from STN Database Accession No. 2017: 232331, Feb. 9, 2017, Chemical Abstracts Service, Columbus, Ohio, US, XP002775032.
Kumar et al., "3-(1H-Indol-2-yl)-1H-pyrazolo[4,3-b]pyridines as Wnt pathway modulators and their preparation," retrieved from STN Database Accession No. 2017: 232415, Feb. 9, 2017, Chemical Abstracts Service, Columbus, Ohio, US, XP002775031.
Kumar et al., "3-(1H-Indol-2-yl)-1H-pyrazolo[4,3-b]pyridines as Wnt pathway modulators and their preparation," retrieved from STN Database Accession No. 2017: 232564, Feb. 9, 2017, Chemical Abstracts Service, Columbus, Ohio, US, XP002775030.
Kumar et al., "3-(1H-Indol-2-yl)-1H-pyrazolo[4,3-b]pyridines as Wnt pathway modulators and their preparation," retrieved from STN Database Accession No. 2017: 233013, Feb. 9, 2017, Chemical Abstracts Service, Columbus, Ohio, US, XP002775029.
Kumar et al., "3-(1H-Indol-2-yl)-1H-pyrazolo[4,3-b]pyridines as Wnt pathway modulators and their preparation," retrieved from STN Database Accession No. 2017: 233418, Feb. 9, 2017, Chemical Abstracts Service, Columbus, Ohio, US, XP002775028.
Kumar et al., "3-(1H-Indol-2-yl)-1H-pyrazolo[4,3-b]pyridines as Wnt pathway modulators and their preparation," retrieved from STN Database Accession No. 2017: 233427, Feb. 9, 2017, Chemical Abstracts Service, Columbus, Ohio, US, XP002775027.
Kumar et al., "3-(1H-Indol-2-yl)-1H-pyrazolo[4,3-b]pyridines as Wnt pathway modulators and their preparation," retrieved from STN Database Accession No. 2017: 233436, Feb. 9, 2017, Chemical Abstracts Service, Columbus, Ohio, US, XP002775026.
Lebel et al., "A rapid, quantitative liquid chromatography-mass spectrometry screening method for 71 active and 11 natural erectile dysfunction ingredients present in potentially adulterated or counterfeit products," J Chromatogr A., May 23, 2014, 1343:143-151.
Lee et al., "Comparative metabolism of sildenafil in liver microsomes of different species by using LC/MS-based multivariate analysis," J of Chromato., Oct. 15, 2011, 879(28):3005-3011.
Li et al., "A highly effective one-pot synthesis of quinolines from o-nitroarylcarbaldehydes," Organic & Biomolecular Chemistry, 2007, 5(1):61-64.
Li et al., "Metabolism of aildenafil in vivo in rats and in vitro in mouse, rat, dog, and human liver microsomes in vitro and in vivo metabolism of aildenafil," Drug Testing and Analysis, 2014, 6(6):552-562.
Li et al., "One-pot Friedlander quinoline synthesis: scope and limitations," Synthesis, 2010, 10:1678-1686.
Lim et al., "Discovery of 1-(1 H-Pyrazolo [4,3-c]pyridin-6-yl)urea Inhibitors of Extracellular Signal-Regulated Kinase (ERK) for the Treatment of Cancers," Journal of Medicinal Chemistry, Jul. 2016, 59(13): 6501-6511.
Lin et al., "2,3,5-Trisubstituted pyridines as selective AKT inhibitors. Part II: Improved drug-like properties and kinase selectivity from azaindazoles," Bioorganic & Medicinal Chemistry Letters 2010, 20(2):679-683.
Lin et al., "Tetrasubstituted pyridines as potent and selective AKT inhibitors: Reduced CYP450 and hERG inhibition of aminopyridines," Bioorg Med Chem Lett. Jan. 15, 2010;20(2):684-688.
Liou et al., "HPK1 is activated by lymphocyte antigen receptors and negatively regulates AP-1," Immunity, Apr. 2000, 12(4): 399-408.
Literature and Patent Chemical Structure Search, Science IP, The CAS Search Service, Jul. 1, 2016, 441 pages.
Literature and Patent Chemical Structure Search, Science IP, The CAS Search Service, Jun. 30, 2016, 200 pages.
Liu et al., "Synthesis and SAR of 1,9-dihydro-9-hydroxypyrazolo[3,4-b]quinolin-4-ones as novel, selective c-Jun N-terminal kinase inhibitors," Bioorg Med Chem Lett., May 15, 2006, 16(10):2590-2594.
Massague et al., "TGFβ Signaling in Growth Control, Cancer, and Heritable Disorders, Cell, Oct. 13, 2000, 103:295-309.
Michelotti et al., "Two Classes of p38a MAP kinase inhibitors having a common core but exhibiting devergent binding modes," 2005, 15:5274-5279.
Miyazaki et al., "Design and effective synthesis of novel templates, 3,7-diphenyl-4-amino-thieno and furo-[3,2-c]pyridines as protein kinase inhibitors and in vitro evaluation targeting angiogenetic kinases," Bioorg Med Chem Lett., Jan. 1, 2007, 17(1):250-254.
Moriyasu et al., "Determination of pharmaceutical adulterants in health foods," Tokyo-to Kenko Anzen Kenkyu Senta Kenkyu Nenpo 2011, 62:25-39 (English Abstract).
Muddassar et al., "Elucidation of binding mode and three dimensional quantitative structure—activity relationship studies of a novel series of protein kinase B/Akt inhibitors," J Mol Model., Feb. 2009, 15(2):183-192.

(56) References Cited

OTHER PUBLICATIONS

Mulvihill et al., "Novel 2-phenylquinolin-7-yl-derived imidazo[1,5-a]pyrazines as potent insulin-like growth factor-I receptor (IGF-IR) inhibitors," Bioorg Med Chem Lett, Feb. 2008, 16(3):1359-1375.
Neuwels et al., "Approach to an adenosine pharmacophore by molecular modeling," Journal de Pharmacie de Belgique, 1992, 47(4):351-363.
Pardanani et al., "Associations and prognostic interactions between circulating levels of hepcidin, ferritin and inflammatory cytokines in primary myelofibrosis," American Journal of Hematology, Feb. 6, 2013, 88:312-316.
Patel et al., "Selectivity criterion for pyrazolo[3,4-b]pyrid[az]ine derivatives as GSK-3 inhibitors: CoMFA and molecular docking studies," European Journal of Medicinal Chemistry (2008), 43(5):949-957.
Peturssion et al., "Protecting Groups in Carbohydrate Chemistry," J. Chem. Educ., Nov. 1, 1997, 74:1297.
Piersanti et al., "Synthesis of Benzo[1,2-d;3,4-d']diimidazole and 1H-Pyrazolo[4,3-b]pyridine as Putative A2A Receptor Antagonists," Organic a& Biomolecular Chemistry, Jul. 13, 2007, 5:2567-2571.
Pitt et al., "Heteroaromatic rings of the future," J Med Chem., May 14, 2009, 52(9):2952-2963.
Pozharskii et al., "Molecular Rings Studded with Jewels," Heterocycles in Life and Society Wiley, 1997, pp. 1-6.
Remington's Pharmaceutical Sciences, 17th Ed., Oct. 1985, p. 1418.
Ross et al., "Molecular Mechanism of Hepcidin-Mediated Ferroportin Internalization Requires Ferroportin Lysines, Not Tyrosines or JAK-STAT," Cell Metabolism, Jun. 6, 2012, 15:905-917.
Sawasdikosol et al., "HPK1 as a novel target for cancer immunotherapy," Immunologic Research, Apr. 4, 2012, 54(1-3): 262-265.
Sawasdikosol et al., "Hematopoietic progenitor kinase 1 (HPK1) influences regulatory T cell functions," The Journal of Immunology, 2012. 188(supplement 1):163, English Abstract.
Shaughnessy et al., "Copper-Catalyzed Amination of Aryl and Alkenyl Electrophiles," Organic Reactions, Chapter 1, 2014, 85: 1-668.
Shen et al., "The fibrodysplasia ossificans progressiva R206H ACVR1 mutation activates BMP-independent chondrogenesis and zebrafish embryo ventralization," Journal of Clinical Investigation, Nov. 2009, 119: 3462-3472.
Shou et al., "Simple means to alleviate sensitivity loss by trifluoroacetic acid (TFA) mobile phases in the hydrophilic interaction chromatography-electrospray tandem mass spectrometric (HILIC-ESI/MS/MS) bioanalysis of basic compounds," Journal of Chromatography B: Analytical Technologies in the Biomedical and Life Sciences, 2005, 825(2):186-192.
Shui et al., "Hematopoietic progenitor kinase 1 negatively regulates T cell receptor signaling and T cell-mediated immune responses," Nat. Immunol., Jan. 2007, 8(1): 84-91.
Smyth et al., "Synthesis and reactivity of 3-amino-1H-pyrazolo[4,3-c]pyridin-4(5H)-ones: development of a novel kinase-focussed library," Tetrahedron, Apr. 2010, 66(15): 2843-2854.
Steinbicker et al "Inhibition of bone morphogenetic protein signaling attenuates anemia associated with inflammation," Blood, May 5, 2011, 117:4915-4923.
Steinbicker et al., "Perturbation of hepcidin expression by BMP type I receptor deletion induces iron overload in mice," Blood, Oct. 13, 2011, 118:4224-4230.
STN Search Report dated Apr. 9, 2018, 7 pages.
STN Search Report dated Aug. 17, 2016, 157 pages.
STN Search Report dated Aug. 25, 2016, 25 pages.
STN Search Report dated Aug. 30, 2016, 31 pages.
STN Search Report dated Aug. 31, 2016, 32 pages.
STN Search Report dated Jan. 27, 2017, 94 pages.
STN Search Report dated Apr. 25, 2018, 19 pages.
STN Search Report dated Jan. 23, 2018, 26 pages.
STN Search Report dated May 9, 2018, 16 pages.
STN Search Report dated Sep. 5, 2017, 26 pages.
STN Search Report dated Sep. 5, 2017, 5 pages.
STN Search Report, dated Sep. 11, 2018, 168 pages.
Structure 1: Substance Search Patent and Non-Patent Databases, Science IP, The CAS Search Service, Jun. 6, 2016, 583 pages.
Structure 2: Substance Search Patent and Non-Patent Databases, Science IP, The CAS Search Service, Jun. 7, 2016, 833 pages.
Structure 3: Substance Search Patent and Non-Patent Databases, Science IP, The CAS Search Service, Jun. 7, 2016, 512 pages.
Structure 4: Substance Search Patent and Non-Patent Databases, Science IP, The CAS Search Service, Jun. 8, 2016, 820 pages.
Subramanyam et al., "6-(4-Pyridinyl)-1H-1,2,3-triazolo [4,5-d]-pyrimidin-4(5H)-one: A Structurally Novel Competitive AMPA Receptor Antagonist," Journal of Medicinal Chemistry, 1995, 38(4):587-589.
Surry and Buchwald, "Dialkylbiaryl Phosphines in Pd-Catalyzed Amination: A User's Guide," Chem. Sci., 2011, 2(1): 27-50.
Taha et al., "Pharmacophore Modeling, Quantitative Structure-Activity Relationship Analysis, and in Silico Screening Reveal Potent Glycogen Synthase Kinase-3β Inhibitory Activities for Cimetidine, Hydroxychloroquine, and Gemifloxacin," J. Med. Chem., 2008, 51(7):2062-2077.
Taylor et al., "ACVR1 Mutations in DIPG: Lessons Learned from FOP," Cancer Research, Sep. 2014, 74:4565-4570.
Taylor et al., "Recurrent activating ACVR1 mutations in diffuse intrinsic pontine glioma.," Nature Genetics, May 2014, 46:457-461.
Tefferi et al., "One Thousand Patients With Primary Myelofibrosis: The Mayo Clinic Experience," Mayo Clinic Proceedings, Jan. 2012, 87:25-33.
Terrett et al.,"Sildenafil (Viagra), a potent and selective inhibitor of type 5 cGMP phosphodiesterase with utility for the treatment of male erectile dysfunction," Bioorganic & Medicinal Chemistry Letters, 1996, 6(15):1819-1824.
Theurl et al., "Pathways for the Regulation of Hepcidin Expression in Anemia of Chronic Disease and Iron Deficiency Anemia In Vivo," Haematologica, Dec. 2011, 96:1761-1769.
Turner et al., "Fibroblast growth factor signalling: from development to cancer," Nature Reviews Cancer, Feb. 2010, 10:116-129.
Vaclavik et al., "Single-laboratory validation study of a method for screening and identification of phosphodiesterase type 5 inhibitors in dietary ingredients and supplements using liquid chromatography/quadrupole-orbital ion trap mass spectrometry: first action 2015. 12," Journal of AOAC International, 2016, 99(1):55-72.
Vymetalova et al., "5-Substituted 3-isopropyl-7-[4-(2-pyridyl)benzyl]amino-1(2)H-pyrazolo[4,3-d]pyrimidines with antiproliferative activity as potent and selective inhibitors of cyclin-dependent kinases," European Journal of Chemistry, 2016, 110:291-301.
Waddell et al., "Benzothiazolylthio Carbapenems: Potent Anti-MRSA Agents," Biorg & Med Chem Lett., 1995, 5(13):1427-1432.
Wang et al., "Activation of the hematopoietic progenitor kinase-1 (HPK1)-dependent stress-activated c-Jun N-terminal kinase (JNK) pathway by transforming growth factor beta (TGF-beta)-activated kinase (TAK1), a kinase mediator of TGF beta signal transduction," J. Biol. Chem., Sep. 1997, 272(36): 22771-22775.
Wang et al., "Down-regulation of B cell receptor signaling by hematopoietic progenitor kinase 1 (HPK-1)-mediated phosphorylation and ubiquitination of activated B cell linker protein (BLNK)," J. Biol. Chem., Mar. 2012, 297(14): 11037-11048.
Wang et al., "Synthesis and evaluation of human phosphodiesterases (PDE) 5 inhibitor analogs as typanosomal PDE inhibitors. Part 1. Sildenafil analogs," Bioorg Med Chem Lett., Apr. 1, 2012, 22(7):2579-2581.
Weinmann et al., "Identification of lorazepam and sildenafil as examples for the application of LC/ionspray-MS and MS-MS with mass spectra library searching in forensic toxicology," Forensic Sci Int., Sep. 11, 2000, 113(1-3):339-344.
Weiss et al.,"Anemia of Chronic Disease," New England Journal of Medicine, Mar. 10, 2005, 352:1011-1023.
Wislicenus "Adolph Strecker's Short Textbook of Organic Chemistry," 1881, Spottiswood, London, pp. 38-39.
Witherington et al., "5-Aryl-pyrazolo[3,4-b]pyridazines: potent inhibitors of glycogen synthase kinase-3 (GSK-3)," Bioorganic & Medicinal Chemistry Letters, 2003, 13(9):1581-1584.

(56) References Cited

OTHER PUBLICATIONS

Witherington et al., "5-Aryl-pyridazines: Potent Inhibitors of Glycogen Synthase Kinase-3 (GSK-3)," Bioorganic & Medicinal Letters, 2003, 13: 1577-1580.
Wuts et al., "Protective Groups in Organic Synthesis," 4th ed., Nov. 19, 2006, 1111 pages.
Xu et al., "Design, synthesis and biological evaluation of deuterated nintedanib for improving pharmacokinetic properties," J. Label Compd. Radiopharm. Feb. 18, 2015, 5: 308-312
Yang et al., "Highly efficient synthesis of fused bicyclic 2,3-diarylpyrimidin-4(3H)-ones via Lewis acid assisted cyclization reaction," Tetrahedron Letters, Mar. 10, 2008, 49(11):1725-1728.
Yeo et al., "New metabolites of hongdenafil, homosildenafil and hydroxyhomosildenafil," Journal of Pharmaceutical and Biomedical Analysis, 2018, 149:586-590.
Yu et al., "BMP type I receptor inhibition reduces heterotopic [corrected] ossification.," Nature Medicine, Dec. 2008, 14:1363-1369.
Zhang et al., "Anti-angiogenic effects of novel cyclin-dependent kinase inhibitors with a pyrazolo[4,3-d]pyrimidine scaffold," Br J Pharmacol., Sep. 2016, 173(17):2645-2656.
Zhao et al., "Iron regulation by hepcidin," Journal of Clinical Investigation, Jun. 2013, 123:2337-2343.
Zhou et al., "Hematopoietic progenitor kinase 1 is a component of transforming growth factor beta-induced c-Jun N-terminal kinase signaling cascade," J. Biol. Chem., May 1999, 274(19): 13133-13138.
Zhu et al., "Characterization of TPN729 metabolites in humans using ultra-performance liquid chromatography/quadrupole time-of-flight mass spectrometry," J Pharm Biomed Anal., Jan. 5, 2016, 117:217-226.
Zhu et al., "Design and Synthesis of Pyridine-pyrazolopyridine based inhibitors of protein kinase B/Akt," Bioorganic and Medicinal Chemistry, Jan. 17, 2007, 15: 2441-2452.
Zhu et al., "Syntheses of potent, selective, and orally bioavailable indazole-pyridine series of protein kinase B/Akt inhibitors with reduced hypotension," J Med Chem., Jun. 28, 2007, 50(13):2990-3003.
Wang et al., "Fragment-based identification and optimization of a class of potent pyrrolo[2,1-f][1,2,4]triazine MAP4K4 inhibitors," Boorg Med Chem Lett., Sep. 15, 2014, 24(18):4546-4552.

* cited by examiner

PYRAZOLOPYRIMIDINE COMPOUNDS AND USES THEREOF

FIELD OF THE INVENTION

The disclosure provides compounds as well as their compositions and methods of use. The compounds modulate activin receptor-like kinase-2 (ALK2) activity and/or Fibroblast Growth Factor Receptors (FGFR) activity and are useful in the treatment of various diseases associated with ALK2 and/or FGFR activity including cancer.

BACKGROUND OF THE INVENTION

Bone morphogenetic protein (BMP) signaling belongs to the transforming growth factor beta (TGF-β) superfamily and TGF-β signaling ligands include more than 25 different ligands: TGF-β growth and differentiation factors, BMPs and Activins. The binding of BMP ligands leads to the assembly of tetrameric receptor complexes composed of two constitutively-active type II receptor serine/threonine kinases (BMPRII, ACTRIIA, or ACTRIIB) and activate two type I receptor serine/threonine kinases (ALK1, ALK2, ALK3, or ALK6). Furthermore, the activated type I receptors phosphorylate BMP receptor responsive SMAD proteins 1/5/8 and the activated SMAD1/5/8 associated with CO-SMAD4 translocate to the nucleus to regulate gene transcription. (Ross, S. L., et al. Cell Metabolism 2012, 15, 905-917; Blobe, G. C., et al. New England Journal of Medicine 2000, 342, 1350-1358).

BMPR kinase activin A receptor, type I (ACVR1) is also called activin receptor-like kinase-2 (ALK2), which is composed of a ligand-binding extracellular domain and a cytoplasmic domain with serine/threonine specificity. ALK2 has been reported to mediate multiple human diseases (Massague, J., et al. Cell 2000, 103, 295-309; Taylor, K. R., et al. Cancer Research 2014, 74, 4565-4570). ALK2 and ALK3 have been shown to play an essential role in regulating the hepcidin levels and affecting the anemia of chronic disease (Andriopoulos, B., et al. Nature Genetics 2009, 41, 482-487; Steinbicker, A. U., et al. Blood 2011, 118, 4224-4230; Steinbicker, A. U., et al. Blood 2011, 117, 4915-4923). Hepcidin is a small peptide hormone primarily synthesized in hepatocytes and reduces both duodenal iron absorption and iron export from monocytes/macrophages by binding to and inducing the internalization and degradation of the iron exporter ferroportin (FPN1) (Theurl, I. et al. Haematologica 2011, 96, 1761-1769; Zhao, N. et al. Journal of Clinical Investigation 2013, 123, 2337-2343). The elevated serum hepcidin levels enhance storage of iron within the reticuloendothelial system and result in reduced iron availability and iron restricted erythropoiesis. Inappropriately increased hepcidin expression causes severe functional iron deficiency anemia in humans and is central to the pathophysiology of anemia of chronic disease (ACD) (Weiss, G. et al. New England Journal of Medicine 2005, 352, 1011-1023).

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recmitment of many intracellular docking proteins. These interactions facilitate the activation of an array of intracellular signaling pathways including Ras-MAPK, AKT-PI3K, and phospholipase C that are important for cellular growth, proliferation and survival (Reviewed in Eswarakumar et al. Cytokine & Growth Factor Reviews, 2005).

Aberrant activation of this pathway either through overexpression of FGF ligands or FGFR or activating mutations in the FGFRs can lead to tumor development, progression, and resistance to conventional cancer therapies. In human cancer, genetic alterations including gene amplification, chromosomal translocations and somatic mutations that lead to ligand-independent receptor activation have been described. Large scale DNA sequencing of thousands of tumor samples has revealed that components of the FGFR pathway are among the most frequently mutated in human cancer. Many of these activating mutations are identical to germline mutations that lead to skeletal dysplasia syndromes. Mechanisms that lead to aberrant ligand-dependent signaling in human disease include overexpression of FGFs and changes in FGFR splicing that lead to receptors with more promiscuous ligand binding abilities (Reviewed in Knights and Cook Pharmacology & Therapeutics, 2010; Turner and Grose, Nature Reviews Cancer, 2010). Therefore, development of inhibitors targeting FGFR may be useful in the clinical treatment of diseases that have elevated FGF or FGFR activity.

The cancer types in which FGF/FGFRs are implicated include, but are not limited to: carcinomas (e.g., bladder, breast, cervical, colorectal, endometrial, gastric, head and neck, kidney, liver, lung, ovarian, prostate); hematopoietic malignancies (e.g., multiple myeloma, chronic lymphocytic lymphoma, adult T cell leukemia, acute myelogenous leukemia, non-Hodgkin lymphoma, myeloproliferative neoplasms, and Waldenstrom's Macroglobulinemia); and other neoplasms (e.g., glioblastoma, melanoma, and rhabdosarcoma). In addition to a role in oncogenic neoplasms, FGFR activation has also been implicated in skeletal and chondrocyte disorders including, but not limited to, achrondroplasia and craniosynostosis syndromes.

Accordingly, there is a need for new compounds that modulate ALK2 activity and/or FGFR activity and for compounds capable of treating diseases that are related to ALK2 activity and/or FGFR activity.

SUMMARY

The present disclosure provides, inter alia, a compound of Formula I:

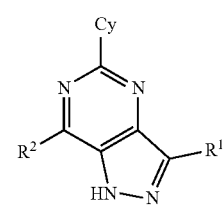

or a pharmaceutically acceptable salt thereof, wherein constituent variables are defined herein.

The present disclosure further provides a pharmaceutical composition comprising a compound of the disclosure, or a pharmaceutically acceptable salt thereof, and at least one pharmaceutically acceptable carrier or excipient.

The present disclosure further provides methods of inhibiting ALK2 activity, which comprises administering to an individual a compound of the disclosure, or a pharmaceutically acceptable salt thereof.

The present disclosure further provides methods of inhibiting FGFR activity, which comprises administering to an individual a compound of the disclosure, or a pharmaceutically acceptable salt thereof.

The present disclosure further provides methods of treating a disease or disorder in a patient comprising administering to the patient a therapeutically effective amount of a compound of the disclosure, or a pharmaceutically acceptable salt thereof.

In some embodiments, the compounds of the present disclosure are inhibitors of ALK2 and/or FGFR activity. In some embodiments, the compounds of the present disclosure are dual ALK2/FGFR inhibitors.

DETAILED DESCRIPTION

Compounds

The present disclosure provides, a compound of Formula I:

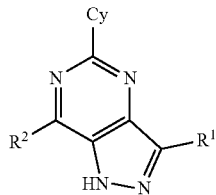

or a pharmaceutically acceptable salt thereof, wherein:

$R^1$ is selected from $Cy^1$, $C_{1-6}$ alkyl, $C_{2-6}$ alkenyl, $C_{2-6}$ alkynyl, $C_{1-6}$ haloalkyl, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NOR^a)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl and $C_{2-6}$ alkynyl are each substituted with 1, 2, 3, or 4 substituents independently selected from $R^{10}$;

$Cy^1$ is selected from $C_{3-14}$ cycloalkyl, 4-14 membered heterocycloalkyl, $C_{6-10}$ aryl and 5-10 membered heteroaryl; wherein the 4-14 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-14 membered heterocycloalkyl is optionally substituted by oxo to form a carbonyl group; and wherein the $C_{3-14}$ cycloalkyl, 4-14 membered heterocycloalkyl, $C_{6-10}$ aryl and 5-10 membered heteroaryl are each optionally substituted with 1, 2, 3 or 4 substituents independently selected from $R^{10}$;

Cy is 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group; wherein when the 4-14 membered heterocycloalkyl of Cy has a fused aromatic ring, the 4-14 membered heterocycloalkyl is directly attached to the pyrazolopyrimidine core structure through a ring-forming atom of the saturated or partially saturated ring; and wherein the 4-14 membered heterocycloalkyl is optionally substituted with 1, 2, 3, 4 or 5 substituents independently selected from $R^{20}$; $R^2$ is selected from H, D, $C_{1-4}$ alkyl, $C_{1-4}$ haloalkyl, $C_{1-4}$ alkoxy and $C_{1-4}$ haloalkoxy;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said C %, alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

or two $R^{10}$ substituents taken together with the carbon atom to which they are attached form a spiro 4-7-membered heterocycloalkyl ring, or a spiro $C_{3-6}$ cycloalkyl ring; wherein each spiro 4-7-membered heterocycloalkyl ring has at least one ring-forming carbon atom and 1, 2 or 3, ring-forming heteroatoms independently selected from N, O, and S; wherein a ring-forming carbon atom of each spiro 4-7-membered heterocycloalkyl ring is optionally substituted by oxo to form a carbonyl group; and wherein the spiro 4-7-membered heterocycloalkyl ring and spiro $C_{3-6}$ cycloalkyl ring are each optionally substituted with 1, 2, 3 or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-10 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$, $NR^{c5}C(O)R^{b5}$, $NR^{c5}C(O)OR^{a5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-4}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$; each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^M$, $NR^{c4}C(O)OR^{a4}$, $NR^{c4}S(O)R^M$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^M$, and $S(O)_2NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^g$;

each $R^a$, $R^c$, and $R^d$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$;

each $R^b$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{10}$;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, carbamyl, $C_{1-6}$ alkyl carbamyl, di($C_{1-6}$ alkyl)carbamyl, aminosulfonyl, $C_{1-6}$ alkylaminosulfonyl and di($C_{1-6}$ alkylaminosulfonyl;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{11}$;

or any $R^{c1}$ and $R^{d1}$ attached to the same N atom, together with the N atom to which they are attached, form a 4-10 membered heterocycloalkyl group optionally substituted with 1, 2, 3 or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkylaminosulfonyl;

each $R^{a2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl- $C_{1-3}$ alkylene, and 5-10 membered heteroaryl-$C_{1-3}$ alkylene are each optionally substituted with 1, 2, 3, or 4 substituents independently selected from $R^{21}$;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_3$-aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{21}$;

each $R^{e2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkylaminosulfonyl;

each $R^{a3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{12}$;

each $R^{a4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{22}$; or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-6}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{22}$;

each $R^{a5}$, $R^{c5}$ and $R^{d5}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c5}$ and $R^{d5}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkylamino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, Cue alkylsulfonylamino, aminosulfonyl, Cue alkylaminosulfonyl, di(Cue alkylaminosulfonyl, aminosulfonylamino, Cue alkylaminosulfonylamino, di(Cue alkylaminosulfonylamino, aminocarbonylamino, Cue alkylaminocarbonylamino, and di(Cue alkylaminocarbonylamino.

In some embodiments, $R^1$ is selected from $Cy^1$, Cue alkyl, $C_{2-6}$ alkenyl, $C_{2-6}$ alkynyl, $C_{1-6}$ haloalkyl, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC$ (O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said Cu, alkyl, C$_{2-6}$ alkenyl and C$_{2-6}$ alkynyl are each substituted with 1 or 2 substituents independently selected from R$^{10}$.

In some embodiments, R$^1$ is selected from Cy$^1$, Cue alkyl, C$_{2-6}$ alkenyl, C$_{2-6}$ alkynyl, C$_{1-6}$ haloalkyl, halo, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, and NR$^c$C(O)OR$^a$; wherein said C$_{1-6}$ alkyl, C$_{2-6}$ alkenyl and C$_{2-6}$ alkynyl are each substituted with 1 or 2 substituents independently selected from R$^{10}$.

In some embodiments, R$^1$ is selected from Cy$^1$, Cue alkyl, C$_{2-6}$ alkenyl, C$_{2-6}$ alkynyl, C$_{1-6}$ haloalkyl, halo, CN, OR$^a$, C(O)R$^b$, C(O)NR$^c$R$^d$, C(O)OR$^a$, OC(O)R$^b$, NR$^c$R$^d$, and NR$^c$C(O)R$^b$; wherein said Cue alkyl, C$_{2-6}$ alkenyl and C$_{1-6}$ alkynyl are each substituted with 1 or 2 substituents independently selected from R$^{10}$.

In some embodiments, R$^1$ is selected from Cy$^1$, Cue haloalkyl, halo, CN, OR$^a$, C(O)R$^b$, C(O)NR$^c$R$^d$, C(O)OR$^a$, OC(O)R$^b$, NR$^c$R$^d$, and NR$^c$C(O)R$^b$.

In some embodiments, R$^1$ is selected from C$_{1-6}$ alkyl, C$_{1-6}$ alkenyl, C$_{1-6}$ alkynyl, CM haloalkyl, halo, CN, OR$^a$, C(O)R$^b$, C(O)NR$^c$R$^d$, C(O)OR$^a$, OC(O)R$^b$, NR$^c$R$^d$, and NR$^c$C(O)R$^b$; wherein said Cue alkyl, C$_{1-6}$ alkenyl and C$_{1-6}$ alkynyl are each substituted with 1 or 2 substituents independently selected from R$^{10}$.

In some embodiments, R$^1$ is selected from C$_{1-6}$ alkyl, C$_{1-6}$ alkenyl, and C$_{1-6}$ alkynyl; wherein said C$_{1-6}$ alkyl, C$_{1-6}$ alkenyl and C$_{1-6}$ alkynyl are each substituted with 1 or 2 substituents independently selected from R$^{10}$.

In some embodiments, R$^1$ is Cy$^1$.

In some embodiments, Cy$^1$ is C$_{3-14}$ cycloalkyl optionally substituted with 1 or 2 substituents independently selected from R$^{10}$. In some embodiments, Cy$^1$ is C$_{3-12}$ cycloalkyl optionally substituted with 1 or 2 substituents independently selected from R$^{10}$. In some embodiments, Cy$^1$ is C$_{4-10}$ cycloalkyl optionally substituted with 1 or 2 substituents independently selected from R$^{10}$. In some embodiments, Cy$^1$ is C$_{3-10}$ cycloalkyl optionally substituted with 1 or 2 substituents independently selected from R$^{10}$. In some embodiments, Cy$^1$ is C$_{4-8}$ cycloalkyl optionally substituted with 1 or 2 substituents independently selected from R$^{10}$. In some embodiments, Cy$^1$ is C$_{5-6}$ cycloalkyl optionally substituted with 1 or 2 substituents independently selected from R$^{10}$.

In some embodiments, Cy$^1$ is 4-14 membered heterocycloalkyl having at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group; and wherein the 4-14 membered heterocycloalkyl is optionally substituted with 1 or 2 substituents independently selected from R$^{10}$. In some embodiments, Cy$^1$ is 4-12 membered heterocycloalkyl, 4-10 membered heterocycloalkyl, 4-8 membered heterocycloalkyl, or 5-6 membered heterocycloalkyl having at least one ring-forming carbon atom and 1, 2, 3, or 4 ring-forming heteroatoms independently selected from N, O, and S; wherein the N and S are optionally oxidized; wherein a ring-forming carbon atom of 4-12 membered heterocycloalkyl, 4-10 membered heterocycloalkyl, 4-8 membered heterocycloalkyl, or 5-6 membered heterocycloalkyl is optionally substituted by oxo to form a carbonyl group; and wherein the 4-14 membered heterocycloalkyl is optionally substituted with 1 or 2 substituents independently selected from R$^{10}$.

In some embodiments, Cy$^1$ is selected from C$_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the C$_{6-10}$ aryl and 5-10 membered heteroaryl are each optionally substituted with 1, 2 or 3 substituents independently selected from R$^{10}$.

In some embodiments, Cy$^1$ is selected from C$_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the C$_{6-10}$ aryl and 5-10 membered heteroaryl are each optionally substituted with 1 or 2 substituents independently selected from R$^{10}$. In some embodiments, Cy$^1$ is C$_{6-10}$ aryl optionally substituted with 1 or 2 substituents independently selected from R$^{10}$. In some embodiments, Cy$^1$ is phenyl optionally substituted with 1 or 2 substituents independently selected from R$^{10}$. In some embodiments, Cy$^1$ is phenyl optionally substituted with 1 R$^{10}$.

In some embodiments, Cy$^1$ is 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the 5-10 membered heteroaryl is optionally substituted with 1 or 2 substituents independently selected from R$^{10}$.

In some embodiments, Cy$^1$ is 5-6 membered heteroaryl; wherein the 5-6 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-6 membered heteroaryl is optionally substituted by oxo to form a carbonyl group; and wherein the 5-6 membered heteroaryl is optionally substituted with 1 or 2 substituents independently selected from R$^{10}$. In some embodiments, Cy$^1$ is phenyl or 5-6 membered heteroaryl; wherein the 5-6 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-6 membered heteroaryl is optionally substituted by oxo to form a carbonyl group; and wherein the phenyl or 5-6 membered heteroaryl is optionally substituted with 1 or 2 substituents independently selected from R$^{10}$.

In some embodiments, Cy$^1$ is pyridinyl optionally substituted with 1 or 2 substituents independently selected from R$^{10}$.

In some embodiments, Cy$^1$ is pyrazolyl optionally substituted with 1 or 2 substituents independently selected from R$^{10}$.

In some embodiments, Cy$^1$ is pyrazolyl, phenyl or pyridinyl, wherein the pyrazolyl, phenyl and pyridinyl are each optionally substituted with 1 or 2 substituents independently selected from R$^{10}$.

In some embodiments, $Cy^1$ is phenyl or pyridinyl, wherein the phenyl and pyridinyl are each optionally substituted with 1 or 2 substituents independently selected from $R^{10}$.

In some embodiments, $Cy^1$ is phenyl, wherein the phenyl is optionally substituted with 1 or 2 substituents independently selected from $R^{10}$.

In some embodiments, $R^{10}$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, and $NR^{c1}R^{d1}$, $NR^{c1}C(O)R^{b1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1 or 2 substituents independently selected from $R^{11}$.

In some embodiments, $R^{10}$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a1}$, 4-10 membered heterocycloalkyl-$C_{1-3}$ alkylene, 5-6 membered heteroaryl-$C_{1-3}$ alkylene, and $C(O)NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, 4-10 membered heterocycloalkyl-$C_{1-3}$ alkylene, and 5-6 membered heteroaryl-$C_{1-3}$ alkylene, are each optionally substituted with 1 or 2 substituents independently selected from $R^{11}$. In some embodiments, $R^{10}$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, and $OR^{a1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{11}$. In some embodiments, $R^{10}$ is selected from $C_{1-6}$ alkyl, $C_{2-6}$ alkenyl, $C_{2-6}$ alkynyl, $C_{1-6}$ haloalkyl, halo, D, CN, and $OR^{a1}$; wherein said $C_{1-6}$ alkyl, $C_{2-6}$ alkenyl and $C_{2-6}$ alkynyl are each optionally substituted with 1 or 2 substituents independently selected from $R^{11}$.

In some embodiments, $R^{10}$ is selected from $C_{1-6}$ alkyl, $C_{2-6}$ alkenyl, and $C_{2-6}$ alkynyl; wherein said $C_{1-6}$ alkyl, $C_{2-6}$ alkenyl and $C_{2-6}$ alkynyl are each optionally substituted with 1 or 2 substituents independently selected from $R^{11}$.

In some embodiments, $R^{10}$ is selected from $C_{1-6}$ alkyl, halo, $C_{3-10}$ cycloalkyl, 4-10 membered heterocycloalkyl, $C_{6-10}$ aryl, 5-10 membered heteroaryl, and $C(O)NR^{c1}R^{d1}$; wherein said $C_{1-6}$ alkyl, $C_{3-10}$ cycloalkyl, 4-10 membered heterocycloalkyl, $C_{6-10}$ aryl, and 5-membered heteroaryl are each optionally substituted with 1 or 2 substituents independently selected from $R^{11}$.

In some embodiments, $R^{10}$ is selected from $C_{3-10}$ cycloalkyl, 4-10 membered heterocycloalkyl, $C_{6-10}$ aryl, and 5-10 membered heteroaryl; wherein said $C_{3-10}$ cycloalkyl, 4-membered heterocycloalkyl, $C_{6-10}$ aryl, and 5-10 membered heteroaryl are each optionally substituted with 1 or 2 substituents independently selected from $R^{11}$.

In some embodiments, $R^{10}$ is $C_{3-10}$ cycloalkyl optionally substituted with 1 or 2 substituents independently selected from $R^{11}$. In some embodiments, $R^{10}$ is $C_{3-6}$ cycloalkyl optionally substituted with 1 or 2 substituents independently selected from $R^{11}$. In some embodiments, $R^{10}$ is cyclohexyl optionally substituted with 1 or 2 substituents independently selected from $R^{11}$. In some embodiments, $R^{10}$ is cyclobutyl optionally substituted with 1 or 2 substituents independently selected from $R^{11}$. In some embodiments, $R^{10}$ is cyclopropyl optionally substituted with 1 or 2 substituents independently selected from $R^{11}$.

In some embodiments, $R^{10}$ is 4-10 membered heterocycloalkyl optionally substituted with 1 or 2 substituents independently selected from $R^{11}$. In some embodiments, $R^{10}$ is 5-6 membered heterocycloalkyl optionally substituted with 1 or 2 substituents independently selected from $R^{11}$. In some embodiments, $R^{10}$ is piperazinyl optionally substituted with 1 or 2 substituents independently selected from $R^{11}$. In some embodiments, $R^{10}$ is pyrrolidinyl optionally substituted with 1 or 2 substituents independently selected from $R^{11}$. In some embodiments, $R^{10}$ is piperidinyl optionally substituted with 1 or 2 substituents independently selected from $R^{11}$. In some embodiments, $R^{10}$ is hexahydropyrrolo[1,2-a]pyrazin-2(1H)-yl optionally substituted with 1 or 2 substituents independently selected from $R^{11}$. In some embodiments, $R^{10}$ is tetrahydropyranyl optionally substituted with 1 or 2 substituents independently selected from $R^{11}$. In some embodiments, $R^{10}$ is morpholino optionally substituted with 1 or 2 substituents independently selected from $R^{11}$.

In some embodiments, $R^{10}$ is $C_{6-10}$ aryl optionally substituted with 1 or 2 substituents independently selected from $R^{11}$. In some embodiments, $R^{10}$ is phenyl optionally substituted with 1 or 2 substituents independently selected from $R^{11}$.

In some embodiments, $R^{10}$ is 5-10 membered heteroaryl optionally substituted with 1 or 2 substituents independently selected from $R^{11}$. In some embodiments, $R^{10}$ is pyridyl optionally substituted with 1 or 2 substituents independently selected from $R^{11}$. In some embodiments, $R^{10}$ is imidazo[1,2-a]pyridyl optionally substituted with 1 or 2 substituents independently selected from $R^{11}$.

In some embodiments, $R^{10}$ is $C_{1-6}$ alkyl, optionally substituted with 1 or 2 substituents independently selected from $R^{11}$. In some embodiments, $R^{10}$ is methyl, optionally substituted with 1 or 2 substituents independently selected from $R^{11}$. In some embodiments, $R^{10}$ is ethyl, optionally substituted with 1 or 2 substituents independently selected from $R^{11}$. In some embodiments, $R^{10}$ is isopropyl, optionally substituted with 1 or 2 substituents independently selected from $R^{11}$.

In some embodiments, $R^{10}$ is $C(O)NR^{c1}R^{d}$. In some embodiments, each $R^{c1}$ and $R^{d1}$ is independently selected from H, and $C_{1-6}$ alkyl. In some embodiments, $R^{10}$ is methylcarbamoyl.

In some embodiments, $R^{10}$ is 4-10 membered heterocycloalkyl-$C_{1-3}$ alkylene optionally substituted with 1 or 2 substituents independently selected from $R^{11}$. In some embodiments, $R^{10}$ is 5-6 membered heterocycloalkyl-$C_{1-3}$ alkylene optionally substituted with 1 or 2 substituents independently selected from $R^{11}$.

In some embodiments, $R^{10}$ is 5-10 membered heteroaryl-$C_{1-3}$ alkylene optionally substituted with 1 or 2 substituents independently selected from $R^{11}$. In some embodiments, $R^{10}$ is 6 membered heteroaryl-$C_{1-3}$ alkylene optionally substituted with 1 or 2 substituents independently selected from $R^{11}$.

In some embodiments, $R^{10}$ is selected from methyl, ethyl, isopropyl, cyclopropyl, cyclobutyl, fluoro, methylcarbamoyl, phenyl, piperazinyl, pyrrolidinyl, morpholino, piperidinyl, pyridinyl, hexahydropyrrolo[1,2-a]pyrazin-2(1H)-yl, tetrahydropyranyl, cyclohexyl, 2-morpholinoethyl, pyridinylmethyl, 2,2,2-trifluoroethyl, and imidazo[1,2-a]pyridin-6-yl; wherein said methyl, ethyl, isopropyl, cyclopropyl, cyclobutyl, methylcarbamoyl, phenyl, piperazinyl, pyrrolidinyl, morpholino, piperidinyl, pyridinyl, hexahydropyrrolo[1,2-a]pyrazin-2(1H)-yl, tetrahydropyranyl, cyclohexyl, 2-morpholinoethyl, pyridinylmethyl, 2,2,2-trifluoroethyl, and imidazo[1,2-a]pyridin-6-yl are each optionally substituted with 1 or 2 substituents independently selected from $R^{11}$.

In some embodiments, $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, and $NR^{c3}C(O)R^{b3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{12}$.

In some embodiments, $R^{11}$ is independently selected from $C_{1-6}$ alkyl, $C_{1-6}$ haloalkyl, halo, 4-10 membered heterocycloalkyl, 5-10 membered heteroaryl, CN, $OR^{a3}$, $C(O)NR^{c3}R^{d3}$, $C(O)R^{b3}$, and $NR^{c3}R^{d3}$, wherein said $C_{1-6}$ alkyl, 4-10 membered heterocycloalkyl, and 5-10 membered heteroaryl are each optionally substituted with 1 or 2 substituents independently selected from $R^{12}$.

In some embodiments, $R^{11}$ is independently selected from methyl, ethyl, 2-hydroxyethyl, 1-hydroxypropan-2-yl, tetrahydro-2H-pyran-4-yl, trifluoromethyl, fluoro, 2-carboxypropan-2-yl, CN, OH, methoxy, dimethylcarbamoyl, methylcarbamoyl, dimethylamine, 1-isobutyryl, morpholino, and pyridinyl.

In some embodiments, $R^{11}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl are each optionally substituted with 1 or 2 substituents independently selected from $R^{12}$.

In some embodiments, $R^{11}$ is independently selected from $C_{1-6}$ alkyl, $C_{2-6}$ alkenyl, and $C_{2-6}$ alkynyl. In some embodiments, $R^{11}$ is $C_{1-6}$ alkyl. In some embodiments, $R^{11}$ is methyl, ethyl, or propyl. In some embodiments, $R^{11}$ is methyl.

In some embodiments, $R^{12}$ is independently selected from $C_{1-6}$ alkyl, $C_{1-6}$ haloalkyl, halo, CN, $OR^{a5}$, and $C(O)OR^{a5}$. In some embodiments, $R^{12}$ is independently selected from $C_{1-6}$ alkyl, C(O)OH, and OH.

In some embodiments, $R^{10}$ is methyl, ethyl, isopropyl, cyclopropyl, cyclobutyl, fluoro, 4-methylpiperazin-1-yl, 4-ethylpiperazin-1-yl, methylcarbamoyl, 1-methylpyrrolidin-3-yl, 1-(2-hydroxyethyl)pyrrolidin-3-yl, 4-(1-hydroxypropan-2-yl)piperazin-1-yl, 4-(tetrahydro-2H-pyran-4-yl)piperazin-1-yl, 4-(2-carboxypropan-2-yl)piperazin-1-yl, 2-methylmorpholino, 3,4-dimethylpiperazin-1-yl, 4-hydroxypiperidin-1-yl, 7-hydroxyhexahydropyrrolo[1,2-a]pyrazin-2(1H)-yl, 2-methoxyethyl, tetrahydro-2H-pyran-4-yl, 4-hydroxycyclohexyl, 1-(dimethylcarbamoyl)piperidin-4-yl, 1-isobutyrylpiperidin-4-yl, 2-morpholinoethyl, 4-methylpiperazin-1-yl, pyridin-4-ylmethyl, 2,2,2-trifluoroethyl, pyridin-4-yl, pyridin-3-yl, 4-cyanophenyl, 2-methylpyridin-4-yl, 6-(dimethylamino)pyridin-3-yl, 5-cyanopyridin-3-yl, 6-cyanopyridin-3-yl, imidazo[1,2-a]pyridin-6-yl, 4-cyano-3-methylphenyl, 4-cyano-2-methylphenyl, 4-cyano-3-fluorophenyl, 4-(methylcarbamoyl)phenyl, 4-(dimethylcarbamoyl)phenyl, 3-fluoro-4-(methylcarbamoyl) phenyl, 3-(6-(methylcarbamoyl)pyridin-3-yl, 3-methylpiperazin-1-yl or 4-methylpiperazin-1-yl.

In some embodiments, $R^{10}$ is 3-methylpiperazin-1-yl or 4-methylpiperazin-1-yl. In some embodiments, $R^{10}$ is (R)-3-methylpiperazin-1-yl.

In some embodiments, $Cy^1$ is 6-(3-methylpiperazin-1-yl) pyridin-3-yl, 4-(4-methylpiperazin-1-yl)phenyl, 3-fluoro-4-(4-methylpiperazin-1-yl)phenyl. 6-(4-methylpiperazin-1-yl) pyridin-3-yl, 4-(4-ethylpiperazin-1-yl)-3-methylphenyl, 4-(methylcarbamoyl)phenyl, 4-(l-methylpyrrolidin-3-yl) phenyl, 4-(1-(2-hydroxy ethylpyrrolidin-3-ylphenyl, 4-(4-(1-hydroxypropan-2-yl)piperazin-1-ylphenyl, 4-(4-(tetrahydro-2H-pyran-4-yl)piperazin-1-ylphenyl, 4-(4-(2-carboxypropan-2-yl)piperazin-1-ylphenyl, 6-(2-methylmorpholino)pyridin-3-yl, 6-(3,4-dimethylpiperazin-1-yl)pyridin-3-yl, 4-(4-hydroxypiperidin-1-ylphenyl, 4-(7-hydroxyhexahydropyrrolo[1,2-a]pyrazin-2(1H)-ylphenyl, 1-(2-methoxyethyl)-1H-pyrazol-4-yl, 1-(tetrahydro-2H-pyran-4-yl)-1H-pyrazol-4-yl, 1-(4-hydroxycyclohexyl)-1H-pyrazol-4-yl, 1-(1-(dimethylcarbamoyl)piperidin-4-yl)-1H-pyrazol-4-yl, 1-(1-isobutyrylpiperidin-4-yl)-1H-pyrazol-4-yl, 1-(2-morpholinoethyl)-1H-pyrazol-4-yl, 6-(4-methylpiperazin-1-yl)pyridin-3-yl, 1-(pyridin-4-ylmethyl)-1H-pyrazol-4-yl, 1-methyl-1H-pyrazol-4-yl, 1-ethyl-1H-pyrazol-4-yl, 1-isopropyl-1H-pyrazol-4-yl, 1-cyclobutyl-1H-pyrazol-4-yl, 1-cyclopropyl-1H-pyrazol-4-yl, 1-(2,2,2-trifluoroethyl)-1H-pyrazol-4-yl, 1-(pyridin-4-yl)-1H-pyrazol-4-yl, 1-(pyridin-3-yl)-1H-pyrazol-4-yl, 1-(4-cyanophenyl)-1H-pyrazol-4-yl, 1-(2-methylpyridin-4-yl)-1H-pyrazol-4-yl, 1-(6-(dimethylamino)pyridin-3-yl)-1H-pyrazol-4-yl, 1-(5-cyanopyridin-3-yl)-1H-pyrazol-4-yl, 1-(6-cyanopyridin-3-yl)-1H-pyrazol-4-yl, 1-(imidazo[1,2-a] pyridin-6-yl)-1H-pyrazol-4-yl, 1-(4-cyano-3-methylphenyl)-1H-pyrazol-4-yl, 1-(4-cyano-2-methylphenyl)-1H-pyrazol-4-yl, 1-(4-cyano-3-fluorophenyl)-1H-pyrazol-4-yl, 1-(4-(methylcarbamoyl)phenyl)-1H-pyrazol-4-yl, 1-(4-(dimethylcarbamoylphenyl)-1H-pyrazol-4-yl, 1-(3-fluoro-4-(methylcarbamoyl)phenyl)-1H-pyrazol-4-yl, and 1-(6-(methylcarbamoyl)pyridin-3-yl)-1H-pyrazol-4-yl.

In some embodiments, $R^2$ is selected from H, D, $C_{1-4}$ alkyl, and $C_{1-4}$ haloalkyl.

In some embodiments, $R^2$ is selected from H and D. In some embodiments, $R^2$ is H. In some embodiments, $R^2$ is D.

In some embodiments, Cy is 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein if the 4-14 membered heterocycloalkyl contains a fused aromatic ring, then the 4-14 membered heterocycloalkyl is directly attached to the pyrazolopyrimidine core structure through a ring-forming atom of the saturated or partially saturated ring; and wherein the 4-14 membered heterocycloalkyl is substituted with 1, 2, 3, 4 or 5 substituents independently selected from $R^{20}$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{3-10}$ aryl-$C_{1-3}$ alkylene, 5-10 membered heteroaryl-$C_{1-3}$ alkylene, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said C %, alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$; wherein at least one $R^{20}$ is selected from $C_{3-10}$ cycloalkyl, 4-10 membered heterocycloalkyl, $C_{6-10}$ aryl, 5-10 membered heteroaryl, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{21}$.

In some embodiments, Cy is 4-14 membered heterocycloalkyl, 4-12 membered heterocycloalkyl, 4-10 membered heterocycloalkyl, 4-8 membered heterocycloalkyl, 5-12 membered heterocycloalkyl, 5-8 membered heterocycloalkyl, 6-11 membered heterocycloalkyl, 6 membered heterocycloalkyl, 7 membered heterocycloalkyl, 8 membered heterocycloalkyl, 9 membered heterocycloalkyl, 10 membered heterocycloalkyl, or 11 membered heterocycloalkyl wherein the 4-14 membered heterocycloalkyl, 4-12 membered heterocycloalkyl, 4-10 membered heterocycloalkyl, 4-8 membered heterocycloalkyl, 5-12 membered heterocycloalkyl, 5-8 membered heterocycloalkyl, 6-11 membered heterocycloalkyl, 6 membered heterocycloalkyl, 7 membered heterocycloalkyl, 8 membered heterocycloalkyl, 9 membered heterocycloalkyl, 10 membered heterocycloalkyl, or 11 membered heterocycloalkyl has at least one ring-forming carbon atom and 1, 2, 3, or 4 ring-forming heteroatoms independently selected from N, O, and S; wherein the N and S are optionally oxidized; wherein if the 4-14 membered heterocycloalkyl contains a fused aromatic ring, then the 4-14 membered heterocycloalkyl, 4-12 membered heterocycloalkyl, 4-membered heterocycloalkyl, 4-8 membered heterocycloalkyl, 5-12 membered heterocycloalkyl, 5-8 membered heterocycloalkyl, 6-11 membered heterocycloalkyl, 6 membered heterocycloalkyl, 7 membered heterocycloalkyl, 8 membered heterocycloalkyl, 9 membered heterocycloalkyl, 10 membered heterocycloalkyl, or 11 membered heterocycloalkyl is directly attached to the pyrazolopyrimidine core structure through a ring-forming atom of the saturated or partially saturated ring; and wherein the 4-14 membered heterocycloalkyl, 4-12 membered heterocycloalkyl, 4-10 membered heterocycloalkyl, 4-8 membered heterocycloalkyl, 5-12 membered heterocycloalkyl, 5-8 membered heterocycloalkyl, 6-11 membered heterocycloalkyl, 6 membered heterocycloalkyl, 7 membered heterocycloalkyl, 8 membered heterocycloalkyl, 9 membered heterocycloalkyl, 10 membered heterocycloalkyl, or 11 membered heterocycloalkyl is substituted with 1, 2, 3, 4 or substituents independently selected from $R^{20}$.

In some embodiments, Cy is 4-14 membered heterocycloalkyl; wherein the 4-14 membered heterocycloalkyl has at least one ring-forming carbon atom and 1, 2, 3, or 4 ring-forming heteroatoms independently selected from N, and O; wherein the N are optionally oxidized; wherein if the 4-14 membered heterocycloalkyl contains a fused aromatic ring, then the 4-14 membered heterocycloalkyl is directly attached to the pyrazolopyrimidine core structure through a ring-forming atom of the saturated or partially saturated ring; and wherein the 4-14 membered heterocycloalkyl is substituted with 1, 2, 3, 4 or 5 substituents independently selected from $R^{20}$.

In some embodiments, Cy is 4-14 membered heterocycloalkyl; wherein the 4-14 membered heterocycloalkyl is a saturated monocyclic ring; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group; and wherein the 4-14 membered heterocycloalkyl is optionally substituted with 1, 2, 3, or 4 substituents independently selected from $R^{20}$.

In some embodiments, Cy is 4-14 membered heterocycloalkyl; wherein the 4-14 membered heterocycloalkyl is a saturated bicyclic ring; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group; and wherein the 4-14 membered heterocycloalkyl is optionally substituted with 1, 2, 3, or 4 substituents independently selected from $R^{20}$.

In some embodiments, Cy is 4-14 membered heterocycloalkyl; wherein the 4-14 membered heterocycloalkyl is a saturated spirocyclic ring; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group; and wherein the 4-14 membered heterocycloalkyl is optionally substituted with 1, 2, 3, or 4 substituents independently selected from $R^{20}$.

In some embodiments, Cy is 4-12 membered heterocycloalkyl; wherein the 4-12 membered heterocycloalkyl has at least one ring-forming carbon atom and 1, 2, 3, or 4 ring-forming heteroatoms independently selected from N, and O; wherein the N are optionally oxidized; wherein if the 4-12 membered heterocycloalkyl contains a fused aromatic ring, then the 4-12 membered heterocycloalkyl is directly attached to the pyrazolopyrimidine core structure through a ring-forming atom of the saturated or partially saturated ring; and wherein the 4-12 membered heterocycloalkyl is substituted with 1, 2, 3, 4 or 5 substituents independently selected from $R^{20}$.

In some embodiments, Cy is 4-12 membered heterocycloalkyl; wherein the 4-12 membered heterocycloalkyl is a saturated monocyclic ring; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-12 membered heterocycloalkyl is optionally substituted by oxo to form a carbonyl group; and wherein the 4-12 membered heterocycloalkyl is optionally substituted with 1, 2, 3, or 4 substituents independently selected from $R^{20}$.

In some embodiments, Cy is 4-12 membered heterocycloalkyl; wherein the 4-12 membered heterocycloalkyl is a saturated bicyclic ring; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-12 membered heterocycloalkyl is optionally substituted by oxo to form a carbonyl group; and wherein the 4-12 membered heterocycloalkyl is optionally substituted with 1, 2, 3, or 4 substituents independently selected from $R^{20}$.

In some embodiments, Cy is 5-12 membered heterocycloalkyl; wherein the 5-12 membered heterocycloalkyl is a saturated spirocyclic ring; wherein the 5-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-12 membered heterocycloalkyl is optionally substituted by oxo to form a carbonyl group; and wherein the 5-12 membered heterocycloalkyl is optionally substituted with 1, 2, 3, or 4 substituents independently selected from $R^{20}$.

In some embodiments, Cy is 6-11 membered heterocycloalkyl; wherein the 6-11 membered heterocycloalkyl has at least one ring-forming carbon atom and 1, 2, 3, or 4 ring-forming heteroatoms independently selected from N, and O; wherein the N are optionally oxidized; wherein if the 6-11 membered heterocycloalkyl contains a fused aromatic ring, then the 6-11 membered heterocycloalkyl is directly attached to the pyrazolopyrimidine core structure through a ring-forming atom of the saturated or partially saturated ring; and wherein the 6-11 membered heterocycloalkyl is substituted with 1, 2, 3, 4 or 5 substituents independently selected from $R^{20}$.

In some embodiments, Cy is 6-11 membered heterocycloalkyl; wherein the 6-11 membered heterocycloalkyl is a saturated monocyclic ring; wherein the 6-11 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 6-11 membered heterocycloalkyl is optionally substituted by oxo to form a carbonyl group; and wherein the 6-11 membered heterocycloalkyl is optionally substituted with 1, 2, 3, or 4 substituents independently selected from $R^{20}$.

In some embodiments, Cy is 6-11 membered heterocycloalkyl; wherein the 6-11 membered heterocycloalkyl is a saturated bicyclic ring; wherein the 6-11 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 6-11 membered heterocycloalkyl is optionally substituted by oxo to form a carbonyl group; and wherein the 6-11 membered heterocycloalkyl is optionally substituted with 1, 2, 3, or 4 substituents independently selected from $R^{20}$.

In some embodiments, Cy is 6-11 membered heterocycloalkyl; wherein the 6-11 membered heterocycloalkyl is a saturated spirocyclic ring; wherein the 6-11 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 6-11 membered heterocycloalkyl is optionally substituted by oxo to form a carbonyl group; and wherein the 6-11 membered heterocycloalkyl is optionally substituted with 1, 2, 3, or 4 substituents independently selected from $R^{20}$.

In some embodiments, Cy is 4-8 membered heterocycloalkyl; wherein the 4-8 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-8 membered heterocycloalkyl is optionally substituted by oxo to form a carbonyl group; wherein when the 4-8 membered heterocycloalkyl of Cy has a fused aromatic ring, the 4-8 membered heterocycloalkyl is directly attached to the pyrazolopyrimidine core structure through a ring-forming atom of the saturated or partially saturated ring; and wherein the 4-8 membered heterocycloalkyl is optionally substituted with 1, 2, 3, or 4 substituents independently selected from $R^{20}$.

In some embodiments, Cy is 4-8 membered heterocycloalkyl; wherein the 4-8 membered heterocycloalkyl is a saturated monocyclic ring; wherein the 4-8 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-8 membered heterocycloalkyl is optionally substituted by oxo to form a carbonyl group; and wherein the 4-8 membered heterocycloalkyl is optionally substituted with 1, 2, 3, or 4 substituents independently selected from $R^{20}$.

In some embodiments, Cy is 4-8 membered heterocycloalkyl; wherein the 4-8 membered heterocycloalkyl is a saturated bicyclic ring; wherein the 4-8 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-8 membered heterocycloalkyl is optionally substituted by oxo to form a carbonyl group; and wherein the 4-8 membered heterocycloalkyl is optionally substituted with 1, 2, 3, or 4 substituents independently selected from $R^{20}$.

In some embodiments, Cy is 5-8 membered heterocycloalkyl; wherein the 5-8 membered heterocycloalkyl is a saturated spirocyclic ring; wherein the 5-8 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-8 membered heterocycloalkyl is optionally substituted by oxo to form a carbonyl group; and wherein the 5-8 membered heterocycloalkyl is optionally substituted with 1, 2, 3, or 4 substituents independently selected from $R^{20}$.

In some embodiments, Cy is 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein the 4-14 membered heterocycloalkyl contains a fused aromatic ring, wherein the 4-14 membered heterocycloalkyl is directly attached to the pyrazolopyrimidine core structure through a ring-forming atom of the saturated or partially saturated ring; and wherein the 4-14 membered heterocycloalkyl is substituted with 1, 2, 3, 4 or 5 substituents independently selected from $R^{20}$.

In some embodiments when Cy is a 4-14 membered heterocycloalkyl, 6-11 membered heterocycloalkyl, 4-8 membered heterocycloalkyl, or 5-8 membered heterocycloalkyl, Cy comprises at least one ring-forming N and Cy is attached to the pyrazolopyrimidine core structure through a N of the heterocycloalkyl.

In some embodiments, $R^{20}$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, and $NR^{c2}C(O)OR^{a2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{21}$.

In some embodiments, $R^{20}$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, $OR^{a2}$, $SR^{a2}$, $C(O)R^{b2}$, $C(O)NR^{c2}R^{d2}$, $C(O)OR^{a2}$, and $NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{21}$.

In some embodiments, $R^{20}$ is selected from $C_{1-6}$ alkyl, $C_{6-10}$ aryl, $OR^{a2}$, $C(O)R^{b2}$, $C(O)NR^{c2}R^{d2}$, and $C(O)OR^{a2}$; wherein said $C_{1-6}$ alkyl and $C_{6-10}$ aryl are each optionally substituted with 1 or 2 substituents independently selected from $R^{21}$.

In some embodiments, $R^{20}$ is independently selected from $C_{1-6}$ alkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1 or 2 substituents independently selected from $R^{21}$.

In some embodiments, $R^{20}$ is $C_{1-6}$ alkyl optionally substituted with 1 or 2 substituents independently selected from $R^{21}$.

In some embodiments, $R^{20}$ is selected from $C_{3-10}$ cycloalkyl, 4-10 membered heterocycloalkyl, $C_{6-10}$ aryl, and 5-10 membered heteroaryl; wherein said $C_{3-10}$ cycloalkyl, 4-membered heterocycloalkyl, $C_{6-10}$ aryl, and 5-10 membered heteroaryl are each optionally substituted with 1 or 2 substituents independently selected from $R^{21}$.

In some embodiments, $R^{20}$ is $C_{6-10}$ aryl optionally substituted with 1 or 2 substituents independently selected from $R^{21}$.

In some embodiments, $R^{20}$ is selected from $OR^{a2}$, $SR^{a2}$, $C(O)R^{b2}$, $C(O)NR^{c2}R^{d2}$, $C(O)OR^{a2}$, and $NR^{c2}R^{d2}$. In some embodiments, $R^{20}$ is selected from $OR^{a2}$, $C(O)R^{b2}$, $C(O)NR^{c2}R^{d2}$, and $C(O)OR^{a2}$.

In some embodiments, $R^{20}$ is selected from $C_{1-6}$ alkyl, $C_{1-6}$ haloalkyl, $C_{3-10}$ cycloalkyl, $C_{6-10}$ aryl, halo, CN, $OR^{a2}$, $C(O)R^{b2}$, $C(O)NR^{c2}R^{d2}$, and $C(O)OR^{a2}$; wherein said $C_{1-6}$ alkyl, $C_{3-10}$ cycloalkyl, and $C_{6-10}$ aryl are each optionally substituted with 1 or 2 substituents independently selected from $R^{21}$.

In some embodiments, $R^{20}$ is selected from methyl, ethyl, isopropyl, 2-fluoroethyl, 2,2-difluoroethyl, cyclopropyl, trifluoromethyl, OH, 4-cyanophenyl, pyrrolidine-1-carbonyl, 3-fluoropyrrolidine-1-carbonyl, cyclopropanecarbonyl, isobutyryl, 2-methoxyacetyl, isopropylcarbamoyl, dimethylcarbamoyl, methoxycarbonyl, ethoxycarbonyl, (2-fluoroethoxy)carbonyl.

In some embodiments, $R^{21}$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{34}$, $SR^{34}$, $C(O)R^{b4}$, $C(O)NR^{c4}R^{d4}$, $C(O)OR^{a4}$, and $NR^{c4}R^{d4}$, $NR^{c4}C(O)R^{b4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{22}$.

In some embodiments, $R^{21}$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, and $OR^{34}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{22}$.

In some embodiments, $R^{21}$ is selected from halo, D, CN, and $OR^{34}$. In some embodiments, $R^{21}$ is selected from halo, CN, and $OR^{34}$. In some embodiments, $R^{21}$ is selected from F, CN, and OH.

In some embodiments, $R^{21}$ is selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl are each optionally substituted with 1 or 2 substituents independently selected from $R^{22}$.

In some embodiments, $R^{21}$ is selected from $C_{3-10}$ cycloalkyl, 4-10 membered heterocycloalkyl, $C_{6-10}$ aryl, and 5-10 membered heteroaryl; wherein said $C_{3-10}$ cycloalkyl, 4-membered heterocycloalkyl, $C_{6-10}$ aryl, and 5-10 membered heteroaryl are each optionally substituted with 1 or 2 substituents independently selected from $R^{22}$.

In some embodiments, each $R^{a2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{21}$.

In some embodiments, each $R^{a2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl; wherein said $C_{1-6}$ alkyl, $C_{2-6}$ alkenyl, and $C_{2-6}$ alkynyl are each optionally substituted with 1 or 2 substituents independently selected from $R^{21}$.

In some embodiments, each $R^{a2}$, $R^{c2}$ and $R^{d2}$ is independently selected from H, $C_{1-6}$ alkyl, and $C_{1-6}$ haloalkyl; wherein said $C_{1-6}$ alkyl is optionally substituted with 1 or 2 substituents independently selected from $R^{21}$.

In some embodiments, each $R^{a2}$, $R^{c2}$ and $R^{d2}$ is independently selected from $C_{3-10}$ cycloalkyl, 4-10 membered heterocycloalkyl, $C_{6-10}$ aryl, and 5-10 membered heteroaryl; wherein said $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{21}$.

In some embodiments, any $R^{c2}$ and $R^{d2}$ attached to the same N atom, together with the N atom to which they are attached, form a 4-10 membered heterocycloalkyl group optionally substituted with 1 or 2 substituents independently selected from $R^{21}$.

In some embodiments, each $R^{a4}$, $R^{c4}$ and $R^{d4}$ is independently selected from H, $C_{1-6}$ alkyl, $C_{2-6}$ alkenyl, $C_{2-6}$ alkynyl, and $C_{1-6}$ haloalkyl. In some embodiments, each $R^{a4}$, $R^{c4}$ and $R^{d4}$ is independently selected from H and $C_{1-6}$ alkyl. In some embodiments, each $R^{a4}$, $R^{c4}$ and $R^{d4}$ is independently $C_{1-6}$ alkyl. In some embodiments, each $R^{a4}$, $R^{c4}$ and $R^{d4}$ is H.

In some embodiments, $R^{b2}$ is selected from $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl are each optionally substituted with 1 or 2 substituents independently selected from $R^{21}$. In some embodiments, $R^{b2}$ is selected from $C_{1-6}$ alkyl, $C_{1-6}$ haloalkyl and $C_{3-10}$ cycloalkyl; wherein said $C_{1-6}$ alkyl and $C_{3-10}$ cycloalkyl are each optionally substituted with 1 or 2 substituents independently selected from $R^{21}$. In some embodiments, $R^{b2}$ is selected from $C_{1-6}$ alkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl are each optionally substituted with 1 or 2 substituents independently selected from $R^{21}$. In some embodiments, $R^{b2}$ is $C_{1-6}$ alkyl optionally substituted with 1 or 2 substituents independently selected from $R^{21}$. In some embodiments, $R^{b2}$ is $C_{3-10}$ cycloalkyl optionally substituted with 1 or 2 substituents independently selected from $R^{21}$. In some embodiments, $R^{b2}$ is 4-10 membered heterocycloalkyl optionally substituted with 1 or 2 substituents independently selected from $R^{21}$.

In some embodiments, Cy is piperidinyl, morpholinyl, azabicyclo[2.2.1]heptanyl, azabicyclo[3.2.1]octanyl, piperazinyl, diazabicyclo[3.2.1]octanyl, 1,4,6,7-tetrahydro-5H-imidazo[4,5-c]pyridin-5-yl, 5,6-dihydroimidazo[1,2-a]pyrazin-7(8H)-yl, 2,5-diazabicyclo[2.2.2]octan-2-yl, 2,5-diazabicyclo[2,2,1]heptan-2-yl, 3-oxopiperazinyl, 5,6,7,8-tetrahydro-1,6-naphthyridin-6-yl, 5,6,7,8-tetrahydroimidazo[1,5-a]pyrazin-7-yl, 4,5,6,7-tetrahydro thiazolo[5,4-c]pyridin-5-yl, 1,4,5,7-tetrahydro-6H-pyrazolo[3,4-c]pyridin-6-yl, 1,4,5,6,7,8-hexahydro-5,8-epiminocyclohepta[c]pyrazol-9-yl, or 2-oxo-3,8-diazabicyclo[3.2.1]octan-8-yl, each optionally substituted with 1, 2, 3, or 4 substituents independently selected from $R^{20}$.

In some embodiments, Cy is piperidinyl, optionally substituted with 1, 2, 3, or 4 substituents independently selected from $R^{20}$.

In some embodiments, Cy is morpholinyl, optionally substituted with 1, 2, 3, or 4 substituents independently selected from $R^{20}$.

In some embodiments, Cy is azabicyclo[2.2.1]heptanyl, optionally substituted with 1, 2, 3, or 4 substituents independently selected from $R^{20}$.

In some embodiments, Cy is azabicyclo[3.2.1]octanyl, optionally substituted with 1, 2, 3, or 4 substituents independently selected from $R^{20}$.

In some embodiments, Cy is piperazinyl, optionally substituted with 1, 2, 3, or 4 substituents independently selected from $R^{20}$.

In some embodiments, Cy is diazabicyclo[3.2.1]octanyl, optionally substituted with 1, 2, 3, or 4 substituents independently selected from $R^{20}$.

In some embodiments, Cy is 1,4,6,7-tetrahydro-5H-imidazo[4,5-c]pyridin-5-yl, optionally substituted with 1, 2, 3, or 4 substituents independently selected from $R^{20}$.

In some embodiments, Cy is 5,6-dihydroimidazo[1,2-a]pyrazin-7(8H)-yl, optionally substituted with 1, 2, 3, or 4 substituents independently selected from $R^{20}$.

In some embodiments, Cy is 2,5-diazabicyclo[2.2.2]octan-2-yl, optionally substituted with 1, 2, 3, or 4 substituents independently selected from $R^{20}$.

In some embodiments, Cy is 3-oxopiperazinyl, optionally substituted with 1, 2, 3, or 4 substituents independently selected from $R^{20}$.

In some embodiments, Cy is 5,6,7,8-tetrahydro-1,6-naphthyridin-6-yl, optionally substituted with 1, 2, 3, or 4 substituents independently selected from $R^{20}$.

In some embodiments, Cy is 5,6,7,8-tetrahydroimidazo[1,5-a]pyrazin-7-yl, optionally substituted with 1, 2, 3, or 4 substituents independently selected from $R^{20}$.

In some embodiments, Cy is 4,5,6,7-tetrahydrothiazolo[5,4-c]pyridin-5-yl, optionally substituted with 1, 2, 3, or 4 substituents independently selected from $R^{20}$.

In some embodiments, Cy is 1,4,5,7-tetrahydro-6H-pyrazolo[3,4-c]pyridin-6-yl, optionally substituted with 1, 2, 3, or 4 substituents independently selected from $R^{20}$.

In some embodiments, Cy is 1,4,5,6,7,8-hexahydro-5,8-epiminocyclohepta[c]pyrazol-9-yl, optionally substituted with 1, 2, 3, or 4 substituents independently selected from $R^{20}$. In some embodiments, Cy is 2-oxo-3,8-diazabicyclo[3.2.1]octan-8-yl, optionally substituted with 1, 2, 3, or 4 substituents independently selected from $R^{20}$.

In some embodiments, Cy is piperidinyl, morpholinyl, azabicyclo[2.2.1]heptanyl, azabicyclo[3.2.1]octanyl, piperazinyl, or diazabicyclo[3.2.1]octanyl. In some embodiments, Cy is piperidinyl. In some embodiments, Cy is morpholinyl. In some embodiments, Cy is azabicyclo[2.2.1]heptanyl. In some embodiments, Cy is azabicyclo[3.2.1]octanyl. In some embodiments, Cy is piperazinyl. In some embodiments, Cy is diazabicyclo[3.2.1]octanyl.

In some embodiments, Cy is

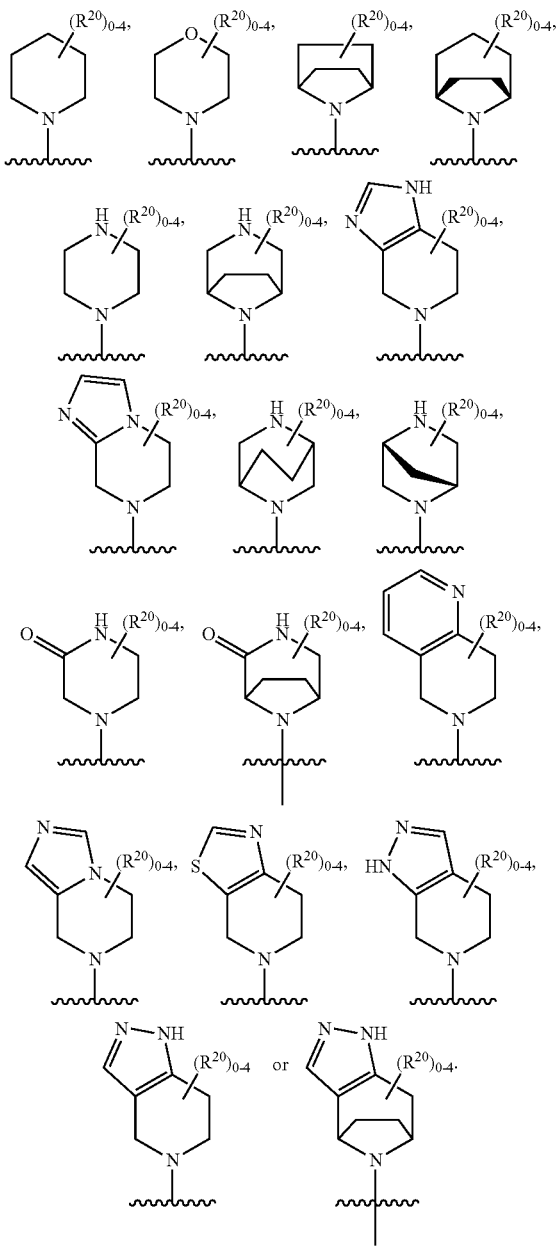

In some embodiments, Cy is

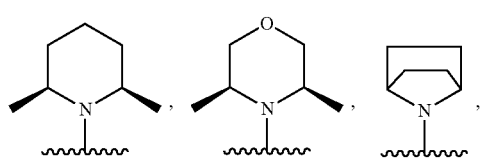

-continued
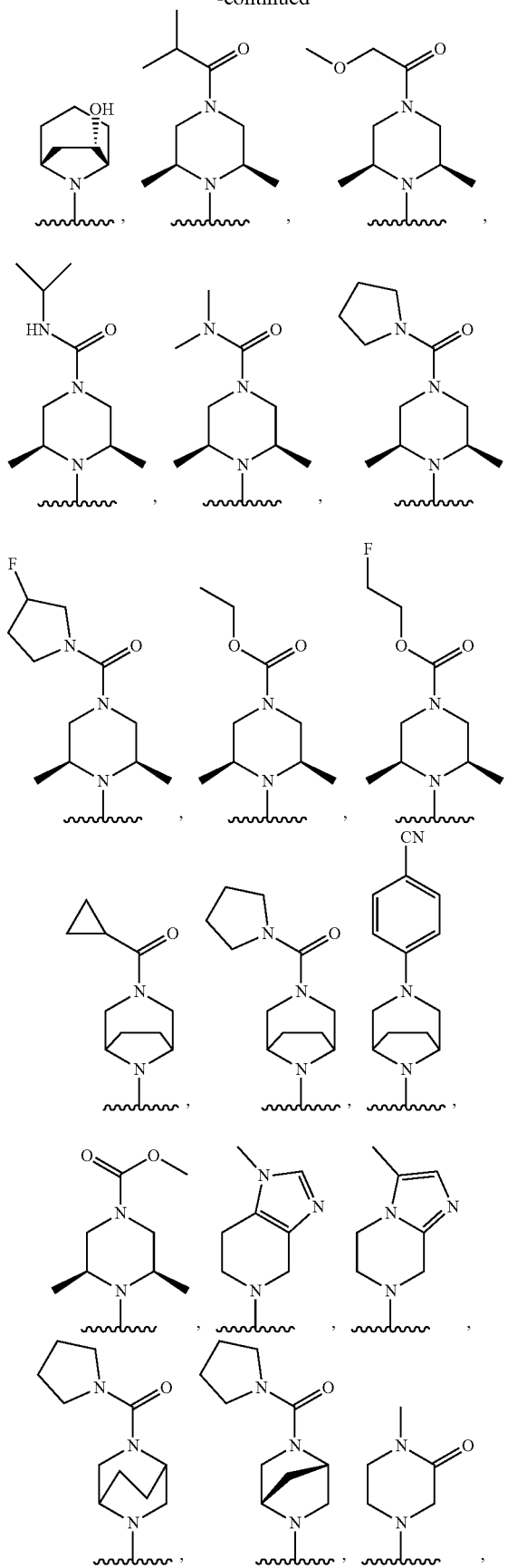
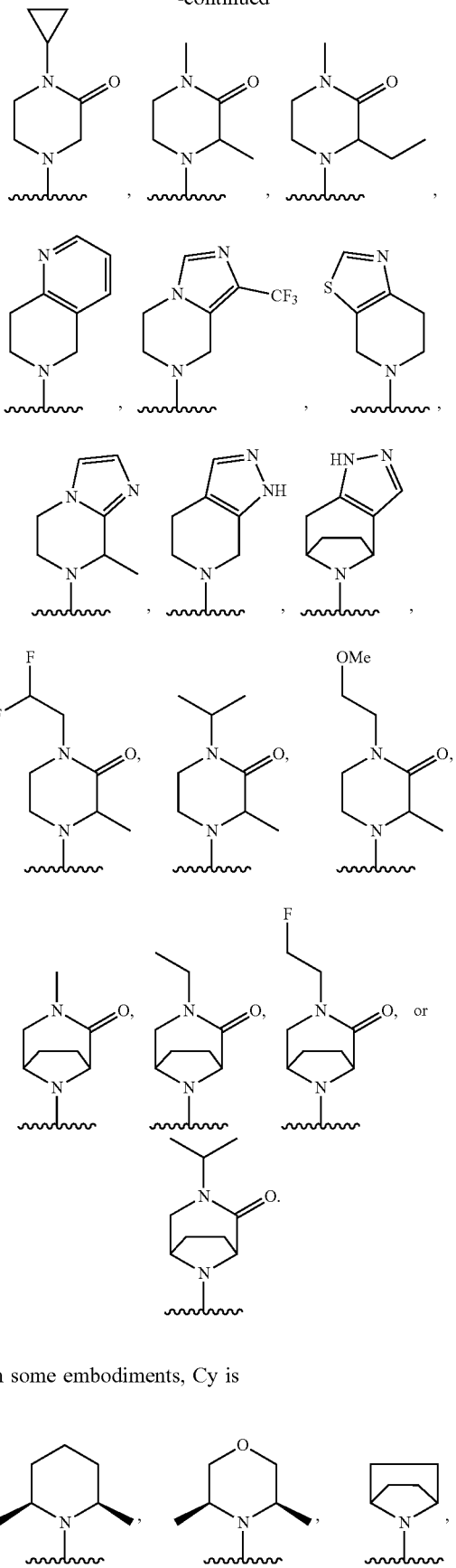
In some embodiments, Cy is
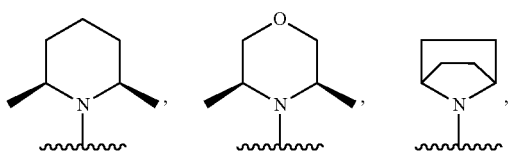

-continued
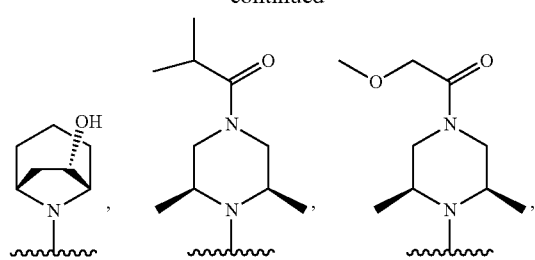
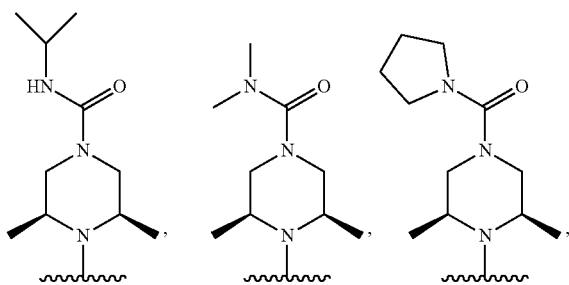
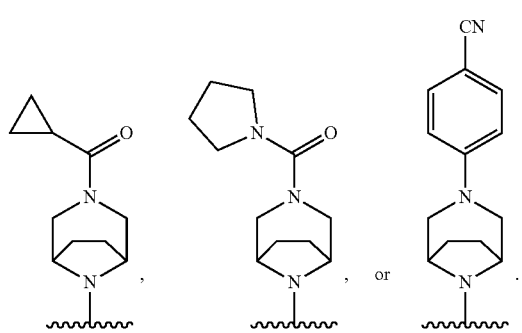
In some embodiments, Cy is
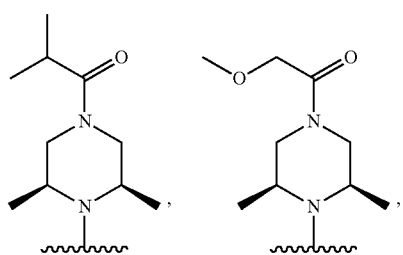
-continued
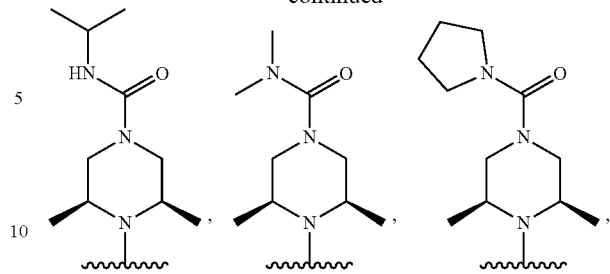
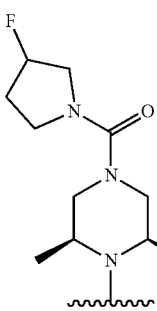, 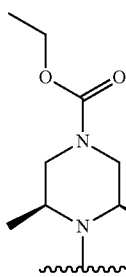, or
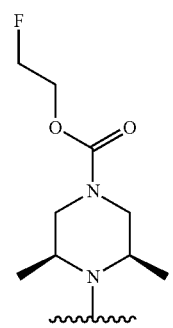.
In some embodiments, Cy is
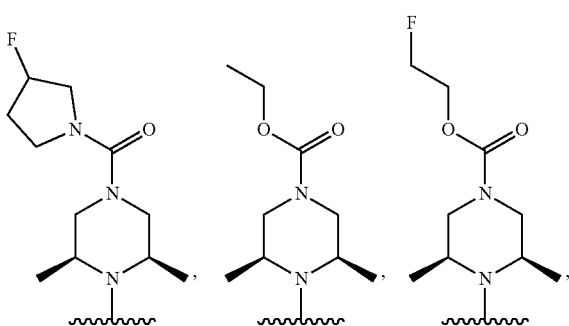
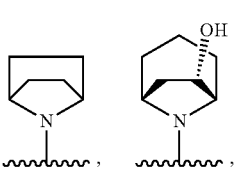, 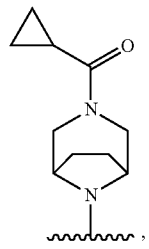.

In some embodiments, Cy is

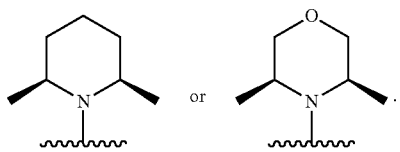

In some embodiments, provided herein is a compound of Formula II:

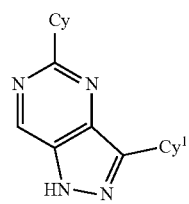

or a pharmaceutically acceptable salt thereof, wherein Cy and Cy¹ are as defined herein.

In some embodiments, provided herein is a compound of Formula III:

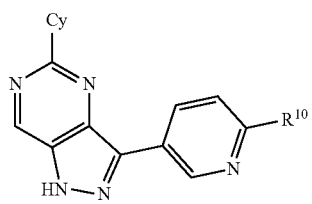

or a pharmaceutically acceptable salt thereof, wherein Cy and $R^{10}$ are as defined herein.

In some embodiments, provided herein is a compound of Formula IV:

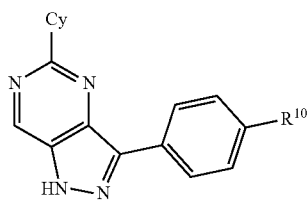

or a pharmaceutically acceptable salt thereof, wherein Cy and $R^{10}$ are as defined herein.

In some embodiments, provided herein is a compound of Formula V:

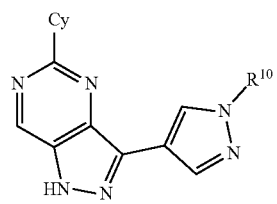

or a pharmaceutically acceptable salt thereof, wherein Cy and $R^{10}$ are as defined herein. In some embodiments, provided herein is a compound of Formula VI:

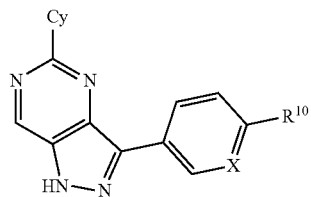

or a pharmaceutically acceptable salt thereof, wherein X is CH, $CR^{10}$ or N and Cy and $R^{10}$ are as defined herein.

In some embodiments, provided herein is a compound of Formula VII:

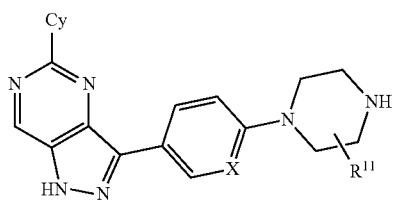

or a pharmaceutically acceptable salt thereof, wherein X is CH, $CR^{10}$ or N and Cy, $R^{10}$ and $R^{11}$ are as defined herein.

In some embodiments, provided herein is a compound of Formula I, or a pharmaceutically acceptable salt thereof, wherein:

$R^1$ is $Cy^1$;

$Cy^1$ is selected from $C_{6-10}$ aryl and 5-10 membered heteroaryl; wherein the 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{10}$;

Cy is 4-14 membered heterocycloalkyl; wherein the 4-14 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-14 membered heterocycloalkyl is optionally substituted by oxo to form a carbonyl group; wherein when the 4-14 membered heterocycloalkyl of Cy has a fused aromatic ring, the 4-14 membered heterocycloalkyl is directly attached to the pyrazolopyrimidine core structure through a ring-forming atom of the saturated or partially saturated ring; and wherein the 4-14 membered heterocycloalkyl is optionally substituted with 1, 2, 3, 4 or 5 substituents independently selected from $R^{20}$;

$R^2$ is H or D;

each $R^{10}$ is independently selected from $C_{1-6}$ alkyl, $C_{1-6}$ haloalkyl, 4-10 membered heterocycloalkyl, halo, D, CN, $OR^{a1}$, $C(O)R^{b1}$, $C(O)NR^{c1}R^{d1}$, $NR^{c1}R^{d1}$, $S(O)_2R^{b1}$, and $S(O)_2NR^{c1}R^{d1}$; wherein said $C_{1-6}$ alkyl and 4-10 membered heterocycloalkyl, are each optionally substituted with 1, 2, 3, or 4 substituents independently selected from $R^{11}$;

each $R^{11}$ is independently selected from $C_{1-6}$ alkyl, $C_{1-6}$ haloalkyl, halo, D, CN, $OR^{a3}$, and $NR^{c3}R^{d3}$;

each $R^{20}$ is independently selected from $C_{1-6}$ alkyl, $C_{1-6}$ haloalkyl, $C_{6-10}$ aryl, halo, D, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein said $C_{1-6}$ alkyl and $C_{6-10}$ aryl are each optionally substituted with 1, 2, 3, or 4 substituents independently selected from $R^{21}$;

each $R^{21}$ is independently selected from $C_{1-6}$ alkyl, $C_{1-6}$ haloalkyl, halo, D, CN, $OR^{a4}$ and $NR^{c4}R^{d4}$;

each $R^{a2}$, $R^{c2}$ and $R^{d2}$ is independently selected from H, $C_{1-6}$ alkyl and $C_{1-6}$ haloalkyl; wherein said $C_{1-6}$ alkyl is optionally substituted with 1 or 2 substituents independently selected from $R^{21}$;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{b2}$ is independently selected from $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl are each optionally substituted with 1, 2, 3, or 4 substituents independently selected from $R^{21}$; and each $R^{a4}$, $R^{c4}$ and $R^{d4}$ is independently selected from H, $C_{1-6}$ alkyl, and $C_{1-6}$ haloalkyl.

In some embodiments, provided herein is a compound of Formula I, or a pharmaceutically acceptable salt thereof, wherein:

$R^1$ is $Cy^1$;

$Cy^1$ is selected from phenyl and 5-6 membered heteroaryl; wherein the 5-6 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-6 membered heteroaryl is optionally substituted by oxo to form a carbonyl group; and wherein the phenyl and 5-6 membered heteroaryl are each optionally substituted with 1 or 2 substituents independently selected from $R^{10}$;

Cy is 4-8 membered heterocycloalkyl; wherein the 4-8 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-8 membered heterocycloalkyl is optionally substituted by oxo to form a carbonyl group; wherein when the 4-8 membered heterocycloalkyl of Cy has a fused aromatic ring, the 4-8 membered heterocycloalkyl is directly attached to the pyrazolopyrimidine core structure through a ring-forming atom of the saturated or partially saturated ring; and wherein the 4-8 membered heterocycloalkyl is optionally substituted with 1 or 2 substituents independently selected from $R^{20}$;

$R^2$ is H or D;

each $R^{10}$ is 4-10 membered heterocycloalkyl optionally substituted with 1 or 2 substituents independently selected from $R^{11}$;

each $R^{11}$ is $C_{1-6}$ alkyl;

each $R^{20}$ is independently selected from $C_{1-6}$ alkyl, $C_{6-10}$ aryl, $OR^{a2}$, $C(O)R^{b2}$, $C(O)NR^{c2}R^{d2}$, and $C(O)OR^{a2}$; wherein said $C_{1-6}$ alkyl and $C_{6-10}$ aryl are each optionally substituted with 1 or 2 substituents independently selected from $R^{21}$;

each $R^{21}$ is independently selected from halo, D, CN, and $OR^{a4}$;

each $R^{a2}$, $R^{c2}$ and $R^{d2}$ is independently selected from H, $C_{1-6}$ alkyl and $C_{1-6}$ haloalkyl; wherein said $C_{1-6}$ alkyl is optionally substituted with 1 or 2 substituents independently selected from $R^{21}$;

or any $R^{c2}$ and $R^{d2}$ attached to the same N atom, together with the N atom to which they are attached, form a 4-10 membered heterocycloalkyl group optionally substituted with 1 or 2 substituents independently selected from $R^{21}$;

each $R^{b2}$ is independently selected from $C_{1-6}$ alkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl are each optionally substituted with 1 or 2 substituents independently selected from $R^{21}$; and $R^{a4}$ is $C_{1-6}$ alkyl.

In some embodiments, provided herein is a compound of Formula I, or a pharmaceutically acceptable salt thereof, wherein:

$R^1$ is $Cy^1$;

$Cy^1$ is selected from $C_{5-6}$ cycloalkyl, 5-6 membered heterocycloalkyl, phenyl and 5-6 membered heteroaryl; wherein the 5-6 membered heterocycloalkyl and 5-6 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-6 membered heteroaryl and 5-6 membered heterocycloalkyl is optionally substituted by oxo to form a carbonyl group; and wherein the $C_{5-6}$ cycloalkyl, 5-6 membered heterocycloalkyl, phenyl and 5-6 membered heteroaryl are each optionally substituted with 1, 2, 3 or 4 substituents independently selected from $R^{10}$;

Cy is 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-12 membered heterocycloalkyl is optionally substituted by oxo to form a carbonyl group; wherein when the 4-12 membered heterocycloalkyl of Cy has a fused aromatic ring, the 4-12 membered heterocycloalkyl is directly attached to the pyrazolopyrimidine core structure through a ring-forming atom of the saturated or partially saturated ring; and wherein the 4-12 membered heterocycloalkyl is optionally substituted with 1, 2, 3, 4 or 5 substituents independently selected from $R^{20}$;

$R^2$ is selected from H, D, $C_{1-6}$ alkyl and $C_{1-6}$ haloalkyl;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, and $NR^{c1}R^{d1}$, $NR^{c1}C(O)R^{b1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1 or 2 substituents independently selected from $R^{11}$;

each $R^{11}$ is independently selected from $C_{1-6}$ alkyl, $C_{1-6}$ haloalkyl, halo, 4-10 membered heterocycloalkyl, 5-10 membered heteroaryl, CN, $OR^{a3}$, $C(O)NR^{c3}R^{d3}$, $C(O)R^{b3}$, and $NR^{c3}R^{d3}$, wherein said $C_{1-6}$ alkyl, 4-10 membered heterocycloalkyl, and 5-10 membered heteroaryl are each optionally substituted with 1 or 2 substituents independently selected from $R^{12}$;

each $R^{12}$ is independently selected from $C_{1-6}$ alkyl, $C_{1-6}$ haloalkyl, halo, CN, $OR^{a5}$, and $C(O)OR^{a5}$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, and $NR^{c2}C(O)OR^{a2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, and $OR^{a4}$;

each $R^{a1}$, $R^{c1}$ and $R^{d1}$ is independently selected from H, and $C_{1-6}$ alkyl;

or any $R^{c1}$ and $R^{d1}$ attached to the same N atom, together with the N atom to which they are attached, form a 4-10 membered heterocycloalkyl group optionally substituted with 1, 2, 3 or 4 substituents independently selected from $R^{11}$;

each $R^{b1}$ is independently selected from $C_{1-6}$ alkyl;

each $R^{a2}$, $R^{c2}$ and $R^{d2}$ is independently selected from H, $C_{1-6}$ alkyl and $C_{1-6}$ haloalkyl; wherein said $C_{1-6}$ alkyl is optionally substituted with 1 or 2 substituents independently selected from $R^{21}$;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{b2}$ is independently selected from $C_{1-6}$ alkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl are each optionally substituted with 1 or 2 substituents independently selected from $R^{21}$;

each $R^{a3}$, $R^{c3}$ and $R^{d3}$ is independently selected from H, $C_{1-6}$ alkyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^{12}$;

each $R^{a4}$ is independently selected from H, and $C_{1-6}$ alkyl; and each $R^{a5}$ is independently selected from H, and $C_{1-6}$ alkyl.

In some embodiments, provided herein is a compound of Formula I, or a pharmaceutically acceptable salt thereof, wherein:

$R^1$ is $Cy^1$;

$Cy^1$ is selected from phenyl and 5-6 membered heteroaryl; wherein the 5-6 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-6 membered heteroaryl is optionally substituted by oxo to form a carbonyl group; and wherein the phenyl and 5-6 membered heteroaryl are each optionally substituted with 1 or 2 substituents independently selected from $R^{10}$;

Cy is 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-12 membered heterocycloalkyl is optionally substituted by oxo to form a carbonyl group; wherein when the 4-12 membered heterocycloalkyl of Cy has a fused aromatic ring, the 4-12 membered heterocycloalkyl is directly attached to the pyrazolopyrimidine core structure through a ring-forming atom of the saturated or partially saturated ring; and wherein the 4-12 membered heterocycloalkyl is optionally substituted with 1, 2 or 3 substituents independently selected from $R^{20}$;

$R^2$ is H or D;

each $R^{10}$ is independently selected from $C_{1-6}$ alkyl, halo, $C_{3-10}$ cycloalkyl, 4-10 membered heterocycloalkyl, $C_{6-10}$ aryl, 5-10 membered heteroaryl, 4-10 membered heterocycloalkyl-$C_{1-3}$ alkylene, 5-6 membered heteroaryl-$C_{1-3}$ alkylene, and $C(O)NR^{c1}R^{d1}$; wherein said $C_{1-6}$ alkyl, $C_{3-10}$ cycloalkyl, 4-10 membered heterocycloalkyl, $C_{6-10}$ aryl, 5-10 membered heteroaryl, 4-10 membered heterocycloalkyl-$C_{1-3}$ alkylene, and 5-6 membered heteroaryl-$C_{1-3}$ alkylene are each optionally substituted with 1 or 2 substituents independently selected from $R^{11}$;

each $R^{11}$ is independently selected from $C_{1-6}$ alkyl, $C_{1-6}$ haloalkyl, halo, 4-10 membered heterocycloalkyl, 5-10 membered heteroaryl, CN, $OR^{a3}$, $C(O)NR^{c3}R^{d3}$, $C(O)R^{b3}$, and $NR^{c3}R^{d3}$, wherein said $C_{1-6}$ alkyl, 4-10 membered heterocycloalkyl, and 5-10 membered heteroaryl are each optionally substituted with 1 or 2 substituents independently selected from $R^{12}$;

each $R^{c1}$ and $R^{d1}$ is independently selected from H, and $C_{1-6}$ alkyl;

each $R^{a3}$, $R^{b3}$, $R^{c3}$ and $R^{d3}$ is independently selected from H, and $C_{1-6}$ alkyl;

each $R^{12}$ is independently selected from $C_{1-6}$ alkyl, C(O) OH, and OH;

each $R^{20}$ is independently selected from $C_{1-6}$ alkyl, $C_{1-6}$ haloalkyl, $C_{3-10}$ cycloalkyl, $C_{6-10}$ aryl, halo, CN, $OR^{a2}$, $C(O)R^{b2}$, $C(O)NR^{c2}R^{d2}$, and $C(O)OR^{a2}$; wherein said $C_{1-6}$ alkyl, $C_{3-10}$ cycloalkyl, and $C_{6-10}$ aryl are each optionally substituted with 1 or 2 substituents independently selected from $R^{21}$;

each $R^{a2}$, $R^{c2}$ and $R^{d2}$ is independently selected from H, $C_{1-6}$ alkyl and $C_{1-6}$ haloalkyl; wherein said $C_{1-6}$ alkyl is optionally substituted with 1 or 2 substituents independently selected from $R^{21}$;

or any $R^{c2}$ and $R^{d2}$ attached to the same N atom, together with the N atom to which they are attached, form a 4-10 membered heterocycloalkyl group optionally substituted with 1 or 2 substituents independently selected from $R^{21}$;

each $R^{b2}$ is independently selected from $C_{1-6}$ alkyl, $C_{3-10}$ cycloalkyl, and 4-10 membered heterocycloalkyl; wherein said Cue alkyl, $C_{3-10}$ cycloalkyl, and 4-10 membered heterocycloalkyl are each optionally substituted with 1 or 2 substituents independently selected from $R^{21}$;

each $R^{21}$ is independently selected from halo, D, CN, and $OR^{a4}$; and each $R^{a4}$ is Cue alkyl.

In some embodiments, provided herein is a compound of Formula II, or a pharmaceutically acceptable salt thereof, wherein:

Cy¹ is pyrazolyl, phenyl or pyridinyl, wherein the pyrazolyl, phenyl or pyridinyl are each optionally substituted with 1 or 2 substituents independently selected from $R^{10}$;

Cy is piperidinyl, morpholinyl, azabicyclo[2.2.1]heptanyl, azabicyclo[3.2.1]octanyl, piperazinyl, diazabicyclo[3.2.1]octanyl, 1,4,6,7-tetrahydro-5H-imidazo[4,5-c]pyridin-5-yl, 5,6-dihydroimidazo[1,2-a]pyrazin-7(8H)-yl, 2,5-diazabicyclo[2.2.2]octan-2-yl, 2,5-diazabicyclo[2.2.1]heptan-2-yl, 3-oxopiperazinyl, 5,6,7,8-tetrahydro-1,6-naphthyridin-6-yl, 5,6,7,8-tetrahydroimidazo[1,5-a]pyrazin-7-yl, 4,5,6,7-tetrahydrothiazolo[5,4-c]pyridin-5-yl, 1,4,5,7-tetrahydro-6H-pyrazolo[3,4-c]pyridin-6-yl, 1,4,5,6,7,8-hexahydro-5,8-epiminocyclohepta[c]pyrazol-9-yl, or 2-oxo-3,8-diazabicyclo[3.2.1]octan-8-yl, each optionally substituted with 1, 2, 3, or 4 substituents independently selected from $R^{20}$;

each $R^{10}$ is methyl, ethyl, isopropyl, cyclopropyl, cyclobutyl, fluoro, 4-methylpiperazin-1-yl, 4-ethylpiperazin-1-yl, methylcarbamoyl, 1-methylpyrrolidin-3-yl, 1-(2-hydroxyethyl)pyrrolidin-3-yl, 4-(1-hydroxypropan-2-ylpiperazin-1-yl, 4-(tetrahydro-2H-pyran-4-yl)piperazin-1-yl, 4-(2-carboxypropan-2-yl)piperazin-1-yl, 2-methylmorpholino, 3,4-dimethylpiperazin-1-yl, 4-hydroxypiperidin-1-yl, 7-hydroxyhexahydropyrrolo[1,2-a]pyrazin-2(1H)-yl, 2-methoxyethyl, tetrahydro-2H-pyran-4-yl, 4-hydroxycyclohexyl, 1-(dimethylcarbamoyl)piperidin-4-yl, 1-isobutyrylpiperidin-4-yl, 2-morpholinoethyl, 4-methylpiperazin-1-yl, pyridin-4-ylmethyl, 2,2,2-trifluoroethyl, pyridin-4-yl, pyridin-3-yl, 4-cyanophenyl, 2-methylpyridin-4-yl, 6-(dimethylamino)pyridin-3-yl, 5-cyanopyridin-3-yl, 6-cyanopyridin-3-yl, imidazo[1,2-a]pyridin-6-yl, 4-cyano-3-methylphenyl, 4-cyano-2-methylphenyl, 4-cyano-3-fluorophenyl, 4-(methylcarbamoyl)phenyl, 4-(dimethylcarbamoyl)phenyl, 3-fluoro-4-(methylcarbamoyl)phenyl, 3-(6-(methylcarbamoyl)pyridin-3-yl, 3-methylpiperazin-1-yl or 4-methylpiperazin-1-yl; and each $R^{20}$ is independently selected from methyl, ethyl, isopropyl, 2-fluoroethyl, 2,2-difluoroethyl, cyclopropyl, trifluoromethyl, OH, 4-cyanophenyl, pyrrolidine-1-carbonyl, 3-fluoropyrrolidine-1-carbonyl, cyclopropanecarbonyl, isobutyryl, 2-methoxyacetyl, isopropylcarbamoyl, dimethylcarbamoyl, methoxycarbonyl, ethoxycarbonyl, (2-fluoroethoxy)carbonyl.

In some embodiments, provided herein is a compound of Formula II, or a pharmaceutically acceptable salt thereof, wherein:

Cy¹ is 6-(3-methylpiperazin-1-yl)pyridin-3-yl, 4-(4-methylpiperazin-1-ylphenyl, 3-fluoro-4-(4-methylpiperazin-1-ylphenyl, 6-(4-methylpiperazin-1-yl)pyridin-3-yl, 4-(4-ethylpiperazin-1-yl)-3-methylphenyl, 4-(methylcarbamoyl) phenyl, 4-(l-methylpyrrolidin-3-yl)phenyl, 4-(1-(2-hydroxyethyl)pyrrolidin-3-yl)phenyl, 4-(4-(1-hydroxypropan-2-yl)piperazin-1-ylphenyl, 4-(4-(tetrahydro-2H-pyran-4-yl)piperazin-1-ylphenyl, 4-(4-(2-carboxypropan-2-yl)piperazin-1-ylphenyl, 6-(2-methylmorpholino)pyridin-3-yl, 6-(3,4-dimethylpiperazin-1-ylpyridin-3-yl, 4-(4-hydroxypiperidin-1-yl)phenyl, 4-(7-hydroxyhexahydropyrrolo[1,2-a]pyrazin-2(1H)-yl)phenyl, 1-(2-methoxyethyl)-1H-pyrazol-4-yl, 1-(tetrahydro-2H-pyran-4-yl)-1H-pyrazol-4-yl, 1-(4-hydroxycyclohexyl)-1H-pyrazol-4-yl, 1-(1-(dimethylcarbamoyl)piperidin-4-yl)-1H-pyrazol-4-yl, 1-(1-isobutyrylpiperidin-4-yl)-1H-pyrazol-4-yl, 1-(2-morpholinoethyl)-1H-pyrazol-4-yl, 6-(4-methylpiperazin-1-yl)pyridin-3-yl, 1-(pyridin-4-ylmethyl)-1H-pyrazol-4-yl, 1-methyl-1H-pyrazol-4-yl, 1-ethyl-1H-pyrazol-4-yl, 1-isopropyl-1H-pyrazol-4-yl, 1-cyclobutyl-1H-pyrazol-4-yl, 1-cyclopropyl-1H-pyrazol-4-yl, 1-(2,2,2-trifluoroethyl)-1H-pyrazol-4-yl, 1-(pyridin-4-yl)-1H-pyrazol-4-yl, 1-(pyridin-3-yl)-1H-pyrazol-4-yl, 1-(4-cyanophenyl)-1H-pyrazol-4-yl, 1-(2-methyl pyridin-4-yl)-1H-pyrazol-4-yl, 1-(6-(dimethylamino)pyridin-3-yl)-1H-pyrazol-4-yl, 1-(5-cyanopyridin-3-yl)-1H-pyrazol-4-yl, 1-(6-cyanopyridin-3-yl)-1H-pyrazol-4-yl, 1-(imidazo)[1,2-a]pyridin-6-yl)-1H-pyrazol-4-yl, 1-(4-cyano-3-methylphenyl)-1H-pyrazol-4-yl, 1-(4-cyano-2-methylphenyl)-1H-pyrazol-4-yl, 1-(4-cyano-3-fluorophenyl)-1H-pyrazol-4-yl, 1-(4-(methylcarbamoyl)phenyl)-1H-pyrazol-4-yl, 1-(4-(dimethylcarbamoylphenyl)-1H-pyrazol-4-yl, 1-(3-fluoro-4-(methylcarbamoylphenyl)-1H-pyrazol-4-yl, 1-(6-(methylcarbamoyl)pyridin-3-yl)-1H-pyrazol-4-yl; and Cy is

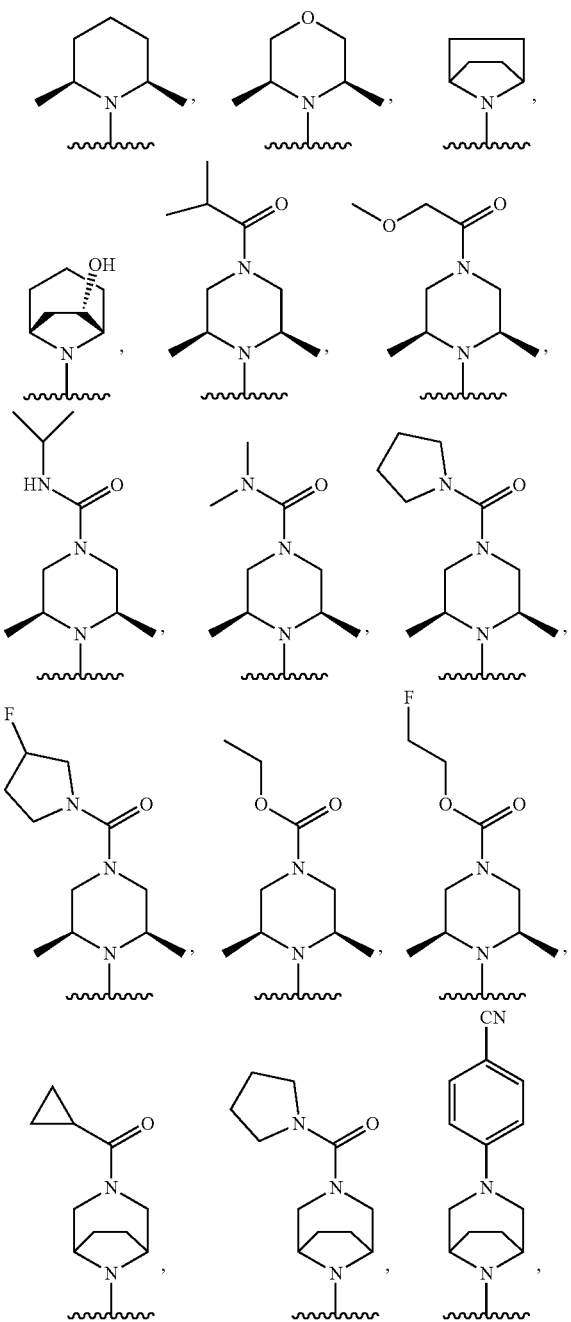

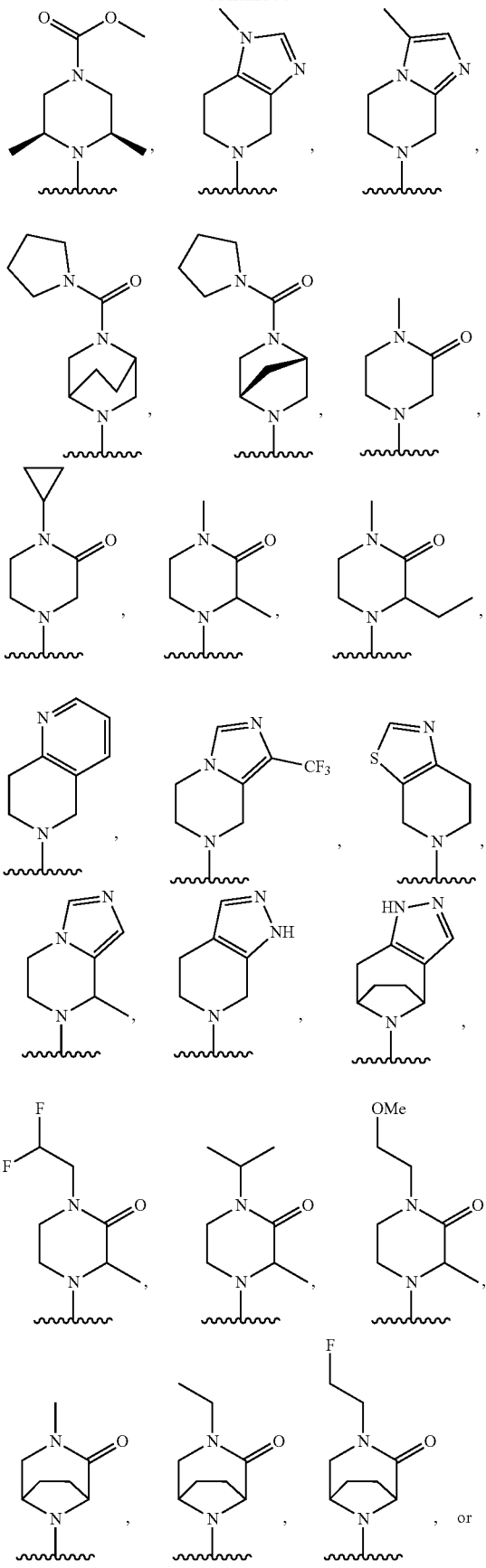

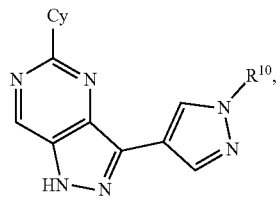

In some embodiments, provided herein is a compound of Formula V $$V$$

or a pharmaceutically acceptable salt thereof, wherein:

Cy is 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-12 membered heterocycloalkyl is optionally substituted by oxo to form a carbonyl group; wherein when the 4-12 membered heterocycloalkyl of Cy has a fused aromatic ring, the 4-12 membered heterocycloalkyl is directly attached to the pyrazolopyrimidine core structure through a ring-forming atom of the saturated or partially saturated ring; and wherein the 4-12 membered heterocycloalkyl is optionally substituted with 1, 2 or 3 substituents independently selected from $R^{20}$;

$R^{10}$ is selected from $C_{1-6}$ alkyl, halo, $C_{3-10}$ cycloalkyl, 4-10 membered heterocycloalkyl, $C_{6-10}$ aryl, 5-10 membered heteroaryl, 4-10 membered heterocycloalkyl-$C_{1-3}$ alkylene, 5-6 membered heteroaryl-$C_{1-3}$ alkylene, and C(O)NR$^{c1}$R$^{d1}$; wherein said $C_{1-6}$ alkyl, $C_{3-10}$ cycloalkyl, 4-10 membered heterocycloalkyl, $C_{6-10}$ aryl, 5-10 membered heteroaryl, 4-10 membered heterocycloalkyl-$C_{1-3}$ alkylene, and 5-6 membered heteroaryl-$C_{1-3}$ alkylene are each optionally substituted with 1 or 2 substituents independently selected from $R^{11}$;

each $R^{11}$ is independently selected from $C_{1-6}$ alkyl, $C_{1-6}$ haloalkyl, halo, 4-10 membered heterocycloalkyl, 5-10 membered heteroaryl, CN, OR$^{a3}$, C(O)NR$^{c3}$R$^{d3}$, C(O)R$^{b3}$, and NR$^{c3}$R$^{d3}$, wherein said $C_{1-6}$ alkyl, 4-10 membered heterocycloalkyl, and 5-10 membered heteroaryl are each optionally substituted with 1 or 2 substituents independently selected from $R^{12}$;

each R$^{c1}$ and R$^{d1}$ is independently selected from H, and $C_{1-6}$ alkyl;

each R$^{a3}$, R$^{b3}$, R$^{c3}$ and R$^{d3}$ is independently selected from H, and $C_{1-6}$ alkyl;

each $R^{12}$ is independently selected from $C_{1-6}$ alkyl, C(O)OH, and OH;

each $R^{20}$ is independently selected from $C_{1-6}$ alkyl, $C_{1-6}$ haloalkyl, $C_{3-10}$ cycloalkyl, $C_{6-10}$ aryl, halo, CN, OR$^{a2}$, C(O)R$^{b2}$, C(O)NR$^{c2}$R$^{d2}$, and C(O)OR$^{a2}$; wherein said $C_{1-6}$ alkyl, $C_{3-10}$ cycloalkyl, and $C_{6-10}$ aryl are each optionally substituted with 1 or 2 substituents independently selected from $R^{21}$;

each $R^{a2}$, $R^{c2}$ and $R^{d2}$ is independently selected from H, $C_{1-6}$ alkyl and $C_{1-6}$ haloalkyl; wherein said $C_{1-6}$ alkyl is optionally substituted with 1 or 2 substituents independently selected from $R^{21}$;

or any $R^{c2}$ and $R^{d2}$ attached to the same N atom, together with the N atom to which they are attached, form a 4-10 membered heterocycloalkyl group optionally substituted with 1 or 2 substituents independently selected from $R^{21}$;

each $R^{b2}$ is independently selected from $C_{1-6}$ alkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl are each optionally substituted with 1 or 2 substituents independently selected from $R^{21}$;

each $R^{21}$ is independently selected from halo, D, CN, and $OR^{a4}$; and each $R^{a4}$ is $C_{1-6}$ alkyl.

In some embodiments, provided herein is a compound of Formula V, or a pharmaceutically acceptable salt thereof, wherein:

Cy is 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-12 membered heterocycloalkyl is optionally substituted by oxo to form a carbonyl group; wherein when the 4-12 membered heterocycloalkyl of Cy has a fused aromatic ring, the 4-12 membered heterocycloalkyl is directly attached to the pyrazolopyrimidine core structure through a ring-forming atom of the saturated or partially saturated ring; and wherein the 4-12 membered heterocycloalkyl is optionally substituted with 1, 2 or 3 substituents independently selected from $R^{20}$; $R^{10}$ is methyl;

each $R^{20}$ is independently selected from $C_{1-6}$ alkyl, $C_{1-6}$ haloalkyl, $C_{3-10}$ cycloalkyl, $C_{6-10}$ aryl, halo, CN, $OR^{a2}$, $C(O)R^{b2}$, $C(O)NR^{c2}R^{d2}$, and $C(O)OR^{a2}$; wherein said $C_{1-6}$ alkyl, $C_{3-10}$ cycloalkyl, and $C_{6-10}$ aryl are each optionally substituted with 1 or 2 substituents independently selected from $R^{21}$;

each $R^{a2}$, $R^{c2}$ and $R^{d2}$ is independently selected from H, $C_{1-6}$ alkyl and $C_{1-6}$ haloalkyl; wherein said $C_{1-6}$ alkyl is optionally substituted with 1 or 2 substituents independently selected from $R^{21}$;

or any $R^{c2}$ and $R^{d2}$ attached to the same N atom, together with the N atom to which they are attached, form a 4-10 membered heterocycloalkyl group optionally substituted with 1 or 2 substituents independently selected from $R^{21}$;

each $R^{b2}$ is independently selected from $C_{1-6}$ alkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl are each optionally substituted with 1 or 2 substituents independently selected from $R^{21}$;

each $R^{21}$ is independently selected from halo, D, CN, and $OR^{a4}$; and each $R^{a4}$ is $C_{1-6}$ alkyl.

In some embodiments, provided herein is a compound of Formula VI, or a pharmaceutically acceptable salt thereof wherein:

X is selected from CH, CF, $CCH_3$ and N;

Cy is 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-12 membered heterocycloalkyl is optionally substituted by oxo to form a carbonyl group; wherein when the 4-12 membered heterocycloalkyl of Cy has a fused aromatic ring, the 4-12 membered heterocycloalkyl is directly attached to the pyrazolopyrimidine core structure through a ring-forming atom of the saturated or partially saturated ring; and wherein the 4-12 membered heterocycloalkyl is optionally substituted with 1, 2 or 3 substituents independently selected from $R^{20}$; $R^{10}$ is selected from 4-10 membered heterocycloalkyl, wherein said 4-10 membered heterocycloalkyl is optionally substituted with 1 or 2 substituents independently selected from $R^{11}$;

each $R^{11}$ is independently selected from $C_{1-6}$ alkyl, and 4-10 membered heterocycloalkyl, $C_{1-6}$ alkyl, and 4-10 membered heterocycloalkyl are each optionally substituted with 1 or 2 substituents independently selected from $R^{12}$;

each $R^{12}$ is independently selected from $C_{1-6}$ alkyl, C(O) OH, and OH;

each $R^{20}$ is independently selected from $C_{1-6}$ alkyl, $C_{1-6}$ haloalkyl, $C_{3-10}$ cycloalkyl, $C_{6-10}$ aryl, halo, CN, $OR^{a2}$, $C(O)R^{b2}$, $C(O)NR^{c2}R^{d2}$, and $C(O)OR^{a2}$; wherein said $C_{1-6}$ alkyl, $C_{3-10}$ cycloalkyl, and $C_{6-10}$ aryl are each optionally substituted with 1 or 2 substituents independently selected from $R^{21}$;

each $R^{a2}$, $R^{c2}$ and $R^{d2}$ is independently selected from H, $C_{1-6}$ alkyl and $C_{1-6}$ haloalkyl; wherein said $C_{1-6}$ alkyl is optionally substituted with 1 or 2 substituents independently selected from $R^{21}$;

or any $R^{c2}$ and $R^{d2}$ attached to the same N atom, together with the N atom to which they are attached, form a 4-10 membered heterocycloalkyl group optionally substituted with 1 or 2 substituents independently selected from $R^{21}$;

each $R^{b2}$ is independently selected from $C_{1-6}$ alkyl, $C_{3-10}$ cycloalkyl, and 4-10 membered heterocycloalkyl; wherein said Cue alkyl, $C_{3-10}$ cycloalkyl, and 4-10 membered heterocycloalkyl are each optionally substituted with 1 or 2 substituents independently selected from $R^{21}$;

each $R^{21}$ is independently selected from halo, D, CN, and $OR^{a4}$; and each $R^{a4}$ is Cue alkyl.

In some embodiments, provided herein is a compound of Formula VII, or a pharmaceutically acceptable salt thereof

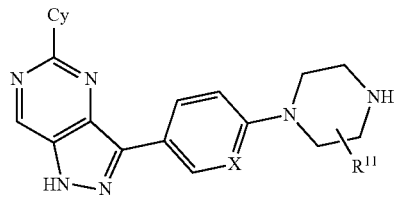

VII wherein:

X is selected from CH, CF, $CCH_3$ and N;

Cy is 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-12 membered heterocycloalkyl is optionally substituted by oxo to form a carbonyl group; wherein when the 4-12 membered heterocycloalkyl of Cy has a fused aromatic ring, the 4-12 membered heterocycloalkyl is directly attached to the pyrazolopyrimidine core structure through a ring-forming atom of the saturated or partially saturated ring; and wherein the 4-12 membered heterocycloalkyl is optionally substituted with 1, 2 or 3 substituents independently selected from $R^{20}$; $R^{11}$ is selected from $C_{1-6}$ alkyl, and 4-10 membered heterocycloalkyl, C$_{1-6}$ alkyl, and 4-10 membered heterocycloalkyl are each optionally substituted with 1 or 2 substituents independently selected from R$^{12}$;

each R$^{12}$ is independently selected from C$_{1-6}$ alkyl, C(O)OH, and OH;

each R$^{20}$ is independently selected from C$_{1-6}$ alkyl, C$_{1-6}$ haloalkyl, C$_{3-10}$ cycloalkyl, C$_{6-10}$ aryl, halo, CN, OR$^{a2}$, C(O)R$^{b2}$, C(O)NR$^{c2}$R$^{d2}$, and C(O)OR$^{a2}$; wherein said C$_{1-6}$ alkyl, C$_{3-10}$ cycloalkyl, and C$_{6-10}$ aryl are each optionally substituted with 1 or 2 substituents independently selected from R$^{21}$;

each R$^{a2}$, R$^{c2}$ and R$^{d2}$ is independently selected from H, C$_{1-6}$ alkyl and C$_{1-6}$ haloalkyl; wherein said C$_{1-6}$ alkyl is optionally substituted with 1 or 2 substituents independently selected from R$^{21}$;

or any R$^{c2}$ and R$^{d2}$ attached to the same N atom, together with the N atom to which they are attached, form a 4-10 membered heterocycloalkyl group optionally substituted with 1 or 2 substituents independently selected from R$^{21}$;

each R$^{b2}$ is independently selected from C$_{1-6}$ alkyl, C$_{3-10}$ cycloalkyl, and 4-10 membered heterocycloalkyl; wherein said C$_{1-6}$ alkyl, C$_{3-10}$ cycloalkyl, and 4-10 membered heterocycloalkyl are each optionally substituted with 1 or 2 substituents independently selected from R$^{21}$;

each R$^{21}$ is independently selected from halo, D, CN, and OR$^{a4}$; and each R$^{a4}$ is C$_{1-6}$ alkyl.

In some embodiments, provided herein is a compound selected from:

5-((2R,6S)-2,6-dimethylpiperidin-1-yl)-3-(6-((R)-3-methylpiperazin-1-yl)pyridin-3-yl)-1H-pyrazolo[4,3-d]pyrimidine;

(3R,5S)-3,5-dimethyl-4-(3-(6-((R)-3-methylpiperazin-1-yl)pyridin-3-yl)-1H-pyrazolo[4,3-d]pyrimidin-5-yl)morpholine;

5-(7-azabicyclo[2.2.1]heptan-7-yl)-3-(6-((R)-3-methylpiperazin-1-yl)pyridin-3-yl)-1H-pyrazolo[4,3-d]pyrimidine;

(1R,5S,6S)-8-(3-(6-((R)-3-methylpiperazin-1-yl)pyridin-3-yl)-1H-pyrazolo[4,3-d]pyrimidin-5-yl)-8-azabicyclo[3.2.1]octan-6-ol;

1-((3R,5S)-3,5-dimethyl-4-(3-(6-((R)-3-methylpiperazin-1-yl)pyridin-3-yl)-1H-pyrazolo[4,3-d]pyrimidin-5-yl)piperazin-1-yl)-2-methylpropan-1-one;

1-((3R,5S)-3,5-dimethyl-4-(3-(6-((R)-3-methylpiperazin-1-yl)pyridin-3-yl)-1H-pyrazolo[4,3-d]pyrimidin-5-yl)piperazin-1-yl)-2-methoxyethan-1-one;

(3R,5S)—N-isopropyl-3,5-dimethyl-4-(3-(6-((R)-3-methylpiperazin-1-yl)pyridin-3-yl)-1H-pyrazolo[4,3-d]pyrimidin-5-yl)piperazine-1-carboxamide;

(3R,5S)—N,N,3,5-tetramethyl-4-(3-(6-((R)-3-methylpiperazin-1-yl)pyridin-3-yl)-1H-pyrazolo[4,3-d]pyrimidin-5-yl)piperazine-1-carboxamide;

((3R,5S)-3,5-dimethyl-4-(3-(6-((R)-3-methylpiperazin-1-yl)pyridin-3-yl)-1H-pyrazolo[4,3-d]pyrimidin-5-yl)piperazin-1-yl)(pyrrolidin-1-yl)methanone;

((3R,5S)-3,5-dimethyl-4-(3-(6-((R)-3-methylpiperazin-1-yl)pyridin-3-yl)-1H-pyrazolo[4,3-d]pyrimidin-5-yl)piperazin-1-yl)(3-fluoropyrrolidin-1-yl)methanone;

Ethyl (3R,5S)-3,5-dimethyl-4-(3-(6-((R)-3-methylpiperazin-1-yl)pyridin-3-yl)-1H-pyrazolo[4,3-d]pyrimidin-5-yl)piperazine-1-carboxylate;

2-Fluoroethyl (3R,5S)-3,5-dimethyl-4-(3-(6-((R)-3-methylpiperazin-1-yl)pyridin-3-yl)-1H-pyrazolo[4,3-d]pyrimidin-5-yl)piperazine-1-carboxylate;

Cyclopropyl((1R,5S)-8-(3-(6-((R)-3-methylpiperazin-1-yl)pyridin-3-yl)-1H-pyrazolo[4,3-d]pyrimidin-5-yl)-3,8-diazabicyclo[3.2.1]octan-3-yl)methanone;

((1R,5S)-8-(3-(6-((R)-3-methylpiperazin-1-yl)pyridin-3-yl)-1H-pyrazolo[4,3-d]pyrimidin-5-yl)-3,8-diazabicyclo[3.2.1]octan-3-yl)(pyrrolidin-1-yl)methanone;

4-((1R,5S)-8-(3-(6-((R)-3-methylpiperazin-1-yl)pyridin-3-yl)-1H-pyrazolo[4,3-d]pyrimidin-5-yl)-3,8-diazabicyclo[3.2.1]octan-3-yl)benzonitrile; and 5-((2R,6S)-2,6-dimethylpiperidin-1-yl)-3-(4-(4-methylpiperazin-1-yl)phenyl)-1H-pyrazolo[4,3-d]pyrimidine, or a pharmaceutically acceptable salt thereof.

In some embodiments, provided herein is a compound selected from:

Methyl (3R,5S)-3,5-dimethyl-4-(3-(6-((R)-3-methylpiperazin-1-yl)pyridin-3-yl)-1H-pyrazolo[4,3-d]pyrimidin-5-yl)piperazine-1-carboxylate;

(R)-5-(1-Methyl-1,4,6,7-tetrahydro-5H-imidazo[4,5-c]pyridin-5-yl)-3-(6-(3-methylpiperazin-1-yl)pyridin-3-yl)-1H-pyrazolo[4,3-d]pyrimidine;

(R)-5-(3-Methyl-5,6-dihydroimidazo[1,2-a]pyrazin-7(8H)-yl)-3-(6-(3-methylpiperazin-1-yl)pyridin-3-yl)-1H-pyrazolo[4,3-d]pyrimidine;

(5-(3-(6-((R)-3-Methylpiperazin-1-yl)pyridin-3-yl)-1H-pyrazolo[4,3-d]pyrimidin-5-yl)-2,5-diazabicyclo[2.2.2]octan-2-yl)(pyrrolidin-1-yl)methanone;

((1S,4S)-5-(3-(6-((R)-3-Methylpiperazin-1-yl)pyridin-3-yl)-1H-pyrazolo[4,3-d]pyrimidin-5-yl)-2,5-diazabicyclo[2.2.1]heptan-2-yl)(pyrrolidin-1-yl)methanone Methyl (3R,5S)-3,5-dimethyl-4-(3-(4-(4-methylpiperazin-1-yl)phenyl)-1H-pyrazolo[4,3-d]pyrimidin-5-yl)piperazine-1-carboxylate;

Methyl (3R,5S)-4-(3-(3-fluoro-4-(4-methylpiperazin-1-yl)phenyl)-1H-pyrazolo[4,3-d]pyrimidin-5-yl)-3,5-dimethylpiperazine-1-carboxylate;

Methyl (3R,5S)-3,5-dimethyl-4-(3-(6-(4-methylpiperazin-1-yl)pyridin-3-yl)-1H-pyrazolo[4,3-d]pyrimidin-5-yl)piperazine-1-carboxylate;

Methyl (3R,5S)-4-(3-(4-(4-ethylpiperazin-1-yl)-3-methylphenyl)-1H-pyrazolo[4,3-d]pyrimidin-5-yl)-3,5-dimethylpiperazine-1-carboxylate;

Methyl (3R,5S)-3,5-dimethyl-4-(3-(4-(methylcarbamoyl)phenyl)-1H-pyrazolo[4,3-d]pyrimidin-5-yl)piperazine-1-carboxylate;

Methyl (3R,5S)-3,5-dimethyl-4-(3-(4-(1-methylpyrrolidin-3-yl)phenyl)-1H-pyrazolo[4,3-d]pyrimidin-5-yl)piperazine-1-carboxylate;

Methyl (3R,5S)-4-(3-(4-(1-(2-hydroxyethyl)pyrrolidin-3-yl)phenyl)-1H-pyrazolo[4,3-d]pyrimidin-5-yl)-3,5-dimethylpiperazine-1-carboxylate;

Methyl (3R,5S)-4-(3-(4-(4-(1-hydroxypropan-2-yl)piperazin-1-yl)phenyl)-1H-pyrazolo[4,3-d]pyrimidin-5-yl)-3,5-dimethylpiperazine-1-carboxylate;

Methyl (3R,5S)-3,5-dimethyl-4-(3-(4-(4-(tetrahydro-2H-pyran-4-yl)piperazin-1-yl)phenyl)-1H-pyrazolo[4,3-d]pyrimidin-5-yl)piperazine-1-carboxylate;

2-(4-(4-(5-((2R,6S)-4-(Methoxycarbonyl)-2,6-dimethylpiperazin-1-yl)-1H-pyrazolo[4,3-d]pyrimidin-3-yl)phenyl)piperazin-1-yl)-2-methylpropanoic acid;

Methyl (3R,5S)-3,5-dimethyl-4-(3-(6-((R)-2-methylmorpholino)pyridin-3-yl)-1H-pyrazolo[4,3-d]pyrimidin-5-yl)piperazine-1-carboxylate;

Methyl (3R,5S)-4-(3-(6-((R)-3,4-dimethylpiperazin-1-yl)pyridin-3-yl)-1H-pyrazolo[4,3-d]pyrimidin-5-yl)-3,5-dimethylpiperazine-1-carboxylate;

Methyl (3R,5S)-4-(3-(4-(4-hydroxypiperidin-1-yl)phenyl)-1H-pyrazolo[4,3-d]pyrimidin-5-yl)-3,5-dimethylpiperazine-1-carboxylate;

Methyl (3R,5S)-4-(3-(4-((7S,8aR)-7-hydroxyhexahydropyrrolo[1,2-a]pyrazin-2(1H)-yl)phenyl)-1H-pyrazolo[4,3-d]pyrimidin-5-yl)-3,5-dimethylpiperazine-1-carboxylate;
1-Methyl-4-(3-(1-methyl-1H-pyrazol-4-yl)-1H-pyrazolo[4,3-d]pyrimidin-5-yl)piperazin-2-one;
1-Cyclopropyl-4-(3-(1-methyl-1H-pyrazol-4-yl)-1H-pyrazolo[4,3-d]pyrimidin-5-yl)piperazin-2-one;
1,3-Dimethyl-4-(3-(1-methyl-1H-pyrazol-4-yl)-1H-pyrazolo[4,3-d]pyrimidin-5-yl)piperazin-2-one;
3-Ethyl-1-methyl-4-(3-(1-methyl-1H-pyrazol-4-yl)-1H-pyrazolo[4,3-d]pyrimidin-5-yl)piperazin-2-one;
6-(3-(1-Methyl-1H-pyrazol-4-yl)-1H-pyrazolo[4,3-d]pyrimidin-5-yl)-5,6,7,8-tetrahydro-1,6-naphthyridine;
3-(1-Methyl-1H-pyrazol-4-yl)-5-(1-(trifluoromethyl)-5,6-dihydroimidazo[1,5-a]pyrazin-7(8H)-yl)-1H-pyrazolo[4,3-d]pyrimidine;
5-(3-(1-Methyl-1H-pyrazol-4-yl)-1H-pyrazolo[4,3-d]pyrimidin-5-yl)-4,5,6,7-tetrahydrothiazolo[5,4-c]pyridine;
3-(1-Methyl-1H-pyrazol-4-yl)-5-(8-methyl-5,6-dihydroimidazo[1,2-a]pyrazin-7(8H)-yl)-1H-pyrazolo[4,3-d]pyrimidine;
3-(1-Methyl-1H-pyrazol-4-yl)-5-(1,4,5,7-tetrahydro-6H-pyrazolo[3,4-c]pyridin-6-yl)-1H-pyrazolo[4,3-d]pyrimidine;
9-(3-(1-Methyl-1H-pyrazol-4-yl)-1H-pyrazolo[4,3-d]pyrimidin-5-yl)-1,4,5,6,7,8-hexahydro-4,7-epiminocyclohepta[c]pyrazole;
1-(2,2-Difluoroethyl)-3-methyl-4-(3-(1-methyl-1H-pyrazol-4-yl)-1H-pyrazolo[4,3-d]pyrimidin-5-yl)piperazin-2-one;
1-Isopropyl-3-methyl-4-(3-(1-methyl-1H-pyrazol-4-yl)-1H-pyrazolo[4,3-d]pyrimidin-5-yl)piperazin-2-one;
1-(2-Methoxyethyl)-3-methyl-4-(3-(1-methyl-1H-pyrazol-4-yl)-1H-pyrazolo[4,3-d]pyrimidin-5-yl)piperazin-2-one;
3-Methyl-8-(3-(1-methyl-1H-pyrazol-4-yl)-1H-pyrazolo[4,3-d]pyrimidin-5-yl)-3,8-diazabicyclo[3.2.1]octan-2-one;
3-Ethyl-8-(3-(1-methyl-1H-pyrazol-4-yl)-1H-pyrazolo[4,3-d]pyrimidin-5-yl)-3,8-diazabicyclo[3.2.1]octan-2-one;
3-(2-Fluoroethyl)-8-(3-(1-methyl-1H-pyrazol-4-yl)-1H-pyrazolo[4,3-d]pyrimidin-5-yl)-3,8-diazabicyclo[3.2.1]octan-2-one;
3-Isopropyl-8-(3-(1-methyl-1H-pyrazol-4-yl)-1H-pyrazolo[4,3-d]pyrimidin-5-yl)-3,8-diazabicyclo[3.2.1]octan-2-one;
8-(3-(1-(2-Methoxyethyl)-1H-pyrazol-4-yl)-1H-pyrazolo[4,3-d]pyrimidin-5-yl)-3-methyl-3,8-diazabicyclo[3.2.1]octan-2-one;
3-Methyl-8-(3-(1-(tetrahydro-2H-pyran-4-yl)-1H-pyrazol-4-yl)-1H-pyrazolo[4,3-d]pyrimidin-5-yl)-3,8-diazabicyclo[3.2.1]octan-2-one;
8-(3-(1-((1r,4S)-4-Hydroxycyclohexyl)-1H-pyrazol-4-yl)-1H-pyrazolo[4,3-d]pyrimidin-5-yl)-3-methyl-3,8-diazabicyclo[3.2.1]octan-2-one;
N,N-Dimethyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)piperidine-1-carboxamide;
8-(3-(1-(1-Isobutyrylpiperidin-4-yl)-1H-pyrazol-4-yl)-1H-pyrazolo[4,3-d]pyrimidin-5-yl)-3-methyl-3,8-diazabicyclo[3.2.1]octan-2-one;
3-Methyl-8-(3-(1-(2-morpholinoethyl)-1H-pyrazol-4-yl)-1H-pyrazolo[4,3-d]pyrimidin-5-yl)-3,8-diazabicyclo[3.2.1]octan-2-one;
3-Methyl-8-(3-(1-(pyridin-4-ylmethyl)-1H-pyrazol-4-yl)-1H-pyrazolo[4,3-d]pyrimidin-5-yl)-3,8-diazabicyclo[3.2.1]octan-2-one;
3-Methyl-8-(3-(6-(4-methylpiperazin-1-yl)pyridin-3-yl)-1H-pyrazolo[4,3-d]pyrimidin-5-yl)-3,8-diazabicyclo[3.2.1]octan-2-one;
8-(3-(1-Ethyl-1H-pyrazol-4-yl)-1H-pyrazolo[4,3-d]pyrimidin-5-yl)-3-methyl-3,8-diazabicyclo[3.2.1]octan-2-one;
8-(3-(1-Isopropyl-1H-pyrazol-4-yl)-1H-pyrazolo[4,3-d]pyrimidin-5-yl)-3-methyl-3,8-diazabicyclo[3.2.1]octan-2-one;
8-(3-(1-Cyclobutyl-1H-pyrazol-4-yl)-1H-pyrazolo[4,3-d]pyrimidin-5-yl)-3-methyl-3,8-diazabicyclo[3.2.1]octan-2-one;
8-(3-(1-Cyclopropyl-1H-pyrazol-4-yl)-1H-pyrazolo[4,3-d]pyrimidin-5-yl)-3-methyl-3,8-diazabicyclo[3.2.1]octan-2-one;
3-Methyl-8-(3-(1-(2,2,2-trifluoroethyl)-1H-pyrazol-4-yl)-1H-pyrazolo[4,3-d]pyrimidin-5-yl)-3,8-diazabicyclo[3.2.1]octan-2-one;
3-Methyl-8-(3-(1-(pyridin-4-yl)-1H-pyrazol-4-yl)-1H-pyrazolo[4,3-d]pyrimidin-5-yl)-3,8-diazabicyclo[3.2.1]octan-2-one;
3-Methyl-8-(3-(1-(pyridin-3-yl)-1H-pyrazol-4-yl)-1H-pyrazolo[4,3-d]pyrimidin-5-yl)-3,8-diazabicyclo[3.2.1]octan-2-one;
4-(4-(5-(3-Methyl-2-oxo-3,8-diazabicyclo[3.2.1]octan-8-yl)-1H-pyrazolo[4,3-d]pyrimidin-3-yl)-1H-pyrazol-1-yl)benzonitrile;
3-Methyl-8-(3-(1-(2-methylpyridin-4-yl)-1H-pyrazol-4-yl)-1H-pyrazolo[4,3-d]pyrimidin-5-yl)-3,8-diazabicyclo[3.2.1]octan-2-one;
8-(3-(1-(6-(Dimethylamino)pyridin-3-yl)-1H-pyrazol-4-yl)-1H-pyrazolo[4,3-d]pyrimidin-5-yl)-3-methyl-3,8-diazabicyclo[3.2.1]octan-2-one;
5-(4-(5-(3-Methyl-2-oxo-3,8-diazabicyclo[3.2.1]octan-8-yl)-1H-pyrazolo[4,3-d]pyrimidin-3-yl)-1H-pyrazol-1-yl)nicotinonitrile;
5-(4-(5-(3-Methyl-2-oxo-3,8-diazabicyclo[3.2.1]octan-8-yl)-1H-pyrazolo[4,3-d]pyrimidin-3-yl)-1H-pyrazol-1-yl)picolinonitrile;
8-(3-(1-(Imidazo[1,2-a]pyridin-6-yl)-1H-pyrazol-4-yl)-1H-pyrazolo[4,3-d]pyrimidin-5-yl)-3-methyl-3,8-diazabicyclo[3.2.1]octan-2-one;
2-Methyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)benzonitrile;
3-Methyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)benzonitrile;
2-Fluoro-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)benzonitrile;
N,N-Dimethyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)benzamide;
N-Methyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)benzamide;
2-Fluoro-N-methyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)benzamide; and
N-Methyl-5-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)picolinamide;

or a pharmaceutically acceptable salt thereof.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$-includes both —NR (CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, vec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The term "amino" refers to a group of formula —NH$_2$.

The term "carbonyl", employed alone or in combination with other terms, refers to a —C(=O)— group, which also may be written as C(O).

As used herein, the term "carbamyl" refers to a group of formula —C(O)NH$_2$.

As used herein, the term "carboxy" refers to a group of formula —C(O)OH.

The term "cyano" or "nitrile" refers to a group of formula-C≡N, which also may be written as —CN.

As used herein, the term "cyano-$C_{1-3}$ alkyl" refers to a group of formula —($C_{1-3}$ alkylene)-CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CH_2F$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an TV-oxide group. In some embodiments, heterocyclic groups may be optionally substituted by 1 or 2 oxo (=O) substituents.

The term "sulfido" refers to a sulfur atom as a divalent substituent, forming a thiocarbonyl group (C=S) when attached to carbon.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$. As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkylaminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkylaminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkylaminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen, nitrogen and phosphorous. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-12 ring atoms including carbon atoms and 1, 2, 3 or 4 heteroatom ring members independently selected from nitrogen, sulfur and oxygen. In some embodiments, the heteroaryl has 5-11 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, isoxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, isoindolyl, benzothiophenyl, benzofuranyl, benzisoxazolyl, imidazo[1,2-b]thiazolyl, purinyl, pyrazolopyrimidinyl (including pyrazolo[1,5-a]pyrimidine and pyrazolo[4,3-d]pyrimidinyl), imidazopyrindinyl (i.e. imidazo[1,2-a]pyridinyl) and the like. In some embodiments, the heteroaryl group is pyridone (e.g., 2-pyridone). Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl. Exemplary six-membered ring heteroaryls are pyridyl, pyrazinyl, pyrimidinyl, triazinyl, isoindolyl, and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic.

In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-14 ring members, 4-12 ring members, 4-10 ring members, 4-8 ring members, 4-7 ring members, 4-6 ring members, 6-11 ring members, 5-12 ring members, 5-8 ring members or any ranges therebetween. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or $S(O)_2$, A-oxide etc) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include azetidinyl, azepanyl, dihydrobenzofuranyl, dihydrofuranyl, dihydropyranyl, morpholino, 3-oxa-9-azaspiro[5.5]undecanyl, 1-oxa-8-azaspiro[4.5]decanyl, piperidinyl, piperazinyl, oxopiperazinyl, pyranyl, pyrrolidinyl, quinuclidinyl, tetrahydrofuranyl, tetrahydropyranyl, 1,2,3,4-tetrahydroquinolinyl, 1,2,3,4-tetrahydroisoquinolinyl, 1,2,3,4-tetrahydronaphthyl, 2,3-dihydro-1H-inden-5-yl, isoindolinyl, tropanyl, and thiomorpholino. Additional Examples of heterocycloalkyl groups include azabicyclo[2.2.1]heptanyl, azabicyclo[3.2.1]octanyl, diazabicyclo[3.2.1]octanyl, 1,4,6,7-tetrahydro-5H-imidazo[4,5-c]pyridin-5-yl, 5,6-dihydroimidazo[1,2-a]pyrazin-7(8H)-yl, 2,5-diazabicyclo[2.2.2]octan-2-yl, 2,5-diazabicyclo[2.2.1]heptan-2-yl, 3-oxopiperazinyl, 5,6,7,8-tetrahydro-1,6-naphthyridin-6-yl, 5,6,7,8-tetrahydroimidazo[1,5-a]pyrazin-7-yl, 4,5,6,7-tetrahydrothiazolo[5,4-c]pyridin-5-yl, 1,4,5,7-tetrahydro-6H-pyrazolo[3,4-c]pyridin-6-yl, 1,4,5,6,7,8-hexahydro-5,8-epiminocyclohepta[c]pyrazol-9-yl, and 2-oxo-3,8-diazabicyclo[3.2.1]octan-8-yl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as δ-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexyl ethyl amine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated. Compounds with two chiral centers can, for example, have (R,R), (R,S), (S,R) or (S,S) configurations.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term, "compound," as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19 and in Stahl et al., Handbook of Pharmaceutical Salts: Properties, Selection, and Use, (Wiley, 2002). In some embodiments, the compounds described herein include the N-oxide forms.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6th Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared, e.g., using a process as illustrated in the schemes below.

Compounds of Formula (Ia) (compounds of Formula (I) wherein $R^2$ is H) with a variety of substitution at positions $R^1$ and Cy such as those described herein can be prepared, using a process as illustrated in Scheme 1. Iodination of 5-chloro-1H-pyrazolo[4,3-d]pyrimidine (1-1) with one of the iodination agents, such as iodine or NIS, forms compounds of Formula (1-2). The NH group of the pyrazole ring of the compounds of Formula (1-2) is protected with a suitable protecting group (e.g., Boc or SEM) to form compounds of Formula (1-3). The iodo substituent in the compounds of Formula (1-3) can be converted into $R^1$ via a number of different cross-coupling reactions, including Suzuki, Sonogashira, Negishi, Buchwald-Hartwig amination, Cu-catalyzed amination and others, to give the compounds of Formula (1-4). The chloro substituent in the compounds of Formula (1-4) can be further converted into Cy via a nucleophilic aromatic substitution (e.g., SNAT) or a number of different cross-coupling reactions, including Buchwald-Hartwig amination, Suzuki, Stille, Negishi, Cu-catalyzed amination and others, to give the compounds of Formula (1-5). Finally, deprotection of the protecting group, e.g. under acidic conditions, such as treatment with HCl or TFA, and/or under basic conditions such as treatment with aqueous ammonium hydroxide results in the formation of the desired compounds of Formula (Ia). Alternatively, compounds of Formula (1-5) can be prepared from compounds of Formula (1-3) by first conducting a nucleophilic aromatic substitution (e.g., SxAr) or a cross-coupling reaction, including Buchwald-Hartwig amination, Suzuki, Cu-catalyzed amination and others to generate compounds of Formula (1-6), followed by a number of different cross-coupling reactions, including Suzuki, Sonogashira, Negishi, Buchwald-Hartwig amination, Cu-catalyzed amination and others, to convert the iodo substituent into $R^1$.

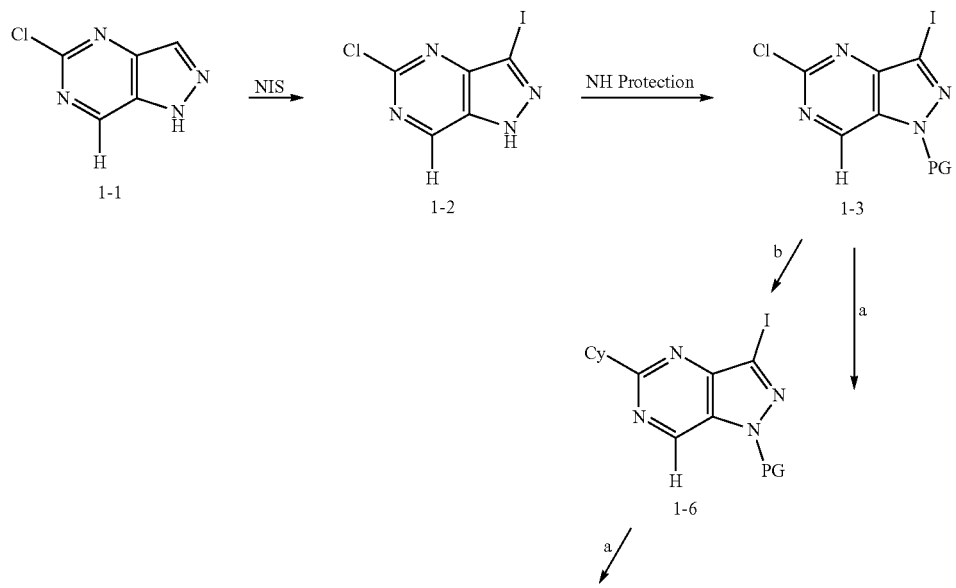

Scheme 1

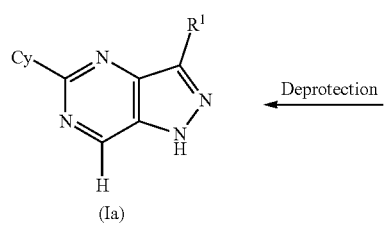 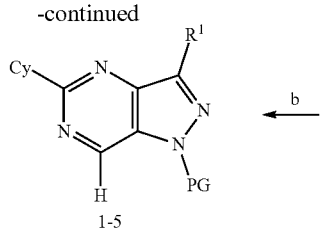 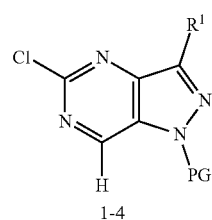

(Ia)            1-5            1-4

(a) Suzuki, Stille, Negishi or Cu cat. amination
(b) S$_N$Ar reaction, Buchwald-Hartwig, Suzuki, Stille, Negishi or Cu cat. amination Compounds of Formula (2-2) (compounds of Formula (I) wherein $R^2$ is H and $Cy^1$ is phenyl or pyridinyl with X is CH or N) with a variety of substitution at positions Cy and $R^{10}$ such as those described herein can be prepared, using a process as illustrated in Scheme 2. Compounds of Formula (1-6) can be converted to compounds of Formula (2-1) via a number of different cross-coupling reactions with a suitable coupling reagent in the presence of a suitable palladium catalyst and a suitable base, including Suzuki, Hiyama, Negishi, Stille cross-coupling reactions and others. Deprotection of the protecting group, e.g. under acidic conditions, such as treatment with HCl or TFA, and/or under basic conditions such as treatment with aqueous ammonium hydroxide results in the formation of the desired compounds of Formula (2-2).

Scheme 2

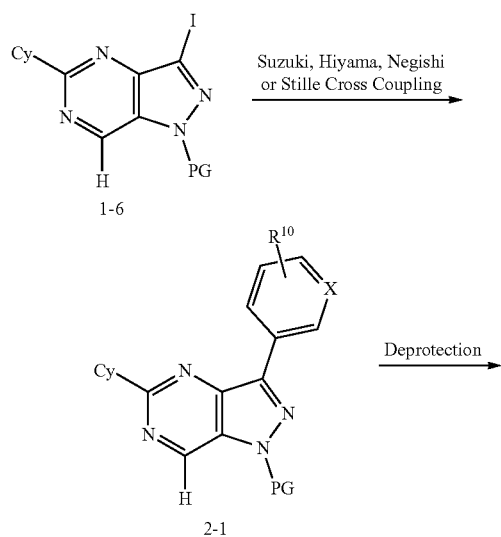

2-2

Compounds of Formula (3-3) (compounds of Formula (I) wherein $R^2$ is H and $Cy^1$ is pyrazol) with a variety of substitution at positions Cy and $R^{10}$ such as those described herein can be prepared, using a process as illustrated in Scheme 3. Compounds of Formula (1-6) can be converted to compounds of Formula (3-1) via a number of different cross-coupling reactions with a suitable coupling reagent in the presence of a suitable palladium catalyst and a suitable base, including Suzuki, Hiyama, Negishi, Stille cross-coupling reactions and others. Compounds of Formula (3-1) can be converted to compounds of Formula (3-2) via a substitution reaction or a cross-coupling reaction, including Buchwald-Hartwig amination, Cu-catalyzed amination and others. Alternatively, compounds of Formula (3-2) can be prepared directly from compounds of Formula (1-6) by a number of different cross-coupling reactions with a suitable coupling reagent in the presence of a suitable palladium catalyst and a suitable base, including Suzuki, Hiyama, Negishi, Stille cross-coupling reactions and others. Deprotection of the protecting group, e.g. under acidic conditions, such as treatment with HCl or TFA, and/or under basic conditions such as treatment with aqueous ammonium hydroxide results in the formation of the desired compounds of Formula (3-3).

Scheme 3

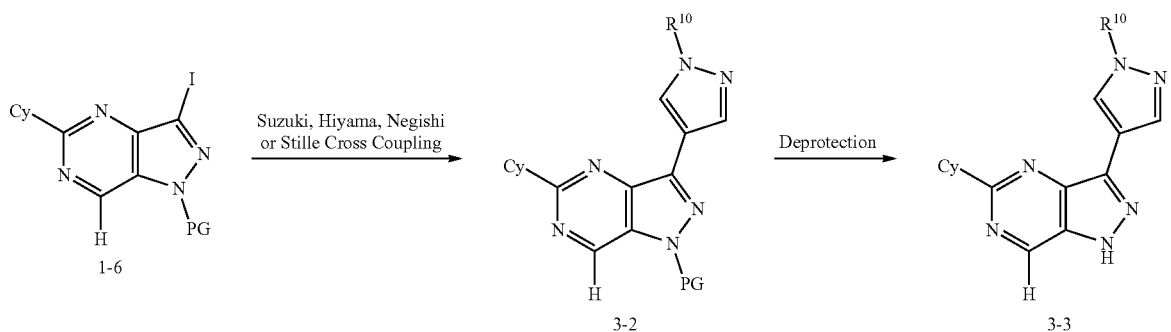

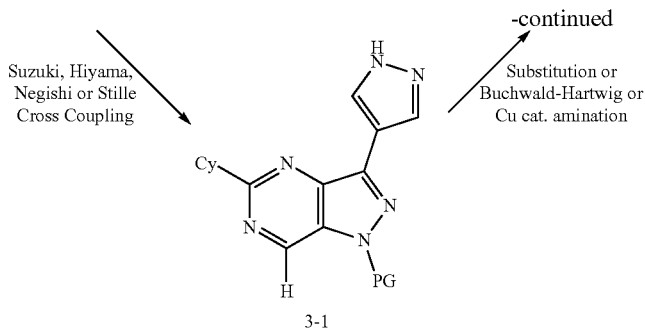

3-1

Compounds of Formula (4-4) (compounds of Formula (I) wherein $R^2$ is H and Cy is substituted piperazine) with a variety of substitution at positions $R^1$ and $R^{20}$ such as those described herein can be prepared, using a process as illustrated in Scheme 4. Compounds of Formula (1-4) can be converted to compounds of Formula (4-1) via a nucleophilic aromatic substitution (e.g., SNAr) or a number of different cross-coupling reactions, including Buchwald-Hartwig amination, Cu-catalyzed amination and others. Selective deprotection of protecting group $PG^2$ (e.g., benzyl, Boc or SEM) generates compounds of Formula (4-2). Alternatively, compounds of Formula (4-2) can be prepared directly from compounds of Formula (1-4) by a nucleophilic aromatic substitution (e.g., $S_NAr$) or a number of different cross-coupling reactions, including Buchwald-Hartwig amination, Cu-catalyzed amination and others. Compounds of Formula (4-2) can be converted to compounds of Formula (4-3) via a substitution reaction or a cross-coupling reaction, including Buchwald-Hartwig amination, Cu-catalyzed amination and others. Deprotection of the protecting group, e.g. under acidic conditions, such as treatment with HCl or TFA, and/or under basic conditions such as treatment with aqueous ammonium hydroxide results in the formation of the desired compounds of Formula (4-4).

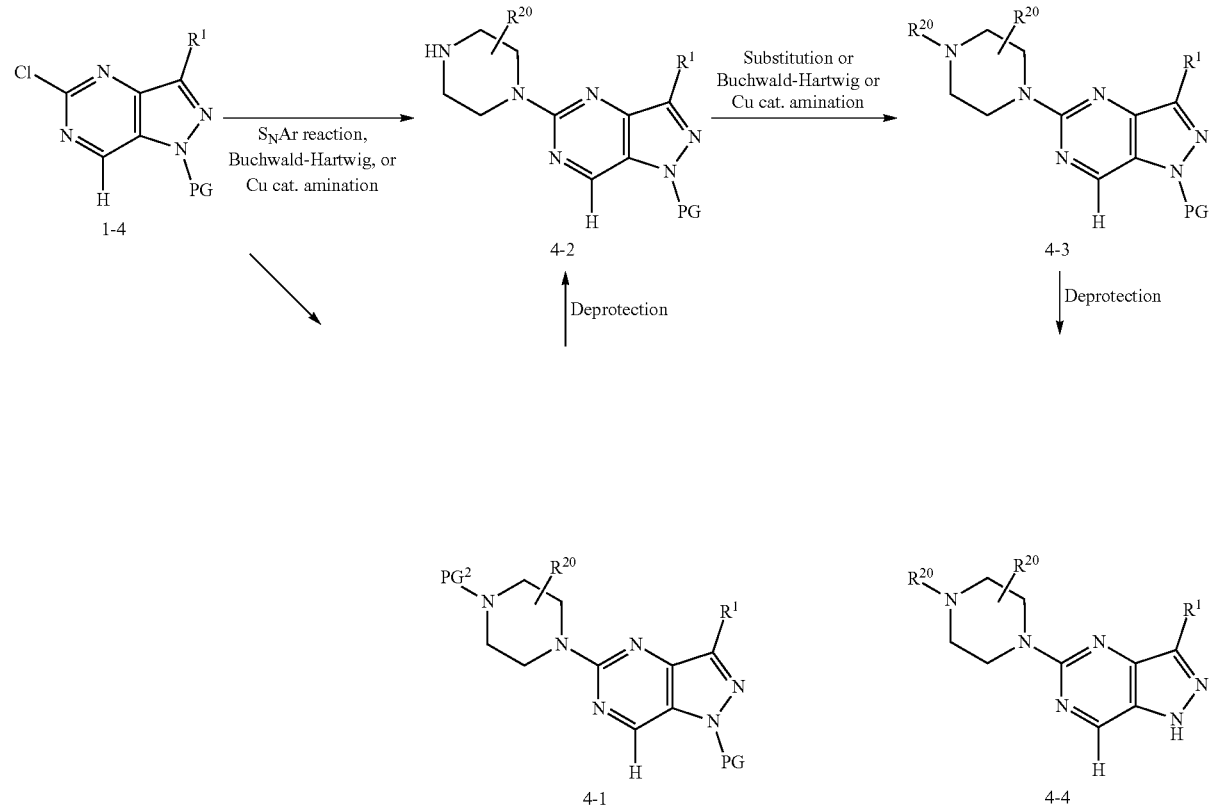

Scheme 4

Compounds of Formula (5-3) (compounds of Formula (I) wherein $R^2$ is H and Cy is 3,8-diazabicyclo[3.2.1]octan-2-one) with a variety of substitution at positions $R^1$ and $R^{20}$ such as those described herein can be prepared, using a process as illustrated in Scheme 5. Compounds of Formula (1-4) can be converted to compounds of Formula (5-1) via a nucleophilic aromatic substitution (e.g., SNAT) or a number of different cross-coupling reactions, including Buchwald-Hartwig amination, Cu-catalyzed amination and others. Compounds of Formula (5-1) can be converted to compounds of Formula (5-2) via a substitution reaction or a cross-coupling reaction, including Buchwald-Hartwig amination, Cu-catalyzed amination and others. Deprotection of the protecting group, e.g. under acidic conditions, such as treatment with HCl or TFA, and/or under basic conditions such as treatment with aqueous ammonium hydroxide results in the formation of the desired compounds of Formula (5-3).

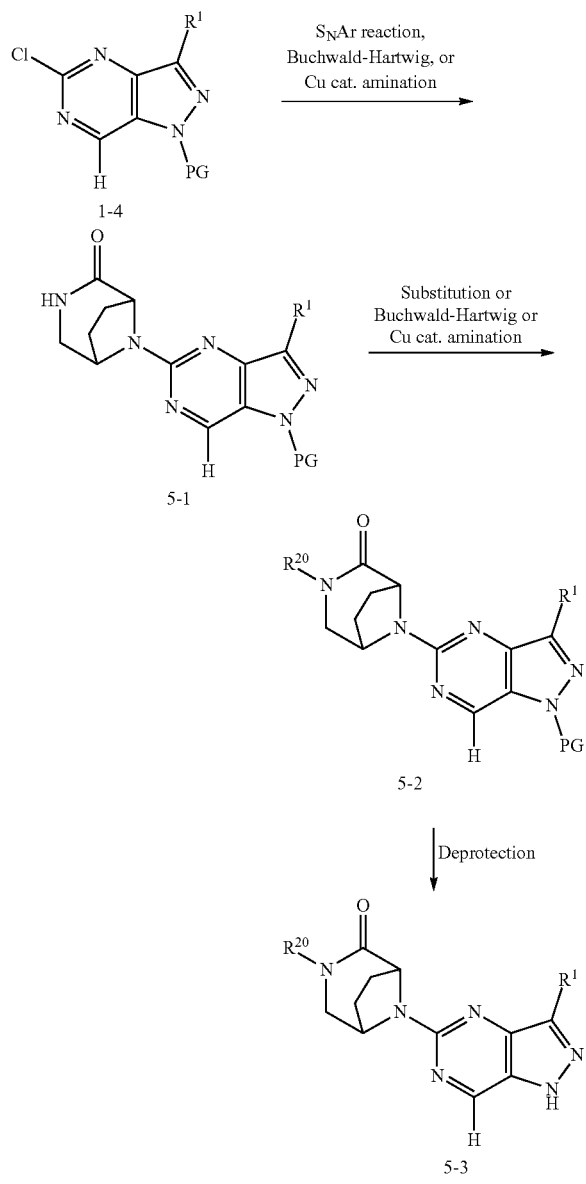

Methods of Use

The present disclosure provides methods of modulating (e.g., inhibiting) ALK2 activity, said method comprising administering to a patient a compound provided herein, or a pharmaceutically acceptable salt thereof. The compounds of the present disclosure can be used alone, in combination with other agents or therapies or as an adjuvant or neoadjuvant for the treatment of diseases or disorders, including cancers. For the uses described herein, any of the compounds of the disclosure, including any of the embodiments thereof, may be used.

In myelofibrosis (MF), a significant proportion of patients develop anemia and become dependent on frequent red blood cell (RBC) transfusions (Tefferi, A. et al. Mayo Clinic Proceedings 2012 87, 25-33). Elevated serum hepcidin levels in patients with MF have been shown to be associated with hemoglobin (Hb) levels, increased requirement for RBC transfusions and reduced survival (Pardanani, A. et al. American Journal of Hematology 2013, 88, 312-316). BMP signaling plays a central role in driving hepcidin transcriptional induction by activating SMAD signaling. In anemia mouse model, the liver-specific deletion of either ALK2 or ALK3 can block the induction of hepcidin production and iron overload (Steinbicker, A. U., et al. Blood 2011, 118, 4224-4230). Therefore, ALK2 inhibition could be useful in combination with ruxolitinib in the treatment of MF patients as the hepcidin-mediated FPN1 internalization and degradation may not require the action of JAK2 (Ross, S. L., et al. Cell Metabolism 2012, 15, 905-917). The ALK2 inhibition may block the negative effect of hepcidin on iron metabolism and improve the anemia in MF patients (Asshoff, M. et al. Blood 2017, 129, 1823-1830).

Fibrodysplasia ossificans progressiva (FOP) is a human rare genetic bone disease and the patients were characterized by extraskeletal bone formation through endochondral ossification (Yu, P B., et al. Nature Medicine 2008, 14, 1363-1369; Fukuda, T. et al. Journal of Biological Chemistry 2009 284, 7149-7156). 95% of FOP patients harbor point mutations in ACVR1/ALK2 and The responsive mutation for classic FOP is 617G>A (R206H) in the intracellular glycine and serine-rich (GS) domain of ALK2 (Shen, Q. et al. Journal of Clinical Investigation 2009, 119, 3462-3472). ALK2 mutations in atypical FOP patients have also been found in other amino acids of the GS domain or protein kinase domain (Fukuda, T. et al. Biochemical and BiophysicalResearch Communications 2008, 377, 905-909). The different ALK2 mutants have been shown to activate BMP signaling without exogenous BMP ligands constitutively and these ALK2 mutants can transmit much stronger BMP signaling upon ligand stimulation (Van Dinther, M. et al. Journal of Bone and Mineral Research 2010, 25, 1208-1215).

Activating mutations in ALK2 have also been identified in diffuse intrapontine gliomas (DIPG), which are highly aggressive glial neoplasms of the ventral pons in the pediatric population. ALK2 was reported as one of the most recurrently mutated gene in DIPG. ALK2 was found to carry nonsynonymous heterozygous somatic mutations in 46 of 195 (24%) cases at five specific residues. Patients with ALK2 mutations were predominantly female (approximately 2:1) and had a younger age of onset (approximately 5 years) and longer overall survival time (approximately 15 months) compared with wild-type IDPG. These ALK2 mutants are highly specific to DIPG and the ALK2 inhibitor LDN-19318917 results in significant inhibition of those ALK2 mutant DIPG cell viability (Taylor, K. R. et al. *Nature Genetics* 2014, 46, 457-461; Buczkowicz, P. et al. Nature Genetics 2014, 46, 451-456).

A method of treating a disease or disorder associated with inhibition of ALK2 activity can include administering to a patient in need thereof a therapeutically effective amount of a compound provided herein, or a pharmaceutically acceptable salt thereof. In some embodiments, the disease or disorder is cancer. Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

Compounds of the present disclosure can inhibit the activity of the FGFR enzyme. For example, compounds of the present disclosure can be used to inhibit activity of an FGFR enzyme in a cell or in an individual or patient in need of inhibition of the enzyme by administering an inhibiting amount of one or more compounds of the present disclosure to the cell, individual, or patient.

As FGFR inhibitors, the compounds of the present disclosure are useful in the treatment of various diseases associated with abnormal expression or activity of the FGFR enzyme or FGFR ligands. Compounds which inhibit FGFR will be useful in providing a means of preventing the growth or inducing apoptosis in tumors, particularly by inhibiting angiogenesis. It is therefore anticipated that compounds of the present disclosure will prove useful in treating or preventing proliferative disorders such as cancers. In particular, tumors with activating mutants of receptor tyrosine kinases or upregulation of receptor tyrosine kinases may be particularly sensitive to the inhibitors.

In certain embodiments, the disclosure provides a method for treating a FGFR-mediated disorder in a patient in need thereof, comprising the step of administering to said patient a compound according to the invention, or a pharmaceutically acceptable composition thereof.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, triple-negative breast cancer, colon cancer and lung cancer (e.g. non-small cell lung cancer and small cell lung cancer). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET), myelodysplasia syndrome (MDS), T-cell acute lymphoblastic lymphoma (T-ALL), multiple myeloma, cutaneous T-cell lymphoma, Waldenstrom's Macroglobulinemia, hairy cell lymphoma, chronic myelogenic lymphoma and Burkitt's lymphoma. Exemplary hematological cancers can also include 8p11 myeloproliferative syndrome. As used herein, the term "8p11 myeloproliferative syndrome" is meant to refer to myeloid/lymphoid neoplasms associated with eosinophilia and abnormalities of FGFR1.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma. Exemplary sarcomas also include lymphosarcoma and leiomyosarcoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma. Exemplary lung cancers also include pavicellular and non-pavicellular carcinoma, bronchial adenoma and pleuropulmonary blastoma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (exocrine pancreatic carcinoma, ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer. Exemplary gastrointestinal cancers also include gall bladder cancer and anal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma). Exemplary genitourinary tract cancers also include renal cell carcinoma and urothelial carcinoma.

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors.

Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease. Exemplary nervous system cancers also include neuro-ectodermal tumors and pineal tumors.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma). Exemplary gynecological cancers also include cancers of the breast (ductal carcinoma, lobular carcinoma, breast sarcoma, triple-negative breast cancer, HER2-positive breast cancer, inflammatory breast cancer, papillary carcinoma), Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids.

In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers. Exemplary head and neck cancers also include tumors of the eye, tumors of the lips and mouth and squamous head and neck cancer.

The compounds of the present disclosure can also be useful in the inhibition of tumor metastases.

In some embodiments, compounds described herein can be used to treat Alzheimer's disease, HIV, or tuberculosis.

In some embodiments, the compounds provided herein may be used to treat tumors producing PGE2 (e.g. Cox-2 overexpressing tumors) and/or adenosine (CD73 and CD39 over-expressing tumors). Overexpression of Cox-2 has been detected in a number of tumors, such as colorectal, breast, pancreatic and lung cancers, where it correlates with a poor prognosis. Overexpression of COX-2 has been reported in hematological cancer models such as RAJI (Burkitt's lymphoma) and U937 (acute promonocytic leukemia) as well as in patient's blast cells. CD73 is up-regulated in various human carcinomas including those of colon, lung, pancreas and ovary. Importantly, higher expression levels of CD73 are associated with tumor neovascularization, invasiveness, and metastasis and with shorter patient survival time in breast cancer.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

As used herein, the term "contacting" refers to the bringing together of the indicated compounds in an in vitro system or an in vivo system such that they are in sufficient physical proximity to interact.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with compounds described herein for treatment of ALK2 and/or FGFR-associated diseases, disorders or conditions, or diseases or conditions as described herein. The agents can be combined with the present compounds in a single dosage form, or the agents can be administered simultaneously or sequentially as separate dosage forms.

I. Immune-Checkpoint Therapies

In some embodiments, the compounds provided herein can be used in combination with one or more immune checkpoint inhibitors for the treatment of cancer as described herein. Compounds of the present disclosure can be used in combination with one or more immune checkpoint inhibitors. Exemplary immune checkpoint inhibitors include inhibitors against immune checkpoint molecules such as CD20, CD28, CD39, CD40, CD 122, CD96, CD73, CD47, GITR, CSF1R, JAK, PBK delta, PBK gamma, TAM, arginase, CD137 (also known as 4-1BB), ICOS, B7-H3, B7-H4, BTLA, CTLA-4, LAGS, TIMS, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAGS, PD-1, TIMS, TIGIT, and VISTA. In some embodiments, the compounds of the disclosure provided herein can be used in combination with one or more agents selected from KIR inhibitors, TIGIT inhibitors, LAIR1 inhibitors, CD 160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab). In some embodiments, the anti-PD-1 monoclonal antibody is ipilumimab.

In some embodiments, the compounds of the disclosure can be used in combination with INCB086550.

In some embodiments, the inhibitor of an immune checkpoint molecule is anti-PD1 antibody, anti-a small molecule PD-L1 antibody, or anti-CTLA-4 antibody. inhibitor. In some embodiments, the small molecule PD-L1 inhibitor has an $IC_{50}$ less than 1 µM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, US 20180016260, US 20180057486, US 20180177784, US 20180177870, US 20180179179, US 20180179197, US 20180179201, and US 20180179202, each of which is incorporated by reference in its entirety for all purposes.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of CSF1R, e.g., an anti-CSF1R antibody. In some embodiments, the anti-CSF1R antibody is IMC-CS4 or RG7155.

In some embodiments, the inhibitor of an immune checkpoint molecule is an inhibitor of LAG3, e.g., an anti-LAG3 antibody. In some embodiments, the anti-LAG3 antibody is BMS-986016, LAG525, IMP321, GSK2831781, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MEDI6469, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO 1, TDO, or arginase. Examples of IDO1 inhibitors include epacadostat, NLG919, BMS-986205, PF-06840003, IOM2983, RG-70099 and LY338196.

An example of an arginase inhibitor is CB-1158.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Examples of agents that may be combined with compounds of the present disclosure include inhibitors of the PI3K-AKT-mTOR pathway, inhibitors of the Raf-MAPK pathway, inhibitors of JAK-STAT pathway, inhibitors of beta catenin pathway, inhibitors of notch pathway, inhibitors of hedgehog pathway, inhibitors of Pirn kinases, and inhibitors of protein chaperones and cell cycle progression. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors for the treatment of diseases, such as cancer. Examples of cancers include solid tumors and liquid tumors, such as blood cancers. For example, the compounds of the present disclosure can be combined with one or more inhibitors of the following kinases for the treatment of cancer: Akt1, Akt2, Akt3, TGF-βR, Pirn, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFJβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABE, ALK and B-Raf. In some embodiments, the compounds of the present disclosure can be combined with one or more of the following inhibitors for the treatment of cancer. Non-limiting examples of inhibitors that can be combined with the compounds of the present disclosure for treatment of cancers include an additional FGFR inhibitor (FGFR1, FGFR2, FGFR3 or FGFR4, e.g., AZD4547, BAY1187982, ARQ087, BGJ398, BIBF1120, TKI258, lucitanib, dovitinib, TAS-120, JNJ-42756493, Debiol347, INCB54828, INCB62079 and INCB63904), a JAK inhibitor (JAK1 and/or JAK2, e.g., ruxolitinib, baricitinib or INCB39110), an IDO inhibitor (e.g., epacadostat and NLG919), an ESDI inhibitor (e.g., GSK2979552, INCB59872 and INCB60003), a TDO inhibitor, a PI3K-delta inhibitor (e.g., INCB50797 and INCB50465), a PI3K-gamma inhibitor such as a PI3K-gamma selective inhibitor, a CSFIR inhibitor (e.g., PLX3397 and LY3022855), a TAM receptor tyrosine kinases (Tyro-3, Axl, and Mer), an angiogenesis inhibitor, an interleukin receptor inhibitor, bromo and extra terminal family members inhibitors (for example, bromodomain inhibitors or BET inhibitors such as OTX015, CPI-0610, INCB54329 and INCB57643) and an adenosine receptor antagonist or combinations thereof. Inhibitors of HD AC such as panobinostat and vorinostat. Inhibitors of c-Met such as onartumzumab, tivantnib, and INC-280. Inhibitors of BTK such as ibrutinib. Inhibitors of mTOR such as rapamycin, sirolimus, temsirolimus, and everolimus. Inhibitors of Raf, such as vemurafenib and dabrafenib. Inhibitors of MEK such as trametinib, selumetinib and GDC-0973. Inhibitors of Hsp90 (e.g., tanespimycin), cyclin dependent kinases (e.g., palbociclib), PARP (e.g., olaparib) and Pirn kinases (LGH447, INCB053914 and SGI-1776) can also be combined with compounds of the present disclosure.

In some embodiments, compounds of the present disclosure can be combined with one or more JAK inhibitors (JAK1 and/or JAK2, e.g., ruxolitinib, baricitinib or INCB39110). In some embodiments, compounds of the present disclosure can be combined with one or more JAK inhibitors (JAK1 and/or JAK2, e.g., ruxolitinib, baricitinib or INCB39110) for the treatment of cancers such as myeloproliferative diseases. For example, the myeloproliferative disease is myelofibrosis. In some embodiments, compounds of the present disclosure can be combined with ruxolitinib, or a pharmaceutically acceptable salt thereof. In some embodiments, compounds of the present disclosure can be combined with ruxolitinib, or a pharmaceutically acceptable salt thereof, for the treatment of myeloproliferative disease such as myelofibrosis.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include bendamustine, nitrogen mustards, ethylenimine derivatives, alkyl sulfonates, nitrosoureas and triazenes, uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, CAR (Chimeric antigen receptor) T cell treatment as a booster for T cell activation, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, abiraterone, afatinib, aflibercept, aldesleukin, alemtuzumab, alitretinoin, allopurinol, altretamine, amsacrine, anastrozole, aphidicolon, arsenic trioxide, asparaginase, axitinib, azacitidine, bevacizumab, bexarotene, baricitinib, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, docetaxel, doxorubicin, droloxafme, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, nofetumomab, oserelin, oxaliplatin, paclitaxel, pamidronate, panitumumab, pazopanib, pegaspargase, pegfdgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafme, revlimid, rituximab, ruxolitinib, sorafenib, streptozocin, sunitinib, sunitinib maleate, tamoxifen, tegafur, temozolomide, teniposide, testolactone, thalidomide, thioguanine, thiotepa, topotecan, toremifene, tositumomab, trastuzumab, tretinoin, triptorelin, uracil mustard, valrubicin, vandetanib, vinblastine, vincristine, Vindesine, vinorelbine, vorinostat and zoledronate.

Other anti-cancer agent(s) include antibody therapeutics such as trastuzumab (Herceptin), antibodies to costimulatory molecules such as CTLA-4 (e.g., ipilimumab or tremelimumab), 4-1BB, antibodies to PD-1 and PD-L1, or antibodies to cytokines (IL-10, TGF-β, etc.). Examples of antibodies to PD-1 and/or PD-L1 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

Other anti-cancer agents include inhibitors of kinases associated cell proliferative disorder. These kinases include but not limited to Aurora-A, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, PAK1, PAK2, PAK3, PAK4, PDK1, PKA, PKC, Rsk and SGK. Other anti-cancer agents also include those that block immune cell migration such as antagonists to chemokine receptors, including CCR2 and CCR4.

The compounds of the present disclosure can further be used in combination with one or more anti-inflammatory agents, steroids, immunosuppressants or therapeutic antibodies. The steroids include but are not limited to 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

The compounds of the present disclosure can also be used in combination with lonafarnib (SCH6636), tipifarnib (R115777), L778123, EMS 214662, tezacitabine (MDL 101731), Sml1, triapine, didox, trimidox and amidox.

The compounds described herein can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds described herein can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds described herein can be combined with dendritic cells immunization to activate potent anti-tumor responses.

The compounds of the present disclosure can be used in combination with bispecific macrocyclic peptides that target Fc alpha or Fc gamma receptor-expressing effectors cells to tumor cells. The compounds of the present disclosure can also be combined with macrocyclic peptides that activate host immune responsiveness.

The compounds of the present disclosure can be used in combination with bone marrow transplant for the treatment of a variety of tumors of hematopoietic origin.

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); Stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and Iodenosine (FddA). Typical suitable NNRTIs include nevirapine (BI-RG-587); delaviradine (BHAP, U-90152); efavirenz (DMP-266); PNU-142721; AG-1549; MKC-442 (l-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

The compounds described herein may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with compound disclosed herein. These include onartumzumab, tivantnib, and INC-280. Agents against Abl (or Bcr-Abl) include imatinib, dasatinib, nilotinib, and ponatinib and those against Aik (or EML4-ALK) include crizotinib.

Angiogenesis inhibitors may be efficacious in some tumors in combination with compounds disclosed herein. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds described herein include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, ternsirolimus, and everolimus may be combined with compounds of the invention. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfdzomib) can also be combined with compounds described herein. In some embodiments, the JAK inhibitor is selective for JAK1 over JAK2 and JAKS.

Other suitable agents for use in combination with compounds described herein include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with compounds described herein include steroids including 17 alphaethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

Other suitable agents for use in combination with compounds described herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds described herein may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabino, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, Vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafme, cyclophosphamide, ifosamide, and droloxafme.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure can be used in combination with bone marrow transplant for the treatment of a variety of tumors of hematopoietic origin.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

When more than one pharmaceutical agent is administered to a patient, they can be administered simultaneously, separately, sequentially, or in combination (e.g., for more than two agents).

Formulation, Dosage Forms and Administration

When employed as pharmaceuticals, the compounds of the present disclosure can be administered in the form of pharmaceutical compositions. Thus the present disclosure provides a composition comprising a compound of Formula (I) or any of the formulas as described herein, a compound as recited in any of the claims and described herein, or a pharmaceutically acceptable salt thereof, or any of the embodiments thereof, and at least one pharmaceutically acceptable carrier or excipient. The pharmaceutical compositions can comprise of a compound described herein and one or more second therapeutic agents as described herein. For example, the second therapeutic agent is a JAK inhibitor such as ruxolitinib. The compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Dmg Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Labeled Compounds and Assay Methods

The compounds of the present disclosure can further be useful in investigations of biological processes in normal and abnormal tissues. Thus, another aspect of the present invention relates to fluorescent dye, spin label, heavy metal or radio-labeled compounds provided herein that would be useful not only in imaging techniques but also in assays, both in vitro and in vivo, for localizing and quantitating ALK2 protein and/or FGFR protein in tissue samples, including human, and for identifying ALK2 ligands and/or FGFR ligands by inhibition binding of a labeled compound. Accordingly, the present invention includes ALK2 binding assays that contain such labeled compounds and FGFR binding assays that contain such labeled compounds.

The present invention further includes isotopically-substituted compounds of the disclosure. An "isotopically-substituted" compound is a compound of the invention where one or more atoms are replaced or substituted by an atom having the same atomic number but a different atomic mass or mass number. Compounds of the invention may contain isotopes in a natural abundance as found in nature. Compounds of the invention may also have isotopes in amounts greater to that found in nature, e.g., synthetically incorporating low natural abundance isotopes into the compounds of the invention so they are enriched in a particularly useful isotope (e.g., $^2$H and $^{13}$C). It is to be understood that a "radio-labeled" compound is a compound that has incorporated at least one isotope that is radioactive (e.g., radionuclide), e.g., $^3$H and $^{14}$C. Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. In some embodiments, the radionuclide is selected from the group consisting of $^3$H, $^{14}$C, $^{125}$I, $^{35}$S and $^{82}$Br. For in vitro ALK2 labeling and competition assays, compounds that incorporate $^3$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful. The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances, (see e.g., A. Kerekes et. al. J. Med. Chem. 2011, 54, 201-210; R. Xu et. al. J. Label Compd. Radiopharm. 2015, 58, 308-312). In particular, substitution at one or more metabolism sites may afford one or more of the therapeutic advantages. Specifically, a labeled compound of the invention can be used in a screening assay to identify and/or evaluate compounds. For example, a newly synthesized or identified compound (i.e., test compound) which is labeled can be evaluated for its ability to bind a ALK2 protein or FGFR protein by monitoring its concentration variation when contacting with the ALK2 protein or FGFR protein, through tracking of the labeling. For example, a test compound (labeled) can be evaluated for its ability to reduce binding of another compound which is known to bind to a ALK2 protein or FGFR protein (i.e., standard compound). Accordingly, the ability of a test compound to compete with the standard compound for binding to the ALK2 protein or FGFR protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, e.g., in the treatment or prevention of diseases or disorders associated with the activity of ALK2 and/or FGFR, such as cancer or infections, which include one or more containers containing a pharmaceutical composition comprising a therapeutically effective amount of a compound of Formula I, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of ALK2 and/or FGFR according to at least one assay described herein.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Haque, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ C$_{18}$ 5 µm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 μm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Example 1. 5-((2R,6S)-2,6-Dimethylpiperidin-1-yl)-3-(6-((R)-3-methylpiperazin-1-yl)pyridin-3-yl)-1H-pyrazolo[4,3-d]pyrimidine

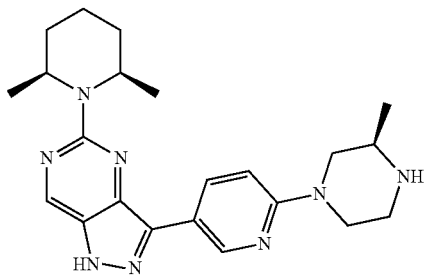 [SMILES: C[C@@H]1CN(c2ccc(-c3n[nH]c4cnc(N5[C@H](C)CCC[C@@H]5C)nc34)cn2)CCN1]

Step 1. 5-Chloro-3-iodo-1-((2-(trimethylsilyl)ethoxy)methyl)-1H-pyrazolo[4,3-d]pyrimidine

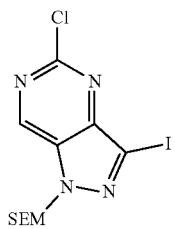 [SMILES: C[Si](C)(C)CCOCn1nc(I)c2nc(Cl)ncc21]

To a solution of 5-chloro-1H-pyrazolo[4,3-d]pyrimidine (9.8 g, 63.4 mmol) in DMF (100 mL) was added A-iodo-succinimide (15.69 g, 69.7 mmol) and the resulting solution was heated to 50° C. After 2 hrs, the reaction mixture was cooled to r.t., diluted with EtOAc and water. The organic layer was washed with brine, dried with $MgSO_4$, filtered and concentrated.

The crude was taken up in 100 mL DMF and NaH (2.79 g, 69.7 mmol, 60% dispersion in mineral oil) was added at 0° C. The mixture was stirred at r.t. for 10 min then 2-(trimethylsilyl)ethoxymethyl chloride (12.37 mL, 69.7 mmol) was added. The resulting mixture was stirred at r.t. After 1 hr, the reaction mixture was diluted with EtOAc and water.

The organic layer was washed with brine, dried with $MgSO_4$, filtered and concentrated. The crude was then purified by CombiFlash Rf+ Lumen. LCMS calculated for $C_{11}H_{17}ClIN_4OSi$ $(M+H)^+$: m/z=411.0; found 411.1.

Step 2. tert-Butyl (R)-2-methyl-4-(5-(4,4,5,5-tetramethyl-1,3,2-dioxaborolan-2-yl)pyridin-2-yl)piperazine-1-carboxylate

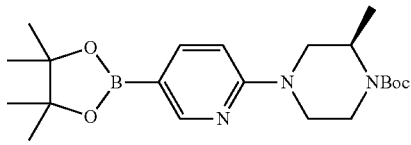 [SMILES: C[C@@H]1CN(c2ccc(B3OC(C)(C)C(C)(C)O3)cn2)CCN1C(=O)OC(C)(C)C]

A mixture of tert-butyl (R)-4-(5-bromopyridin-2-yl)-2-methylpiperazine-1-carboxylate (1.84 g, 5.16 mmol), bis(pinacolato)diboron (1.836 g, 7.23 mmol), potassium acetate (1.521 g, 15.49 mmol), and dichloro[1,1'-bis(diphenylphosphino)ferrocene]palladium (II) dichloromethane adduct (0.422 g, 0.516 mmol) in dioxane (25.8 mL) under $N_2$ was heated to 85° C.

After 16 hrs, the reaction mixture was cooled to r.t, quenched with water and EtOAc, and filtered through celite. The organic layer was washed with brine, dried with $MgSO_4$, filtered and concentrated. The crude was then purified by CombiFlash Rf+ Lumen. LCMS calculated for $C_{15}H_{25}BN_3O_4$ $(M-C_6H_9)^+$: m/z=322.2; found 322.2.

Step 3. tert-Butyl (R)-4-(5-(5-chloro-1-((2-(trimethylsilyl)ethoxy)methyl)-1H-pyrazolo[4,3-d]pyrimidin-3-yl)pyridin-2-yl)-2-methylpiperazine-1-carboxylate

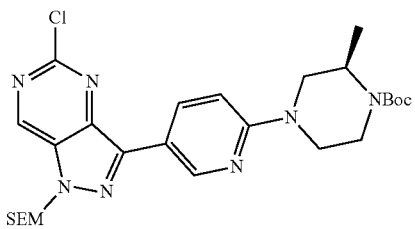 [SMILES: C[C@@H]1CN(c2ccc(-c3nn(COCC[Si](C)(C)C)c4cnc(Cl)nc34)cn2)CCN1C(=O)OC(C)(C)C]

A mixture of 5-chloro-3-iodo-1-((2-(trimethylsilyl)ethoxy)methyl)-1H-pyrazolo[4,3-d]pyrimidine (2.444 g, 5.95 mmol), to/7-butyl (R)-2-methyl-4-(5-(4,4,5,5-tetramethyl-1,3,2-dioxaborolan-2-yl)pyridin-2-yl)piperazine-1-carboxylate (2.00 g, 4.96 mmol), potassium carbonate (2.056 g, 14.88 mmol) and dichloro[1,1'-bis(diphenylphosphino)ferrocene]palladium (II) dichloromethane adduct (1.215 g, 1.488 mmol) in dioxane (39.7 mL) and water (9.92 mL) was heated to 90° C. under $N_2$. After 20 hrs, the reaction mixture was cooled to r.t., quenched with water and EtOAc, then filtered through celite. The organic layer was washed with brine, dried with $MgSO_4$ and purified by CombiFlash Rf+ Lumen. LCMS calculated for $C_{26}H_{39}ClN_7O_3Si$ (M+H)$^+$: m/z=560.3; found 560.3.

Step 4. 5-((2R,6S)-2,6-Dimethylpiperidin-1-yl)-3-(6-((R)-3-methylpiperazin-1-yl)pyridin-3-yl)-1H-pyrazolo[4,3-d]pyrimidine A solution of tert-butyl (R)-4-(5-(5-chloro-1-((2-(trimethylsilyl)ethoxy)methyl)-1H-pyrazolo[4,3-d]pyrimidin-3-yl)pyridin-2-yl)-2-methylpiperazine-1-carboxylate (38 mg, 0.068 mmol), N,N-diisopropylethylamine (0.059 mL, 0.339 mmol) and cis-2,6-dimethylpiperidine (0.046 mL, 0.339 mmol) in 1-methyl-2-pyrrolidinone (1 mL) was heated to 120° C. After 4 days, the reaction was cooled to r.t., diluted with water and extracted with EtOAc. The organic layer was washed with brine, dried with $Na_2SO_4$ and concentrated. The crude was taken up in 1 mL DCM and 1 mL TFA and stirred at r.t. for 2 hrs. The solvent was then removed under vacuum. The crude was then taken up in 1 mL MeOH and 0.7 mL $NH_4OH$ (aq) was added. The resulting mixture was stirred at r.t. for 5 min and purified with prep-LCMS (XBridge C18 column, eluting with a gradient of acetonitrile/water containing 0.1% TFA, at flow rate of 60 mL/min). LCMS calculated for $C_{22}H_{31}N_8$(M+H)$^+$: m/z=407.3; found 407.3. The product was isolated as the TFA salt.

Example 2. (3R,5S)-3,5-Dimethyl-4-(3-(6-((R)-3-methylpiperazin-1-yl)pyridin-3-yl)-1H-pyrazolo[4,3-d]pyrimidin-5-yl)morpholine

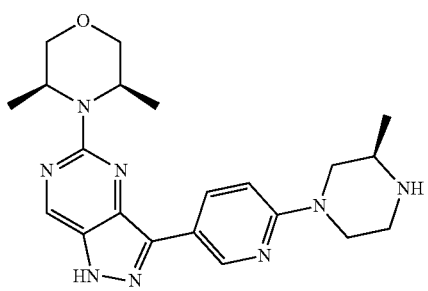 [SMILES: C[C@@H]1CN(c2ccc(-c3n[nH]c4cnc(N5[C@H](C)COC[C@@H]5C)nc34)cn2)CCN1]

This compound was prepared according to the procedures described in Example 1, using cis-3,5-dimethylmorpholine instead of cis-2,6-dimethylpiperidine as starting material. LCMS calculated for $C_{21}H_{29}N_8O$ (M+H)$^+$: m/z=409.2; found: 409.3. The product was isolated as the TFA salt.

Example 3. 5-(7-Azabicyclo[2.2.1]heptan-7-yl)-3-(6-((R)-3-methylpiperazin-1-yl)pyridin-3-yl)-1H-pyrazolo[4,3-d]pyrimidine

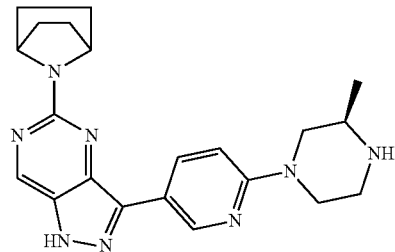 [SMILES: C[C@@H]1CN(c2ccc(-c3n[nH]c4cnc(N5C6CCC5CC6)nc34)cn2)CCN1]

This compound was prepared according to the procedures described in Example 1, using 7-azabicyclo[2.2.1]heptane instead of cis-2,6-dimethylpiperidine as starting material. LCMS calculated for $C_{21}H_{27}N_8$(M+H)$^+$: m/z=391.2; found: 391.3. The product was isolated as the TFA salt.

Example 4. (1R,5S,6S)-8-(3-(6-((R)-3-Methylpiperazin-1-yl)pyridin-3-yl)-1H-pyrazolo[4,3-d]pyrimidin-5-yl)-8-azabicyclo[3.2.1]octan-6-ol

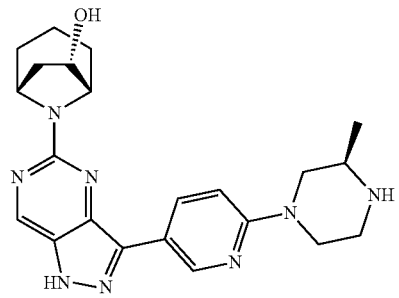 [SMILES: C[C@@H]1CN(c2ccc(-c3n[nH]c4cnc(N5[C@@H]6CCC[C@H]5[C@@H](O)C6)nc34)cn2)CCN1]

This compound was prepared according to the procedures described in Example 1, using (1R,5S,6S)-8-azabicyclo[3.2.1]octan-6-ol instead of cis-2,6-dimethylpiperidine as starting material. LCMS calculated for $C_{22}H_{29}N_8O$ (M+H)$^+$: m/z=421.2; found: 421.2. The product was isolated as the TFA salt.

Example 5. 1-((3R,5S)-3,5-Dimethyl-4-(3-(6-((R)-3-methylpiperazin-1-yl)pyridin-3-yl)-1H-pyrazolo[4,3-d]pyrimidin-5-yl)piperazin-1-yl)-2-methylpropan-1-one

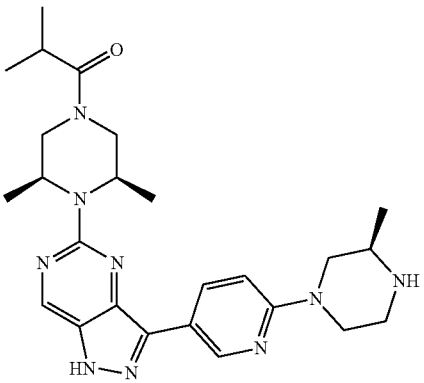 [SMILES: CC(C)C(=O)N1C[C@@H](C)N(c2ncc3[nH]nc(-c4ccc(N5CCN[C@H](C)C5)nc4)c3n2)[C@@H](C)C1]

Step 1. tert-Butyl (R)-4-(5-(5-((2R,6S)-4-benzyl-2,6-dimethylpiperazin-1-yl)-1-((2-(trimethylsilyl)ethoxy)methyl)-1H-pyrazolo[4,3-d]pyrimidin-3-yl)pyridin-2-yl)-2-methylpiperazine-1-carboxylate

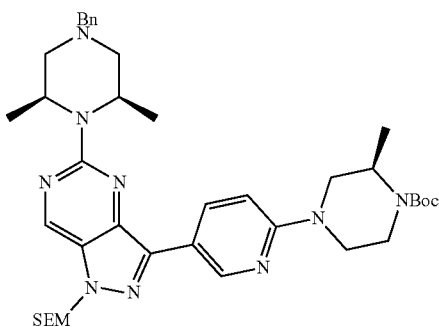 [SMILES: C[C@@H]1CN(c2ccc(-c3nn(COCC[Si](C)(C)C)c4cnc(N5[C@H](C)CN(Cc6ccccc6)C[C@@H]5C)nc34)cn2)CCN1C(=O)OC(C)(C)C]

To a microwave vial was added tert-butyl (R)-4-(5-(5-chloro-1-((2-(trimethylsilyl)ethoxy)methyl)-1H-pyrazolo[4,3-d]pyrimidin-3-yl)pyridin-2-yl)-2-methylpiperazine-1-carboxylate (380 mg, 0.678 mmol, see Example 1, Step 3), 1-benzyl-cis-3,5-dimethylpiperazine (770 mg, 3.77 mmol) and N,N-diisopropylethylamine (1.185 mL, 6.78 mmol) in 1-methyl-2-pyrrolidinone (3 mL). The reaction mixture was heated to 150° C. under microwave for 42 hrs.

The reaction was then cooled to r.t., diluted with water and extracted with EtOAc. The organic layer was washed with brine, dried with $Na_2SO_4$, filtered and concentrated. The crude residue was taken up in 2 mL DCM and N,N-diisopropylethylamine (1.185 mL, 6.78 mmol) and di-tert-butyl dicarbonate (0.315 mL, 1.357 mmol) was added. The mixture was stirred at r.t. for 2 hrs. The reaction was then quenched with water, extracted with DCM, washed with brine and dried with $Na_2SO_4$. The crude was purified by CombiFlash Rf+ Lumen. LCMS calculated for $C_{39}H_{58}N_9O_3Si$ (M+H)$^+$: m/z=728.4; found 728.5.

Step 2. tert-Butyl (R)-4-(5-(5-((2R,6S)-2,6-Dimethylpiperazin-1-yl)-1-((2-(trimethylsilyl)ethoxy)methyl)-1H-pyrazolo[4,3-d]pyrimidin-3-yl)pyridin-2-yl)-2-methylpiperazine-1-carboxylate

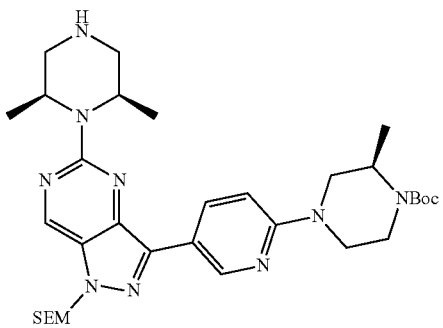 [SMILES: C[C@@H]1CN(c2ccc(-c3nn(COCC[Si](C)(C)C)c4cnc(N5[C@H](C)CNC[C@@H]5C)nc34)cn2)CCN1C(=O)OC(C)(C)C]

A mixture of tert-butyl (R)-4-(5-(5-((2R,6S)-4-benzyl-2,6-dimethylpiperazin-1-yl)-1-((2-(trimethylsilyl)ethoxy)methyl)-1H-pyrazolo[4,3-d]pyrimidin-3-yl)pyridin-2-yl)-2-methylpiperazine-1-carboxylate (108 mg, 0.148 mmol), palladium on carbon (10%, 23.7 mg, 0.022 mmol) and ammonium formate (94 mg, 1.483 mmol) was taken up in methanol (2 mL) under $N_2$ and heated to 60° C. After 22 hrs, the reaction mixture was cooled to r.t., diluted with EtOAc, filtered through celite, and concentrated in vacuo. The obtained crude product was used in the next step without further purification. LCMS calculated for $C_{32}H_{52}N_9O_3Si$ (M+H)$^+$: m/z=638.4; found 638.5.

Step 3. 1-((3R,5S)-3,5-Dimethyl-4-(3-(6-((R)-3-methylpiperazin-1-yl)pyridin-3-yl)-1H-pyrazolo[4,3-d]pyrimidin-5-yl)piperazin-1-yl)-2-methylpropan-1-one A solution of tert-butyl (R)-4-(5-(5-((2R,6S)-2,6-dimethylpiperazin-1-yl)-1-((2-(trimethylsilyl)ethoxy)methyl)-1H-pyrazolo[4,3-d]pyrimidin-3-yl)pyridin-2-yl)-2-methylpiperazine-1-carboxylate (14 mg, 0.022 mmol) in 0.5 mL DCM was added triethylamine (0.012 mL, 0.088 mmol) and isobutyryl chloride (4.60 µL, 0.044 mmol). The reaction mixture was stirred at r.t. for 18 hrs. The reaction was then diluted with water and extracted with EtOAc. The organic layer was washed with brine, dried with $Na_2SO_4$ and concentrated. The crude was taken up in 1 mL DCM and 1 mL TFA and stirred at r.t. for 2 hrs. The solvent was then removed in vacuo. The crude was then taken up in 1 mL MeOH and 0.7 mL $NH_4OH$ (aq) was added. The resulting mixture was stirred at r.t. for 5 min and purified with prep-LCMS (XBridge C18 column, eluting with a gradient of acetonitrile/water containing 0.1% TFA, at flow rate of 60 mL/min). LCMS calculated for $C_{25}H_{36}N_9O$ (M+H)$^+$: m/z=478.3; found 478.3. $^1$H NMR (600 MHz, DMSO) δ 13.47 (s, 1H), 9.43 (s, 1H), 9.21 (d, J=2.3 Hz, 1H), 9.07 (s, 1H), 8.46 (dd, J=8.9, 2.3 Hz, 1H), 7.11 (d, J=9.0 Hz, 1H), 4.86 (m, 2H), 4.47-4.37 (m, 3H), 4.03 (m, 1H), 3.48-3.27 (m, 4H), 3.25-2.85 (m, 4H), 1.31 (d, J=6.5 Hz, 3H), 1.27-1.13 (m, 6H), 1.1 (d, J=6.4 Hz, 3H), 1.05 (d, J=6.9 Hz, 3H) ppm. The product was isolated as the TFA salt.

Example 6. 1-((3R,5S)-3,5-Dimethyl-4-(3-(6-((R)-3-methylpiperazin-1-yl)pyridin-3-yl)-1H-pyrazolo[4,3-d]pyrimidin-5-yl)piperazin-1-yl)-2-methoxyethan-1-one

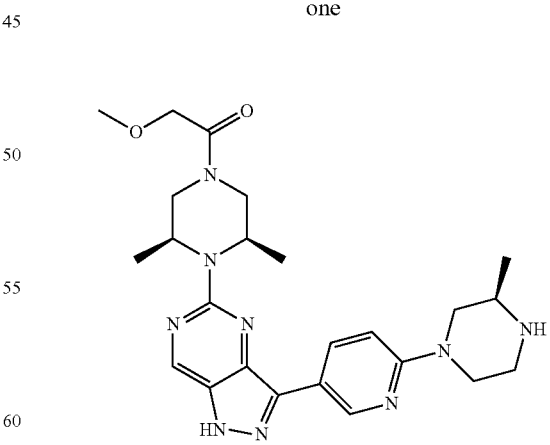

This compound was prepared according to the procedures described in Example 5, using 2-methoxyacetyl chloride instead of isobutyryl chloride as starting material. LCMS calculated for $C_{24}H_{34}N_9O_2$ (M+H)$^+$: m/z=480.3; found: 480.3. The product was isolated as the TFA salt.

Example 7. (3R,5S)—N-isopropyl-3,5-dimethyl-4-(3-(6-((R)-3-methylpiperazin-1-yl)pyridin-3-yl)-1H-pyrazolo[4,3-d]pyrimidin-5-yl)piperazine-1-carboxamide

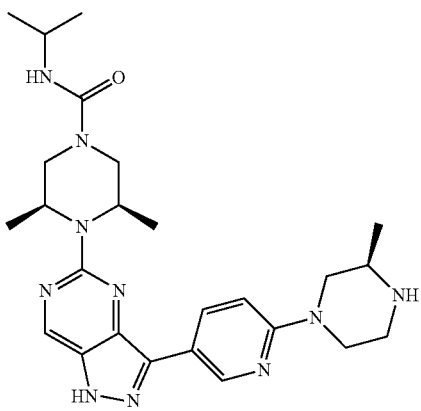 [SMILES: CC(C)NC(=O)N1C[C@@H](C)N(c2ncc3[nH]nc(-c4ccc(N5CCN[C@H](C)C5)nc4)c3n2)[C@@H](C)C1]

This compound was prepared according to the procedures described in Example 5, using isopropyl isocyanate instead of isobutyryl chloride as starting material. LCMS calculated for $C_{25}H_{37}N_{10}O$ (M+H)$^+$: m/z=493.3; found: 493.4. The product was isolated as the TFA salt.

Example 8. (3R,5S)—N,N,3,5-tetramethyl-4-(3-(6-((R)-3-methylpiperazin-1-yl)pyridin-3-yl)-1H-pyrazolo[4,3-d]pyrimidin-5-yl)piperazine-1-carboxamide

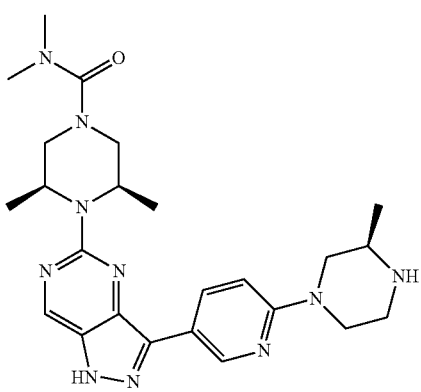 [SMILES: C[C@@H]1CN(c2ccc(-c3n[nH]c4cnc(N5[C@H](C)CN(C(=O)N(C)C)C[C@@H]5C)nc34)cn2)CCN1]

This compound was prepared according to the procedures described in Example 5, using dimethylcarbamoyl chloride instead of isobutyryl chloride as starting material. LCMS calculated for $C_{24}H_{35}N_{10}O$ (M+H)$^+$: m/z=479.3; found: 479.4. $^1$H NMR (600 MHz, DMSO) δ 13.41 (s, 1H), 9.31 (s, 1H), 9.21 (d, J=2.2 Hz, 1H), 9.07 (s, 1H), 8.47 (dd, J=8.9, 2.4 Hz, 1H), 7.11 (m, 1H), 4.83 (m, 2H), 4.43 (m, 2H), 3.56 (d, J=12.6 Hz, 2H), 3.44-3.05 (m, 4H), 3.01-2.92 (m, 3H), 2.87 (s, 6H), 1.33 (d, J=6.8 Hz, 6H), 1.30 (d, J=6.6 Hz, 3H) ppm. The product was isolated as the TFA salt.

Example 9. ((3R,5S)-3,5-Dimethyl-4-(3-(6-((R)-3-methylpiperazin-1-yl)pyridin-3-yl)-1H-pyrazolo[4,3-d]pyrimidin-5-yl)piperazin-1-yl)(pyrrolidin-1-yl)methanone

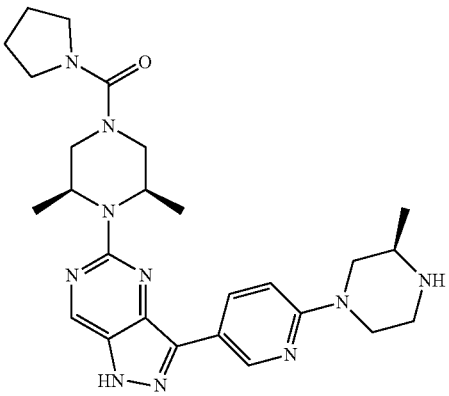 [SMILES: C[C@@H]1CN(c2ccc(-c3n[nH]c4cnc(N5[C@H](C)CN(C(=O)N6CCCC6)C[C@@H]5C)nc34)cn2)CCN1]

Step 1. ((3R,5S)-3,5-Dimethylpiperazin-1-yl) (pyrrolidin-1-yl)methanone

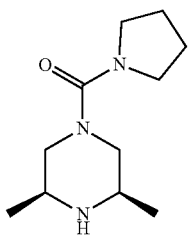

To a solution of cis-2,6-dimethylpiperazine (0.057 g, 0.5 mmol) in 2.5 mL DCM was added pyrrolidine-1-carbonyl chloride (0.066 mL, 0.600 mmol). The resulting solution was stirred at r.t. for 16 hrs. The reaction was then quenched with water, extracted with EtOAc, washed with brine and dried with $Na_2SO_4$. The obtained crude product was used in the next step without further purification. LCMS calculated for $C_{11}H_{22}N_3O$ (M+H)$^+$: m/z=212.2; found 212.2.

Step 2. ((3R,5S)-3,5-Dimethyl-4-(3-(6-((R)-3-methylpiperazin-1-yl)pyridin-3-yl)-1H-pyrazolo[4,3-d]pyrimidin-5-yl)piperazin-1-yl) (pyrrolidin-1-yl) methanone A solution of tert-butyl (R)-4-(5-(5-chloro-1-((2-(trimethylsilyl)ethoxy)methyl)-1H-pyrazolo[4,3-d]pyrimidin-3-yl)pyridin-2-yl)-2-methylpiperazine-1-carboxylate (30 mg, 0.054 mmol, see Example 1, Step 3), ((3R,5S)-3,5-dimethylpiperazin-1-yl)(pyrrolidin-1-yl)methanone (106 mg, 0.5 mmol), N,N-diisopropylethylamine (0.2 mL, 1.145 mmol) in 1-methyl-2-pyrrolidinone (1 mL) was heated to 120° C. After 5 days, the reaction was cooled to r.t., diluted with water and extracted with EtOAc. The organic layer was washed with brine, dried with $Na_2SO_4$ and concentrated.

The crude was taken up in 1 mL DCM and 1 mL TFA and stirred at r.t. for 2 hrs. The solvent was then removed in vacuo. The crude was then taken up in 1 mL MeOH and 0.7 mL NH$_4$OH (aq) was added. The resulting mixture was stirred at r.t. for 5 min and purified with prep-LCMS (XBridge C18 column, eluting with a gradient of acetonitrile/water containing 0.1% TFA, at flow rate of 60 mL/min). LCMS calculated for $C_{26}H_{37}N_{10}O$ (M+H)$^+$: m/z=505.3; found 505.5. The product was isolated as the TFA salt.

Example 10. ((3R,5S)-3,5-Dimethyl-4-(3-(6-((R)-3-methylpiperazin-1-yl)pyridin-3-yl)-1H-pyrazolo[4,3-d]pyrimidin-5-yl)piperazin-1-yl)(3-fluoropyrrolidin-1-yl)methanone

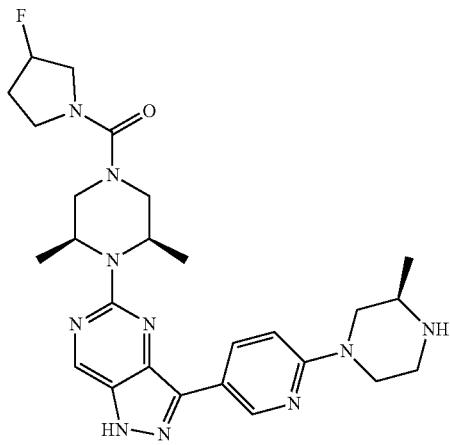 [SMILES: C[C@@H]1CN(c2ccc(-c3n[nH]c4cnc(N5[C@H](C)CN(C(=O)N6CCC(F)C6)C[C@@H]5C)nc34)cn2)CCN1]

Step 1. ((3R,5S)-3,5-Dimethylpiperazin-1-yl)(3-fluoropyrrolidin-1 yl)methanone

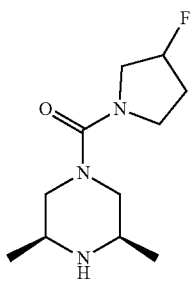 [SMILES: C[C@@H]1CN(C(=O)N2CCC(F)C2)C[C@H](C)N1]

To a solution of 3-fluoropyrrolidine hydrochloride (0.104 g, 0.825 mmol) and N,N-diisopropylethylamine (0.437 mL, 2.500 mmol) in 3 mL DCM was added triphosgene (0.074 g, 0.25 mmol) in 0.5 mL DCM and the resulting mixture was stirred at r.t. After 4 hrs, N,N-diisopropylethylamine (0.437 mL, 2.500 mmol) and cis-2,6-dimethylpiperazine (0.057 g, 0.500 mmol) was added and the resulting mixture was stirred at r.t. After 20 hrs, the reaction was quenched with water, extracted with DCM, washed with brine and dried with Na$_2$SO$_4$. The obtained crude product was used in the next step without further purification. LCMS calculated for $C_{11}H_{21}FN_3O$ (M+H)$^+$: m/z=230.2; found 230.3.

Step 2. ((3R,5S)-3,5-Dimethyl-4-(3-(6-((R)-3-methylpiperazin-1-yl)pyridin-3-yl)-1H-pyrazolo[4,3-d]pyrimidin-5-yl)piperazin-1-yl) (3-fluoropyrrolidin-1-yl) methanone This compound was prepared according to the procedures described in Example 9, using ((3R,5S)-3,5-dimethylpiperazin-1-yl)(3-fluoropyrrolidin-1-yl)methanone instead of ((3R,5S)-3,5-dimethylpiperazin-1-yl)(pyrrolidin-1-yl)methanone as starting material. LCMS calculated for $C_{26}H_{36}FN_{10}O$ (M+H)$^+$: m/z=523.3; found: 523.5. The product was isolated as the TFA salt.

Example 11. Ethyl (3R,5S)-3,5-dimethyl-4-(3-(6-((R)-3-methylpiperazin-1-yl)pyridin-3-yl)-1H-pyrazolo[4,3-d]pyrimidin-5-yl)piperazine-1-carboxylate

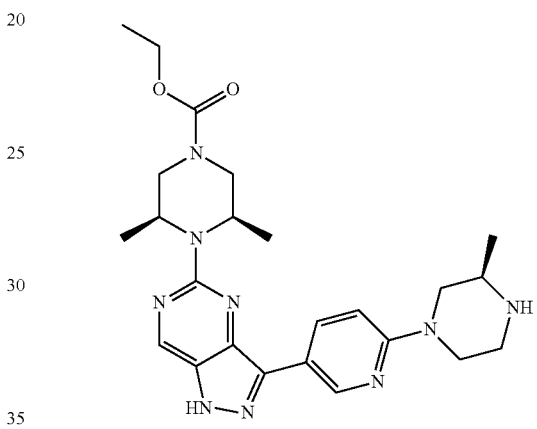

This compound was prepared according to the procedures described in Example 9, using ethyl chloroformate instead of pyrrolidine-1-carbonyl chloride as starting material. LCMS calculated for $C_{24}H_{34}N_9O_2$ (M+H)$^+$: m/z=480.3; found: 480.3. The product was isolated as the TFA salt.

Example 12. 2-Fluoroethyl (3R,5S)-3,5-dimethyl-4-(3-(6-((R)-3-methylpiperazin-1-yl)pyridin-3-yl)-1H-pyrazolo[4,3-d]pyrimidin-5-yl)piperazine-1-carboxylate

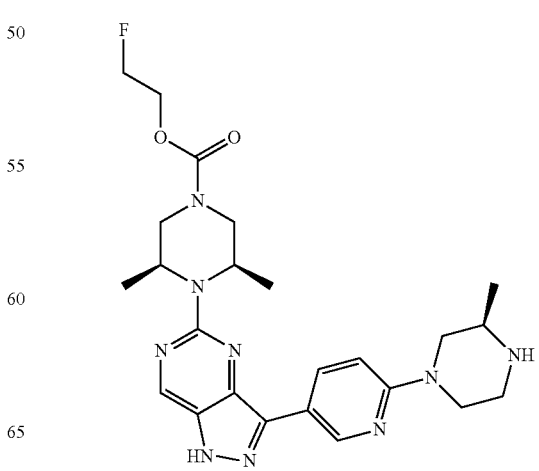

This compound was prepared according to the procedures described in Example 9, using 2-fluoroethyl chloroformate instead of pyrrolidine-1-carbonyl chloride as starting material. LCMS calculated for $C_{24}H_{33}FN_9O_2(M+H)^+$: m/z=498.3; found: 498.3. The product was isolated as the TFA salt.

Example 13. Cyclopropyl((1R,5S)-8-(3-(6-((R)-3-methylpiperazin-1-yl)pyridin-3-yl)-1H-pyrazolo[4,3-d]pyrimidin-5-yl)-3,8-diazabicyclo[3.2.1]octan-3-yl)methanone

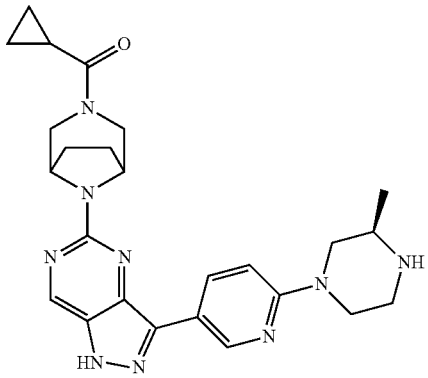 [SMILES: C[C@@H]1CN(c2ccc(-c3n[nH]c4cnc(N5C6CCC5CN(C(=O)C5CC5)C6)nc34)cn2)CCN1]

Step 1. ((R, 5S)-3,8-Diazabicyclo[3.2.1]octan-3-yl)(cyclopropyl)methanone

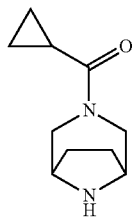 [SMILES: O=C(C1CC1)N1CC2CCC(C1)N2]

To a solution of tert-butyl (1R,5SS)-3,8-diazabicyclo[3.2.1]octane-8-carboxylate (100 mg, 0.471 mmol) in 2.4 mL DCM was added triethylamine (263 μL, 1.884 mmol) and cyclopropanecarbonyl chloride (85 μL, 0.942 mmol) and the resulting solution was stirred at r.t. After 20 hrs, the reaction was quenched with water, extracted with DCM, washed with brine and dried with $Na_2SO_4$. The crude was taken up in 1 mL DCM and 1 mL TFA was added. The reaction mixture was stirred at r.t. After 1 hr, the solvent was removed in vacuo. The obtained crude product was used in the next step without further purification. LCMS calculated for $C_{10}H_{17}N_2O$ $(M+H)^+$: m/z=181.1; found 181.1.

Step 2. Cyclopropyl((R, 5S)-8-(3-(6-((R)-3-methylpiperazin-1-yl)pyridin-3-yl)-1H-pyrazolo[4,3-d]pyrimidin-5-yl)-3,8-diazabicyclo[3.2.1]octan-3-yl)methanone This compound was prepared according to the procedures described in Example 9, using ((1R,5S)-3,8-diazabicyclo[3.2.1]octan-3-yl)(cyclopropyl)methanone instead of ((3R,5S)-3,5-dimethylpiperazin-1-yl)(pyrrolidin-1-yl)methanone as starting material. LCMS calculated for $C_{25}H_{32}N_9O$ $(M+H)^+$: m/z=474.3; found: 474.3. The product was isolated as the TFA salt.

Example 14. ((1R,5S)-8-(3-(6-((R)-3-Methylpiperazin-1-yl)pyridin-3-yl)-1H-pyrazolo[4,3-d]pyrimidin-5-yl)-3,8-diazabicyclo[3.2.1]octan-3-yl)(pyrrolidin-1-yl)methanone

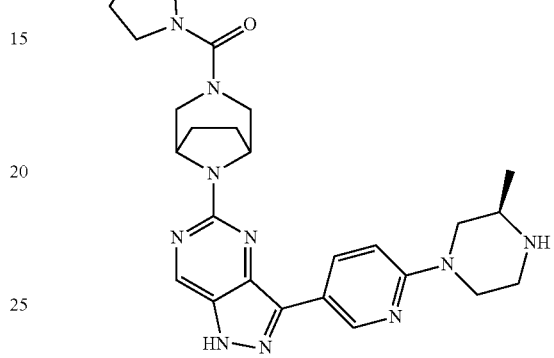

This compound was prepared according to the procedures described in Example 13, using pyrrolidine-1-carbonyl chloride instead of cyclopropanecarbonyl chloride as starting material. LCMS calculated for $C_{26}H_{35}N_{10}O$ $(M+H)^+$: m/z=503.3; found: 503.3. $^1$H NMR (600 MHz, DMSO) δ 13.46 (s, 1H), 9.19 (d, J=2.2 Hz, 1H), 9.06 (s, 1H), 8.87 (s, 1H), 8.46 (dd, J=8.9, 2.3 Hz, 1H), 7.13 (d, J=9.0 Hz, 1H), 4.79 (m, 2H), 4.49-4.35 (m, 2H), 3.60 (dd, J=12.5, 2.4 Hz, 2H), 3.46-3.30 (m, 2H), 3.28-3.20 (m, 4H), 3.20-3.05 (m, 4H), 3.01-2.93 (dd, J=13.8, 10.7 Hz, 1H), 1.95-1.83 (m, 4H), 1.76-1.69 (m, 4H), 1.30 (d, J=6.4 Hz, 3H) ppm. The product was isolated as the TFA salt.

Example 15. 4-((1R,5S)-8-(3-(6-((R)-3-Methylpiperazin-1-yl)pyridin-3-yl)-1H-pyrazolo[4,3-d]pyrimidin-5-yl)-3,8-diazabicyclo[3.2.1]octan-3-yl)benzonitrile

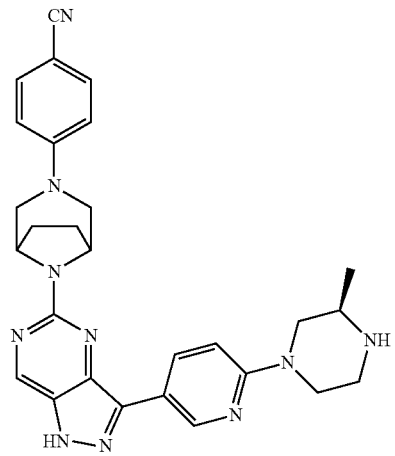 [SMILES: C[C@@H]1CN(c2ccc(-c3n[nH]c4cnc(N5C6CCC5CN(c5ccc(C#N)cc5)C6)nc34)cn2)CCN1]

Step 1. 4-((R, 5S)-3,8-Diazabicyclo[3.2.1]octan-3-yl)benzonitrile

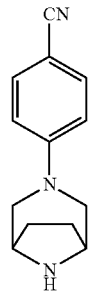 [SMILES: N#Cc1ccc(N2CC3CCC(C2)N3)cc1]

A mixture of tert-butyl (1R,5S)-3,8-diazabicyclo[3.2.1]octane-8-carboxylate (100 mg, 0.471 mmol), 4-bromobenzonitrile (129 mg, 0.707 mmol), sodium tert-butoxide (67.9 mg, 0.707 mmol), RuPhos Pd G3 (19.70 mg, 0.024 mmol) and RuPhos (11.0 mg, 0.024 mmol) in 2.4 mL THF was heated to 80° C. After 16 hrs, the reaction was diluted with EtOAc, filtered through celite, and concentrated. The crude was purified by CombiFlash Rf+ Lumen. The obtained product was then taken up in 1 mL DCM and 1 mL TFA was added. The reaction mixture was stirred at r.t. After 1 hr, the solvent was removed in vacuo. The obtained crude product was used in the next step without further purification.

Step 2. 4-((1R,5S)-8-(3-(6-((R)-3-Methylpiperazin-1-yl)pyridin-3-yl)-1H-pyrazolo[4,3-d]pyrimidin-5-yl)-3,8-diazabicyclo[3.2.1]octan-3-yl)benzonitrile This compound was prepared according to the procedures described in Example 9, using 4-((1R,5S)-3,8-diazabicyclo[3.2.1]octan-3-yl)benzonitrile instead of ((3R,5S)-3,5-dimethylpiperazin-1-yl)(pyrrolidin-1-yl)methanone as starting material. LCMS calculated for $C_{28}H_{31}N_{10}$ (M+H)$^+$: m/z=507.3; found: 507.3. The product was isolated as the TFA salt.

Example 16. 5-((2R,6S)-2,6-Dimethylpiperidin-1-yl)-3-(4-(4-methylpiperazin-1-yl)phenyl)-1H-pyrazolo[4,3-d]pyrimidine

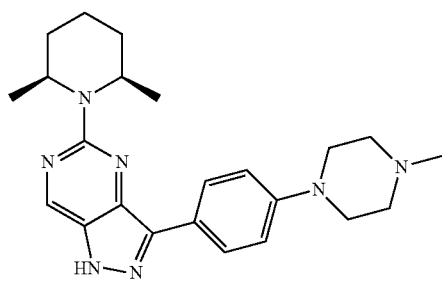

Step 1. 5-Chloro-3-(4-(4-methylpiperazin-1-yl)phenyl)-1-((2-(trimethylsilyl)ethoxy)methyl)-1H-pyrazolo[4,3-d]pyrimidine

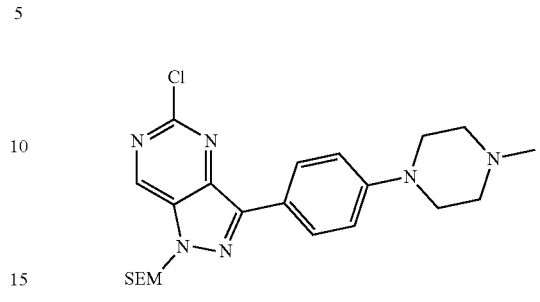

This compound was prepared according to the procedures described in Example 1, Step 3, using (4-(4-methylpiperazin-1-yl)phenyl)boronic acid instead of tert-butyl (R)-2-methyl-4-(5-(4,4,5,5-tetramethyl-1,3,2-dioxaborolan-2-yl)pyridin-2-yl)piperazine-1-carboxylate as starting material. LCMS calculated for $C_{22}H_{32}ClN_6OSi$ (M+H)$^+$: m/z=459.2; found: 459.3.

Step 2. 5-((2R,6S)-2,6-Dimethylpiperidin-1-yl)-3-(4-(4-methylpiperazin-1-yl)phenyl)-1H-pyrazolo[4,3-d]pyrimidine This compound was prepared according to the procedures described in Example 1, Step 4, using 5-chloro-3-(4-(4-methylpiperazin-1-yl)phenyl)-1-((2-(trimethylsilyl)ethoxy)methyl)-1H-pyrazolo[4,3-d]pyrimidine instead of tert-butyl (R)-4-(5-(5-chloro-1-((2-(trimethylsilyl)ethoxy)methyl)-1H-pyrazolo[4,3-d]pyrimidin-3-yl)pyridin-2-yl)-2-methylpiperazine-1-carboxylate as starting material. LCMS calculated for $C_{23}H_{32}N_7$ (M+H)$^+$: m/z=406.3; found: 406.3. The product was isolated as the TFA salt.

Example 17. Methyl (3R,5S)-3,5-dimethyl-4-(3-(6-((R)-3-methylpiperazin-1-yl)pyridin-3-yl)-1H-pyrazolo[4,3-d]pyrimidin-5-yl)piperazine-1-carboxylate

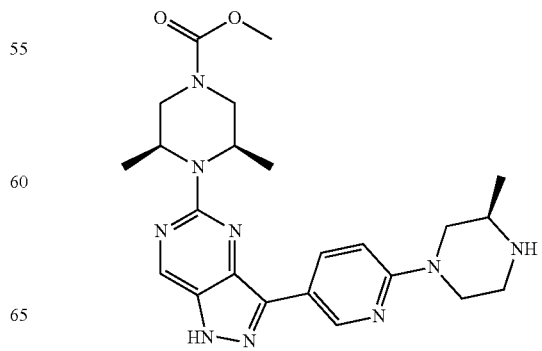

This compound was prepared according to the procedures described in Example 9, using methyl chloroformate instead of pyrrolidine-1-carbonyl chloride as starting material. LCMS calculated for $C_{23}H_{32}N_9O_2$ (M+H)$^+$: m/z=466.3; found: 466.1. The product was isolated as the TFA salt.

Example 18. (R)-5-(1-Methyl-1,4,6,7-tetrahydro-5H-imidazo[4,5-c]pyridin-5-yl)-3-(6-(3-methylpiperazin-1-yl)pyridin-3-yl)-1H-pyrazolo[4,3-d]pyrimidine

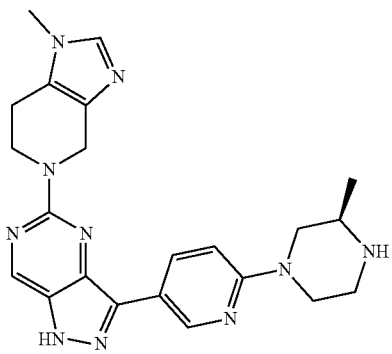 [SMILES: C[C@@H]1CN(c2ccc(-c3n[nH]c4cnc(N5CCc6c(ncn6C)C5)nc34)cn2)CCN1]

This compound was prepared according to the procedures described in Example 1, using 1-methyl-4,5,6,7-tetrahydro-1H-imidazo[4,5-c]pyridine instead of cis-2,6-dimethylpiperidine as starting material. LCMS calculated for $C_{22}H_{27}N_{10}$ (M+H)$^+$: m/z=431.2; found: 431.1. The product was isolated as the TFA salt.

Example 19. (R)-5-(3-Methyl-5,6-dihydroimidazo[1,2-a]pyrazin-7(8H)-yl)-3-(6-(3-methylpiperazin-1-yl)pyridin-3-yl)-1H-pyrazolo[4,3-d]pyrimidine

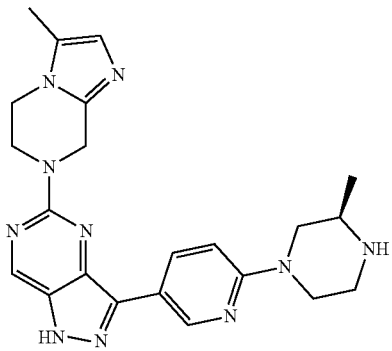 [SMILES: Cc1cnc2n1CCN(c1ncc3[nH]nc(-c4ccc(N5CCN[C@H](C)C5)nc4)c3n1)C2]

Step 1. tert-Butyl (R)-4-(5-(5-(3-bromo-5,6-dihydroimidazo[1,2-a]pyrazin-7(8H)-yl)-1-((2-(trimethylsilyl)ethoxy)methyl)-1H-pyrazolo[4,3-d]pyrimidin-3-yl)pyridin-2-yl)-2-methylpiperazine-1-carboxylate

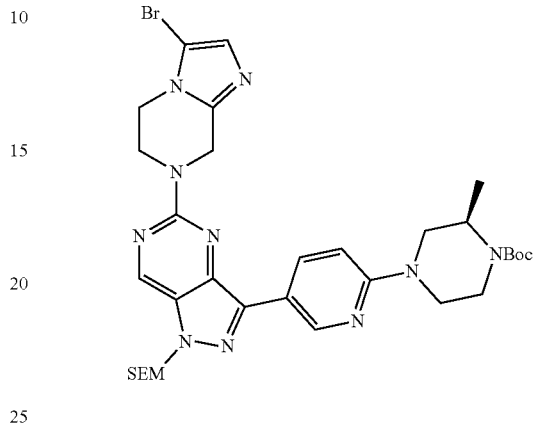

A solution of tert-butyl (R)-4-(5-(5-chloro-1-((2-(trimethylsilyl)ethoxy)methyl)-1H-pyrazolo[4,3-d]pyrimidin-3-yl)pyridin-2-yl)-2-methylpiperazine-1-carboxylate (100 mg, 0.179 mmol, see Example 1, Step 3), 3-bromo-5,6,7,8-tetrahydroimidazo[1,2-a]pyrazine (108 mg, 0.536 mmol), and N,N-diisopropylethylamine (0.280 mL, 1.607 mmol) in 1-methyl-2-pyrrolidinone (2 mL) was combined and heated to 120° C. After 3 days, the reaction was cooled to r.t., diluted with water and extracted with EtOAc. The organic layer was washed with brine, dried with $Na_2SO_4$ and concentrated. The crude was then purified by CombiFlash Rf+ Lumen. LCMS calculated for $C_{32}H_{46}BrN_{10}O_3Si$ (M-$C_6H_9$)$^+$: m/z=725.3; found 725.4.

Step 2. (R)-5-(3-Methyl-5,6-dihydroimidazo[1,2-a]pyrazin-7(8H)-yl)-3-(6-(3-methylpiperazin-1-yl)pyridin-3-yl)-1H-pyrazolo[4,3-d]pyrimidine A solution of tert-butyl (R)-4-(5-(5-(3-bromo-5,6-dihydroimidazo[1,2-a]pyrazin-7(8H)-yl)-1-((2-(trimethylsilyl)ethoxy)methyl)-1H-pyrazolo[4,3-d]pyrimidin-3-yl)pyridin-2-yl)-2-methylpiperazine-1-carboxylate (20 mg, 0.028 mmol), 2,4,6-trimethyl-1,3,5,2,4,6-trioxatriborinane (17.30 mg, 0.138 mmol), XPhos Pd G2 (4.34 mg, 5.51 µmol), and potassium phosphate (23.40 mg, 0.110 mmol) in dioxane (1 mL) and water (0.1 mL) was heated to 75° C. After 20 hrs, the reaction was cooled to r.t., diluted with water and extracted with EtOAc. The organic layer was washed with brine, dried with $Na_2SO_4$ and concentrated. The crude was taken up in 1 mL MeOH and 1 mL HCl (4 M solution in dioxane) and stirred at 60° C. for 2 hrs. The resulting mixture was purified with prep-LCMS (XBridge C18 column, eluting with a gradient of acetonitrile/water containing 0.1% TFA, at flow rate of 60 mL/min). LCMS calculated for $C_{22}H_{27}N_{10}$ (M+H)$^+$: m/z=431.2; found 431.4. The product was isolated as the TFA salt.

Example 20. (5-(3-(6-((R)-3-Methylpiperazin-1-yl)pyridin-3-yl)-1H-pyrazolo[4,3-d]pyrimidin-5-yl)-2,5-diazabicyclo[2.2.2]octan-2-yl)(pyrrolidin-1-yl)methanone

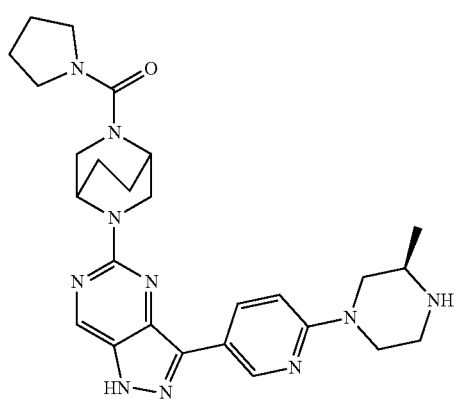 [SMILES: C[C@@H]1CN(c2ccc(-c3n[nH]c4cnc(N5CC6CCC5CN6C(=O)N5CCCC5)nc34)cn2)CCN1]

This compound was prepared according to the procedures described in Example 14, using tert-butyl 2,5-diazabicyclo[2.2.2]octane-2-carboxylate instead of tert-butyl (1R,5S)-3,8-diazabicyclo[3.2.1]octane-8-carboxylate as starting material. LCMS calculated for $C_{26}H_{35}N_{10}O$ (M+H)$^+$: m/z=503.3; found: 503.2. The product was isolated as the TFA salt.

Example 21. ((1S,4S)-5-(3-(6-((R)-3-Methylpiperazin-1-yl)pyridin-3-yl)-1H-pyrazolo[4,3-d]pyrimidin-5-yl)-2,5-diazabicyclo[2.2.1]heptan-2-yl)(pyrrolidin-1-yl)methanone

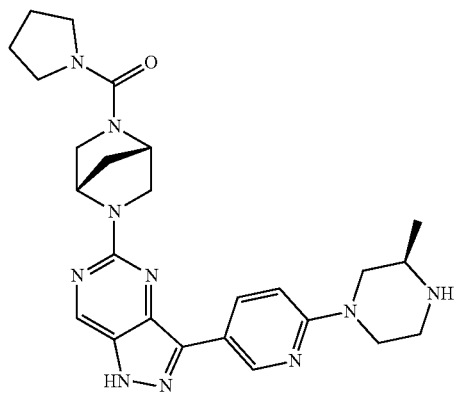 [SMILES: C[C@@H]1CN(c2ccc(-c3n[nH]c4cnc(N5C[C@@H]6C[C@H]5CN6C(=O)N5CCCC5)nc34)cn2)CCN1]

This compound was prepared according to the procedures described in Example 14, using tert-butyl (1S,4S)-2,5-diazabicyclo[2.2.1]heptane-2-carboxylate instead of tert-butyl (1R,5S)-3,8-diazabicyclo[3.2.1]octane-8-carboxylate as starting material. LCMS calculated for $C_{25}H_{33}N_{10}O$ (M+H)$^+$: m/z=489.3; found: 489.1. The product was isolated as the TFA salt.

Example 22. Methyl (3R,5S)-3,5-dimethyl-4-(3-(4-(4-methylpiperazin-1-yl)phenyl)-1H-pyrazolo[4,3-d]pyrimidin-5-yl)piperazine-1-carboxylate

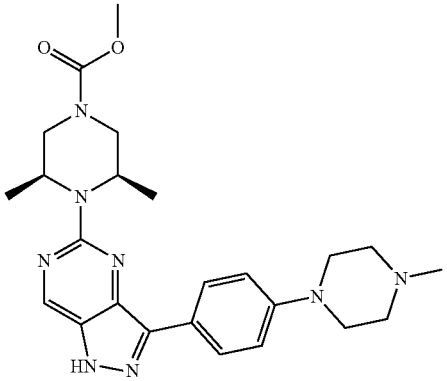

Step 1. Methyl (3R,5S)-4-(3-iodo-1-((2-(trimethylsilyl)ethoxy)methyl)-1H-pyrazolo[4,3-d]pyrimidin-5-yl)-3,5-dimethylpiperazine-1-carboxylate

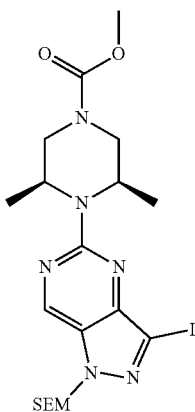 [SMILES: COC(=O)N1C[C@@H](C)N(c2ncc3c(n2)c(I)nn3COCC[Si](C)(C)C)[C@@H](C)C1]

A solution of 5-chloro-3-iodo-1-((2-(trimethylsilyl)ethoxy)methyl)-1H-pyrazolo[4,3-d]pyrimidine (1.368 g, 3.33 mmol, see Example 1, Step 1), methyl (3R,5S)-3,5-dimethylpiperazine-1-carboxylate (1.721 g, 9.99 mmol), and N,N-diisopropylethylamine (3.49 mL, 19.98 mmol) in 1-methyl-2-pyrrolidinone (20 mL) was heated to 120° C. After 5 days, the reaction mixture was cooled to r.t., quenched with water and EtOAc. The organic layer was washed with brine, dried with MgSO$_4$ and purified by CombiFlash Rf+ Lumen. LCMS calculated for $C_{19}H_{32}IN_6O_3Si$ (M+H)$^+$: m/z=547.1; found 547.1.

Step 2. Methyl (3R,5S)-3,5-dimethyl-4-(3-(4-(4-methylpiperazin-1-yl)phenyl)-1H-pyrazolo[4,3-d]pyrimidin-5-yl)piperazine-1-carboxylate A solution of methyl (3R,5S)-4-(3-iodo-1-((2-(trimethylsilyl)ethoxy)methyl)-1H-pyrazolo[4,3-d]pyrimidin-5-yl)-3,5-dimethylpiperazine-1-carboxylate (400 mg, 0.732 mmol), (4-(4-methylpiperazin-1-yl)phenyl)boronic acid (483 mg, 2.196 mmol), XPhos Pd G2 (86 mg, 0.110 mmol), and potassium phosphate (621 mg, 2.93 mmol) in dioxane (10 mL) and water (1 mL) was heated to 70° C. After 20 hrs, the reaction was cooled to r.t., diluted with water and extracted with EtOAc. The organic layer was washed with brine, dried with Na$_2$SO$_4$ and concentrated. The crude was taken up in 5 mL MeOH and 4 mL HCl (4M in dioxane) and stirred at 60° C. for 1 hr. The resulting mixture was purified with prep-LCMS (XBridge C18 column, eluting with a gradient of acetonitrile/water containing 0.1% TFA, at flow rate of 60 mL/min). LCMS calculated for C$_{24}$H$_{33}$N$_8$O$_2$ (M+H)$^+$: m/z=465.3; found 465.4. $^1$H NMR (500 MHz, DMSO) δ 9.77 (s, 1H), 9.05 (s, 1H), 8.31 (m, 2H), 7.15 (m, 2H), 4.85 (m, 2H), 3.96 (m, 4H), 3.68 (s, 3H), 3.55 (d, J=12.2 Hz, 2H), 3.18 (m, 4H), 3.04 (m, 2H), 2.89 (m, 3H), 1.23 (s, 3H), 1.21 (s, 3H) ppm. The product was isolated as the TFA salt.

Example 23. Methyl (3R,5S)-4-(3-(3-fluoro-4-(4-methylpiperazin-1-yl)phenyl)-1H-pyrazolo[4,3-d]pyrimidin-5-yl)-3,5-dimethylpiperazine-1-carboxylate

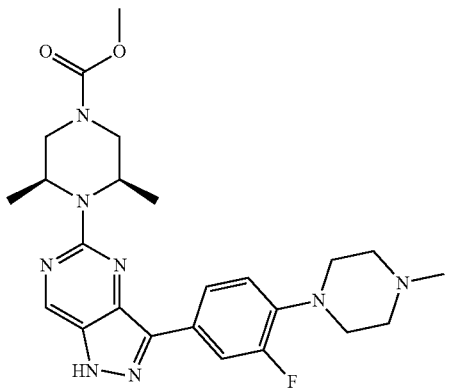

This compound was prepared according to the procedures described in Example 22, using 1-(2-fluoro-4-(4,4,5,5-tetramethyl-1,3,2-dioxaborolan-2-yl)phenyl)-4-methylpiperazine instead of (4-(4-methylpiperazin-1-yl)phenyl)boronic acid as starting material. LCMS calculated for C$_{24}$H$_{32}$FN$_8$O$_2$(M+H)$^+$: m/z=483.3; found: 483.5. The product was isolated as the TFA salt.

Example 24. Methyl (3R,5S)-3,5-dimethyl-4-(3-(6-(4-methylpiperazin-1-yl)pyridin-3-yl)-1H-pyrazolo[4,3-d]pyrimidin-5-yl)piperazine-1-carboxylate

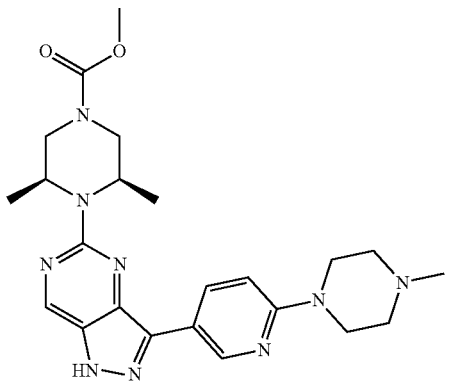

Step 1. Methyl (3R,5S)-4-(3-(6-fluoropyridin-3-yl)-1-((2-(trimethylsilyl)ethoxy)methyl)-1H-pyrazolo[4,3-d]pyrimidin-5-yl)-3,5-dimethylpiperazine-1-carboxylate

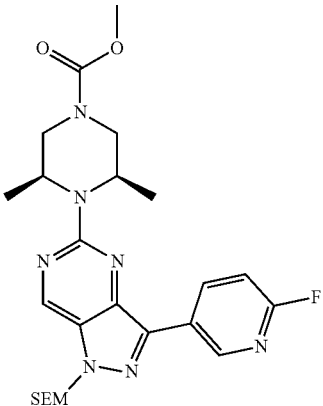 [SMILES: COC(=O)N1C[C@@H](C)N(c2ncc3c(n2)c(-c2ccc(F)nc2)nn3COCC[Si](C)(C)C)[C@@H](C)C1]

A solution of methyl (3R,5S)-4-(3-iodo-1-((2-(trimethylsilyl)ethoxy)methyl)-1H-pyrazolo[4,3-d]pyrimidin-5-yl)-3,5-dimethylpiperazine-1-carboxylate (100 mg, 0.183 mmol, see Example 22, Step 1), (6-fluoropyridin-3-yl)boronic acid (77 mg, 0.549 mmol), Xphos Pd G2 (21.60 mg, 0.027 mmol), and potassium phosphate (136 mg, 0.640 mmol) in dioxane (1.6 mL) and water (0.16 mL) was heated to 75° C. After 20 hrs, the reaction was cooled to r.t., diluted with water and extracted with EtOAc. The organic layer was washed with brine, dried with Na$_2$SO$_4$ and concentrated. The crude was used directly in the next step. LCMS calculated for C$_{24}$H$_{35}$FN$_7$O$_3$Si (M+H)$^+$: m/z=516.3; found 516.3.

Step 2. Methyl (3R,5S)-3,5-dimethyl-4-(3-(6-(4-methylpiperazin-1-yl)pyridin-3-yl)-1H-pyrazolo[4,3-d]pyrimidin-5-yl)piperazine-1-carboxylate A solution of methyl (3R,5S)-4-(3-(6-fluoropyridin-3-yl)-1-((2-(trimethylsilyl)ethoxy)methyl)-1H-pyrazolo[4,3-d]pyrimidin-5-yl)-3,5-dimethylpiperazine-1-carboxylate (20 mg, 0.039 mmol), 1-methylpiperazine (11.65 mg, 0.116 mmol), and N,N-diisopropylethylamine (135 µL, 0.776 mmol) in DMSO (1 mL) was heated to 120° C. After 20 hrs, the reaction was cooled to r.t., diluted with water and extracted with EtOAc. The organic layer was washed with brine, dried with Na$_2$SO$_4$ and concentrated. The crude was taken up in 1 mL MeOH and 0.8 mL HCl (4M in dioxane) and stirred at 60° C. for 2 hrs. The resulting mixture was purified with prep-LCMS (XBridge C18 column, eluting with a gradient of acetonitrile/water containing 0.1% TFA, at flow rate of 60 mL/min). LCMS calculated for C$_{23}$H$_{32}$N$_9$O$_2$ (M+H)$^+$: m/z=466.3; found: 466.3. The product was isolated as the TFA salt.

Example 25. Methyl (3R,5S)-4-(3-(4-(4-ethylpiperazin-1-yl)-3-methylphenyl)-1H-pyrazolo[4,3-d]pyrimidin-5-yl)-3,5-dimethylpiperazine-1-carboxylate

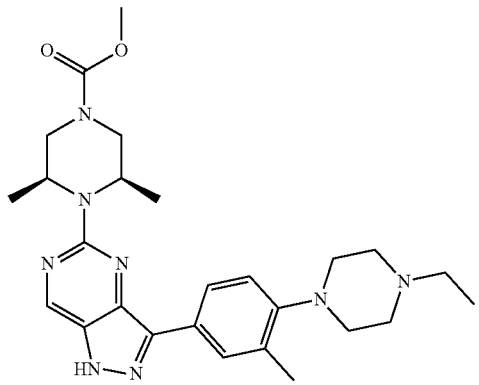 [SMILES: CCN1CCN(c2ccc(-c3n[nH]c4cnc(N5[C@H](C)CN(C(=O)OC)C[C@@H]5C)nc34)cc2C)CC1]

Step 1.
1-(4-Bromo-2-chlorophenyl)-4-ethylpiperazine

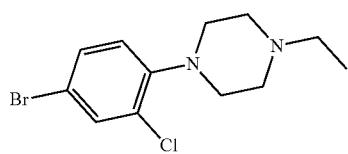 [SMILES: CCN1CCN(c2ccc(Br)cc2Cl)CC1]

A solution of 1-(4-bromo-2-chlorophenyl)piperazine (100 mg, 0.363 mmol), acetaldehyde (61 µL, 1.09 mmol), and sodium triacetoxyhydroborate (231 mg, 1.09 mmol) in DCM (5 mL) was stirred at r.t. for 20 hrs. The reaction mixture was then diluted with water and extracted with DCM. The organic layer was washed with brine, dried with Na$_2$SO$_4$ and concentrated. The crude was purified by CombiFlash Rf+ Lumen. LCMS calculated for C$_{12}$H$_{17}$BrClN$_2$ (M+H)$^+$: m/z=303.0; found 303.0.

Step 2. 1-(2-Chloro-4-(4,4,5,5-tetramethyl-1,3,2-dioxaborolan-2-yl)phenyl)-4-ethylpiperazine

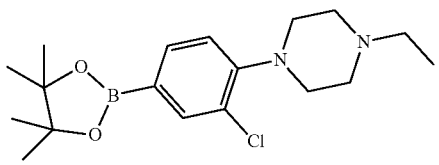 [SMILES: CCN1CCN(c2ccc(B3OC(C)(C)C(C)(C)O3)cc2Cl)CC1]

A solution of 1-(4-bromo-2-chlorophenyl)-4-ethylpiperazine (78.6 mg, 0.259 mmol), bis(pinacolato)diboron (65.7 mg, 0.259 mmol), PdCl$_2$dppf.DCM (31.7 mg, 0.039 mmol), and potassium acetate (76 mg, 0.777 mmol) in dioxane (2.59 mL) was heated to 85° C. for 20 hrs. The reaction mixture was cooled to r.t., diluted with EtOAc and filtered through celite. The organic layer was concentrated and purified by CombiFlash Rf+ Lumen. LCMS calculated for C$_{18}$H$_{29}$BClN$_2$O$_2$(M+H)$^+$: m/z=351.2; found 351.1.

Step 3. Methyl (3R,5S)-4-(3-(3-chloro-4-(4-ethylpiperazin-1-yl)phenyl)-1-((2-(trimethylsilyl)ethoxy)methyl)-1H-pyrazolo[4,3-d]pyrimidin-5-yl)-3,5-dimethylpiperazine-1-carboxylate

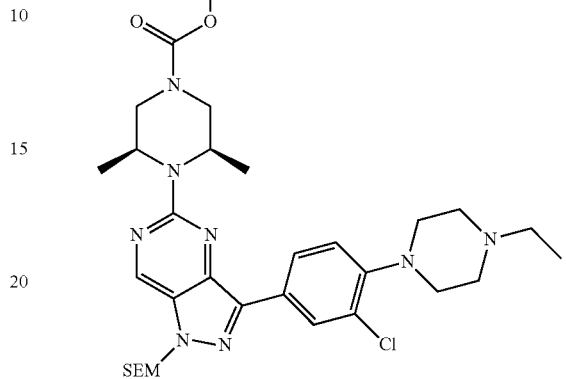

A solution of methyl (3R,5S)-4-(3-iodo-1-((2-(trimethylsilyl)ethoxy)methyl)-1H-pyrazolo[4,3-d]pyrimidin-5-yl)-3,5-dimethylpiperazine-1-carboxylate (49.7 mg, 0.091 mmol, see Example 22, Step 1), 1-(2-chloro-4-(4,4,5,5-tetramethyl-1,3,2-dioxaborolan-2-yl)phenyl)-4-ethylpiperazine (32.1 mg, 0.091 mmol), Xphos Pd G2 (14.40 mg, 0.018 mmol), and potassium phosphate (58.3 mg, 0.274 mmol) in dioxane (2 mL) and water (0.2 mL) was heated to 75° C. After 20 hrs, the reaction mixture was cooled to r.t., diluted with water and EtOAc. The organic layer was concentrated and purified by CombiFlash Rf+ Lumen. LCMS calculated for C$_{31}$H$_{48}$ClN$_8$O$_3$Si (M+H)$^+$: m/z=643.3; found 643.4.

Step 4. Methyl (3R,5S)-4-(3-(4-(4-ethylpiperazin-1-yl)-3-methylphenyl)-1H-pyrazolo[4,3-d]pyrimidin-5-yl)-3,5-dimethylpiperazine-1-carboxylate A solution of methyl (3R,5S)-4-(3-(3-chloro-4-(4-ethylpiperazin-1-yl)phenyl)-1-((2-(trimethylsilyl)ethoxy)methyl)-1H-pyrazolo[4,3-d]pyrimidin-5-yl)-3,5-dimethylpiperazine-1-carboxylate (30 mg, 0.047 mmol), 2,4,6-trimethyl-1,3,5,2,4,6-trioxatriborinane (65 µL, 0.47 mmol), Xphos Pd G2 (18.35 mg, 0.023 mmol), and potassium phosphate (49.5 mg, 0.233 mmol) in dioxane (2 mL) and water (0.200 mL) was heated to 75° C. After 20 hrs, the reaction was cooled to r.t., diluted with water and extracted with EtOAc. The organic layer was washed with brine, dried with Na$_2$SO$_4$ and concentrated. The crude was taken up in 1 mL MeOH and 0.8 mL HCl (4M in dioxane) and stirred at 60° C. for 2 hrs. The resulting mixture was purified with prep-LCMS (XBridge C18 column, eluting with a gradient of acetonitrile/water containing 0.1% TFA, at flow rate of 60 mL/min). LCMS calculated for C$_{25}$H$_{35}$N$_8$O$_2$ (M+H)$^+$: m/z=493.3; found 493.1. The product was isolated as the TFA salt.

Example 26. Methyl (3R,5S)-3,5-dimethyl-4-(3-(4-(methylcarbamoyl)phenyl)-1H-pyrazolo[4,3-d]pyrimidin-5-yl)piperazine-1-carboxylate

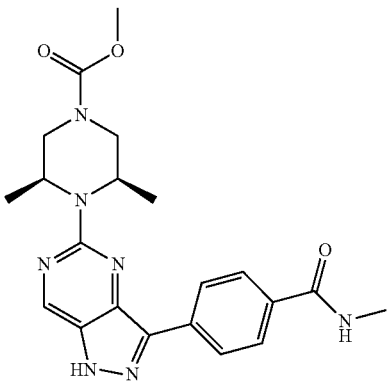

This compound was prepared according to the procedures described in Example 22, using (4-(methylcarbamoyl)phenyl)boronic acid instead of (4-(4-methylpiperazin-1-yl)phenyl)boronic acid as starting material. LCMS calculated for $C_{21}H_{26}N_7O_3$ (M+H)$^+$: m/z=424.2; found: 424.1. The product was isolated as the TFA salt.

Example 27. Methyl (3R,5S)-3,5-dimethyl-4-(3-(4-(1-methylpyrrolidin-3-yl)phenyl)-1H-pyrazolo[4,3-d]pyrimidin-5-yl)piperazine-1-carboxylate

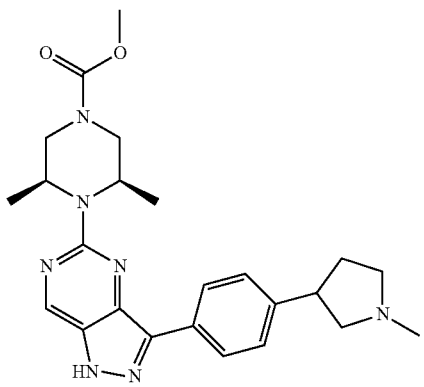

Step 1. 1-Methyl-3-(4-(4,4,5,5-tetramethyl-1,3,2-dioxaborolan-2-yl)phenyl)pyrrolidine

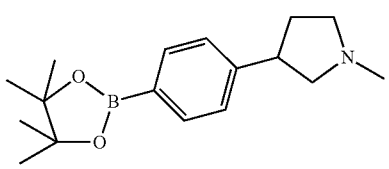

A solution of 3-(4-bromophenyl)-1-methylpyrrolidine (0.23 g, 0.958 mmol), bis(pinacolato)diboron (0.340 g, 1.341 mmol), PdCl$_2$dppf.DCM (0.078 g, 0.096 mmol), and potassium acetate (0.282 g, 2.87 mmol) in dioxane (4.79 mL) was heated to 85° C. for 16 hrs. The reaction mixture was cooled to r.t., diluted with EtOAc and filtered through celite. The organic layer was concentrated and purified by CombiFlash Rf+ Lumen. LCMS calculated for $C_{17}H_{27}BNO_2$(M+H)$^+$: m/z=288.2; found 288.2.

Step 2. Methyl (3R,5S)-3,5-dimethyl-4-(3-(4-(1-methylpyrrolidin-3-yl)phenyl)-1H-pyrazolo[4,3-d]pyrimidin-5-yl)piperazine-1-carboxylate A solution of methyl (3R,5S)-4-(3-iodo-1-((2-(trimethylsilyl)ethoxy)methyl)-1H-pyrazolo[4,3-d]pyrimidin-5-yl)-3,5-dimethylpiperazine-1-carboxylate (25 mg, 0.046 mmol, see Example 22, Step 1), 1-methyl-3-(4-(4,4,5,5-tetramethyl-1,3,2-dioxaborolan-2-yl)phenyl)pyrrolidine (39.4 mg, 0.137 mmol), Xphos Pd G2 (7.2 mg, 9.2 μmol), and potassium phosphate (34.0 mg, 0.160 mmol) in dioxane (1 mL) and water (0.1 mL) was heated to 75° C. After 20 hrs, the reaction was cooled to r.t., diluted with water and extracted with EtOAc. The organic layer was washed with brine, dried with Na$_2$SO$_4$ and concentrated. The crude was taken up in 1 mL MeOH and 0.8 mL HCl (4M in dioxane) and stirred at 60° C. for 2 hrs. The resulting mixture was purified with prep-LCMS (XBridge C18 column, eluting with a gradient of acetonitrile/water containing 0.1% TFA, at flow rate of 60 mL/min). LCMS calculated for $C_{24}H_{32}N_7O_2$ (M+H)$^+$: m/z=450.3; found 450.2. The product was isolated as the TFA salt.

Example 28. Methyl (3R,5S)-4-(3-(4-(1-(2-hydroxyethyl)pyrrolidin-3-yl)phenyl)-1H-pyrazolo[4,3-d]pyrimidin-5-yl)-3,5-dimethylpiperazine-1-carboxylate

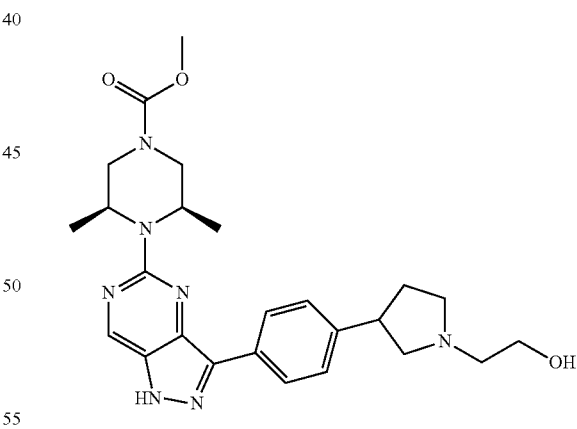

Step 1. 3-(4-Bromophenyl)-1-(2-((tert-butyldimethylsilyl)oxy)ethyl)pyrrolidine

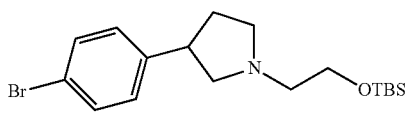 [SMILES: CC(C)(C)[Si](C)(C)OCCN1CCC(c2ccc(Br)cc2)C1]

A solution of 2-((tert-butyldimethylsilyl)oxy)acetaldehyde (0.239 mL, 1.257 mmol), 3-(4-bromophenyl)pyrrolidine hydrochloride (110 mg, 0.419 mmol), and sodium triacetoxyhydroborate (266 mg, 1.257 mmol) in DCM (5 mL) was stirred at r.t. for 20 hrs. The reaction mixture was then diluted with water and extracted with DCM. The organic layer was washed with brine, dried with $Na_2SO_4$ and concentrated. The crude was purified by CombiFlash Rf+ Lumen. LCMS calculated for $C_{18}H_{31}BrNOSi$ $(M+H)^+$: m/z=384.1; found 384.1.

Step 2. 1-(2-((tert-Butyldimethylsilyl)oxy)ethyl)-3-(4-(4,4,5,5-tetramethyl-1,3,2-dioxaborolan-2-yl)phenyl)pyrrolidine

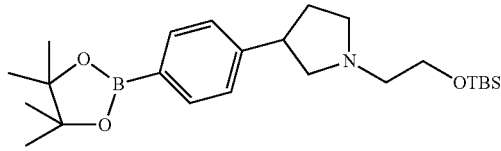 [SMILES: CC1(C)OB(c2ccc(C3CCN(CCO[Si](C)(C)C(C)(C)C)C3)cc2)OC1(C)C]

A solution of 3-(4-bromophenyl)-1-(2-((tert-butyldimethylsilyl)oxy)ethyl)pyrrolidine (205 mg, 0.533 mmol), bis(pinacolato)diboron (190 mg, 0.747 mmol), PdCl$_2$dppf.DCM (65.3 mg, 0.080 mmol), and potassium acetate (157 mg, 1.600 mmol) in dioxane (4 mL) was heated to 85° C. for 16 hrs. The reaction mixture was cooled to r.t., diluted with EtOAc and filtered through celite. The organic layer was concentrated and purified by CombiFlash Rf+ Lumen. LCMS calculated for $C_{24}H_{43}BNO_3Si$ $(M+H)^+$: m/z=432.3; found 432.2.

Step 3. Methyl (3R,5S)-4-(3-(4-(1-(2-hydroxyethyl)pyrrolidin-3-yl)phenyl)-1H-pyrazolo[4,3-d]pyrimidin-5-yl)-3,5-dimethylpiperazine-1-carboxylate A solution of methyl (3R,5S)-4-(3-iodo-1-((2-(trimethylsilyl)ethoxy)methyl)-1H-pyrazolo[4,3-d]pyrimidin-5-yl)-3,5-dimethylpiperazine-1-carboxylate (30 mg, 0.055 mmol, see Example 22, Step 1), 1-(2-((tert-butyldimethylsilyl)oxy)ethyl)-3-(4-(4,4,5,5-tetramethyl-1,3,2-dioxaborolan-2-yl)phenyl)pyrrolidine (230 mg, 0.533 mmol), Xphos Pd G2 (25.9 mg, 0.033 mmol), and potassium phosphate (69.9 mg, 0.329 mmol) in dioxane (2 mL) and water (0.2 mL) was heated to 75° C. After 20 hrs, the reaction was cooled to r.t., diluted with water and extracted with EtOAc. The organic layer was washed with brine, dried with $Na_2SO_4$ and concentrated. The crude was taken up in 1 mL MeOH and 0.8 mL HCl (4M in dioxane) and stirred at 60° C. for 2 hrs. The resulting mixture was purified with prep-LCMS (XBridge C18 column, eluting with a gradient of acetonitrile/water containing 0.1% TFA, at flow rate of 60 mL/min). LCMS calculated for $C_{25}H_{34}N_7O_3$ $(M+H)^+$: m/z=480.3; found 480.3. The product was isolated as the TFA salt.

Example 29. Methyl (3R,5S)-4-(3-(4-(4-(1-hydroxypropan-2-yl)piperazin-1-yl)phenyl)-1H-pyrazolo[4,3-d]pyrimidin-5-yl)-3,5-dimethylpiperazine-1-carboxylate This compound was prepared according to the procedures described in Example 28, using 1-(4-bromophenyl)piperazine and 1-((tert-butyldimethylsilyl)oxy)propan-2-one instead of 3-(4-bromophenyl)pyrrolidine hydrochloride and 2-((tert-butyldimethylsilyl)oxy)acetaldehyde as starting material. LCMS calculated for $C_{26}H_{37}N_8O_3$ $(M+H)^+$: m/z=509.3; found: 509.5. The product was isolated as the TFA salt.

Example 30. Methyl (3R,5S)-3,5-dimethyl-4-(3-(4-(4-(tetrahydro-2H-pyran-4-yl)piperazin-1-yl)phenyl)-1H-pyrazolo[4,3-d]pyrimidin-5-yl)piperazine-1-carboxylate

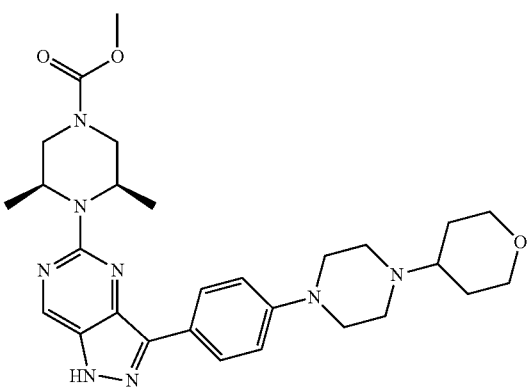 [SMILES: COC(=O)N1C[C@@H](C)N(c2ncc3[nH]nc(-c4ccc(N5CCN(C6CCOCC6)CC5)cc4)c3n2)[C@@H](C)C1]

This compound was prepared according to the procedures described in Example 28, using 1-(4-bromophenyl)piperazine and tetrahydro-4H-pyran-4-one instead of 3-(4-bromophenyl)pyrrolidine hydrochloride and 2-((tert-butyldimethylsilyl)oxy)acetaldehyde as starting material. LCMS calculated for $C_{28}H_{39}N_8O_3$ $(M+H)^+$: m/z=535.3; found: 535.2. The product was isolated as the TFA salt.

Example 31. 2-(4-(4-(5-((2R,6S)-4-(Methoxycarbonyl)-2,6-dimethylpiperazin-1-yl)-1H-pyrazolo[4,3-d]pyrimidin-3-yl)phenyl)piperazin-1-yl)-2-methylpropanoic acid

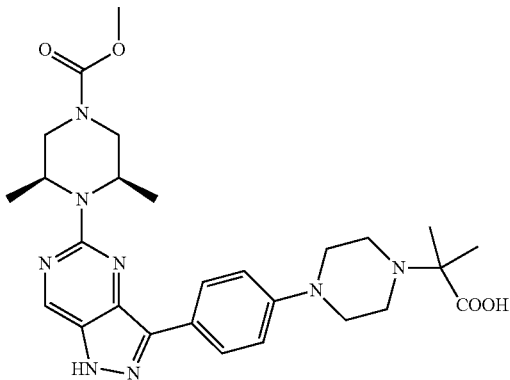 [SMILES: COC(=O)N1C[C@@H](C)N(c2ncc3[nH]nc(-c4ccc(N5CCN(C(C)(C)C(=O)O)CC5)cc4)c3n2)[C@@H](C)C1]

Step 1. tert-Butyl 2-(4-(4-bromophenyl)piperazin-1-yl)-2-methylpropanoate

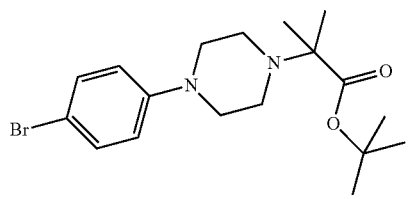 [SMILES: CC(C)(C)OC(=O)C(C)(C)N1CCN(c2ccc(Br)cc2)CC1]

A mixture of 1-(4-bromophenyl)piperazine (138 mg, 0.572 mmol), tert-butyl 2-bromo-2-methylpropanoate (0.320 mL, 1.717 mmol), and potassium carbonate (395 mg, 2.86 mmol) in acetonitrile (5 mL) was heated to 85° C. for 3 days. The reaction mixture was then diluted with EtOAc and water. The organic layer was washed with brine, dried with Na$_2$SO$_4$ and concentrated. The crude was purified by CombiFlash Rf+ Lumen. LCMS calculated for C$_{18}$H$_{28}$BrN$_2$O$_2$(M+H)$^+$: m/z=383.1; found 383.3.

Step 2. tert-Butyl 2-methyl-2-(4-(4-(4,4,5,5-tetramethyl-1,3,2-dioxaborolan-2-yl)phenyl)piperazin-1-yl)propanoate

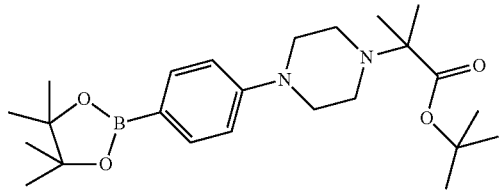 [SMILES: CC(C)(C)OC(=O)C(C)(C)N1CCN(c2ccc(B3OC(C)(C)C(C)(C)O3)cc2)CC1]

A solution of tert-butyl 2-(4-(4-bromophenyl)piperazin-1-yl)-2-methylpropanoate (153 mg, 0.399 mmol), bis(pinacolato)diboron (142 mg, 0.559 mmol), PdCl$_2$dppf.DCM (48.9 mg, 0.060 mmol), and potassium acetate (118 mg, 1.197 mmol) in dioxane (3 mL) was heated to 85° C. for 20 hrs. The reaction mixture was cooled to r.t., diluted with EtOAc and filtered through celite. The organic layer was concentrated and purified by CombiFlash Rf+ Lumen. LCMS calculated for C$_{24}$H$_{40}$BN$_2$O$_4$(M+H)$^+$: m/z=431.3; found 431.5.

Step 3. 2-(4-(4-(5-((2R,6S)-4-(Methoxycarbonyl)-2,6-dimethylpiperazin-1-yl)-1H-pyrazolo[4,3-d]pyrimidin-3-yl)phenyl)piperazin-1-yl)-2-methylpropanoic acid A solution of methyl (3R,5S)-4-(3-iodo-1-((2-(trimethylsilyl)ethoxy)methyl)-1H-pyrazolo [4,3-d]pyrimidin-5-yl)-3,5-dimethylpiperazine-1-carboxylate (60 mg, 0.110 mmol, see Example 22, Step 1), tert-butyl 2-methyl-2-(4-(4-(4,4,5,5-tetramethyl-1,3,2-dioxaborolan-2-yl)phenyl)piperazin-1-yl)propanoate (135 mg, 0.314 mmol), Xphos Pd G2 (12.96 mg, 0.016 mmol), and potassium phosphate (93 mg, 0.439 mmol) in dioxane (1.5 mL) and water (0.150 mL) was heated to 70° C. After 20 hrs, the reaction was cooled to r.t., diluted with water and extracted with EtOAc. The organic layer was washed with brine, dried with Na$_2$SO$_4$ and concentrated. The crude was taken up in 1 mL MeOH and 0.8 mL HCl (4M in dioxane) and stirred at 60° C. for 2 hrs. The resulting mixture was purified with prep-LCMS (XBridge C18 column, eluting with a gradient of acetonitrile/water containing 0.1% TFA, at flow rate of 60 mL/min). LCMS calculated for C$_{27}$H$_{37}$N$_8$O$_4$ (M+H)$^+$: m/z=537.3; found 537.4. The product was isolated as the TFA salt.

Example 32. Methyl (3R,5S)-3,5-dimethyl-4-(3-(6-((R)-2-methylmorpholino)pyridin-3-yl)-1H-pyrazolo[4,3-d]pyrimidin-5-yl)piperazine-1-carboxylate

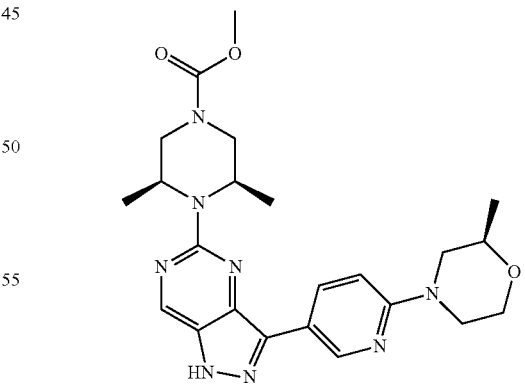

This compound was prepared according to the procedures described in Example 24, using (R)-2-methylmorpholine hydrochloride instead of 1-methylpiperazine as starting material. LCMS calculated for C$_{23}$H$_{31}$N$_8$O$_3$ (M+H)$^+$: m/z=467.2; found: 467.3. The product was isolated as the TFA salt.

Example 33. Methyl (3R,5S)-4-(3-(6-((R)-3,4-dimethylpiperazin-1-yl)pyridin-3-yl)-1H-pyrazolo[4,3-d]pyrimidin-5-yl)-3,5-dimethylpiperazine-1-carboxylate

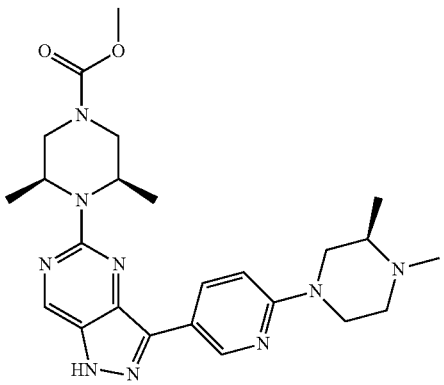

This compound was prepared according to the procedures described in Example 24, using (R)-1,2-dimethylpiperazine dihydrochloride instead of 1-methylpiperazine as starting material. LCMS calculated for $C_{24}H_{34}N_9O_2$ (M+H)$^+$: m/z=480.3; found: 480.3. The product was isolated as the TFA salt.

Example 34. Methyl (3R,5S)-4-(3-(4-(4-hydroxypiperidin-1-yl)phenyl)-1H-pyrazolo[4,3-d]pyrimidin-5-yl)-3,5-dimethylpiperazine-1-carboxylate

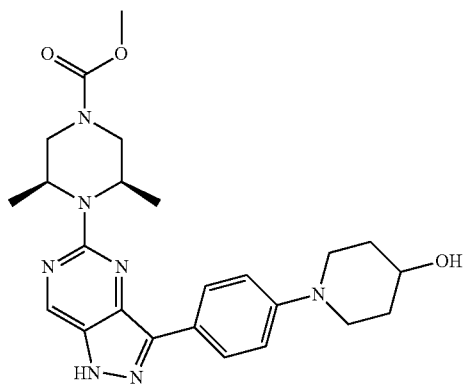 [SMILES: COC(=O)N1C[C@@H](C)N(c2ncc3[nH]nc(-c4ccc(N5CCC(O)CC5)cc4)c3n2)[C@@H](C)C1]

Step 1. Methyl (3R,5S)-4-(3-(4-chlorophenyl)-1-((2-(trimethylsilyl)ethoxy)methyl)-1H-pyrazolo[4,3-d]pyrimidin-5-yl)-3,5-dimethylpiperazine-1-carboxylate

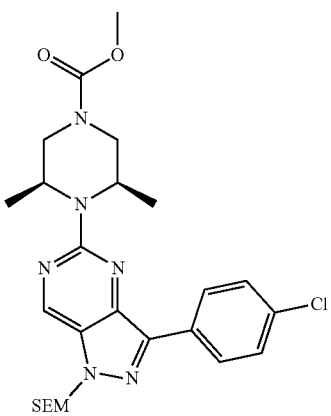 [SMILES: COC(=O)N1C[C@@H](C)N(c2ncc3c(n2)c(-c2ccc(Cl)cc2)nn3COCC[Si](C)(C)C)[C@@H](C)C1]

A solution of methyl (3R,5S)-4-(3-iodo-1-((2-(trimethylsilyl)ethoxy)methyl)-1H-pyrazolo[4,3-d]pyrimidin-5-yl)-3,5-dimethylpiperazine-1-carboxylate (500 mg, 0.915 mmol, see Example 22, Step 1), (4-chlorophenyl)boronic acid (0.286 g, 1.830 mmol), Pd$_2$(dba)$_3$ (0.042 g, 0.046 mmol), tri(o-tolyl)phosphine (0.056 g, 0.183 mmol), and potassium phosphate (0.777 g, 3.66 mmol) in DMF (5 mL) was heated to 80° C. After 2 days, the reaction mixture was cooled to r.t., diluted with EtOAc and filtered through celite. The organic layer was washed with brine, dried with Na$_2$SO$_4$ and concentrated. The organic layer was concentrated and purified by CombiFlash Rf+ Lumen. LCMS calculated for $C_{25}H_{36}ClN_6O_3Si$ (M+H)$^+$: m/z=531.2; found 531.3.

Step 2. Methyl (3R,5S)-4-(3-(4-(4-hydroxypiperidin-1-yl)phenyl)-1H-pyrazolo[4,3-d]pyrimidin-5-yl)-3,5-dimethylpiperazine-1-carboxylate A solution of methyl (3R,5S)-4-(3-(4-chlorophenyl)-1-((2-(trimethylsilyl)ethoxy)methyl)-1H-pyrazolo[4,3-d]pyrimidin-5-yl)-3,5-dimethylpiperazine-1-carboxylate (12 mg, 0.023 mmol), piperidin-4-ol (4.57 mg, 0.045 mmol), RuPhos Pd G3 (2.83 mg, 3.39 µmol), RuPhos (1.6 mg, 3.4 µmol), and sodium tert-butoxide (10.9 mg, 0.113 mmol) in THF (1 mL) was heated to 85° C. After 20 hrs, the reaction was cooled to r.t., diluted with water and extracted with EtOAc. The organic layer was washed with brine, dried with Na$_2$SO$_4$ and concentrated. The crude was taken up in 1 mL MeOH and 0.8 mL HCl (4M in dioxane) and stirred at 60° C. for 2 hrs. The resulting mixture was purified with prep-LCMS (XBridge C18 column, eluting with a gradient of acetonitrile/water containing 0.1% TFA, at flow rate of 60 mL/min). LCMS calculated for $C_{24}H_{32}N_7O_3$ (M+H)$^+$: m/z=466.3; found 466.4. The product was isolated as the TFA salt.

Example 35. Methyl (3R,5S)-4-(3-(4-((7S,8aR)-7-hydroxyhexahydropyrrolo[1,2-a]pyrazin-2(1H)-yl)phenyl)-1H-pyrazolo[4,3-d]pyrimidin-5-yl)-3,5-dimethylpiperazine-1-carboxylate

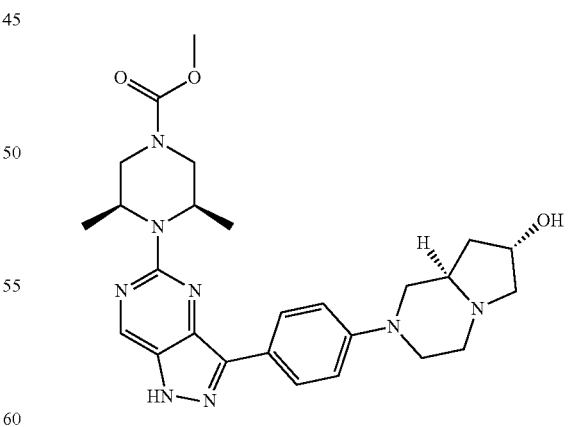

This compound was prepared according to the procedures described in Example 34, using (7S,8aR)-octahydropyrrolo[1,2-a]pyrazin-7-ol dihydrochloride instead of piperidin-4-ol as starting material. LCMS calculated for $C_{26}H_{35}N_8O_3$ (M+H)$^+$: m/z=507.3; found: 507.4. The product was isolated as the TFA salt.

Example 36. 1-Methyl-4-(3-(1-methyl-1H-pyrazol-4-yl)-1H-pyrazolo[4,3-d]pyrimidin-5-yl)piperazin-2-one

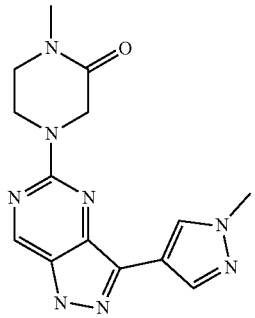 [SMILES: CN1CCN(c2ncc3[nH]nc(-c4cnn(C)c4)c3n2)CC1=O]

Step 1. 5-Chloro-3-(1-methyl-1H-pyrazol-4-yl)-1-((2-(trimethylsilyl)ethoxy)methyl)-1H-pyrazolo[4,3-d]pyrimidine

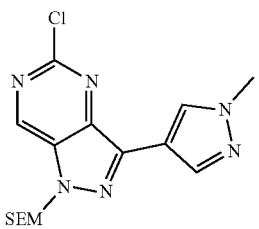 [SMILES: Cn1cc(-c2nn(COCC[Si](C)(C)C)c3cnc(Cl)nc23)cn1]

A solution of 5-chloro-3-iodo-1-((2-(trimethylsilyl)ethoxy)methyl)-1H-pyrazolo[4,3-d]pyrimidine (1.0 g, 2.435 mmol), 1-methyl-4-(4,4,5,5-tetramethyl-1,3,2-dioxaborolan-2-yl)-1H-pyrazole (0.507 g, 2.435 mmol), Xphos Pd G2 (0.192 g, 0.243 mmol), and potassium phosphate (1.550 g, 7.30 mmol) in dioxane (15 mL) and water (1.5 mL) was heated to 75° C. After 20 hrs, the reaction mixture was cooled to r.t., quenched with water and EtOAc. The organic layer was washed with brine, dried with $Na_2SO_4$ and purified by CombiFlash Rf+ Lumen. LCMS calculated for $C_{15}H_{22}ClN_6OSi$ (M+H)$^+$: m/z=365.1; found 365.1.

Step 2. 1-Methyl-4-(3-(1-methyl-1H-pyrazol-4-yl)-1H-pyrazolo[4,3-d]pyrimidin-5-yl)piperazin-2-one A solution of 5-chloro-3-(1-methyl-1H-pyrazol-4-yl)-1-((2-(trimethylsilyl)ethoxy)methyl)-1H-pyrazolo[4,3-d]pyrimidine (40 mg, 0.110 mmol), 1-methylpiperazin-2-one hydrochloride (33.0 mg, 0.219 mmol), and N,N-diisopropylethylamine (56.7 mg, 0.438 mmol) in dioxane (1 mL) was heated to 100° C. After 20 hrs, the reaction was cooled to r.t., diluted with water and extracted with EtOAc. The organic layer was washed with brine, dried with $Na_2SO_4$ and concentrated. The crude was taken up in 1 mL MeOH and 1 mL HCl (4 M solution in dioxane) and stirred at 60° C. for 2 hrs. The resulting mixture was purified with prep-LCMS (XBridge C18 column, eluting with a gradient of acetonitrile/water containing 0.1% TFA, at flow rate of 60 mL/min). LCMS calculated for $C_{14}H_{17}N_8O$ (M+H)$^+$: m/z=313.1; found 313.1. The product was isolated as the TFA salt.

Example 37. 1-Cyclopropyl-4-(3-(1-methyl-1H-pyrazol-4-yl)-1H-pyrazolo[4,3-d]pyrimidin-5-yl)piperazin-2-one

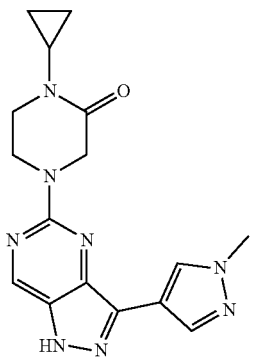 [SMILES: Cn1cc(-c2n[nH]c3cnc(N4CCN(C5CC5)C(=O)C4)nc23)cn1]

This compound was prepared according to the procedures described in Example 36, using 1-cyclopropylpiperazin-2-one instead of 1-methylpiperazin-2-one hydrochloride as starting material. LCMS calculated for $C_{16}H_{19}N_8O$ (M+H)$^+$: m/z=339.2; found: 339.0. The product was isolated as the TFA salt.

Example 38. 1,3-Dimethyl-4-(3-(1-methyl-1H-pyrazol-4-yl)-1H-pyrazolo[4,3-d]pyrimidin-5-yl)piperazin-2-one

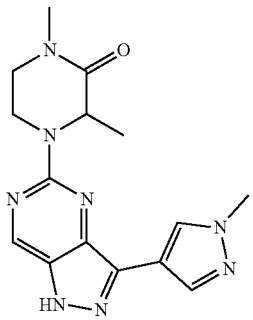 [SMILES: CC1C(=O)N(C)CCN1c1ncc2[nH]nc(-c3cnn(C)c3)c2n1]

A solution of 5-chloro-3-(1-methyl-1H-pyrazol-4-yl)-1-((2-(trimethylsilyl)ethoxy)methyl)-1H-pyrazolo[4,3-d]pyrimidine (40 mg, 0.110 mmol, see Example 36, Step 1), 1,3-dimethylpiperazin-2-one hydrochloride (27.1 mg, 0.164 mmol), RuPhos (10.2 mg, 0.022 mmol), RuPhos Pd G3 (18.3 mg, 0.022 mmol), and sodium tert-butoxide (31.6 mg, 0.329 mmol) in THF (1 mL) was heated to 85° C. After 20 hrs, the reaction was cooled to r.t., diluted with water and extracted with EtOAc. The organic layer was washed with brine, dried with $Na_2SO_4$ and concentrated. The crude was taken up in 1 mL MeOH and 1 mL HCl (4 M solution in dioxane) and stirred at 60° C. for 2 hrs. The resulting mixture was purified with prep-LCMS (XBridge C18 column, eluting with a gradient of acetonitrile/water containing 0.1% TFA, at flow rate of 60 mL/min). LCMS calculated for $C_{15}H_{19}N_8O$ (M+H)$^+$: m/z=327.2; found 327.1. The product was isolated as the TFA salt.

Example 39. 3-Ethyl-1-methyl-4-(3-(1-methyl-1H-pyrazol-4-yl)-1H-pyrazolo[4,3-d]pyrimidin-5-yl)piperazin-2-one

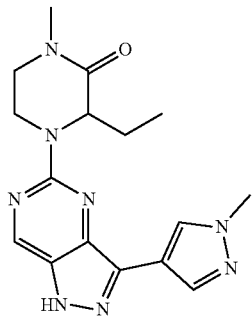 [SMILES: CCC1C(=O)N(C)CCN1c1ncc2[nH]nc(-c3cnn(C)c3)c2n1]

This compound was prepared according to the procedures described in Example 38, using 3-ethyl-1-methylpiperazin-2-one instead of 1,3-dimethylpiperazin-2-one hydrochloride as starting material. LCMS calculated for $C_{16}H_{21}N_8O$ (M+H)$^+$: m/z=341.2; found: 341.2. The product was isolated as the TFA salt.

Example 40. 6-(3-(1-Methyl-1H-pyrazol-4-yl)-1H-pyrazolo[4,3-d]pyrimidin-5-yl)-5,6,7,8-tetrahydro-1,6-naphthyridine

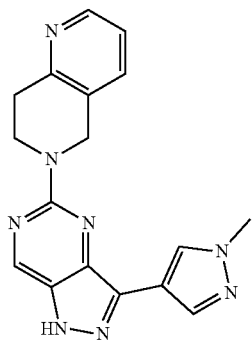 [SMILES: Cn1cc(-c2n[nH]c3cnc(N4CCc5ncccc5C4)nc23)cn1]

This compound was prepared according to the procedures described in Example 38, using 5,6,7,8-tetrahydro-1,6-naphthyridine instead of 1,3-dimethylpiperazin-2-one hydrochloride as starting material. LCMS calculated for $C_{17}H_{17}N_8$ (M+H)$^+$: m/z=333.2; found: 333.2. The product was isolated as the TFA salt.

Example 41. 3-(1-Methyl-1H-pyrazol-4-yl)-5-(1-(trifluoromethyl)-5,6-dihydroimidazo[1,5-a]pyrazin-7(8H)-yl)-1H-pyrazolo[4,3-d]pyrimidine

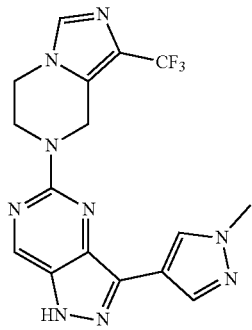 [SMILES: Cn1cc(-c2n[nH]c3cnc(N4CCn5cnc(C(F)(F)F)c5C4)nc23)cn1]

This compound was prepared according to the procedures described in Example 38, using 1-(trifluoromethyl)-5,6,7,8-tetrahydroimidazo[1,5-a]pyrazine instead of 1,3-dimethylpiperazin-2-one hydrochloride as starting material. LCMS calculated for $C_{16}H_{15}F_3N_9$ (M+H)$^+$: m/z=390.1; found: 390.0. The product was isolated as the TFA salt.

Example 42. 5-(3-(1-Methyl-1H-pyrazol-4-yl)-1H-pyrazolo[4,3-d]pyrimidin-5-yl)-4,5,6,7-tetrahydrothiazolo[5,4-c]pyridine

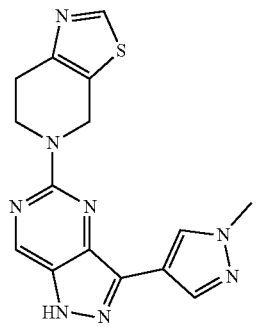 [SMILES: Cn1cc(-c2n[nH]c3cnc(N4CCc5ncsc5C4)nc23)cn1]

This compound was prepared according to the procedures described in Example 38, using 4,5,6,7-tetrahydrothiazolo[5,4-c]pyridine hydrochloride instead of 1,3-dimethylpiperazin-2-one hydrochloride as starting material. LCMS calculated for $C_{15}H_{15}N_8S$ (M+H)$^+$: m/z=339.1; found: 339.1. The product was isolated as the TFA salt.

Example 43. 3-(1-Methyl-1H-pyrazol-4-yl)-5-(8-methyl-5,6-dihydroimidazo[1,2-a]pyrazin-7(8H)-yl)-1H-pyrazolo[4,3-d]pyrimidine

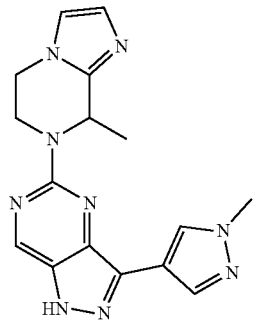 [SMILES: CC1c2nccn2CCN1c1ncc2[nH]nc(-c3cnn(C)c3)c2n1]

This compound was prepared according to the procedures described in Example 38, using 8-methyl-5,6,7,8-tetrahydroimidazo[1,2-a]pyrazine instead of 1,3-dimethylpiperazin-2-one hydrochloride as starting material. LCMS calculated for $C_{16}H_{18}N_9$(M+H)$^+$: m/z=336.2; found: 336.0. The product was isolated as the TFA salt.

Example 44. 3-(1-Methyl-1H-pyrazol-4-yl)-5-(1,4,5,7-tetrahydro-6H-pyrazolo[3,4-c]pyridin-6-yl)-1H-pyrazolo[4,3-d]pyrimidine

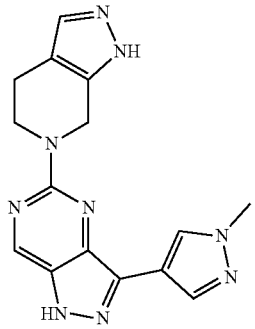 [SMILES: Cn1cc(-c2n[nH]c3cnc(N4CCc5cn[nH]c5C4)nc23)cn1]

This compound was prepared according to the procedures described in Example 36, using 4,5,6,7-tetrahydro-3H-imidazo[4,5-c]pyridine instead of 1-methylpiperazin-2-one hydrochloride as starting material. LCMS calculated for $C_{15}H_{16}N_9(M+H)^+$: m/z=322.2; found: 322.2. The product was isolated as the TFA salt.

Example 45. 9-(3-(1-Methyl-1H-pyrazol-4-yl)-1H-pyrazolo[4,3-d]pyrimidin-5-yl)-1,4,5,6,7,8-hexahydro-4,7-epiminocyclohepta[c]pyrazole

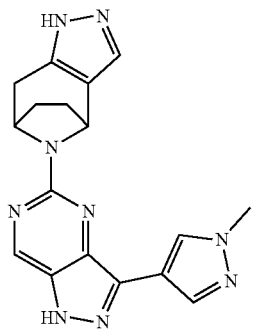 [SMILES: Cn1cc(-c2n[nH]c3cnc(N4C5CCC4c4cn[nH]c4C5)nc23)cn1]

This compound was prepared according to the procedures described in Example 36, using 1,4,5,6,7,8-hexahydro-4,7-epiminocyclohepta[c]pyrazole dihydrochloride instead of 1-methylpiperazin-2-one hydrochloride as starting material. LCMS calculated for $C_{17}H_{18}N_9 (M+H)^+$: m/z=348.2; found: 348.2. The product was isolated as the TFA salt.

Example 46. 1-(2,2-Difluoroethyl)-3-methyl-4-(3-(1-methyl-1H-pyrazol-4-yl)-1H-pyrazolo[4,3-d]pyrimidin-5-yl)piperazin-2-one

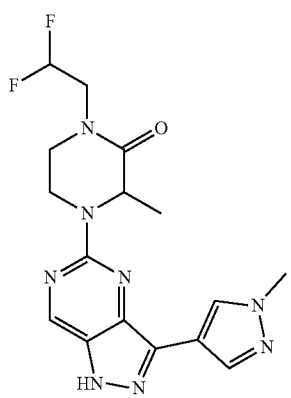 [SMILES: CC1C(=O)N(CC(F)F)CCN1c1ncc2[nH]nc(-c3cnn(C)c3)c2n1]

Step 1. 3-Methyl-4-(3-(1-methyl-1H-pyrazol-4-yl)-1-((2-(trimethylsilyl)ethoxy)methyl)-1H-pyrazolo[4,3-d]pyrimidin-5-yl)piperazin-2-one

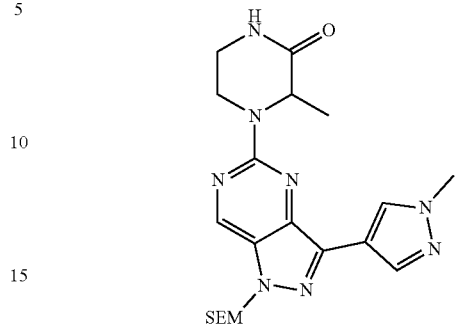

A solution of 5-chloro-3-(1-methyl-1H-pyrazol-4-yl)-1-((2-(trimethylsilyl)ethoxy)methyl)-1H-pyrazolo[4,3-d]pyrimidine (610 mg, 1.672 mmol, see Example 36, Step 1), 3-methylpiperazin-2-one (620 mg, 5.43 mmol), and N,N-diisopropylethylamine (1460 µL, 8.36 mmol) in DMF (7 mL) was heated at 120° C. After 2 days, the reaction mixture was cooled to r.t., quenched with water and EtOAc. The organic layer was washed with brine, dried with $Na_2SO_4$ and purified by CombiFlash Rf+ Lumen. LCMS calculated for $C_{20}H_{31}N_8O_2Si (M+H)^+$: m/z=443.2; found 443.5.

Step 2. 1-(2,2-Difluoroethyl)-3-methyl-4-(3-(1-methyl-1H-pyrazol-4-yl)-1H-pyrazolo[4,3-d]pyrimidin-5-yl)piperazin-2-one A solution of 3-methyl-4-(3-(1-methyl-1H-pyrazol-4-yl)-1-((2-(trimethylsilyl)ethoxy)methyl)-1H-pyrazolo[4,3-d]pyrimidin-5-yl)piperazin-2-one (25 mg, 0.056 mmol) in THF (1 mL) was added to a vial containing sodium hydride (2.71 mg, 0.068 mmol, 60%). The suspension was added DMF (1 mL) and the resulting solution was stirred at r.t. After 1 hr, 2-bromo-1,1-difluoroethane (13.5 µL, 0.169 mmol) was added and the solution was stirred at 60° C. After 2 hrs, the reaction was cooled to r.t., diluted with water and extracted with EtOAc. The organic layer was washed with brine, dried with $Na_2SO_4$ and concentrated. The crude was taken up in 1 mL MeOH and 1 mL HCl (4 M solution in dioxane) and stirred at 60° C. for 2 hrs. The resulting mixture was purified with prep-LCMS (XBridge C18 column, eluting with a gradient of acetonitrile/water containing 0.1% TFA, at flow rate of 60 mL/min). LCMS calculated for $C_{16}H_{19}F_2N_8O (M+H)^+$: m/z=377.2; found 377.0. The product was isolated as the TFA salt.

Example 47. 1-Isopropyl-3-methyl-4-(3-(1-methyl-1H-pyrazol-4-yl)-1H-pyrazolo[4,3-d]pyrimidin-5-yl)piperazin-2-one

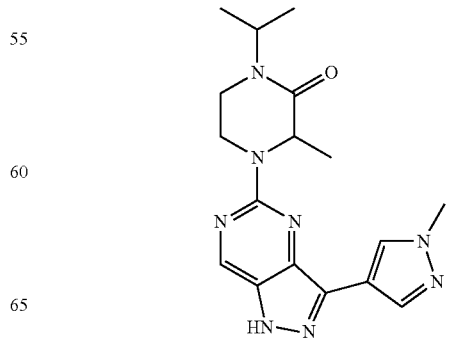

This compound was prepared according to the procedures described in Example 46, using 2-bromopropane instead of 2-bromo-1,1-difluoroethane as starting material. LCMS calculated for $C_{17}H_{23}N_8O$ (M+H)$^+$: m/z=355.2; found: 355.1. The product was isolated as the TFA salt.

Example 48. 1-(2-Methoxyethyl)-3-methyl-4-(3-(1-methyl-1H-pyrazol-4-yl)-1H-pyrazolo[4,3-d]pyrimidin-5-yl)piperazin-2-one

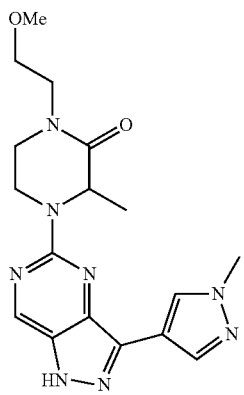 [SMILES: COCCN1CCN(c2ncc3[nH]nc(-c4cnn(C)c4)c3n2)C(C)C1=O]

This compound was prepared according to the procedures described in Example 46, using 1-bromo-2-methoxyethane instead of 2-bromo-1,1-difluoroethane as starting material. LCMS calculated for $C_{17}H_{23}N_8O_2$ (M+H)$^+$: m/z=371.2; found: 371.1. The product was isolated as the TFA salt.

Example 49. 3-Methyl-8-(3-(1-methyl-1H-pyrazol-4-yl)-1H-pyrazolo[4,3-d]pyrimidin-5-yl)-3,8-diazabicyclo[3.2.1]octan-2-one

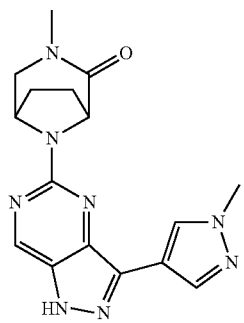 [SMILES: CN1CC2CCC(C1=O)N2c1ncc2[nH]nc(-c3cnn(C)c3)c2n1]

Step 1. 8-(3-(1-Methyl-1H-pyrazol-4-yl)-1-((2-(trimethylsilyl)ethoxy)methyl)-1H-pyrazolo[4,3-d]pyrimidin-5-yl)-3,8-diazabicyclo[3.2.1]octan-2-one

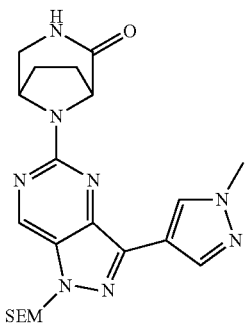 [SMILES: Cn1cc(-c2nn(COCC[Si](C)(C)C)c3cnc(N4C5CCC4C(=O)NC5)nc23)cn1]

A solution of 5-chloro-3-(1-methyl-1H-pyrazol-4-yl)-1-((2-(trimethylsilyl)ethoxy)methyl)-1H-pyrazolo[4,3-d]pyrimidine (200 mg, 0.548 mmol, see Example 36, Step 1), 3,8-diazabicyclo[3.2.1]octan-2-one (138 mg, 1.096 mmol), and N,N-diisopropylethylamine (383 µl, 2.192 mmol) in DMF (3 mL) was heated to 120° C. After 2 days, the reaction mixture was cooled to r.t., quenched with water and EtOAc. The organic layer was washed with brine, dried with Na$_2$SO$_4$ and purified by CombiFlash Rf+ Lumen. LCMS calculated for $C_{21}H_{31}N_8O_2Si$ (M+H)$^+$: m/z=455.2; found 455.4.

Step 2. 3-Methyl-8-(3-(1-methyl-1H-pyrazol-4-yl)-1H-pyrazolo[4,3-d]pyrimidin-5-yl)-3,8-diazabicyclo[3.2.1]octan-2-one A solution of 8-(3-(1-methyl-1H-pyrazol-4-yl)-1-((2-(trimethylsilyl)ethoxy)methyl)-1H-pyrazolo[4,3-d]pyrimidin-5-yl)-3,8-diazabicyclo[3.2.1]octan-2-one (45 mg, 0.099 mmol) in THF (1 mL) was added to a vial containing sodium hydride (4.75 mg, 0.119 mmol, 60%). The suspension was added DMF (1 mL) and the resulting solution was stirred at r.t. After 1 hr, iodomethane (148 µL, 0.297 mmol) was added and the solution was stirred at rt. After 2 hrs, the reaction was diluted with water and extracted with EtOAc. The organic layer was washed with brine, dried with Na$_2$SO$_4$ and concentrated. The crude was taken up in 1 mL MeOH and 1 mL HCl (4 M solution in dioxane) and stirred at 60° C. for 2 hrs. The resulting mixture was purified with prep-LCMS (XBridge C18 column, eluting with a gradient of acetonitrile/water containing 0.1% TFA, at flow rate of 60 mL/min). LCMS calculated for $C_{16}H_{19}N_8O$ (M+H)$^+$: m/z=339.2; found 339.2. The product was isolated as the TFA salt.

Example 50. 3-Ethyl-8-(3-(1-methyl-1H-pyrazol-4-yl)-1H-pyrazolo[4,3-d]pyrimidin-5-yl)-3,8-diazabicyclo[3.2.1]octan-2-one

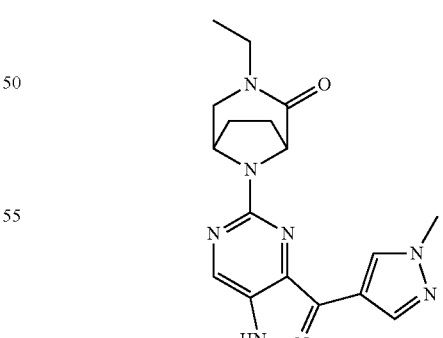

This compound was prepared according to the procedures described in Example 49, using iodoethane instead of iodomethane as starting material. LCMS calculated for $C_{17}H_{21}N_8O$ (M+H)$^+$: m/z=353.2; found: 353.1. The product was isolated as the TFA salt.

Example 51. 3-(2-Fluoroethyl)-8-(3-(1-methyl-1H-pyrazol-4-yl)-1H-pyrazolo[4,3-d]pyrimidin-5-yl)-3,8-diazabicyclo[3.2.1]octan-2-one

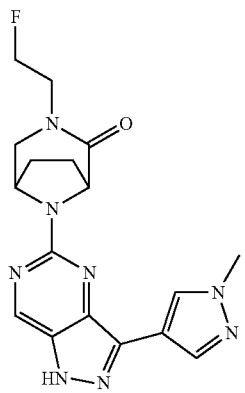 [SMILES: Cn1cc(-c2n[nH]c3cnc(N4C5CCC4C(=O)N(CCF)C5)nc23)cn1]

This compound was prepared according to the procedures described in Example 49, using 1-bromo-2-fluoroethane instead of iodomethane as starting material. LCMS calculated for $C_{17}H_{20}FN_8O$ (M+H)$^+$: m/z=371.4; found: 371.1. The product was isolated as the TFA salt.

Example 52. 3-Isopropyl-8-(3-(1-methyl-1H-pyrazol-4-yl)-1H-pyrazolo[4,3-d]pyrimidin-5-yl)-3,8-diazabicyclo[3.2.1]octan-2-one

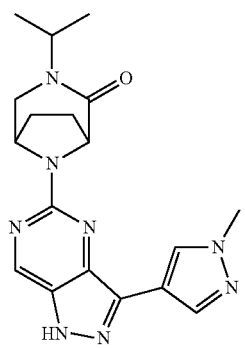 [SMILES: CC(C)N1CC2CCC(C1=O)N2c1ncc2[nH]nc(-c3cnn(C)c3)c2n1]

This compound was prepared according to the procedures described in Example 49, using 2-bromopropane instead of iodomethane as starting material. LCMS calculated for $C_{18}H_{23}N_8O$ (M+H)$^+$: m/z=367.2; found: 367.1. The product was isolated as the TFA salt.

Example 53. 8-(3-(1-(2-Methoxyethyl)-1H-pyrazol-4-yl)-1H-pyrazolo[4,3-d]pyrimidin-5-yl)-3-methyl-3,8-diazabicyclo[3.2.1]octan-2-one

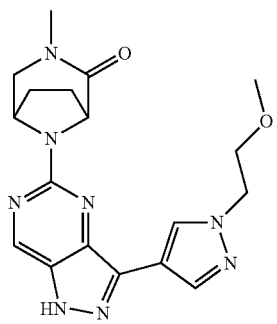 [SMILES: COCCn1cc(-c2n[nH]c3cnc(N4C5CCC4C(=O)N(C)C5)nc23)cn1]

Step 1. 8-(3-Iodo-1-((2-(trimethylsilyl)ethoxy)methyl)-1H-pyrazolo[4,3-d]pyrimidin-5-yl)-3,8-diazabicyclo[3.2.1]octan-2-one

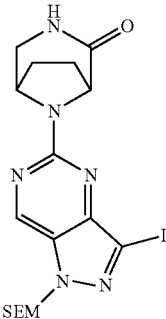 [SMILES: C[Si](C)(C)CCOCn1nc(I)c2nc(N3C4CCC3C(=O)NC4)ncc21]

A solution of 3,8-diazabicyclo[3.2.1]octan-2-one (98 mg, 0.779 mmol), 5-chloro-3-iodo-1-((2-(trimethylsilyl)ethoxy)methyl)-1H-pyrazolo[4,3-d]pyrimidine (160 mg, 0.390 mmol, see Example 1, Step 1), and N,N-diisopropylethylamine (272 µL, 1.558 mmol) in DMSO (2 mL) was heated to 120° C. After 20 hrs, the reaction mixture was cooled to r.t., quenched with water and EtOAc. The organic layer was washed with brine, dried with Na$_2$SO$_4$ and purified by CombiFlash Rf+ Lumen. LCMS calculated for $C_{17}H_{26}IN_6O_2Si$ (M+H)$^+$: m/z=501.1; found 501.0.

Step 2. 8-(3-Iodo-1-((2-(trimethylsilyl) ethoxy)methyl)-1H-pyrazolo[4,3-d]pyrimidin-5-yl)-3-methyl-3,8-diazabicyclo[3.2.1]octan-2-one

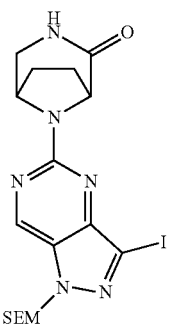 [SMILES: C[Si](C)(C)CCOCn1nc(I)c2nc(N3C4CCC3C(=O)NC4)ncc21]

A solution of 8-(3-iodo-1-((2-(trimethylsilyl)ethoxy)methyl)-1H-pyrazolo[4,3-d]pyrimidin-5-yl)-3,8-diazabicyclo[3.2.1]octan-2-one (500 mg, 0.999 mmol) in THF (3 mL) was added to a vial containing sodium hydride (48.0 mg, 1.199 mmol, 60%). The suspension was added DMF (3 mL) and the resulting solution was stirred at r.t. After 1 hr, iodomethane (187 µL, 3.00 mmol) was added and the resulting solution was stirred at r.t. After 2 hrs, the reaction was diluted with water and extracted with EtOAc. The organic layer was washed with brine, dried with Na$_2$SO$_4$ and purified by CombiFlash Rf+ Lumen. LCMS calculated for $C_{18}H_{28}IN_6O_2Si$ (M+H)$^+$: m/z=515.1; found 515.0.

Step 3. 8-(3-(1-(2-Methoxyethyl)-1H-pyrazol-4-yl)-1H-pyrazolo[4,3-d]pyrimidin-5-yl)-3-methyl-3,8-diazabicyclo[3.2.1]octan-2-one A solution of 8-(3-iodo-1-((2-(trimethylsilyl)ethoxy)methyl)-1H-pyrazolo[4,3-d]pyrimidin-5-yl)-3-methyl-3,8-diazabicyclo[3.2.1]octan-2-one (30 mg, 0.058 mmol), 1-(2- methoxyethyl)-4-(4,4,5,5-tetramethyl-1,3,2-dioxaborolan-2-yl)-1H-pyrazole (44.1 mg, 0.175 mmol), Xphos Pd G2 (4.6 mg, 5.8 μmol), and potassium phosphate (49.5 mg, 0.233 mmol) in dioxane (1 mL) and water (0.1 mL) was heated to 80° C. After 20 hrs, the reaction was cooled to r.t., diluted with water and extracted with EtOAc. The organic layer was washed with brine, dried with $Na_2SO_4$ and concentrated. The crude was taken up in 1 mL DCM and 1 mL TFA and stirred at r.t. for 2 hrs. The solvent was then removed in vacuo. The crude was then taken up in 1 mL MeOH and 0.7 mL $NH_4OH$ (aq) was added. The resulting mixture was stirred at r.t. for 5 min and purified with prep-LCMS (XBridge C18 column, eluting with a gradient of acetonitrile/water containing 0.1% TFA, at flow rate of 60 mL/min). LCMS calculated for $C_{18}H_{23}N_8O_2$ $(M+H)^+$: m/z=383.2; found 383.2. The product was isolated as the TFA salt.

Example 54. 3-Methyl-8-(3-(1-(tetrahydro-2H-pyran-4-yl)-1H-pyrazol-4-yl)-1H-pyrazolo[4,3-d]pyrimidin-5-yl)-3,8-diazabicyclo[3.2.1]octan-2-one

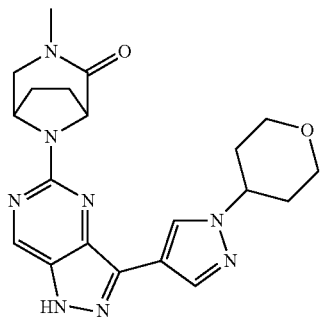 [SMILES: CN1CC2CCC(C1=O)N2c1ncc2[nH]nc(-c3cnn(C4CCOCC4)c3)c2n1]

This compound was prepared according to the procedures described in Example 53, using 1-(tetrahydro-2H-pyran-4-yl)-4-(4,4,5,5-tetramethyl-1,3,2-dioxaborolan-2-yl)-1H-pyrazole instead of 1-(2-methoxyethyl)-4-(4,4,5,5-tetramethyl-1,3,2-dioxaborolan-2-yl)-1H-pyrazole as starting material. LCMS calculated for $C_{20}H_{25}N_8O_2$ $(M+H)^+$: m/z=409.2; found: 409.2. The product was isolated as the TFA salt.

Example 55. 8-(3-(1-((1r,4S)-4-Hydroxycyclohexyl)-1H-pyrazol-4-yl)-1H-pyrazolo[4,3-d]pyrimidin-5-yl)-3-methyl-3,8-diazabicyclo[3.2.1]octan-2-one

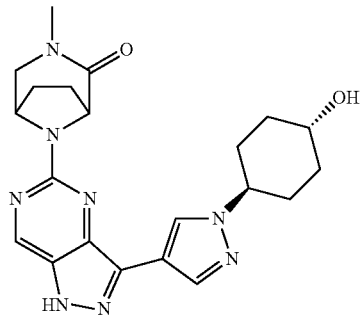 [SMILES: CN1CC2CCC(C1=O)N2c1ncc2[nH]nc(-c3cnn([C@H]4CC[C@H](O)CC4)c3)c2n1]

This compound was prepared according to the procedures described in Example 53, using 1-((1r,4r)-4-((tert-butyldimethylsilyl)oxy)cyclohexyl)-4-(4,4,5,5-tetramethyl-1,3,2-dioxaborolan-2-yl)-1H-pyrazole instead of 1-(2-methoxyethyl)-4-(4,4,5,5-tetramethyl-1,3,2-dioxaborolan-2-yl)-1H-pyrazole as starting material. LCMS calculated for $C_{21}H_{27}N_8O_2$ $(M+H)^+$: m/z=423.2; found: 423.2. The product was isolated as the TFA salt.

Example 56. N,N-Dimethyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)piperidine-1-carboxamide

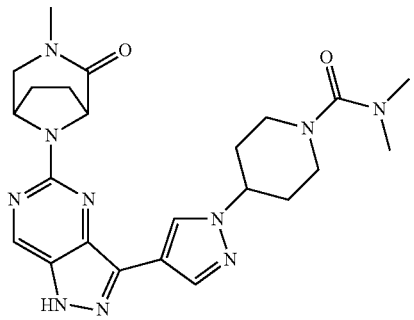 [SMILES: CN(C)C(=O)N1CCC(n2cc(-c3n[nH]c4cnc(N5C6CCC5C(=O)N(C)C6)nc34)cn2)CC1]

This compound was prepared according to the procedures described in Example 53, using N,N-dimethyl-4-(4-(4,4,5,5-tetramethyl-1,3,2-dioxaborolan-2-yl)-1H-pyrazol-1-yl)piperidine-1-carboxamide instead of 1-(2-methoxyethyl)-4-(4,4,5,5-tetramethyl-1,3,2-dioxaborolan-2-yl)-1H-pyrazole as starting material. LCMS calculated for $C_{23}H_{31}N_{10}O_2$ $(M+H)^+$: m/z=479.3; found: 479.4. The product was isolated as the TFA salt.

Example 57. 8-(3-(1-(1-Isobutyrylpiperidin-4-yl)-1H-pyrazol-4-yl)-1H-pyrazolo[4,3-d]pyrimidin-5-yl)-3-methyl-3,8-diazabicyclo[3.2.1]octan-2-one

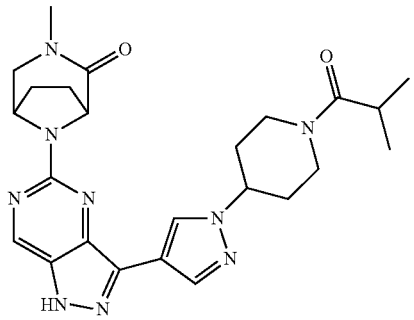 [SMILES: CC(C)C(=O)N1CCC(n2cc(-c3n[nH]c4cnc(N5C6CCC5C(=O)N(C)C6)nc34)cn2)CC1]

This compound was prepared according to the procedures described in Example 53, using 2-methyl-1-(4-(4-(4,4,5,5-tetramethyl-1,3,2-dioxaborolan-2-yl)-1H-pyrazol-1-yl)piperidin-1-yl)propan-1-one instead of 1-(2-methoxyethyl)-4-(4,4,5,5-tetramethyl-1,3,2-dioxaborolan-2-yl)-1H-pyrazole as starting material. LCMS calculated for $C_{24}H_{32}N_9O_2$ $(M+H)^+$: m/z=478.3; found: 478.1. The product was isolated as the TFA salt.

Example 58. 3-Methyl-8-(3-(1-(2-morpholinoethyl)-1H-pyrazol-4-yl)-1H-pyrazolo[4,3-d]pyrimidin-5-yl)-3,8-diazabicyclo[3.2.1]octan-2-one

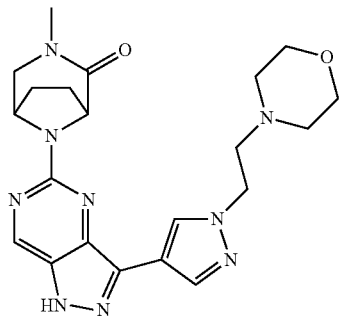 [SMILES: CN1CC2CCC(C1=O)N2c1ncc2[nH]nc(-c3cnn(CCN4CCOCC4)c3)c2n1]

This compound was prepared according to the procedures described in Example 53, using 4-(2-(4-(4,4,5,5-tetramethyl-1,3,2-dioxaborolan-2-yl)-1H-pyrazol-1-yl)ethyl)morpholine instead of 1-(2-methoxyethyl)-4-(4,4,5,5-tetramethyl-1,3,2-dioxaborolan-2-yl)-1H-pyrazole as starting material. LCMS calculated for $C_{21}H_{28}N_9O_2$ (M+H)$^+$: m/z=438.2; found: 438.4. The product was isolated as the TFA salt.

Example 59. 3-Methyl-8-(3-(1-(pyridin-4-ylmethyl)-1H-pyrazol-4-yl)-1H-pyrazolo[4,3-d]pyrimidin-5-yl)-3,8-diazabicyclo[3.2.1]octan-2-one

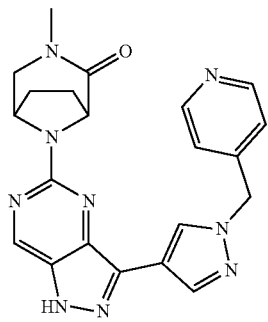 [SMILES: CN1CC2CCC(C1=O)N2c1ncc2[nH]nc(-c3cnn(Cc4ccncc4)c3)c2n1]

This compound was prepared according to the procedures described in Example 53, using 4-((4-(4,4,5,5-tetramethyl-1,3,2-dioxaborolan-2-yl)-1H-pyrazol-1-yl)methyl)pyridine instead of 1-(2-methoxyethyl)-4-(4,4,5,5-tetramethyl-1,3,2-dioxaborolan-2-yl)-1H-pyrazole as starting material. LCMS calculated for $C_{21}H_{22}N_9O$ (M+H)$^+$: m/z=416.2; found: 416.3. The product was isolated as the TFA salt.

Example 60. 3-Methyl-8-(3-(6-(4-methylpiperazin-1-yl)pyridin-3-yl)-1H-pyrazolo[4,3-d]pyrimidin-5-yl)-3,8-diazabicyclo[3.2.1]octan-2-one

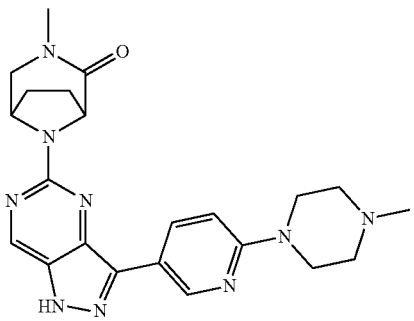 [SMILES: CN1CCN(c2ccc(-c3n[nH]c4cnc(N5C6CCC5C(=O)N(C)C6)nc34)cn2)CC1]

This compound was prepared according to the procedures described in Example 53, using 1-methyl-4-(5-(4,4,5,5-tetramethyl-1,3,2-dioxaborolan-2-yl)pyridin-2-yl)piperazine instead of 1-(2-methoxyethyl)-4-(4,4,5,5-tetramethyl-1,3,2-dioxaborolan-2-yl)-1H-pyrazole as starting material. LCMS calculated for $C_{22}H_{28}N_9O$ (M+H)$^+$: m/z=434.2; found: 434.2. The product was isolated as the TFA salt.

Example 61. 8-(3-(1-Ethyl-1H-pyrazol-4-yl)-1H-pyrazolo[4,3-d]pyrimidin-5-yl)-3-methyl-3,8-diazabicyclo[3.2.1]octan-2-one

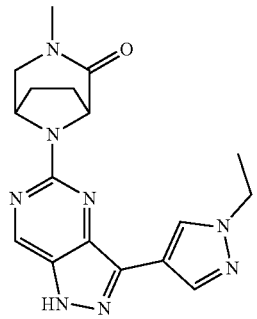 [SMILES: CCn1cc(-c2n[nH]c3cnc(N4C5CCC4C(=O)N(C)C5)nc23)cn1]

This compound was prepared according to the procedures described in Example 53, using 1-ethyl-4-(4,4,5,5-tetramethyl-1,3,2-dioxaborolan-2-yl)-1H-pyrazole instead of 1-(2-methoxyethyl)-4-(4,4,5,5-tetramethyl-1,3,2-dioxaborolan-2-yl)-1H-pyrazole as starting material. LCMS calculated for $C_{17}H_{21}N_8O$ (M+H)$^+$: m/z=353.2; found: 353.2. The product was isolated as the TFA salt.

Example 62. 8-(3-(1-Isopropyl-1H-pyrazol-4-yl)-1H-pyrazolo[4,3-d]pyrimidin-5-yl)-3-methyl-3,8-diazabicyclo[3.2.1]octan-2-one

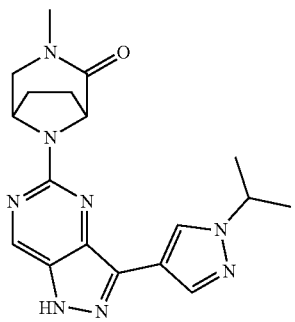 [SMILES: CC(C)n1cc(-c2n[nH]c3cnc(N4C5CCC4C(=O)N(C)C5)nc23)cn1]

This compound was prepared according to the procedures described in Example 53, using 1-isopropyl-4-(4,4,5,5-tetramethyl-1,3,2-dioxaborolan-2-yl)-1H-pyrazole instead of 1-(2-methoxyethyl)-4-(4,4,5,5-tetramethyl-1,3,2-dioxaborolan-2-yl)-1H-pyrazole as starting material. LCMS calculated for $C_{18}H_{23}N_8O$ (M+H)$^+$: m/z=367.2; found: 367.3. The product was isolated as the TFA salt.

Example 63 and Example 64. 8-(3-(1-Cyclobutyl-1H-pyrazol-4-yl)-1H-pyrazolo[4,3-d]pyrimidin-5-yl)-3-methyl-3,8-diazabicyclo[3.2.1]octan-2-one, two enantiomers peak 1

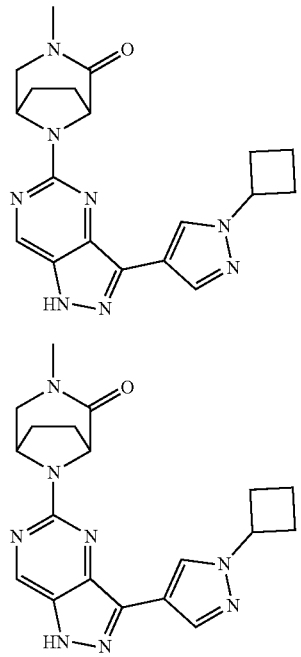

peak 2

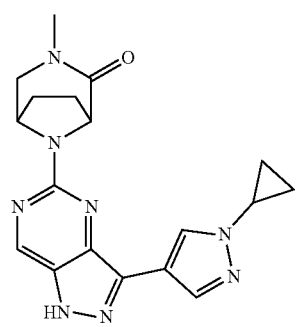

The racemic mixture was prepared according to the procedures described in Example 53, using 1-cyclobutyl-4-(4,4,5,5-tetramethyl-1,3,2-dioxaborolan-2-yl)-1H-pyrazole instead of 1-(2-methoxyethyl)-4-(4,4,5,5-tetramethyl-1,3,2-dioxaborolan-2-yl)-1H-pyrazole as starting material. LCMS calculated for $C_{19}H_{23}N_8O$ (M+H)$^+$: m/z=379.2; found: 379.2. The product was isolated as the TFA salt. Then, the two enantiomers were separated with chiral SFC (Amylose-1, 2×250 mm, eluting with 40% MeOH in $CO_2$, at flow rate of 60 mL/min). Example 63: peak 1, $t_R$=3.3 min. Example 64: peak 2, $t_R$=4.1 min; $^1$H NMR (500 MHz, DMSO) δ 13.29 (s, 1H), 9.05 (s, 1H), 8.42 (s, 1H), 8.14 (s, 1H), 5.01-4.90 (m, 2H), 4.78 (d, J=6.8 Hz, 1H), 3.70-3.61 (m, 1H), 3.09 (d, J=11.7 Hz, 1H), 2.64 (s, 3H), 2.59-2.39 (m, 4H), 2.33-2.23 (m, 1H), 2.23-2.14 (m, 1H), 2.04-1.76 (m, 4H) ppm.

Example 65 and Example 66. 8-(3-(1-Cyclopropyl-1H-pyrazol-4-yl)-1H-pyrazolo[4,3-d]pyrimidin-5-yl)-3-methyl-3,8-diazabicyclo[3.2.1]octan-2-one, two enantiomers peak 1

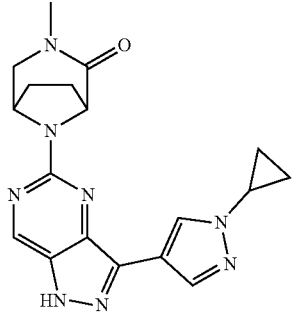

peak 2

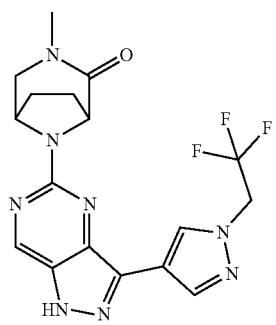 [SMILES: CN1CC2CCC(C1=O)N2c1ncc2[nH]nc(-c3cnn(CC(F)(F)F)c3)c2n1]

The racemic mixture was prepared according to the procedures described in Example 53, using 1-cyclopropyl-4-(4,4,5,5-tetramethyl-1,3,2-dioxaborolan-2-yl)-1H-pyrazole instead of 1-(2-methoxyethyl)-4-(4,4,5,5-tetramethyl-1,3,2-dioxaborolan-2-yl)-1H-pyrazole as starting material. LCMS calculated for $C_{18}H_{21}N_8O$ (M+H)$^+$: m/z=365.2; found: 365.2. The product was isolated as the TFA salt. Then, the two enantiomers were separated with chiral SFC (Amylose-1, 2×250 mm, eluting with 40% MeOH in $CO_2$, at flow rate of 60 mL/min). Example 65: peak 1, $t_R$=3.1 min. Example 66: peak 2, $t_R$=3.9 min; $^1$H NMR (500 MHz, DMSO) δ 13.28 (s, 1H), 9.05 (s, 1H), 8.38 (s, 1H), 8.08 (s, 1H), 4.97-4.88 (m, 1H), 4.77 (d, J=6.8 Hz, 1H), 3.88-3.80 (m, 1H), 3.68-3.59 (m, 1H), 3.09 (d, J=11.8 Hz, 1H), 2.64 (s, 3H), 2.33-1.84 (m, 4H), 1.16-0.96 (m, 4H) ppm.

Example 67. 3-Methyl-8-(3-(1-(2,2,2-trifluoroethyl)-1H-pyrazol-4-yl)-1H-pyrazolo[4,3-d]pyrimidin-5-yl)-3,8-diazabicyclo[3.2.1]octan-2-one

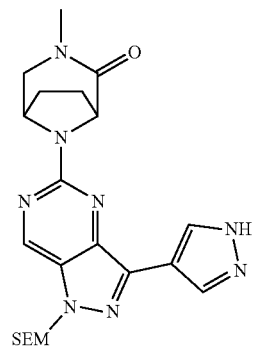 [SMILES: CN1CC2CCC(C1=O)N2c1ncc2c(n1)c(-c1cn[nH]c1)nn2COCC[Si](C)(C)C]

Step 1. 8-(3-(1H-pyrazol-4-yl)-1-((2-(trimethylsilyl)ethoxy)methyl)-1H-pyrazolo[4,3-d]pyrimidin-5-yl)-3-methyl-3,8-diazabicyclo[3.2.1]octan-2-one A solution of 8-(3-iodo-1-((2-(trimethylsilyl)ethoxy)methyl)-1H-pyrazolo[4,3-d]pyrimidin-5-yl)-3-methyl-3,8-diazabicyclo[3.2.1]octan-2-one (210 mg, 0.408 mmol, see Example 53, Step 2), 4-(4,4,5,5-tetramethyl-1,3,2-dioxaborolan-2-yl)-1H-pyrazole (238 mg, 1.225 mmol), XPhos Pd G2 (32.1 mg, 0.041 mmol), and potassium phosphate (347 mg, 1.633 mmol) in dioxane (5 mL) and water (0.5 mL) was heated to 80° C. After 20 hrs, the reaction was cooled to r.t., diluted with water and extracted with EtOAc. The organic layer was washed with brine, dried with $Na_2SO_4$ and purified by CombiFlash Rf+ Lumen. LCMS calculated for $C_{21}H_{31}N_8O_2Si$ $(M+H)^+$: m/z=455.2; found 455.4.

Step 2. 3-Methyl-8-(3-(1-(2,2,2-trifluoroethyl)-1H-pyrazol-4-yl)-1H-pyrazolo[4,3-d]pyrimidin-5-yl)-3,8-diazabicyclo[3.2.1]octan-2-one A mixture of 8-(3-(1H-pyrazol-4-yl)-1-((2-(trimethylsilyl)ethoxy)methyl)-1H-pyrazolo[4,3-d]pyrimidin-5-yl)-3-methyl-3,8-diazabicyclo[3.2.1]octan-2-one (40 mg, 0.088 mmol), 1,1,1-trifluoro-2-iodoethane (17.2 μL, 0.176 mmol), and $Cs_2CO_3$ (86 mg, 0.264 mmol) in DMF (0.880 mL) was heated to 50° C. After 20 hrs, the reaction was diluted with water and extracted with EtOAc. The organic layer was washed with brine, dried with $Na_2SO_4$ and concentrated. The crude was taken up in 1 mL DCM and 1 mL TFA and stirred at r.t. for 2 hrs. The solvent was then removed in vacuo. The crude was then taken up in 1 mL MeOH and 0.7 mL $NH_4OH$ (aq) was added. The resulting mixture was stirred at r.t. for 5 min and purified with prep-LCMS (XBridge C18 column, eluting with a gradient of acetonitrile/water containing 0.1% TFA, at flow rate of 60 mL/min). LCMS calculated for $C_{17}H_{18}F_3N_8O$ $(M+H)^+$: m/z=407.4; found 407.3. The product was isolated as the TFA salt.

Example 68. 3-Methyl-8-(3-(1-(pyridin-4-yl)-1H-pyrazol-4-yl)-1H-pyrazolo[4,3-d]pyrimidin-5-yl)-3,8-diazabicyclo[3.2.1]octan-2-one

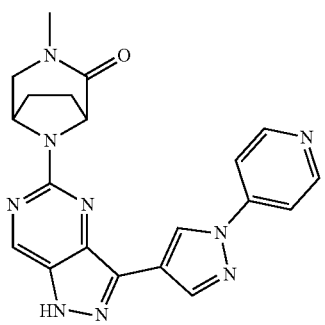 [SMILES: CN1CC2CCC(C1=O)N2c1ncc2[nH]nc(-c3cnn(-c4ccncc4)c3)c2n1]

This compound was prepared according to the procedures described in Example 53, using 4-(4-(4,4,5,5-tetramethyl-1,3,2-dioxaborolan-2-yl)-1H-pyrazol-1-yl)pyridine instead of 1-(2-methoxyethyl)-4-(4,4,5,5-tetramethyl-1,3,2-dioxaborolan-2-yl)-1H-pyrazole as starting material. LCMS calculated for $C_{20}H_{20}N_9O$ $(M+H)^+$: m/z=402.2; found: 402.3. The product was isolated as the TFA salt.

Example 69. 3-Methyl-8-(3-(1-(pyridin-3-yl)-1H-pyrazol-4-yl)-1H-pyrazolo[4,3-d]pyrimidin-5-yl)-3,8-diazabicyclo[3.2.1]octan-2-one

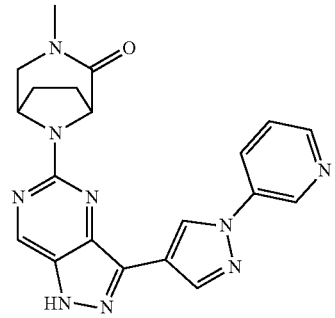 [SMILES: CN1CC2CCC(C1=O)N2c1ncc2[nH]nc(-c3cnn(-c4cccnc4)c3)c2n1]

This compound was prepared according to the procedures described in Example 53, using 3-(4-(4,4,5,5-tetramethyl-1,3,2-dioxaborolan-2-yl)-1H-pyrazol-1-yl)pyridine instead of 1-(2-methoxyethyl)-4-(4,4,5,5-tetramethyl-1,3,2-dioxaborolan-2-yl)-1H-pyrazole as starting material. LCMS calculated for $C_{20}H_{20}N_9O$ $(M+H)^+$: m/z=402.2; found: 402.4. The product was isolated as the TFA salt.

Example 70. 4-(4-(5-(3-Methyl-2-oxo-3,8-diazabicyclo[3.2.1]octan-8-yl)-1H-pyrazolo[4,3-d]pyrimidin-3-yl)-1H-pyrazol-1-yl)benzonitrile

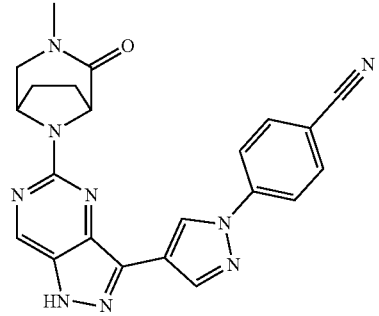 [SMILES: CN1CC2CCC(C1=O)N2c1ncc2[nH]nc(-c3cnn(-c4ccc(C#N)cc4)c3)c2n1]

This compound was prepared according to the procedures described in Example 53, using 4-(4-(4,4,5,5-tetramethyl-1,3,2-dioxaborolan-2-yl)-1H-pyrazol-1-yl)benzonitrile instead of 1-(2-methoxyethyl)-4-(4,4,5,5-tetramethyl-1,3,2-dioxaborolan-2-yl)-1H-pyrazole as starting material. LCMS calculated for $C_{22}H_{20}N_9O$ $(M+H)^+$: m/z=426.2; found: 426.3. The product was isolated as the TFA salt.

Example 71. 3-Methyl-8-(3-(1-(2-methylpyridin-4-yl)-1H-pyrazol-4-yl)-1H-pyrazolo[4,3-d]pyrimidin-5-yl)-3,8-diazabicyclo[3.2.1]octan-2-one

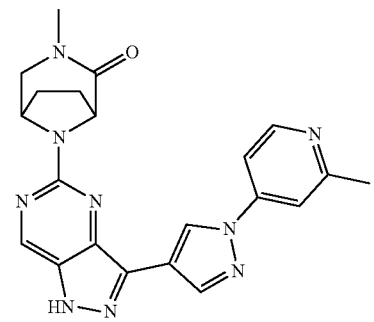 [SMILES: Cc1cc(-n2cc(-c3n[nH]c4cnc(N5C6CCC5C(=O)N(C)C6)nc34)cn2)ccn1]

A solution of 8-(3-(1H-pyrazol-4-yl)-1-((2-(trimethylsilyl)ethoxy)methyl)-1H-pyrazolo[4,3-d]pyrimidin-5-yl)-3-methyl-3,8-diazabicyclo[3.2.1]octan-2-one (40 mg, 0.088 mmol, see Example 67, Step 1), (2-methylpyridin-4-yl)boronic acid (36.1 mg, 0.264 mmol), copper (II) acetate (24.0 mg, 0.132 mmol), and pyridine (21.4 µL, 0.264 mmol) in DCM (1 mL) was stirred at 50° C. After 20 hrs, the reaction was cooled to r.t., diluted with water and extracted with DCM. The organic layer was washed with brine, dried with $Na_2SO_4$ and concentrated. The crude was taken up in 1 mL DCM and 1 mL TFA and stirred at r.t. for 2 hrs. The solvent was then removed in vacuo. The crude was then taken up in 1 mL MeOH and 0.7 mL $NH_4OH$ (aq) was added. The resulting mixture was stirred at r.t. for 5 min and purified with prep-LCMS (XBridge C18 column, eluting with a gradient of acetonitrile/water containing 0.1% TFA, at flow rate of 60 mL/min). LCMS calculated for $C_{21}H_{22}N_9O$ (M+H)$^+$: m/z=416.2; found 416.4. The product was isolated as the TFA salt.

Example 72. 8-(3-(1-(6-(Dimethylamino)pyridin-3-yl)-1H-pyrazol-4-yl)-1H-pyrazolo[4,3-d]pyrimidin-5-yl)-3-methyl-3,8-diazabicyclo[3.2.1]octan-2-one

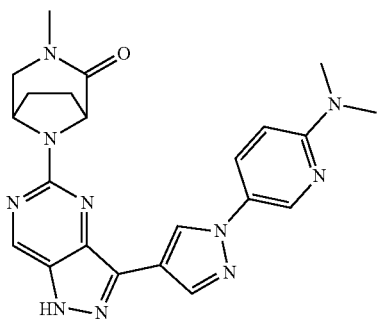 [SMILES: CN1CC2CCC(C1=O)N2c1ncc2[nH]nc(-c3cnn(-c4ccc(N(C)C)nc4)c3)c2n1]

This compound was prepared according to the procedures described in Example 71, using (6-(dimethylamino)pyridin-3-yl)boronic acid instead of (2-methylpyridin-4-yl)boronic acid as starting material. LCMS calculated for $C_{22}H_{25}N_{10}O$ (M+H)$^+$: m/z=445.2; found: 445.4. The product was isolated as the TFA salt.

Example 73. 5-(4-(5-(3-Methyl-2-oxo-3,8-diazabicyclo[3.2.1]octan-8-yl)-1H-pyrazolo[4,3-d]pyrimidin-3-yl)-1H-pyrazol-1-yl)nicotinonitrile

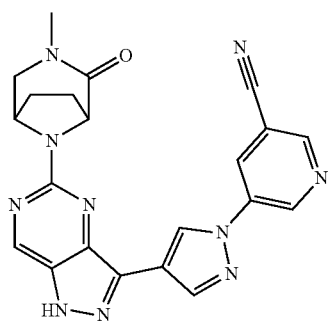 [SMILES: CN1CC2CCC(C1=O)N2c1ncc2[nH]nc(-c3cnn(-c4cncc(C#N)c4)c3)c2n1]

This compound was prepared according to the procedures described in Example 71, using (5-cyanopyridin-3-yl)boronic acid instead of (2-methylpyridin-4-yl)boronic acid as starting material. LCMS calculated for $C_{21}H_{19}N_{10}O$ (M+H)$^+$: m/z=427.2; found: 427.4. The product was isolated as the TFA salt.

Example 74. 5-(4-(5-(3-Methyl-2-oxo-3,8-diazabicyclo[3.2.1]octan-8-yl)-1H-pyrazolo[4,3-d]pyrimidin-3-yl)-1H-pyrazol-1-yl)picolinonitrile

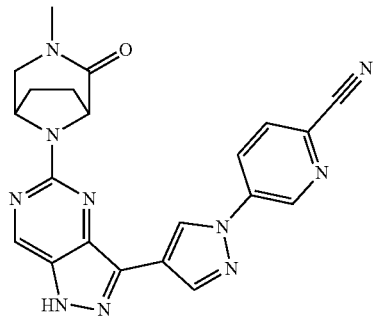 [SMILES: CN1CC2CCC(C1=O)N2c1ncc2[nH]nc(-c3cnn(-c4ccc(C#N)nc4)c3)c2n1]

This compound was prepared according to the procedures described in Example 71, using 5-(4,4,5,5-tetramethyl-1,3,2-dioxaborolan-2-yl)picolinonitrile instead of (2-methylpyridin-4-yl)boronic acid as starting material. LCMS calculated for $C_{21}H_{19}N_{10}O$ (M+H)$^+$: m/z=427.2; found: 427.2. The product was isolated as the TFA salt.

Example 75. 8-(3-(1-(Imidazo[1,2-a]pyridin-6-yl)-1H-pyrazol-4-yl)-1H-pyrazolo[4,3-d]pyrimidin-5-yl)-3-methyl-3,8-diazabicyclo[3.2.1]octan-2-one

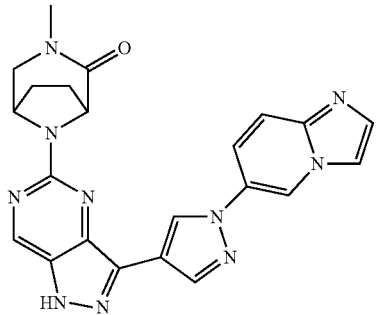 [SMILES: CN1CC2CCC(C1=O)N2c1ncc2[nH]nc(-c3cnn(-c4ccc5nccn5c4)c3)c2n1]

This compound was prepared according to the procedures described in Example 71, using imidazo[1,2-a]pyridin-6-ylboronic acid instead of (2-methylpyridin-4-yl)boronic acid as starting material. LCMS calculated for $C_{22}H_{21}N_{10}O$ (M+H)$^+$: m/z=441.2; found: 441.4. The product was isolated as the TFA salt.

Example 76. 2-Methyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)benzonitrile

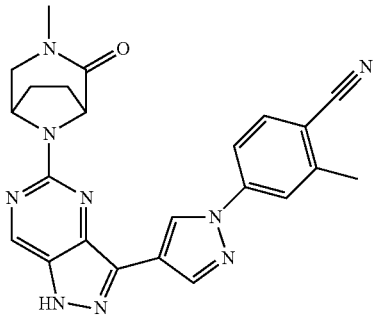 [SMILES: Cc1cc(-n2cc(-c3n[nH]c4cnc(N5C6CCC5C(=O)N(C)C6)nc34)cn2)ccc1C#N]

This compound was prepared according to the procedures described in Example 71, using (4-cyano-3-methylphenyl)boronic acid instead of (2-methylpyridin-4-yl)boronic acid as starting material. LCMS calculated for $C_{23}H_{22}N_9O$ $(M+H)^+$: m/z=440.2; found: 440.1. The product was isolated as the TFA salt.

Example 77. 3-Methyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)benzonitrile

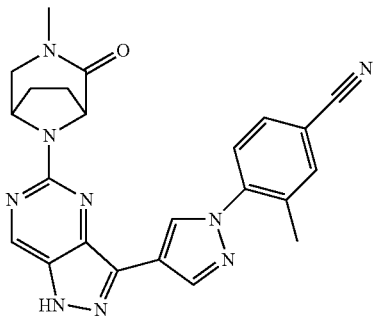 [SMILES: Cc1cc(C#N)ccc1-n1cc(-c2n[nH]c3cnc(N4C5CCC4C(=O)N(C)C5)nc23)cn1]

This compound was prepared according to the procedures described in Example 71, using (4-cyano-2-methylphenyl)boronic acid instead of (2-methylpyridin-4-yl)boronic acid as starting material. LCMS calculated for $C_{23}H_{22}N_9O$ $(M+H)^+$: m/z=440.2; found: 440.3. The product was isolated as the TFA salt.

Example 78. 2-Fluoro-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)benzonitrile

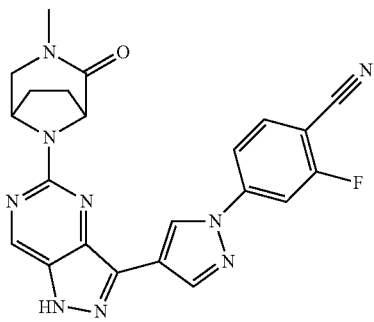 [SMILES: CN1CC2CCC(C1=O)N2c1ncc2[nH]nc(-c3cnn(-c4ccc(C#N)c(F)c4)c3)c2n1]

This compound was prepared according to the procedures described in Example 71, using (4-cyano-3-fluorophenyl)boronic acid instead of (2-methylpyridin-4-yl)boronic acid as starting material. LCMS calculated for $C_{22}H_{19}FN_9O$ $(M+H)^+$: m/z=444.2; found: 444.1. The product was isolated as the TFA salt.

Example 79. N,N-Dimethyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)benzamide

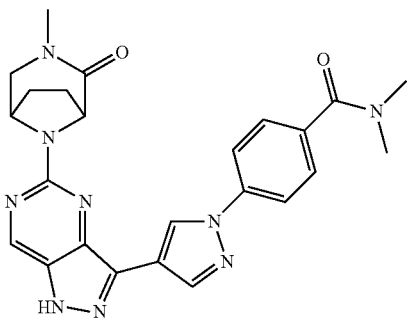 [SMILES: CN(C)C(=O)c1ccc(-n2cc(-c3n[nH]c4cnc(N5C6CCC5C(=O)N(C)C6)nc34)cn2)cc1]

This compound was prepared according to the procedures described in Example 71, using (4-(dimethylcarbamoyl)phenyl)boronic acid instead of (2-methylpyridin-4-yl)boronic acid as starting material. LCMS calculated for $C_{24}H_{26}N_9O_2$ $(M+H)^+$: m/z=472.2; found: 472.4. The product was isolated as the TFA salt.

Example 80. N-Methyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)benzamide

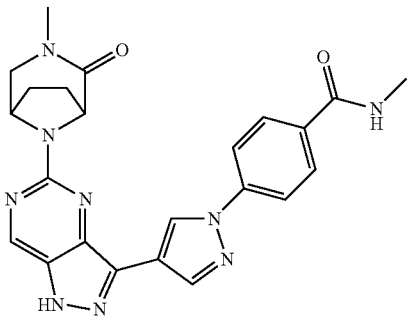 [SMILES: CNC(=O)c1ccc(-n2cc(-c3n[nH]c4cnc(N5C6CCC5C(=O)N(C)C6)nc34)cn2)cc1]

This compound was prepared according to the procedures described in Example 71, using (4-(methylcarbamoyl)phenyl)boronic acid instead of (2-methylpyridin-4-yl)boronic acid as starting material. LCMS calculated for $C_{23}H_{24}N_9O_2$ $(M+H)^+$: m/z=458.2; found: 458.4. The product was isolated as the TFA salt.

Example 81. 2-Fluoro-N-methyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)benzamide

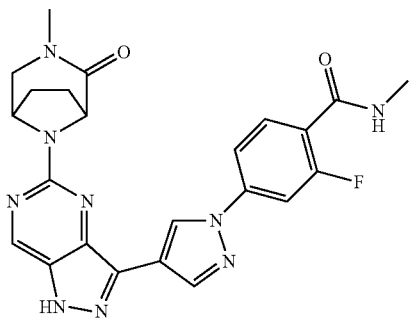 [SMILES: CNC(=O)c1ccc(-n2cc(-c3n[nH]c4cnc(N5C6CCC5C(=O)N(C)C6)nc34)cn2)cc1F]

This compound was prepared according to the procedures described in Example 71, using (3-fluoro-4-(methylcarbamoyl)phenyl)boronic acid instead of (2-methylpyridin-4-yl) boronic acid as starting material. LCMS calculated for $C_{23}H_{23}FN_9O_2(M+H)^+$: m/z=476.2; found: 476.2. The product was isolated as the TFA salt.

Example 82. N-Methyl-5-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)picolinamide

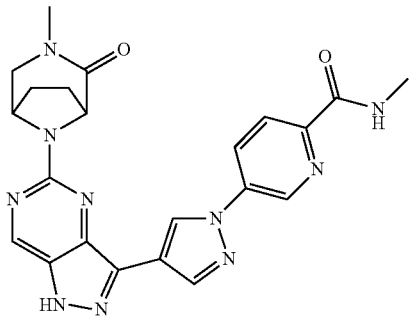 [SMILES: CNC(=O)c1ccc(-n2cc(-c3n[nH]c4cnc(N5C6CCC5C(=O)N(C)C6)nc34)cn2)cn1]

This compound was prepared according to the procedures described in Example 71, using N-methyl-5-(4,4,5,5-tetramethyl-1,3,2-dioxaborolan-2-yl)picolinamide instead of (2-methylpyridin-4-yl)boronic acid as starting material. LCMS calculated for $C_{22}H_{23}N_{10}O_2$ $(M+H)^+$: m/z=459.2; found: 459.2. The product was isolated as the TFA salt.

Example A. ALK2 HTRF Assay

ALK2 (aa 147-end) was obtained from BPS biosciences. The enzymatic assays were conducted in white 384-well polystyrene plates in a final volume of 8 μL. The inhibitors were serially diluted in DMSO and added to the plate wells prior to addition of the other reaction components. The assays were carried out at 25° C. in the assay buffer (50 mM HEPES, pH 7.1, 10% Glycerol, 0.01% Brij50, 10 mM $MgCl_2$, 1 mM EGTA, 5 mM DTT, and 0.01% BSA), containing 50 nM LANCE Ultra ULight™-DNA Topoisomerase 2-alpha peptide (Perkin Elmer TRF0130), and 3 uM, 100 uM or 1 mM ATP (as specified). The final concentration of DMSO in the assay was 1% and the enzyme concentration was 2.5 nM for ALK2. The reactions were allowed to proceed for 2-4 hr after which, the reaction was quenched by addition of EDTA at a final concentration of 20 mM along with 1.5 nM LANCE Ultra Europium-anti-phospho-DNA Topoisomerase 2-alpha (Thr1342) antibody (Perkin Elmer TRF0218). The reaction was read on a PHERAstar FS plate reader (BMG Labtech). $IC_{50}$ determination was performed by fitting percent control activity versus the log of the inhibitor concentration using the IDBS XLFit and GraphPad Prism 5.0 software.

Compounds of the present disclosure, as exemplified in the Examples, showed $IC_{50}$ values in the following ranges: $+=IC_{50} \leq 100$ nM; $++=100$ nM$<IC_{50} \leq 500$ nM; $+++=500$ nM$<IC_{50} \leq 2000$ nM; $++++=IC_{50}>2000$ nM. NT=Not tested. Results are shown in Table 1.

Example B. ALK2 Cellular Assay

HeLa cells were cultured in MEM media with 10% FBS. Recombinant human BMP-7 was obtained from R&D Systems (cat #354-BP) and phospho SMAD1 (S463/S465) HTRF kit was purchased from Cisbio (63ADKO62PEH). HeLa cells were plated in 96 well flat bottomed plate at 50,000 cells per well and incubated overnight. Next day, media was removed and 50 μL of fresh complete media was added. 5 μL compound was added to cells (3 μM final concentration at highest) and incubated for 60 min at 37° C. 200 ng/ml BMP-7 was added and incubated for 30 min at 37° C. After incubation, the media was removed, washed 2×PBS, and proceeded with HTRF kit according to Cisbio HTRF kit instructions for measuring the Phospho SMAD1 (S463/S465). Finally, both the donor and acceptor were added into 384 well plates and incubated at room temperature overnight and the HTRF signal was measured via Pherastar the next day.

Compounds of the present disclosure, as exemplified in the Examples, showed $Eu^{3+}$ Cryptate fluorescent values in the following ranges: *=PSMAD≤100 nM; =100 nM<PSMAD≤500 nM; *=500 nM<PSMAD≤2000 nM. NT=Not tested. Results are shown in Table 1.

TABLE 1

| Ex # | ALK2 3 μM $IC_{50}$ | ALK2 100 μM $IC_{50}$ | ALK2 1 mM $IC_{50}$ | ALK2 Cellular Assay PSMAD |
|---|---|---|---|---|
| 1 | + | + | + | ** |
| 2 | + | ++ | +++ | ** |
| 3 | + | + | ++ | ** |
| 4 | + | + | + | ** |
| 5 | + | ++ | ++ | *** |
| 6 | + | + | + | ** |
| 7 | + | ++ | ++ | ** |
| 8 | + | + | + | ** |
| 9 | + | + | + | * |
| 10 | + | + | + | * |
| 11 | + | + | + | ** |
| 12 | + | + | + | * |
| 13 | + | + | ++ | ** |
| 14 | + | + | ++ | ** |
| 15 | + | ++ | +++ | *** |
| 16 | + | NT | ++ | *** |
| 17 | + | + | + | * |
| 18 | + | + | ++ | ** |
| 19 | + | + | ++ | ** |
| 20 | + | + | ++ | ** |
| 21 | + | + | ++ | *** |
| 22 | + | + | + | * |
| 23 | + | + | ++ | ** |
| 24 | + | + | + | * |

TABLE 1-continued

| Ex # | ALK2 3 μM IC$_{50}$ | ALK2 100 μM IC$_{50}$ | ALK2 1 mM IC$_{50}$ | ALK2 Cellular Assay PSMAD |
|---|---|---|---|---|
| 25 | + | + | NT | ** |
| 26 | + | NT | ++++ | NT |
| 27 | + | NT | ++ | ** |
| 28 | + | + | NT | * |
| 29 | + | + | NT | * |
| 30 | + | + | NT | ** |
| 31 | + | + | NT | * |
| 32 | + | + | ++ | ** |
| 33 | + | + | + | * |
| 34 | ++ | NT | ++++ | *** |
| 35 | + | NT | ++ | ** |
| 36 | +++ | +++ | NT | NT |
| 37 | NT | NT | NT | NT |
| 38 | ++ | +++ | NT | NT |
| 39 | NT | NT | NT | NT |
| 40 | +++ | +++ | NT | NT |
| 41 | +++ | +++ | NT | NT |
| 42 | NT | NT | NT | NT |
| 43 | NT | NT | NT | NT |
| 44 | +++ | +++ | NT | NT |
| 45 | +++ | +++ | NT | NT |
| 46 | NT | NT | NT | NT |
| 47 | NT | NT | NT | NT |
| 48 | NT | NT | NT | NT |
| 49 | +++ | ++++ | NT | NT |
| 50 | NT | NT | NT | NT |
| 51 | ++ | +++ | NT | NT |
| 52 | NT | NT | NT | NT |
| 53 | NT | NT | NT | NT |
| 54 | NT | NT | NT | NT |
| 55 | NT | NT | NT | NT |
| 56 | NT | NT | NT | NT |
| 57 | +++ | +++ | NT | NT |
| 58 | +++ | +++ | NT | NT |
| 59 | +++ | +++ | NT | NT |
| 60 | + | +++ | NT | NT |
| 61 | +++ | +++ | NT | NT |
| 62 | NT | NT | NT | NT |
| 63 | NT | NT | NT | NT |
| 64 | ++ | +++ | NT | NT |
| 65 | NT | NT | NT | NT |
| 66 | NT | NT | NT | NT |
| 67 | NT | NT | NT | NT |
| 68 | +++ | ++++ | NT | NT |
| 69 | NT | NT | NT | NT |
| 70 | +++ | ++++ | NT | NT |
| 71 | +++ | +++ | NT | NT |
| 72 | +++ | +++ | NT | NT |
| 73 | NT | NT | NT | NT |
| 74 | NT | NT | NT | NT |
| 75 | +++ | +++ | NT | NT |
| 76 | +++ | +++ | NT | NT |
| 77 | NT | NT | NT | NT |
| 78 | NT | NT | NT | NT |
| 79 | ++ | +++ | NT | NT |
| 80 | NT | NT | NT | NT |
| 81 | +++ | +++ | NT | NT |
| 82 | +++ | +++ | NT | NT |

Example C. FGFR Enzymatic Assay

The inhibitor potency of the exemplified compounds was determined in an enzyme discontinuous assay that measures peptide phosphorylation using FRET measurements to detect product formation. Inhibitors were serially diluted in DMSO and a volume of 0.2 μL was transferred to the wells of a 384-well plate. For the isoforms of FGFR (−1, −2, −3 wild-type and mutant isoforms, −4) including phosphorylated (P) and un-phosphorylated (UP) proteins, a 5 μL/well volume of enzyme diluted in assay buffer (50 mM HEPES, 10 mM MgCl$_2$, 1 mM EGTA, 0.01% Tween-20, 5 mM DTT, pH 7.5) was added to the plate and pre-incubated with inhibitor for 5 to 15 minutes at ambient temperature. Appropriate controls (enzyme blank and enzyme with no inhibitor) were included on the plate. The reaction was initiated by the addition of a 5 μL/well volume containing both biotinylated EQEDEPEGDYFEWLE (SEQ ID: 1) peptide substrate and ATP in assay buffer. The 10 μL/well reaction concentration of the peptide substrate was 500 nM whereas the ATP concentration was maintained near or below the ATP K$_m$ for each FGFR isoform. The ATP K$_m$ values were pre-determined for each FGFR isoform in a separate series of experiments. The reaction plate was incubated at 25° C. for 1 hr and the reactions were ended with the addition of 5 μL/well of quench solution (50 mM Tris, 150 mM NaCl, 0.5 mg/mL BSA, pH 7.8; 45 mM EDTA, 600 nM staurosporin, with Perkin Elmer Lance Reagents at 3.75 nM Eu-antibody PY20 and 180 nM APC-Streptavidin). The plate was allowed to equilibrate for ~10 minutes at ambient temperature before scanning on a PheraStar plate reader (BMG Labtech) instrument.

Either GraphPad prism or XLfit was used to analyze the data. The IC$_{50}$ values were derived by fitting the data to a four parameter logistic equation producing a sigmoidal dose-response curve with a variable Hill coefficient. Prism equation: $Y = Bottom + (Top - Bottom)/(1 + 10^{((LogIC_{50} - X) * Hill\ slope)})$;

XLfit equation: $Y = (A + ((B-A)/(1 + ((X/C)^D))))$ where $X$ is the logarithm of inhibitor concentration and $Y$ is the response.

Compounds of the present disclosure, as exemplified in the Examples, showed IC$_{50}$ values in the following ranges: $+=IC_{50} \leq 100$ nM; $++=100$ nM$<IC_{50} \leq 500$ nM; $+++=500$ nM$<IC_{50} \leq 2000$ nM; $++++=IC_{50}>2000$ nM. NT=Not tested. Results are shown in Table 2.

Example D. pFGFR2 and pFGFR1,3 Functional Cell HTRF Assay

To measure phosphorylated Fibroblast Growth Factor Receptor 2 (FGFR2), KATOIII cells (Human Gastric Carcinoma) were purchased from ATCC and maintained in Iscove's with 20% FBS (Gibco/Life Technologies). For the pFGFR2 assay, KATOIII cells were plated overnight in 5% FBS and Iscove's medium at $5 \times 10^4$ cells/well into Corning 96-well flat-bottom tissue culture treated plates. The next morning, 50 μl of fresh media with 0.5% FBS was incubated in the presence or absence of a concentration range of test compounds also at 50 μl, for 1 hour at 37° C., 5% CO$_2$. Cell were washed with PBS, and lysed with Cell Signaling Lysis Buffer with standard Protease inhibitors for 45 min at room temperature. 4 μl total of Cis Bio Anti Phospho-YAP d2 and Cis Bio Anti Phospho-YAP Cryptate together were added to the lysate and mixed well (following directions of the kit). 16 μl was then transferred to 384 well Greiner white plates and stored at 4° C. overnight in the dark. Plates were read on the Pherastar plate reader at 665 nm and 620 nm wavelengths. IC$_{50}$ determination was performed by fitting the curve of inhibitor percent inhibition versus the log of the inhibitor concentration using the GraphPad Prism 5.0 software.

To measure phosphorylated Fibroblast Growth Factor Receptor 1 and 3 (FGF1 and FGFR3), in house stable cell lines BAF3-TEL-FGFR1 or BAF3-TEL-FGFR3 were maintained in RPMI with 10% FBS and 1 µg/ml puromycin (Gibco/Life Technologies). For the assay, 12 nl of BAF3-TEL-FGFR1 or BAF3-TEL-FGFR3 cells in serum free and puromycin free RPMI media at 1×10$^6$ cell/ml were added to 384 Greiner white plate already containing 20 nl dots of compounds at a concentration range. The plates were gently shaken (100 rpm) for 2 minutes at room temperature to mix well and incubated for 2 hours in a single layer at 37° C., 5% CO$_2$. 4 µl/well of 1/25 dilution of lysis buffer #3 (Cis Bio) was added with standard Protease inhibitors and shaken at 200 rpm at room temperature for 20 minutes. 4 µl total of the Cis Bio Tb-pFGFR Ab (10 ng) and d2-FGFR3 (1 ng) together were added to the lysate and mixed well. Plates were sealed and incubated at room temperature overnight in the dark. Plates were read on the Pherastar plate reader at 665 nm and 620 nm wavelengths. IC$_{50}$ determination was performed by fitting the curve of inhibitor percent inhibition versus the log of the inhibitor concentration using the GraphPad Prism 5.0 software.

Compounds of the present disclosure, as exemplified in the Examples, showed IC$_{50}$ values in the following ranges: +=IC$_{50}$≤100 nM; ++=100 nM<IC$_{50}$≤500 nM; +++=500 nM<IC$_{50}$≤2000 nM; ++++=IC$_{50}$>2000 nM. NT=Not tested. Results are shown in Table 2.

Example E. Luminescent Viability Assay (LVA, FGFR3)

RT112 cells were purchased from ATCC (Manassas, Va.) and maintained in RPMI, 10% FBS (Gibco/Life Technologies). To measure the effect of test compounds on the viability of cells, the cells were plated with RPMI 10% FBS (5×10$^3$ cells/well/in 50 µL) into black 96-well Greiner polystyrene in the presence or absence of 50 µl of a concentration range of test compounds. After 3 days, 100 µl of CellTiter-Glo Reagent (Promega) was added. Luminescence was read with a TopCount (PerkinElmer). IC$_{50}$ determination was performed by fitting the curve of percent inhibition versus the log of the inhibitor concentration using the GraphPad Prism 5.0 software.

Compounds of the present disclosure, as exemplified in the Examples, showed IC$_{50}$ values in the following ranges: +=IC$_{50}$≤100 nM; ++=100 nM<IC$_{50}$≤500 nM; +++=500 nM<IC$_{50}$≤2000 nM; ++++=IC$_{50}$>2000 nM. NT=Not tested. Results are shown in Table 2.

TABLE 2

| Ex # | FGFR3 (UP) IC$_{50}$ (nM) | FGFR2 (P) IC$_{50}$ (nM) | FGFR1 (UP) IC$_{50}$ (nM) | FGFR2 (UP) IC$_{50}$ (nM) | FGFR1 HTRF IC$_{50}$ | FGFR2 HTRF IC$_{50}$ | FGFR3 HTRF IC$_{50}$ | LVA, FGFR3 IC$_{50}$ |
|---|---|---|---|---|---|---|---|---|
| 1 | + | + | ++ | NT | NT | NT | NT | NT |
| 2 | + | ++ | ++ | NT | NT | NT | NT | NT |
| 3 | ++ | NT | +++ | ++ | NT | NT | NT | NT |
| 4 | + | + | ++ | NT | NT | NT | NT | NT |
| 5 | ++++ | ++++ | ++++ | NT | NT | NT | NT | NT |
| 6 | +++ | NT | ++++ | +++ | NT | NT | NT | NT |
| 7 | +++ | +++ | +++ | NT | NT | NT | NT | NT |
| 8 | NT | NT | NT | NT | NT | NT | NT | NT |
| 9 | ++ | NT | +++ | ++ | NT | NT | NT | NT |
| 10 | +++ | NT | +++ | +++ | NT | NT | NT | NT |
| 11 | +++ | NT | +++ | +++ | NT | NT | NT | NT |
| 12 | ++ | NT | +++ | ++ | NT | NT | NT | NT |
| 13 | ++ | NT | +++ | ++ | NT | NT | NT | NT |
| 14 | ++++ | NT | ++++ | ++++ | NT | NT | NT | NT |
| 15 | ++++ | ++++ | ++++ | NT | NT | NT | NT | NT |
| 16 | ++ | NT | ++ | ++ | NT | NT | NT | NT |
| 17 | + | NT | ++ | + | NT | NT | NT | NT |
| 18 | ++ | ++ | ++ | NT | NT | NT | NT | NT |
| 19 | ++ | ++ | +++ | NT | NT | NT | NT | NT |
| 20 | ++++ | NT | +++ | +++ | NT | NT | NT | NT |
| 21 | ++++ | NT | ++++ | ++++ | NT | NT | NT | NT |
| 22 | ++ | NT | +++ | ++ | NT | NT | NT | NT |
| 23 | ++ | NT | ++ | ++ | NT | NT | NT | NT |
| 24 | ++ | NT | +++ | ++ | NT | NT | NT | NT |
| 25 | NT | NT | NT | NT | NT | NT | NT | NT |
| 26 | ++ | NT | +++ | ++ | NT | NT | NT | NT |
| 27 | NT | NT | NT | NT | NT | NT | NT | NT |
| 28 | ++ | NT | +++ | ++ | NT | NT | NT | NT |
| 29 | +++ | NT | ++ | +++ | NT | NT | NT | NT |
| 30 | ++ | NT | +++ | ++ | NT | NT | NT | NT |
| 31 | ++ | NT | +++ | ++ | NT | NT | NT | NT |
| 32 | ++ | NT | ++++ | +++ | NT | NT | NT | NT |
| 33 | + | NT | ++ | ++ | NT | NT | NT | NT |
| 34 | +++ | NT | ++++ | +++ | NT | NT | NT | NT |
| 35 | NT | NT | NT | NT | NT | NT | NT | NT |
| 36 | ++ | ++ | +++ | NT | NT | NT | NT | NT |
| 37 | ++ | +++ | ++++ | NT | NT | NT | NT | NT |
| 38 | + | + | ++ | NT | NT | NT | NT | ++ |
| 39 | + | + | ++ | NT | NT | NT | NT | ++ |

TABLE 2-continued

| Ex # | FGFR3 (UP) IC$_{50}$ (nM) | FGFR2 (P) IC$_{50}$ (nM) | FGFR1 (UP) IC$_{50}$ (nM) | FGFR2 (UP) IC$_{50}$ (nM) | FGFR1 HTRF IC$_{50}$ | FGFR2 HTRF IC$_{50}$ | FGFR3 HTRF IC$_{50}$ | LVA, FGFR3 IC$_{50}$ |
|---|---|---|---|---|---|---|---|---|
| 40 | + | ++ | +++ | NT | NT | NT | NT | +++ |
| 41 | + | ++ | ++ | NT | NT | NT | NT | ++ |
| 42 | + | ++ | +++ | NT | NT | NT | NT | ++ |
| 43 | ++ | ++ | +++ | NT | NT | NT | NT | NT |
| 44 | + | + | ++ | NT | NT | NT | NT | +++ |
| 45 | + | + | + | + | +++ | NT | ++ | ++ |
| 46 | + | + | ++ | NT | NT | NT | NT | ++ |
| 47 | + | ++ | +++ | NT | NT | NT | NT | +++ |
| 48 | ++ | +++ | ++++ | NT | NT | NT | NT | NT |
| 49 | + | + | + | + | +++ | NT | + | ++ |
| 50 | + | + | ++ | NT | ++ | NT | ++ | ++ |
| 51 | + | ++ | ++ | NT | NT | NT | NT | +++ |
| 52 | + | + | ++ | NT | ++NT | NT | ++ | ++ |
| 53 | + | + | ++ | NT | NT | NT | NT | +++ |
| 54 | + | + | ++ | NT | NT | NT | NT | +++ |
| 55 | + | + | ++ | NT | NT | NT | NT | ++++ |
| 56 | + | + | ++ | NT | NT | NT | NT | +++ |
| 57 | + | + | ++ | NT | NT | NT | NT | +++ |
| 58 | + | + | ++ | NT | NT | NT | NT | +++ |
| 59 | + | + | ++ | NT | NT | NT | NT | +++ |
| 60 | + | + | + | NT | NT | NT | NT | ++ |
| 61 | + | + | ++ | NT | NT | NT | + | ++ |
| 62 | + | + | ++ | NT | NT | NT | ++ | ++ |
| 63 | ++ | +++ | ++++ | NT | NT | NT | NT | NT |
| 64 | + | + | + | + | NT | + | + | + |
| 65 | +++ | +++ | ++++ | NT | NT | NT | NT | NT |
| 66 | + | + | + | NT | NT | + | + | + |
| 67 | + | ++ | ++ | NT | NT | NT | ++ | NT |
| 68 | + | + | + | + | NT | + | + | ++ |
| 69 | + | + | + | NT | NT | NT | + | ++ |
| 70 | + | + | + | + | NT | + | + | + |
| 71 | + | + | + | NT | NT | + | + | + |
| 72 | + | + | + | + | NT | + | + | ++ |
| 73 | + | + | ++ | NT | NT | NT | NT | +++ |
| 74 | + | + | + | NT | NT | NT | NT | ++ |
| 75 | + | + | + | NT | NT | NT | NT | +++ |
| 76 | + | + | + | + | NT | + | + | + |
| 77 | + | ++ | +++ | NT | NT | NT | NT | +++ |
| 78 | + | + | ++ | NT | NT | NT | NT | ++ |
| 79 | + | + | + | + | NT | NT | + | NT |
| 80 | + | + | + | + | NT | NT | NT | +++ |
| 81 | + | + | + | NT | NT | + | + | + |
| 82 | + | + | + | NT | NT | NT | ++ | NT |

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:
1. A compound of Formula I:

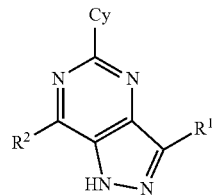

or a pharmaceutically acceptable salt thereof, wherein:
$R^1$ is selected from $Cy^1$, $C_{2-6}$ alkenyl, $C_{2-6}$ alkynyl, $C_{1-6}$ haloalkyl, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NOR^a)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{2-6}$ alkenyl and $C_{2-6}$ alkynyl are each substituted with 1, 2, 3, or 4 substituents independently selected from $R^{10}$;

$Cy^1$ is selected from $C_{3-8}$ cycloalkyl, 4-12 membered heterocycloalkyl, $C_{6-10}$ aryl and 5-10 membered heteroaryl; wherein the 4-12 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-12 membered heterocycloalkyl is optionally substituted by oxo to form a carbonyl group; and wherein the $C_{3-8}$ cycloalkyl, 4-12 membered heterocycloalkyl, $C_{6-10}$ aryl and 5-10 membered heteroaryl are each optionally substituted with 1, 2, 3 or 4 substituents independently selected from $R^{10}$;

Cy is 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-12 membered heterocycloalkyl is optionally substituted by oxo to form a carbonyl group; wherein when the 4-12 membered heterocycloalkyl of Cy has a fused aromatic ring, the 4-12 membered heterocycloalkyl is directly attached to the pyrazolopyrimidine core structure through a ring-forming atom of the saturated or partially saturated ring; and wherein the 4-12 membered heterocycloalkyl is optionally substituted with 1, 2, 3, 4 or 5 substituents independently selected from $R^{20}$;

$R^2$ is selected from H, D, $C_{1-4}$ alkyl, $C_{1-4}$ haloalkyl, $C_{1-4}$ alkoxy and $C_{1-4}$ haloalkoxy;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

or two $R^{10}$ substituents taken together with the carbon atom to which they are attached form a spiro 4-7-membered heterocycloalkyl ring, or a spiro $C_{3-6}$ cycloalkyl ring; wherein each spiro 4-7-membered heterocycloalkyl ring has at least one ring-forming carbon atom and 1, 2 or 3, ring-forming heteroatoms independently selected from N, O, and S; wherein a ring-forming carbon atom of each spiro 4-7-membered heterocycloalkyl ring is optionally substituted by oxo to form a carbonyl group; and wherein the spiro 4-7-membered heterocycloalkyl ring and spiro $C_{3-6}$ cycloalkyl ring are each optionally substituted with 1, 2, 3 or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$ $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$ $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-10 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$, $NR^{c5}C(O)R^{b5}$, $NR^{c5}C(O)OR^{a5}$, $NR^{c5}S(O)R^{b5}$, $NR^{c5}S(O)_2R^{b5}$, $NR^{c5}S(O)_2NR^{c5}R^{d5}$ $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)$ $NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$ $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)R^{b4}$, $NR^{c4}S(O)_2R^{b4}$, $NR^{c4}S(O)_2NR^{c4}R^{d4}$ $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a6}$, $SR^{a6}$, $C(O)R^{b6}$, $C(O)NR^{c6}R^{d6}$, $C(O)OR^{a6}$, $NR^{c6}R^{d6}$ $NR^{c6}C(O)R^{b6}$, $NR^{6}C(O)OR^{a6}$ $NR^{c6}S(O)R^{b6}$, $NR^{c6}S(O)_2R^{b6}$, $NR^{c6}S(O)_2NR^{c6}R^{d6}$ $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^g$;

each $R^a$, $R^c$, and $R^d$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3 or 4 substituents independently selected from $R^{10}$;

each $R^b$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{10}$;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{11}$;

or any $R^{c1}$ and $R^{d1}$ attached to the same N atom, together with the N atom to which they are attached, form a 4-10 membered heterocycloalkyl group optionally substituted with 1, 2, 3 or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, and di($C_{1-6}$ alkyl)aminosulfonyl;

each $R^{a2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{21}$;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, and 5-10 membered heteroaryl-$C_{1-3}$ alkylene are each optionally substituted with 1, 2, 3, or 4 substituents independently selected from $R^{21}$;

each $R^{e2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, and di($C_{1-6}$ alkyl)aminosulfonyl;

each $R^{a3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{13}$ alkylene are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{12}$;

each $R^{a4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene; wherein said $C_{1-6}$ alkyl, $C_{2-6}$ alkenyl, $C_{2-6}$ alkynyl, $C_{3-6}$ cycloalkyl, phenyl, 5-6 membered heteroaryl, 4-7 membered heterocycloalkyl, $C_{3-6}$ cycloalkyl-$C_{1-3}$ alkylene, 4-7 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, 3, or 4 substituents independently selected from $R^{22}$;

each $R^{a5}$, $R^{c5}$ and $R^{d5}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c5}$ and $R^{d5}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The compound of claim 1, wherein $R^1$ is selected from $Cy^1$, $C_{1-6}$ haloalkyl, halo, CN, $OR^a$, $C(O)R^b$, $C(O)NR^cR^d$, $C(O)OR^a$, $OC(O)R^b$, $NR^cR^d$, and $NR^cC(O)R^b$.

3. The compound of claim 1, wherein $R^1$ is $Cy^1$.

4. The compound of claim 1, wherein $Cy^1$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2 or 3 substituents independently selected from $R^{10}$.

5. The compound of claim 1, wherein $Cy^1$ is $C_{6-10}$ aryl optionally substituted with 1 or 2 substituents independently selected from $R^{10}$.

6. The compound of claim 1, wherein $Cy^1$ is phenyl optionally substituted with 1 or 2 substituents independently selected from $R^{10}$.

7. The compound of claim 1, wherein $Cy^1$ is 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the 5-10 membered heteroaryl is optionally substituted with 1 or 2 substituents independently selected from $R^{10}$.

8. The compound of claim 1, wherein $Cy^1$ is 5-6 membered heteroaryl; wherein the 5-6 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-6 membered heteroaryl is optionally substituted by oxo to form a carbonyl group; and wherein the 5-6 membered heteroaryl is optionally substituted with 1 or 2 substituents independently selected from $R^{10}$.

9. The compound of claim 1, wherein $Cy^1$ is pyridinyl optionally substituted with 1 or 2 substituents independently selected from $R^{10}$.

10. The compound of claim 1, wherein $Cy^1$ is selected from pyrazolyl, phenyl and pyridinyl, wherein the pyrazolyl, phenyl and pyridinyl are each optionally substituted with 1 or 2 substituents independently selected from $R^{10}$.

11. The compound of claim 1, wherein $R^{10}$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a1}$, 4-10 membered heterocycloalkyl-$C_{1-3}$ alkylene, 5-6 membered heteroaryl-$C_{1-3}$ alkylene, and $C(O)NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, 4-10 membered heterocycloalkyl-$C_{1-3}$ alkylene, and 5-6 membered heteroaryl-$C_{1-3}$ alkylene are each optionally substituted with 1 or 2 substituents independently selected from $R^H$.

12. The compound of claim 1, wherein $R^{10}$ is selected from $C_{1-6}$ alkyl, halo, $C_{3-10}$ cycloalkyl, 4-10 membered heterocycloalkyl, $C_{6-10}$ aryl, 5-10 membered heteroaryl, 4-10 membered heterocycloalkyl-$C_{1-3}$ alkylene, 5-6 membered heteroaryl-$C_{1-3}$ alkylene, and $C(O)NR^{c1}R^{d1}$; wherein said $C_{1-6}$ alkyl, $C_{3-10}$ cycloalkyl, 4-10 membered heterocycloalkyl, $C_{6-10}$ aryl, 5-10 membered heteroaryl, 4-10 membered heterocycloalkyl-$C_{1-3}$ alkylene, and 5-6 membered heteroaryl-$C_{1-3}$ alkylene, are each optionally substituted with 1 or 2 substituents independently selected from $R^{11}$.

13. The compound of claim 1, wherein $R^{10}$ is 4-10 membered heterocycloalkyl optionally substituted with 1 or 2 substituents independently selected from RH.

14. The compound of claim 1, wherein $R^{10}$ is 5-6 membered heterocycloalkyl optionally substituted with 1 or 2 substituents independently selected from $R^{11}$.

15. The compound of claim 1, wherein $R^{10}$ is piperazinyl optionally substituted with 1 or 2 substituents independently selected from $R^{11}$.

16. The compound of claim 1, wherein $R^{10}$ is selected from methyl, ethyl, isopropyl, cyclopropyl, cyclobutyl, fluoro, methylcarbamoyl, phenyl, piperazinyl, pyrrolidinyl, morpholino, piperidinyl, pyridinyl, hexahydropyrrolo[1,2-a]pyrazin-2(1H)-yl, tetrahydropyranyl, cyclohexyl, 2-morpholinoethyl, pyridinylmethyl, 2,2,2-trifluoroethyl, and imidazo[1,2-a]pyridin-6-yl; wherein said methyl, ethyl, isopropyl, cyclopropyl, cyclobutyl, methylcarbamoyl, phenyl, piperazinyl, pyrrolidinyl, morpholino, piperidinyl, pyridinyl, hexahydropyrrolo[1,2-a]pyrazin-2(1H)-yl, tetrahydropyranyl, cyclohexyl, 2-morpholinoethyl, pyridinylmethyl, 2,2,2-trifluoroethyl, and imidazo[1,2-a]pyridin-6-yl are each optionally substituted with 1 or 2 substituents independently selected from $R^{11}$.

17. The compound of claim 1, wherein $R^{11}$ is independently selected from $C_{1-6}$ alkyl, $C_{1-6}$ haloalkyl, halo, 4-10 membered heterocycloalkyl, 5-10 membered heteroaryl, CN, $OR^{a3}$, $C(O)NR^{c3}R^{d3}$, $C(O)R^{b3}$, and $NR^{c3}R^{d3}$, wherein said $C_{1-6}$ alkyl, 4-10 membered heterocycloalkyl, and 5-10 membered heteroaryl are each optionally substituted with 1 or 2 substituents independently selected from $R^{12}$.

18. The compound of claim 1, wherein $R^{11}$ is independently selected from $C_{1-6}$ alkyl, $C_{2-6}$ alkenyl, and $C_{2-6}$ alkynyl.

19. The compound of claim 1, wherein $R^{11}$ is $C_{1-6}$ alkyl.

20. The compound of claim 1, wherein $R^{11}$ is methyl.

21. The compound of claim 1, wherein $R^{10}$ is methyl, ethyl, isopropyl, cyclopropyl, cyclobutyl, fluoro, methylpiperazin-1-yl, 4-ethylpiperazin-1-yl, methylcarbamoyl, 1-methylpyrrolidin-3-yl, 1-(2-hydroxyethyl)pyrrolidin-3-yl, 4-(1-hydroxypropan-2-yl)piperazin-1-yl, 4-(tetrahydro-2H-pyran-4-yl)piperazin-1-yl, 4-(2-carboxypropan-2-yl)piperazin-1-yl, 2-methylmorpholino, 3,4-dimethylpiperazin-1-yl, 4-hydroxypiperidin-1-yl, 7-hydroxyhexahydropyrrolo[1,2-a]pyrazin-2(1H)-yl, 2-methoxyethyl, tetrahydro-2H-pyran-4-yl, 4-hydroxycyclohexyl, 1-(dimethylcarbamoyl)piperidin-4-yl, 1-isobutyrylpiperidin-4-yl, 2-morpholinoethyl, 4-methylpiperazin-1-yl, pyridin-4-ylmethyl, 2,2,2-trifluoroethyl, pyridin-4-yl, pyridin-3-yl, 4-cyanophenyl, 2-methylpyridin-4-yl, 6-(dimethylamino)pyridin-3-yl, 5-cyanopyridin-3-yl, 6-cyanopyridin-3-yl, 4-cyano-3-methylphenyl, 4-cyano-2-methylphenyl, 4-cyano-3-fluorophenyl, 4-(methylcarbamoyl)phenyl, 4-(dimethylcarbamoyl)phenyl, 3-fluoro-4-(methylcarbamoyl)phenyl, 3-(6-(methylcarbamoyl)pyridin-3-yl, 3-methylpiperazin-1-yl or 4-methylpiperazin-1-yl.

22. The compound of claim 1, wherein $R^2$ is H.

23. The compound of claim 1, wherein Cy is 4-8 membered heterocycloalkyl; wherein the 4-8 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-8 membered heterocycloalkyl is optionally substituted by oxo to form a carbonyl group; wherein when the 4-8 membered heterocycloalkyl of Cy has a fused aromatic ring, the 4-8 membered heterocycloalkyl is directly attached to the pyrazolopyrimidine core structure through a ring-forming atom of the saturated or partially saturated ring; and wherein the 4-8 membered heterocycloalkyl is optionally substituted with 1, 2, 3, or 4 substituents independently selected from $R^{20}$.

24. The compound of claim 1, wherein $R^{20}$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, $OR^{a2}$, $SR^{a2}$, $C(O)R^{b2}$, $C(O)NR^{c2}R^{d2}$, $C(O)OR^{a2}$, and $NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{21}$.

25. The compound of claim 1, wherein $R^{20}$ is selected from $C_{1-6}$ alkyl, $C_{1-6}$ haloalkyl, $C_{3-10}$ cycloalkyl, $C_{6-10}$ aryl, halo, CN, $OR^{a2}$, $C(O)R^{b2}$, $C(O)NR^{c2}R^{d2}$, and $C(O)OR^{a2}$; wherein said $C_{1-6}$ alkyl, $C_{3-10}$ cycloalkyl, and $C_{6-10}$ aryl are each optionally substituted with 1 or 2 substituents independently selected from $R^{21}$.

26. The compound of claim 1, wherein each $R^{20}$ is $C_{1-6}$ alkyl optionally substituted with 1 or 2 substituents independently selected from $R^{21}$.

27. The compound of claim 1, wherein $R^{20}$ is $C_{6-10}$ aryl optionally substituted with 1 or 2 substituents independently selected from $R^{21}$.

28. The compound of claim 1, wherein $R^{20}$ is selected from $OR^{a2}$, $C(O)R^{b2}$, $C(O)NR^{c2}R^{d2}$, and $C(O)OR^{a2}$.

29. The compound of claim 1, wherein $R^{21}$ is selected from halo, CN, and $OR^{a4}$.

30. The compound of claim 1, wherein each $R^{a2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl; wherein said $C_{1-6}$ alkyl, $C_{2-6}$ alkenyl, and $C_{2-6}$ alkynyl are each optionally substituted with 1 or 2 substituents independently selected from $R^{21}$.

31. The compound of claim 1, wherein each $R^{a2}$, $R^{c2}$ and $R^{d2}$ is independently selected from H, $C_{1-6}$ alkyl, and $C_{1-6}$ haloalkyl; wherein said $C_{1-6}$ alkyl is optionally substituted with 1 or 2 substituents independently selected from $R^{21}$.

32. The compound of claim 1, wherein any $R^{c2}$ and $R^{d2}$ attached to the same N atom, together with the N atom to which they are attached, form a 4-10 membered heterocycloalkyl group optionally substituted with 1 or 2 substituents independently selected from $R^{21}$.

33. The compound of claim 1, wherein $R^{b2}$ is selected from $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl are each optionally substituted with 1 or 2 substituents independently selected from $R^{21}$.

34. The compound of claim 1, wherein each $R^{a4}$, $R^{c4}$ and $R^{d4}$ is independently selected from H and $C_{1-6}$ alkyl.

35. The compound of claim 1, wherein each $R^{a4}$, $R^{c4}$ and $R^{d4}$ is independently $C_{1-6}$ alkyl.

36. The compound of claim 1, wherein Cy is piperidinyl, morpholinyl, azabicyclo[2.2.1]heptanyl, azabicyclo[3.2.1]octanyl, piperazinyl, diazabicyclo[3.2.1]octanyl, 1,4,6,7-tetrahydro-5H-imidazo[4,5-c]pyridin-5-yl, 5,6-dihydroimidazo[1,2-a]pyrazin-7(8H)-yl, 2,5-diazabicyclo[2.2.2]octan-2-yl, 2,5-diazabicyclo[2.2.1]heptan-2-yl, 3-oxopiperazinyl, 5,6,7,8-tetrahydro-1,6-naphthyridin-6-yl, 5,6,7,8-tetrahydroimidazo[1,5-a]pyrazin-7-yl, 4,5,6,7-tetrahydrothiazolo[5,4-c]pyridin-5-yl, 1,4,5,7-tetrahydro-6H-pyrazolo[3,4-c]pyridin-6-yl, 1,4,5,6,7,8-hexahydro-5,8-epiminocyclohepta[c]pyrazol-9-yl, or 2-oxo-3,8-diazabicyclo[3.2.1]octan-8-yl, each optionally substituted with 1, 2, 3, or 4 substituents independently selected from $R^{20}$.

37. The compound of claim 1, wherein Cy is

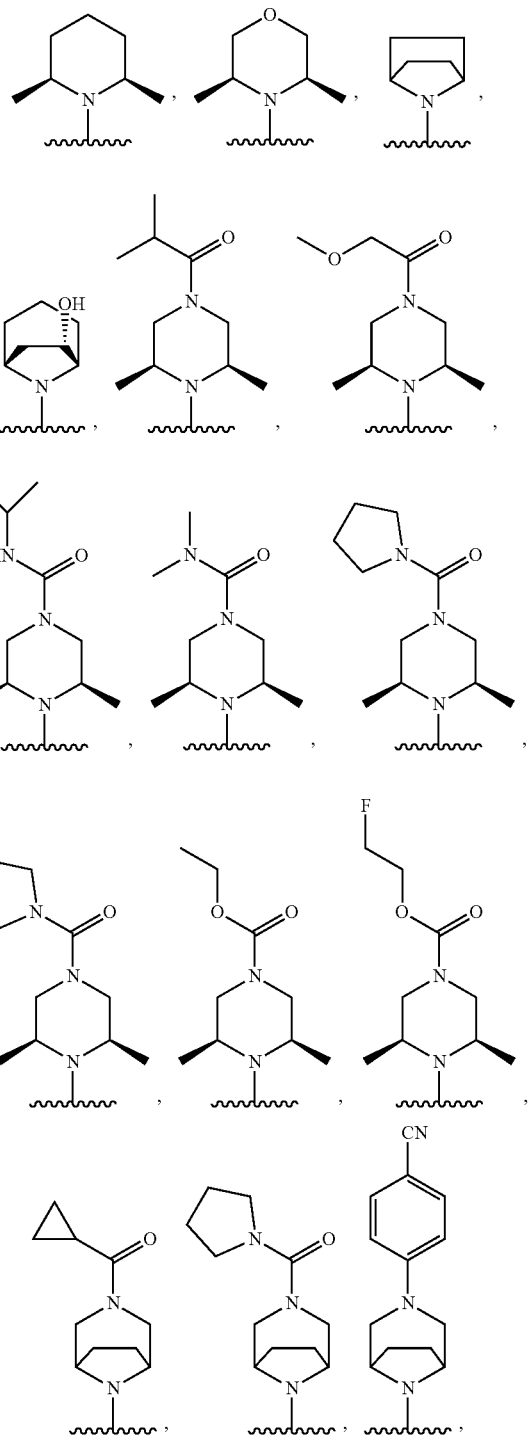

147

-continued

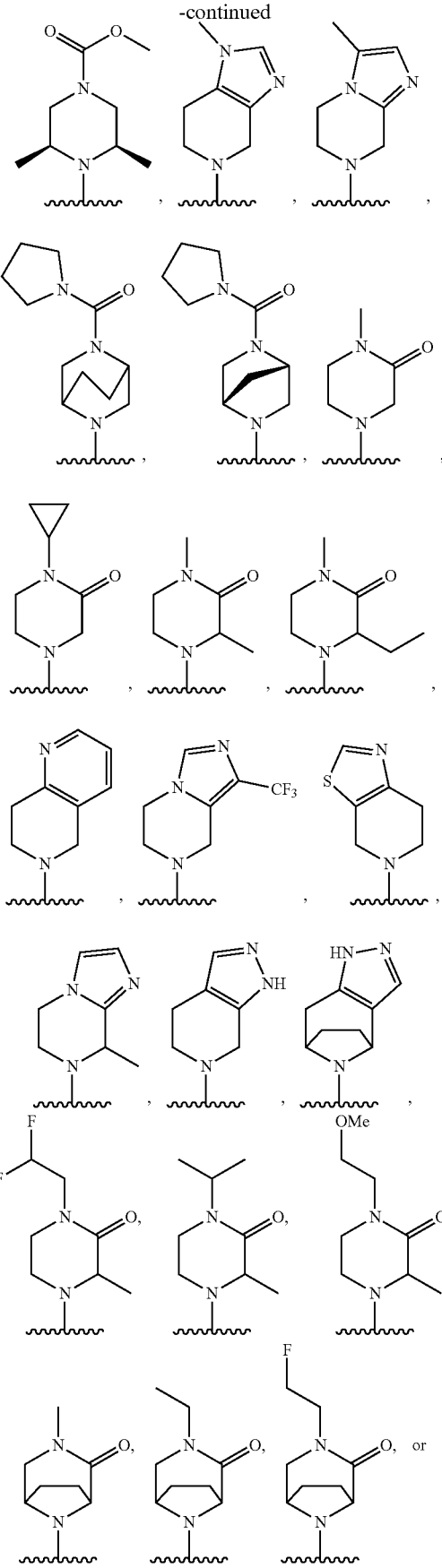

148

-continued

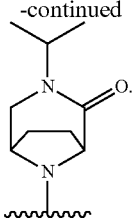

38. The compound of claim 1, wherein the compound is a compound of Formula II:

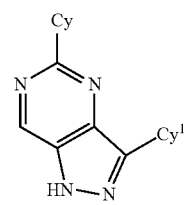

II or a pharmaceutically acceptable salt thereof.

39. The compound of claim 1, wherein the compound is a compound of Formula III:

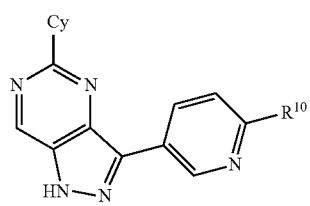

III or a pharmaceutically acceptable salt thereof.

40. The compound of claim 1, wherein the compound is a compound of Formula IV:

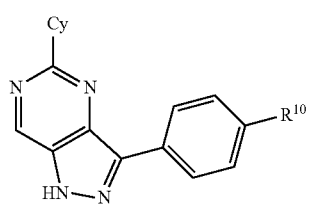

IV or a pharmaceutically acceptable salt thereof.

41. The compound of claim 1, wherein the compound is a compound of Formula V:

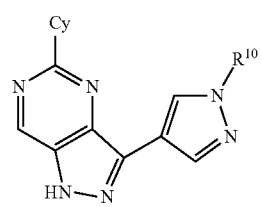

V or a pharmaceutically acceptable salt thereof.

42. The compound of claim 1, wherein:

$R^1$ is $Cy^1$;

$Cy^1$ is selected from $C_{5-6}$ cycloalkyl, 5-6 membered heterocycloalkyl, phenyl and 5-6 membered heteroaryl; wherein the 5-6 membered heterocycloalkyl and 5-6 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-6 membered heteroaryl and 5-6 membered heterocycloalkyl is optionally substituted by oxo to form a carbonyl group; and wherein the $C_{5-6}$ cycloalkyl, 5-6 membered heterocycloalkyl, phenyl and 5-6 membered heteroaryl are each optionally substituted with 1, 2, 3 or 4 substituents independently selected from $R^{10}$;

Cy is 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-12 membered heterocycloalkyl is optionally substituted by oxo to form a carbonyl group; wherein when the 4-12 membered heterocycloalkyl of Cy has a fused aromatic ring, the 4-12 membered heterocycloalkyl is directly attached to the pyrazolopyrimidine core structure through a ring-forming atom of the saturated or partially saturated ring; and wherein the 4-12 membered heterocycloalkyl is optionally substituted with 1, 2, 3, 4 or 5 substituents independently selected from $R^{20}$;

$R^2$ is selected from H, D, $C_{1-4}$ alkyl and $C_{1-4}$ haloalkyl;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, and $NR^{c1}R^{d1}$, $NR^{c1}C(O)R^{b1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1 or 2 substituents independently selected from $R^{11}$;

each $R^{11}$ is independently selected from $C_{1-6}$ alkyl, $C_{1-6}$ haloalkyl, halo, 4-10 membered heterocycloalkyl, 5-10 membered heteroaryl, CN, $OR^{a3}$, $C(O)NR^{c3}R^{d3}$, $C(O)R^{b3}$, and $NR^{c3}R^{d3}$, wherein said $C_{1-6}$ alkyl, 4-10 membered heterocycloalkyl, and 5-10 membered heteroaryl are each optionally substituted with 1 or 2 substituents independently selected from $R^{12}$;

each $R^{12}$ is independently selected from $C_{1-6}$ alkyl, $C_{1-6}$ haloalkyl, halo, CN, $OR^{a5}$, and $C(O)OR^{a5}$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, and $NR^{c2}C(O)OR^{a2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, and $OR^{a4}$;

each $R^{a1}$, $R^{c1}$ and $R^{d1}$ is independently selected from H, and $C_{1-6}$ alkyl;

or any $R^{c1}$ and $R^{d1}$ attached to the same N atom, together with the N atom to which they are attached, form a 4-10 membered heterocycloalkyl group optionally substituted with 1, 2, 3 or 4 substituents independently selected from $R^{11}$;

each $R^{b1}$ is independently selected from $C_{1-6}$ alkyl;

each $R^{a2}$, $R^{c2}$ and $R^{d2}$ is independently selected from H, $C_{1-6}$ alkyl and $C_{1-6}$ haloalkyl;

wherein said $C_{1-6}$ alkyl is optionally substituted with 1 or 2 substituents independently selected from $R^{21}$;

or any $R^{c2}$ and $R^{d2}$ attached to the same N atom, together with the N atom to which they are attached, form a 4-10 membered heterocycloalkyl group optionally substituted with 1, 2, 3 or 4 substituents independently selected from $R^{21}$;

each $R^{b2}$ is independently selected from $C_{1-6}$ alkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl are each optionally substituted with 1 or 2 substituents independently selected from $R^{21}$;

each $R^{a3}$, $R^{c3}$ and $R^{d3}$ is independently selected from H, $C_{1-6}$ alkyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{1-6}$ haloalkyl, $C_{3-6}$ cycloalkyl, phenyl, 5-6 membered heteroaryl, and 4-7 membered heterocycloalkyl; wherein said $C_{1-6}$ alkyl, $C_{3-6}$ cycloalkyl, phenyl, 5-6 membered heteroaryl, and 4-7 membered heterocycloalkyl, are each optionally substituted with 1, 2, 3, or 4 substituents independently selected from $R^{12}$;

each $R^{a4}$ is independently selected from H, and $C_{1-6}$ alkyl; and each $R^{a5}$ is independently selected from H, and $C_{1-6}$ alkyl.

43. The compound of claim 1, wherein:

$R^1$ is $Cy^1$;

$Cy^1$ is selected from phenyl and 5-6 membered heteroaryl; wherein the 5-6 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-6 membered heteroaryl is optionally substituted by oxo to form a carbonyl group; and wherein the phenyl and 5-6 membered heteroaryl are each optionally substituted with 1 or 2 substituents independently selected from $R^{10}$;

Cy is 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-12 membered heterocycloalkyl is optionally substituted by oxo to form a carbonyl group; wherein when the 4-12 membered heterocycloalkyl of Cy has a fused aromatic ring, the 4-12 membered heterocycloalkyl is directly attached to the pyrazolopyrimidine core structure through a ring-forming atom of the saturated or partially saturated ring; and wherein the 4-12 membered heterocycloalkyl is optionally substituted with 1,2 or 3 substituents independently selected from $R^{20}$;

$R^2$ is H or D;

each $R^{10}$ is independently selected from $C_{1-6}$ alkyl, halo, $C_{3-10}$ cycloalkyl, 4-10 membered heterocycloalkyl, $C_{6-10}$ aryl, 5-10 membered heteroaryl, 4-10 membered heterocycloalkyl-$C_{1-3}$ alkylene, 5-6 membered heteroaryl-$C_{1-3}$ alkylene, and $C(O)NR^{c1}R^{d1}$; wherein said $C_{1-6}$ alkyl, $C_{3-10}$ cycloalkyl, 4-10 membered heterocycloalkyl, $C_{6-10}$ aryl, 5-10 membered heteroaryl, 4-10 membered heterocycloalkyl-$C_{1-3}$ alkylene, and 5-6 membered heteroaryl-$C_{1-3}$ alkylene are each optionally substituted with 1 or 2 substituents independently selected from $R^{11}$;

each $R^{11}$ is independently selected from $C_{1-6}$ alkyl, $C_{1-6}$ haloalkyl, halo, 4-10 membered heterocycloalkyl, 5-10 membered heteroaryl, CN, $OR^{a3}$, $C(O)NR^{c3}R^{d3}$, $C(O)R^{b3}$, and $NR^{c3}R^{d3}$, wherein said $C_{1-6}$ alkyl, 4-10 membered heterocycloalkyl, and 5-10 membered heteroaryl are each optionally substituted with 1 or 2 substituents independently selected from $R^{12}$;

each $R^{c1}$ and $R^{d1}$ is independently selected from H, and $C_{1-6}$ alkyl;

each $R^{a3}$, $R^{b3}$, $R^{c3}$ and $R^{d3}$ is independently selected from H, and $C_{1-6}$ alkyl;

each $R^{12}$ is independently selected from $C_{1-6}$ alkyl, C(O)OH, and OH;

each $R^{20}$ is independently selected from $C_{1-6}$ alkyl, $C_{1-6}$ haloalkyl, $C_{3-10}$ cycloalkyl, $C_{6-10}$ aryl, halo, CN, $OR^{a2}$, $C(O)R^{b2}$, $C(O)NR^{c2}R^{d2}$, and $C(O)OR^{a2}$; wherein said $C_{1-6}$ alkyl, $C_{3-10}$ cycloalkyl, and $C_{6-10}$ aryl are each optionally substituted with 1 or 2 substituents independently selected from $R^{21}$;

each $R^{a2}$, $R^{c2}$ and $R^{d2}$ is independently selected from H, $C_{1-6}$ alkyl and $C_{1-6}$ haloalkyl; wherein said $C_{1-6}$ alkyl is optionally substituted with 1 or 2 substituents independently selected from $R^{21}$;

or any $R^{c2}$ and $R^{d2}$ attached to the same N atom, together with the N atom to which they are attached, form a 4-10 membered heterocycloalkyl group optionally substituted with 1 or 2 substituents independently selected from $R^{21}$;

each $R^{b2}$ is independently selected from $C_{1-6}$ alkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl are each optionally substituted with 1 or 2 substituents independently selected from $R^{21}$;

each $R^{21}$ is independently selected from halo, D, CN, and $OR^{a4}$; and each $R^{a4}$ is $C_{1-6}$ alkyl.

44. The compound of claim 1, wherein the compound is a compound of Formula V:

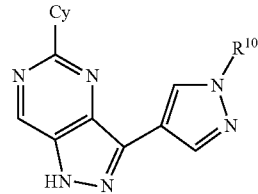

V or a pharmaceutically acceptable salt thereof, wherein:

Cy is 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-12 membered heterocycloalkyl is optionally substituted by oxo to form a carbonyl group; wherein when the 4-12 membered heterocycloalkyl of Cy has a fused aromatic ring, the 4-12 membered heterocycloalkyl is directly attached to the pyrazolopyrimidine core structure through a ring-forming atom of the saturated or partially saturated ring; and wherein the 4-12 membered heterocycloalkyl is optionally substituted with 1, 2 or 3 substituents independently selected from $R^{20}$;

$R^{10}$ is selected from $C_{1-6}$ alkyl, halo, $C_{3-10}$ cycloalkyl, 4-10 membered heterocycloalkyl, $C_{6-10}$ aryl, 5-10 membered heteroaryl, 4-10 membered heterocycloalkyl-$C_{1-3}$ alkylene, 5-6 membered heteroaryl-$C_{1-3}$ alkylene, and $C(O)NR^{c1}R^{d1}$; wherein said $C_{1-6}$ alkyl, $C_{3-10}$ cycloalkyl, 4-10 membered heterocycloalkyl, $C_{6-10}$ aryl, 5-10 membered heteroaryl, 4-10 membered heterocycloalkyl-$C_{1-3}$ alkylene, and 5-6 membered heteroaryl-$C_{1-3}$ alkylene are each optionally substituted with 1 or 2 substituents independently selected from $R^{11}$;

each $R^{11}$ is independently selected from $C_{1-6}$ alkyl, $C_{1-6}$ haloalkyl, halo, 4-10 membered heterocycloalkyl, 5-10 membered heteroaryl, CN, $OR^{a3}$, $C(O)NR^{c3}R^{d3}$, $C(O)R^{b3}$, and $NR^{c3}R^{d3}$, wherein said $C_{1-6}$ alkyl, 4-10 membered heterocycloalkyl, and 5-10 membered heteroaryl are each optionally substituted with 1 or 2 substituents independently selected from $R^{12}$;

each $R^{c1}$ and $R^{d1}$ is independently selected from H, and $C_{1-6}$ alkyl;

each $R^{a3}$, $R^{b3}$, $R^{c3}$ and $R^{d3}$ is independently selected from H, and $C_{1-6}$ alkyl;

each $R^{12}$ is independently selected from $C_{1-6}$ alkyl, C(O)OH, and OH;

each $R^{20}$ is independently selected from $C_{1-6}$ alkyl, $C_{1-6}$ haloalkyl, $C_{3-10}$ cycloalkyl, $C_{6-10}$ aryl, halo, CN, $OR^{a2}$, $C(O)R^{b2}$, $C(O)NR^{c2}R^{d2}$, and $C(O)OR^{a2}$; wherein said $C_{1-6}$ alkyl, $C_{3-10}$ cycloalkyl, and $C_{6-10}$ aryl are each optionally substituted with 1 or 2 substituents independently selected from $R^{21}$;

each $R^{a2}$, $R^{c2}$ and $R^{d2}$ is independently selected from H, $C_{1-6}$ alkyl and $C_{1-6}$ haloalkyl;

wherein said $C_{1-6}$ alkyl is optionally substituted with 1 or 2 substituents independently selected from $R^{21}$;

or any $R^{c2}$ and $R^{d2}$ attached to the same N atom, together with the N atom to which they are attached, form a 4-10 membered heterocycloalkyl group optionally substituted with 1 or 2 substituents independently selected from $R^{21}$;

each $R^{b2}$ is independently selected from $C_{1-6}$ alkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl are each optionally substituted with 1 or 2 substituents independently selected from $R^{21}$;

each $R^{21}$ is independently selected from halo, D, CN, and $OR^{a4}$; and each $R^{a4}$ is $C_{1-6}$ alkyl.

45. The compound of claim 1, wherein the compound is a compound of Formula VI, or a pharmaceutically acceptable salt thereof:

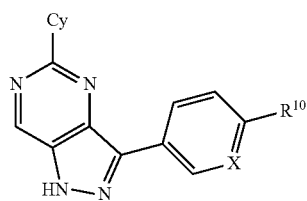

VI wherein:

X is selected from CH, CF, CCH$_3$ and N;

Cy is 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of 4-12 membered heterocycloalkyl is optionally substituted by oxo to form a carbonyl group; wherein when the 4-12 membered heterocycloalkyl of Cy has a fused aromatic ring, the 4-12 membered heterocycloalkyl is directly attached to the pyrazolopyrimidine core structure through a ring-forming atom of the saturated or partially saturated ring; and wherein the 4-12 membered heterocycloalkyl is optionally substituted with 1, 2 or 3 substituents independently selected from $R^{20}$;

$R^{10}$ is selected from 4-10 membered heterocycloalkyl, wherein said 4-10 membered heterocycloalkyl is optionally substituted with 1 or 2 substituents independently selected from $R^{11}$;

each $R^{11}$ is independently selected from $C_{1-6}$ alkyl, and 4-10 membered heterocycloalkyl, $C_{1-6}$ alkyl, and 4-10 membered heterocycloalkyl are each optionally substituted with 1 or 2 substituents independently selected from $R^{12}$;

each $R^{12}$ is independently selected from $C_{1-6}$ alkyl, C(O)OH, and OH;

each $R^{20}$ is independently selected from $C_{1-6}$ alkyl, $C_{1-6}$ haloalkyl, $C_{3-10}$ cycloalkyl, $C_{6-10}$ aryl, halo, CN, $OR^{a2}$, $C(O)R^{b2}$, $C(O)NR^{c2}R^{d2}$, and $C(O)OR^{a2}$; wherein said $C_{1-6}$ alkyl, $C_{3-10}$ cycloalkyl, and $C_{6-10}$ aryl are each optionally substituted with 1 or 2 substituents independently selected from $R^{21}$;

each $R^{a2}$, $R^{c2}$ and $R^{d2}$ is independently selected from H, $C_{1-6}$ alkyl and $C_{1-6}$ haloalkyl;

wherein said $C_{1-6}$ alkyl is optionally substituted with 1 or 2 substituents independently selected from $R^{21}$;

or any $R^{c2}$ and $R^{d2}$ attached to the same N atom, together with the N atom to which they are attached, form a 4-10 membered heterocycloalkyl group optionally substituted with 1 or 2 substituents independently selected from $R^{21}$;

each $R^{b2}$ is independently selected from $C_{1-6}$ alkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl are each optionally substituted with 1 or 2 substituents independently selected from $R^{21}$;

each $R^{21}$ is independently selected from halo, D, CN, and $OR^{a4}$; and each $R^{a4}$ is $C_{1-6}$ alkyl.

46. The compound of claim 1, wherein the compound is selected from:

5-((2R,6S)-2,6-dimethylpiperidin-1-yl)-3-(6-((R)-3-methylpiperazin-1-yl)pyridin-3-yl)-1H-pyrazolo[4,3-d]pyrimidine;

(3R,5S)-3, 5-dimethyl-4-(3-(6-((R)-3-methylpiperazin-1-yl)pyridin-3-yl)-1H-pyrazolo[4,3-d]pyrimidin-5-yl)morpholine;

5-(7-azabicyclo[2.2.1]heptan-7-yl)-3-(6-((R)-3-methylpiperazin-1-yl)pyridin-3-yl)-1H-pyrazolo[4,3-d]pyrimidine;

(1R,5S,6S)-8-(3-(6-((R)-3-methylpiperazin-1-yl)pyridin-3-yl)-1H-pyrazolo[4,3-d]pyrimidin-5-yl)-8-azabicyclo[3.2.1]octan-6-ol;

1-((3R,5S)-3, 5-dimethyl-4-(3-(6-((R)-3-methylpiperazin-1-yl)pyridin-3-yl)-1H-pyrazolo[4,3-d]pyrimidin-5-yl)piperazin-1-yl)-2-methylpropan-1-one;

1-((3R,5S)-3, 5-dimethyl-4-(3-(6-((R)-3-methylpiperazin-1-yl)pyridin-3-yl)-1H-pyrazolo[4,3-d]pyrimidin-5-yl)piperazin-1-yl)-2-methoxyethan-1-one;

(3R,5S)-N-isopropyl-3,5-dimethyl-4-(3-(6-((R)-3-methylpiperazin-1-yl)pyridin-3-yl)-1H-pyrazolo[4,3-d]pyrimidin-5-yl)piperazine-1-carboxamide;

(3R,5S)-N,N,3,5-tetramethyl-4-(3-(6-((R)-3-methylpiperazin-1-yl)pyridin-3-yl)-1H-pyrazolo[4,3-d]pyrimidin-5-yl)piperazine-1-carboxamide;

((3R,5S)-3, 5-dimethyl-4-(3-(6-((R)-3-methylpiperazin-1-yl)pyridin-3-yl)-1H-pyrazolo[4,3-d]pyrimidin-5-yl)piperazin-1-yl)(pyrrolidin-1-yl)methanone;

((3R,5S)-3, 5-dimethyl-4-(3-(6-((R)-3-methylpiperazin-1-yl)pyridin-3-yl)-1H-pyrazolo[4,3-d]pyrimidin-5-yl)piperazin-1-yl)(3-fluoropyrrolidin-1-yl)methanone;

Ethyl (3R,5S)-3,5-dimethyl-4-(3-(6-((R)-3-methylpiperazin-1-yl)pyridin-3-yl)-1H-pyrazolo[4,3-d]pyrimidin-5-yl)piperazine-1-carboxylate;

2-Fluoroethyl (3R,5S)-3,5-dimethyl-4-(3-(6-((R)-3-methylpiperazin-1-yl)pyridin-3-yl)-1H-pyrazolo[4,3-d]pyrimidin-5-yl)piperazine-1-carboxylate;

Cyclopropyl((1R,5S)-8-(3-(6-((R)-3-methylpiperazin-1-yl)pyridin-3-yl)-1H-pyrazolo[4,3-d]pyrimidin-5-yl)-3, 8-diazabicyclo[3.2.1]octan-3-yl)methanone;

((1R,5S)-8-(3-(6-((R)-3-methylpiperazin-1-yl)pyridin-3-yl)-1H-pyrazolo[4,3-d]pyrimidin-5-yl)-3, 8-diazabicyclo[3.2.1]octan-3-yl)(pyrrolidin-1-yl)methanone;

4-((1R,5S)-8-(3-(6-((R)-3-methylpiperazin-1-yl)pyridin-3-yl)-1H-pyrazolo[4,3-d]pyrimidin-5-yl)-3,8-diazabicyclo[3.2.1]octan-3-yl)benzonitrile; and 5-((2R,6S)-2,6-dimethylpiperidin-1-yl)-3-(4-(4-methylpiperazin-1-yl)phenyl)-1H-pyrazolo[4,3-d]pyrimidine, or a pharmaceutically acceptable salt thereof.

47. The compound of claim 1, wherein the compound is selected from:

Methyl (3R,5S)-3,5-dimethyl-4-(3-(6-((R)-3-methylpiperazin-1-yl)pyridin-3-yl)-1H-pyrazolo[4,3-d]pyrimidin-5-yl)piperazine-1-carboxylate;

(R)-5-(1-Methyl-1,4,6,7-tetrahydro-5H-imidazo[4,5-c]pyridin-5-yl)-3-(6-(3-methylpiperazin-1-yl)pyridin-3-yl)-1H-pyrazolo[4,3-d]pyrimidine;
(R)-5-(3-Methyl-5,6-dihydroimidazo[1,2-a]pyrazin-7(8H)-yl)-3-(6-(3-methylpiperazin-1-yl)pyridin-3-yl)-1H-pyrazolo[4,3-d]pyrimidine;
(5-(3-(6-((R)-3-Methylpiperazin-1-yl)pyridin-3-yl)-1H-pyrazolo[4,3-d]pyrimidin-5-yl)-2,5-diazabicyclo[2.2.2]octan-2-yl)(pyrrolidin-1-yl)methanone;
((1S,4S)-5-(3-(6-((R)-3-Methylpiperazin-1-yl)pyridin-3-yl)-1H-pyrazolo[4,3-d]pyrimidin-5-yl)-2,5-diazabicyclo[2.2.1]heptan-2-yl)(pyrrolidin-1-yl)methanone
Methyl (3R,5S)-3,5-dimethyl-4-(3-(4-(4-methylpiperazin-1-yl)phenyl)-1H-pyrazolo[4,3-d]pyrimidin-5-yl)piperazine-1-carboxylate;
Methyl (3R,5S)-4-(3-(3-fluoro-4-(4-methylpiperazin-1-yl)phenyl)-1H-pyrazolo[4,3-d]pyrimidin-5-yl)-3,5-dimethylpiperazine-1-carboxylate;
Methyl (3R,5S)-3,5-dimethyl-4-(3-(6-(4-methylpiperazin-1-yl)pyridin-3-yl)-1H-pyrazolo[4,3-d]pyrimidin-5-yl)piperazine-1-carboxylate;
Methyl (3R,5S)-4-(3-(4-(4-ethylpiperazin-1-yl)-3-methylphenyl)-1H-pyrazolo[4,3-d]pyrimidin-5-yl)-3,5-dimethylpiperazine-1-carboxylate;
Methyl (3R,5S)-3,5-dimethyl-4-(3-(4-(methylcarbamoyl)phenyl)-1H-pyrazolo[4,3-d]pyrimidin-5-yl)piperazine-1-carboxylate;
Methyl (3R,5S)-3,5-dimethyl-4-(3-(4-(1-methylpyrrolidin-3-yl)phenyl)-1H-pyrazolo[4,3-d]pyrimidin-5-yl)piperazine-1-carboxylate;
Methyl (3R,5S)-4-(3-(4-(1-(2-hydroxyethyl)pyrrolidin-3-yl)phenyl)-1H-pyrazolo[4,3-d]pyrimidin-5-yl)-3,5-dimethylpiperazine-1-carboxylate;
Methyl (3R,5S)-4-(3-(4-(4-(1-hydroxypropan-2-yl)piperazin-1-yl)phenyl)-1H-pyrazolo[4,3-d]pyrimidin-5-yl)-3,5-dimethylpiperazine-1-carboxylate;
Methyl (3R,5S)-3,5-dimethyl-4-(3-(4-(4-(tetrahydro-2H-pyran-4-yl)piperazin-1-yl)phenyl)-1H-pyrazolo[4,3-d]pyrimidin-5-yl)piperazine-1-carboxylate;
2-(4-(4-(5-((2R,6S)-4-(Methoxycarbonyl)-2,6-dimethylpiperazin-1-yl)-1H-pyrazolo[4,3-d]pyrimidin-3-yl)phenyl)piperazin-1-yl)-2-methylpropanoic acid;
Methyl (3R,5S)-3,5-dimethyl-4-(3-(6-((R)-2-methylmorpholino)pyridin-3-yl)-1H-pyrazolo[4,3-d]pyrimidin-5-yl)piperazine-1-carboxylate;
Methyl (3R,5S)-4-(3-(6-((R)-3,4-dimethylpiperazin-1-yl)pyridin-3-yl)-1H-pyrazolo[4,3-d]pyrimidin-5-yl)-3,5-dimethylpiperazine-1-carboxylate;
Methyl (3R,5S)-4-(3-(4-(4-hydroxypiperidin-1-yl)phenyl)-1H-pyrazolo[4,3-d]pyrimidin-5-yl)-3,5-dimethylpiperazine-1-carboxylate;
Methyl (3R,5S)-4-(3-(4-((7S,8aR)-7-hydroxyhexahydropyrrolo[1,2-a]pyrazin-2(1H)-yl)phenyl)-1H-pyrazolo[4,3-d]pyrimidin-5-yl)-3,5-dimethylpiperazine-1-carboxylate;
1-Methyl-4-(3-(1-methyl-1H-pyrazol-4-yl)-1H-pyrazolo[4,3-d]pyrimidin-5-yl)piperazin-2-one;
1-Cyclopropyl-4-(3-(1-methyl-1H-pyrazol-4-yl)-1H-pyrazolo[4,3-d]pyrimidin-5-yl)piperazin-2-one;
1,3-Dimethyl-4-(3-(1-methyl-1H-pyrazol-4-yl)-1H-pyrazolo[4,3-d]pyrimidin-5-yl)piperazin-2-one;
3-Ethyl-1-methyl-4-(3-(1-methyl-1H-pyrazol-4-yl)-1H-pyrazolo[4,3-d]pyrimidin-5-yl)piperazin-2-one;
6-(3-(1-Methyl-1H-pyrazol-4-yl)-1H-pyrazolo[4,3-d]pyrimidin-5-yl)-5,6,7,8-tetrahydro-1,6-naphthyridine;
3-(1-Methyl-1H-pyrazol-4-yl)-5-(1-(trifluoromethyl)-5,6-dihydroimidazo[1,5-a]pyrazin-7(8H)-yl)-1H-pyrazolo[4,3-d]pyrimidine;
5-(3-(1-Methyl-1H-pyrazol-4-yl)-1H-pyrazolo[4,3-d]pyrimidin-5-yl)-4,5,6,7-tetrahydrothiazolo[5,4-c]pyridine;
3-(1-Methyl-1H-pyrazol-4-yl)-5-(8-methyl-5, 6-dihydroimidazo[1,2-a]pyrazin-7(8H)-yl)-1H-pyrazolo[4,3-d]pyrimidine;
3-(1-Methyl-1H-pyrazol-4-yl)-5-(1,4,5,7-tetrahydro-6H-pyrazolo[3,4-c]pyridin-6-yl)-1H-pyrazolo[4,3-d]pyrimidine;
9-(3-(1-Methyl-1H-pyrazol-4-yl)-1H-pyrazolo[4,3-d]pyrimidin-5-yl)-1,4,5,6,7,8-hexahydro-4,7-epiminocyclohepta[c]pyrazole;
1-(2,2-Difluoroethyl)-3-methyl-4-(3-(1-methyl-1H-pyrazol-4-yl)-1H-pyrazolo[4,3-d]pyrimidin-5-yl)piperazin-2-one;
1-Isopropyl-3-methyl-4-(3-(1-methyl-1H-pyrazol-4-yl)-1H-pyrazolo[4,3-d]pyrimidin-5-yl)piperazin-2-one;
1-(2-Methoxyethyl)-3-methyl-4-(3-(1-methyl-1H-pyrazol-4-yl)-1H-pyrazolo[4,3-d]pyrimidin-5-yl)piperazin-2-one;
3-Methyl-8-(3-(1-methyl-1H-pyrazol-4-yl)-1H-pyrazolo[4,3-d]pyrimidin-5-yl)-3,8-diazabicyclo[3.2.1]octan-2-one;
3-Ethyl-8-(3-(1-methyl-1H-pyrazol-4-yl)-1H-pyrazolo[4,3-d]pyrimidin-5-yl)-3,8-diazabicyclo[3.2.1]octan-2-one;
3-(2-Fluoroethyl)-8-(3-(1-methyl-1H-pyrazol-4-yl)-1H-pyrazolo[4,3-d]pyrimidin-5-yl)-3,8-diazabicyclo[3.2.1]octan-2-one;
3-Isopropyl-8-(3-(1-methyl-1H-pyrazol-4-yl)-1H-pyrazolo[4,3-d]pyrimidin-5-yl)-3, 8-diazabicyclo[3.2.1]octan-2-one;
8-(3-(1-(2-Methoxyethyl)-1H-pyrazol-4-yl)-1H-pyrazolo[4,3-d]pyrimidin-5-yl)-3-methyl-3,8-diazabicyclo[3.2.1]octan-2-one;
3-Methyl-8-(3-(1-(tetrahydro-2H-pyran-4-yl)-1H-pyrazol-4-yl)-1H-pyrazolo[4,3-d]pyrimidin-5-yl)-3,8-diazabicyclo[3.2.1]octan-2-one;
8-(3-(1-(((1r,4S)-4-Hydroxycyclohexyl)-1H-pyrazol-4-yl)-1H-pyrazolo[4,3-d]pyrimidin-5-yl)-3-methyl-3,8-diazabicyclo[3.2.1]octan-2-one;
N,N-Dimethyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)piperidine-1-carboxamide;
8-(3-(1-(1-Isobutyrylpiperidin-4-yl)-1H-pyrazol-4-yl)-1H-pyrazolo[4,3-d]pyrimidin-5-yl)-3-methyl-3, 8-diazabicyclo[3.2.1]octan-2-one;
3-Methyl-8-(3-(1-(2-morpholinoethyl)-1H-pyrazol-4-yl)-1H-pyrazolo[4,3-d]pyrimidin-5-yl)-3,8-diazabicyclo[3.2.1]octan-2-one;
3-Methyl-8-(3-(1-(pyridin-4-ylmethyl)-1H-pyrazol-4-yl)-1H-pyrazolo[4,3-d]pyrimidin-5-yl)-3,8-diazabicyclo[3.2.1]octan-2-one;
3-Methyl-8-(3-(6-(4-methylpiperazin-1-yl)pyridin-3-yl)-1H-pyrazolo[4,3-d]pyrimidin-5-yl)-3,8-diazabicyclo[3.2.1]octan-2-one;
8-(3-(1-Ethyl-1H-pyrazol-4-yl)-1H-pyrazolo[4,3-d]pyrimidin-5-yl)-3-methyl-3, 8-diazabicyclo[3.2.1]octan-2-one;
8-(3-(1-Isopropyl-1H-pyrazol-4-yl)-1H-pyrazolo[4,3-d]pyrimidin-5-yl)-3-methyl-3, 8-diazabicyclo[3.2.1]octan-2-one;

8-(3-(1-Cyclobutyl-1H-pyrazol-4-yl)-1H-pyrazolo[4,3-d]pyrimidin-5-yl)-3-methyl-3, 8-diazabicyclo[3.2.1]octan-2-one;

8-(3-(1-Cyclopropyl-1H-pyrazol-4-yl)-1H-pyrazolo[4,3-d]pyrimidin-5-yl)-3-methyl-3, 8-diazabicyclo[3.2.1]octan-2-one;

3-Methyl-8-(3-(1-(2,2,2-trifluoroethyl)-1H-pyrazol-4-yl)-1H-pyrazolo[4,3-d]pyrimidin-5-yl)-3,8-diazabicyclo[3.2.1]octan-2-one;

3-Methyl-8-(3-(1-(pyridin-4-yl)-1H-pyrazol-4-yl)-1H-pyrazolo[4,3-d]pyrimidin-5-yl)-3,8-diazabicyclo[3.2.1]octan-2-one;

3-Methyl-8-(3-(1-(pyridin-3-yl)-1H-pyrazol-4-yl)-1H-pyrazolo[4,3-d]pyrimidin-5-yl)-3,8-diazabicyclo[3.2.1]octan-2-one;

4-(4-(5-(3-Methyl-2-oxo-3, 8-diazabicyclo[3.2.1]octan-8-yl)-1H-pyrazolo[4,3-d]pyrimidin-3-yl)-1H-pyrazol-1-yl)benzonitrile;

3-Methyl-8-(3-(1-(2-methylpyridin-4-yl)-1H-pyrazol-4-yl)-1H-pyrazolo[4,3-d]pyrimidin-5-yl)-3,8-diazabicyclo[3.2.1]octan-2-one;

8-(3-(1-(6-(Dimethylamino)pyridin-3-yl)-1H-pyrazol-4-yl)-1H-pyrazolo[4,3-d]pyrimidin-5-yl)-3-methyl-3,8-diazabicyclo[3.2.1]octan-2-one;

5-(4-(5-(3-Methyl-2-oxo-3, 8-diazabicyclo[3.2.1]octan-8-yl)-1H-pyrazolo[4,3-d]pyrimidin-3-yl)-1H-pyrazol-1-yl)nicotinonitrile;

5-(4-(5-(3-Methyl-2-oxo-3, 8-diazabicyclo[3.2.1]octan-8-yl)-1H-pyrazolo[4,3-d]pyrimidin-3-yl)-1H-pyrazol-1-yl)picolinonitrile;

8-(3-(1-(Imidazo[1,2-a]pyridin-6-yl)-1H-pyrazol-4-yl)-1H-pyrazolo[4,3-d]pyrimidin-5-yl)-3-methyl-3, 8-diazabicyclo[3.2.1]octan-2-one;

2-Methyl-4-(4-(5-(3-methyl-2-oxo-3, 8-diazabicyclo[3.2.1]octan-8-yl)-1H-pyrazolo[4,3-d]pyrimidin-3-yl)-1H-pyrazol-1-yl)benzonitrile;

3-Methyl-4-(4-(5-(3-methyl-2-oxo-3, 8-diazabicyclo[3.2.1]octan-8-yl)-1H-pyrazolo[4,3-d]pyrimidin-3-yl)-1H-pyrazol-1-yl)benzonitrile;

2-Fluoro-4-(4-(5-(3-methyl-2-oxo-3, 8-diazabicyclo[3.2.1]octan-8-yl)-1H-pyrazolo[4,3-d]pyrimidin-3-yl)-1H-pyrazol-1-yl)benzonitrile;

N,N-Dimethyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)benzamide;

N-Methyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)benzamide;

2-Fluoro-N-methyl-4-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)benzamide; and N-Methyl-5-(4-(5-(3-methyl-2-oxo-3,8-diazabicyclo[3.2.1]octan-8-yl)-1H-pyrazolo[4,3-d]pyrimidin-3-yl)-1H-pyrazol-1-yl)picolinamide;

or a pharmaceutically acceptable salt thereof.

48. A pharmaceutical composition comprising a compound of claim 1, or a pharmaceutically acceptable salt thereof, and at least one pharmaceutically acceptable carrier or excipient.

\* \* \* \* \*

UNITED STATES PATENT AND TRADEMARK OFFICE
CERTIFICATE OF CORRECTION

PATENT NO. : 11,111,247 B2
APPLICATION NO. : 16/580766
DATED : September 7, 2021
INVENTOR(S) : Oleg Vechorkin et al.

It is certified that error appears in the above-identified patent and that said Letters Patent is hereby corrected as shown below:

In the Claims

Column 137, Line 65, Claim 1, delete "$NR^{c1}C(O)OR^{a1}$" and insert -- $NR^{c1}C(O)OR^{a1}$, --;

Column 138, Line 12, Claim 1, delete "attached" and insert -- attached, --;

Column 138, Line 31, Claim 1, delete "$NR^{c3}R^{d3}$" and insert -- $NR^{c3}R^{d3}$, --;

Column 138, Lines 32-33, Claim 1, delete "$NR^{c3}S(O)_2NR^{c3}R^{d3}$" and insert -- $NR^{c3}S(O)_2NR^{c3}R^{d3}$, --;

Column 138, Lines 50-51, Claim 1, delete "$NR^{c5}S(O)_2NR^{c5}R^{d5}$" and insert -- $NR^{c5}S(O)_2NR^{c5}R^{d5}$, --;

Column 139, Line 4, Claim 1, delete "$S(O)R^{b2}$" and insert -- $S(O)R^{b2}$, --;

Column 139, Lines 22-23, Claim 1, delete "$NR^{c4}S(O)_2NR^{c4}R^{d4}$" and insert -- $NR^{c4}S(O)_2NR^{c4}R^{d4}$, --;

Column 139, Line 39, Claim 1, delete "$NR^{c6}R^{d6}$" and insert -- $NR^{c6}R^{d6}$, --;

Column 139, Line 39, Claim 1, delete "$NR^{6}C(O)OR^{a6}$" and insert -- $NR^{c6}C(O)OR^{a6}$, --;

Column 139, Line 40, Claim 1, delete "$NR^{c6}S(O)_2NR^{c6}R^{d6}$" and insert -- $NR^{c6}S(O)_2NR^{c6}R^{d6}$, --;

Column 141, Line 40, Claim 1, delete "heteroaryl-$C_{13}$" and insert -- heteroaryl-$C_{1-3}$ --.

Column 143, Line 65, Claim 11, delete "$R^H$." and insert -- $R^{11}$. --.

Column 144, Line 11, Claim 13, delete "RH." and insert -- $R^{11}$. --.

Column 144, Line 58, Claim 21, before "4-cyano" insert -- imidazo[1,2- a]pyridin-6-yl, --.

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,111,247 B2

Column 149, Line 37, Claim 42, after "$C_{3-10}$" insert -- cycloalkyl-$C_{1-3}$ --;

Column 150, Line 48, Claim 42, delete "$R'^{12}$;" and insert -- $R^{12}$; --.

Column 151, Line 10, Claim 43, delete "1,2" and insert -- 1, 2 --.

Column 154, Line 15, Claim 46, delete "3, 5" and insert -- 3,5 --;

Column 154, Line 24, Claim 46, delete "o1;" and insert -- ol; --;

Column 154, Line 25, Claim 46, delete "3, 5" and insert -- 3,5 --;

Column 154, Line 28, Claim 46, delete "3, 5" and insert -- 3,5 --;

Column 154, Line 37, Claim 46, delete "3, 5" and insert -- 3,5 --;

Column 154, Line 40, Claim 46, delete "3, 5" and insert -- 3,5 --;

Column 154, Line 54, Claim 46, delete "3, 8" and insert -- 3,8 --.

Column 155, Line 12, Claim 47, delete "methanone" and insert -- methanone; --;

Column 156, Lines 1-2, Claim 47, delete "5, 6" and insert -- 5,6 --;

Column 156, Line 7, Claim 47, delete "5, 6" and insert -- 5,6 --;

Column 156, Line 35, Claim 47, delete "3, 8" and insert -- 3,8 --;

Column 156, Line 51, Claim 47, delete "3, 8" and insert -- 3,8 --;

Column 156, Line 63, Claim 47, delete "3, 8" and insert -- 3,8 --;

Column 156, Line 66, Claim 47, delete "3, 8" and insert -- 3,8 --;

Column 157, Line 2, Claim 47, delete "3, 8" and insert -- 3,8 --;

Column 157, Line 5, Claim 47, delete "3, 8" and insert -- 3,8 --;

Column 157, Line 16, Claim 47, delete "3, 8" and insert -- 3,8 --;

Column 157, Line 25, Claim 47, delete "3, 8" and insert -- 3,8 --;

Column 157, Line 28, Claim 47, delete "3, 8" and insert -- 3,8 --;

Column 158, Line 2, Claim 47, delete "3, 8" and insert -- 3,8 --;

Column 158, Line 4, Claim 47, delete "3, 8" and insert -- 3,8 --;

Column 158, Line 7, Claim 47, delete "3, 8" and insert -- 3,8 --;

Column 158, Line 10, Claim 47, delete "3, 8" and insert -- 3,8 --.

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: synthetic peptide

<400> SEQUENCE: 1

Glu Gln Glu Asp Glu Pro Glu Gly Asp Tyr Phe Glu Trp Leu Glu
1               5                   10                  15